(12) United States Patent
Omura et al.

(10) Patent No.: US 8,438,067 B2
(45) Date of Patent: May 7, 2013

(54) MEDICAL RESOURCE STORAGE AND MANAGEMENT APPARATUS AND MEDICAL SUPPLY MANAGEMENT SYSTEM

(75) Inventors: Shiro Omura, Tokyo (JP); Hideaki Hirobe, Tokyo (JP); Yoshihito Omura, Tokyo (JP); Takehiko Imura, Tokyo (JP)

(73) Assignee: Tosho Inc., Tokyo (JP)

( * ) Notice: Subject to any disclaimer, the term of this patent is extended or adjusted under 35 U.S.C. 154(b) by 1525 days.

(21) Appl. No.: 11/661,733

(22) PCT Filed: Aug. 23, 2005

(86) PCT No.: PCT/JP2005/015290
§ 371 (c)(1),
(2), (4) Date: May 8, 2007

(87) PCT Pub. No.: WO2006/027951
PCT Pub. Date: Mar. 16, 2006

(65) Prior Publication Data
US 2008/0065264 A1  Mar. 13, 2008

(30) Foreign Application Priority Data

| Sep. 3, 2004 | (JP) | 2004-256901 |
| Sep. 3, 2004 | (JP) | 2004-256926 |
| Sep. 3, 2004 | (JP) | 2004-256955 |
| Sep. 3, 2004 | (JP) | 2004-256987 |
| Sep. 14, 2004 | (JP) | 2004-266868 |
| Dec. 1, 2004 | (JP) | 2004-348692 |

(51) Int. Cl.
*G06Q 20/00* (2012.01)

(52) U.S. Cl.
USPC .................. 705/23; 705/22; 705/28

(58) Field of Classification Search .............. 705/22, 705/23, 28; 700/231
See application file for complete search history.

(56) References Cited

U.S. PATENT DOCUMENTS

| 6,272,394 B1 | 8/2001 | Lipps |
| 6,609,047 B1 * | 8/2003 | Lipps ........................ 700/231 |
| 2001/0032035 A1 * | 10/2001 | Holmes et al. ............. 700/231 |

FOREIGN PATENT DOCUMENTS

| JP | 07-257714 | 10/1995 |
| JP | 9503732 | 4/1997 |
| JP | 09-315525 | 12/1997 |

(Continued)

OTHER PUBLICATIONS

Int'l Search Report, Oct. 25, 2005.

(Continued)

*Primary Examiner* — Elaine Gort
(74) *Attorney, Agent, or Firm* — Matthew B. Dernier, Esq.; Gibson & Dernier LLP

(57) ABSTRACT

Locations of storage on a rack 70 for arranging and storing medical resources are partitioned by a partition member 75. A medical resource detecting member 73 and a retrieval guidance member 72 are provided in each partition on the rack. By configuring the partition member 75 to be removable from a depression 71 in the rack 70, and by providing an input for configuration in a control unit 30 to designate whether or not the partition member 75 is inserted, the control unit 30 is operable to collectively process medical resource detecting members 73 and retrieval guidance members 72. In this way, a large variety of large and small medical resources can be stored for automatic management.

2 Claims, 98 Drawing Sheets

FOREIGN PATENT DOCUMENTS

| | | |
|---|---|---|
| JP | 2001505518 A | 4/2001 |
| JP | 2001-198194 | 7/2001 |
| JP | 2002-011072 | 1/2002 |
| JP | 2002-259778 | 9/2002 |
| JP | 2002-293414 | 10/2002 |
| WO | WO 95/03587 | 2/1995 |
| WO | WO 97/14104 | 4/1997 |

OTHER PUBLICATIONS

International Search Report of International Application PCT/JP2005/015290.

International Search Report of International Application PCT/JP2005/015290, Oct. 25, 2005.

* cited by examiner

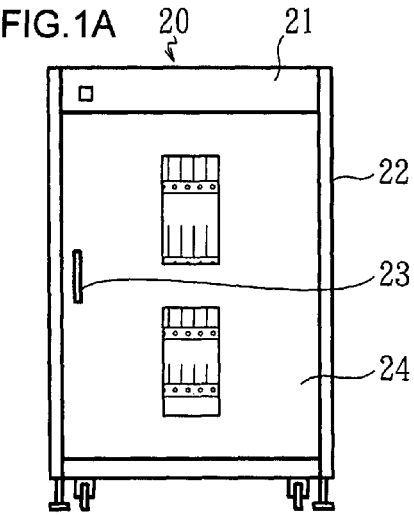
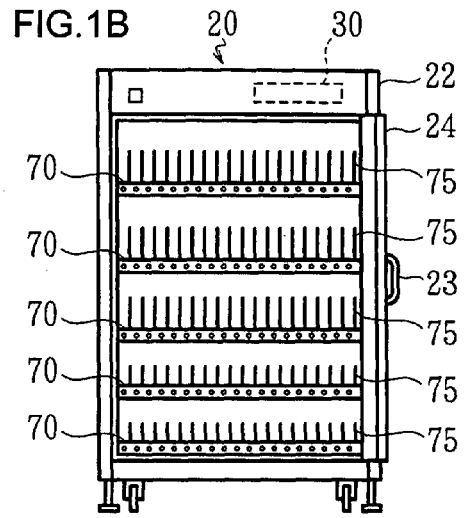
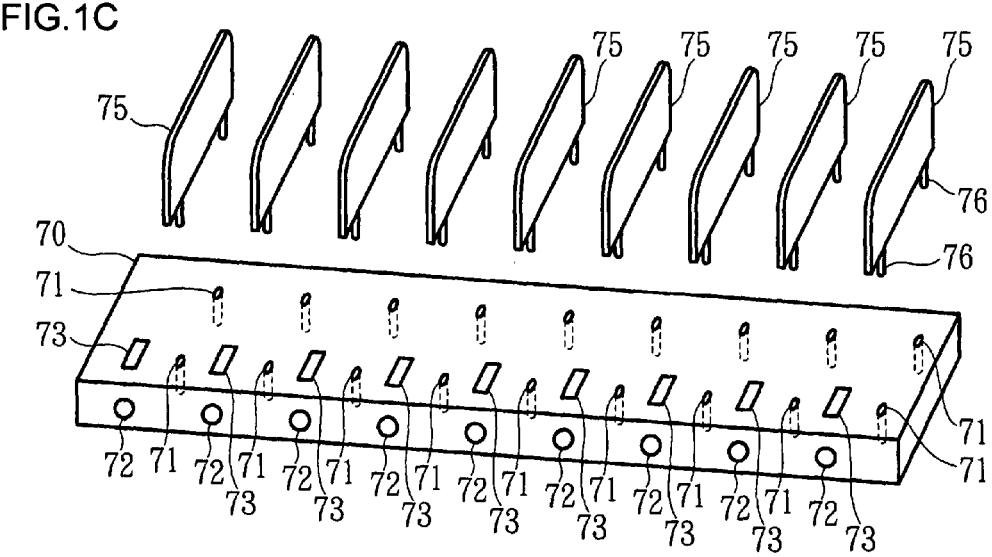
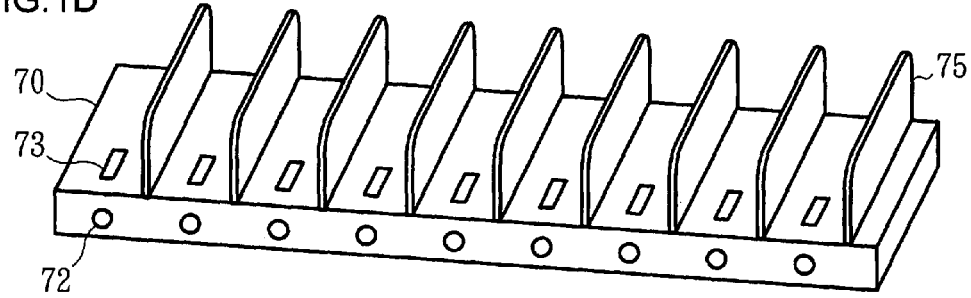

FIG.4A 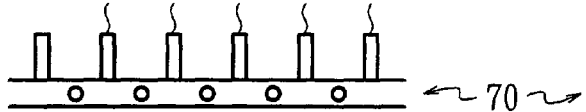 FIG.4B 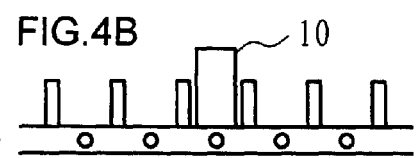
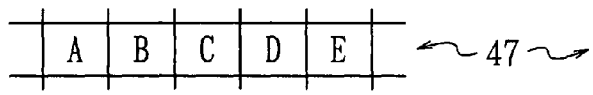 ← 70 →
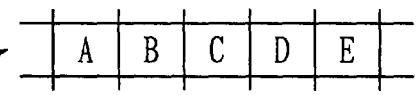
← 47 →
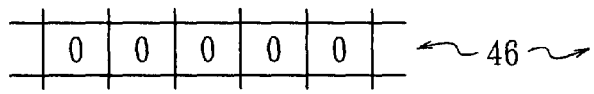 ← 46 →
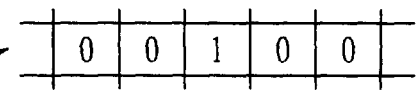
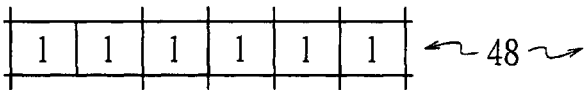 ← 48 →
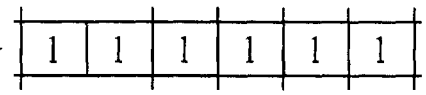
70 → 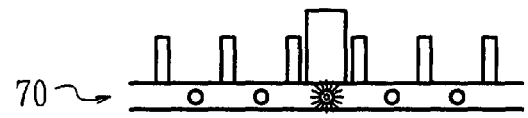

FIG.5A 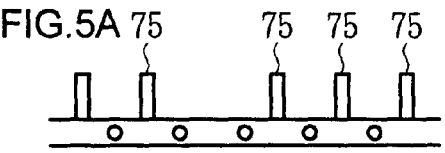 FIG.5B 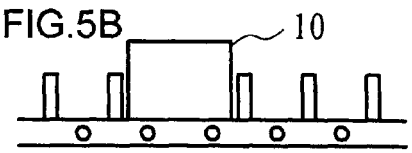
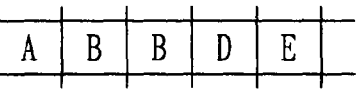 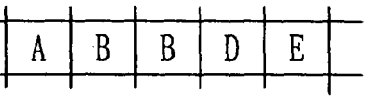
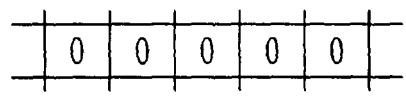 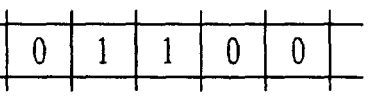
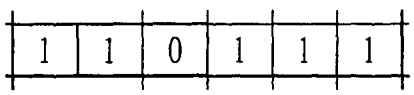 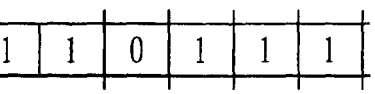
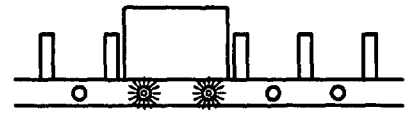
FIG.5C 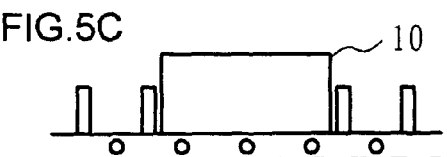 FIG.5D 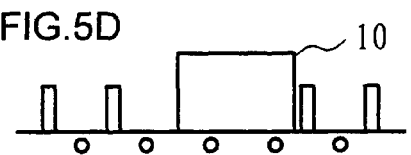
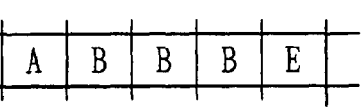 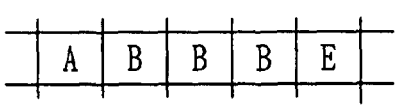
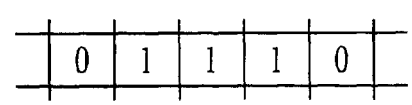 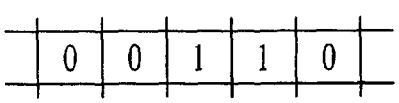
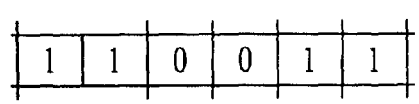 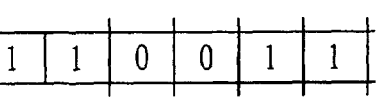
 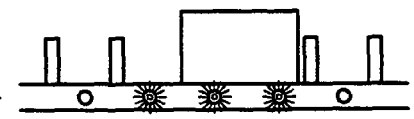

```
IN OPERATION  PATIENT INFORMATION  xxxxxxx
                                   0000000
DATE AND TIME 2004.8.26            ******

No.    MEDICAL        NO. OF      DATE AND TIME
       RESOURCE NAME  ITEMS
***    *** TUBE       ONE         2004.8.26 15:00
 ⋮      ⋮              ⋮             ⋮

[CONFIGURE] [REGISTER] [CONFIRM] [TALLY] [REPLENISH]
```

```
                    INFORMATION ON
REPLENISHMENT       OPERATOR         xxxxxxx
                    REPLENISHING     0000000
DATE AND TIME 2004.8.26              ******

[REGISTERED]  [NEW REGISTRATION]     [RETURN]
```

```
REGISTERED                    LOCATION AVAILABILITY
DATE AND TIME 2004.8.26  [OCCUPIED]  [EMPTY]

MEDICAL         NO. OF EMPTY
ADDRESS    No.      RESOURCE NAME   LOCATIONS
***        ***      *** TUBE        ONE            [▲]
***        ***      *** TUBE        THREE
 ⋮          ⋮        ⋮               ⋮             [▼]
```

39d, 39e, 39f, 39f

FIG. 13A 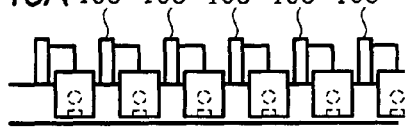 FIG. 13B 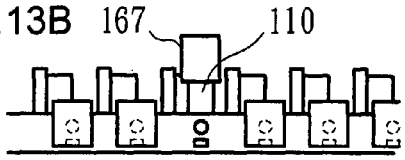
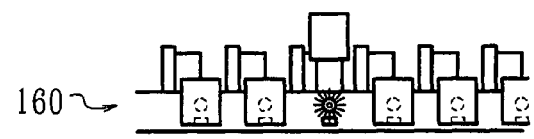

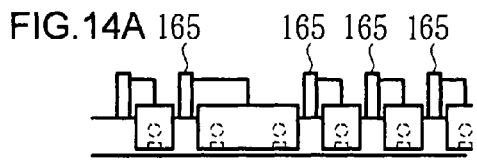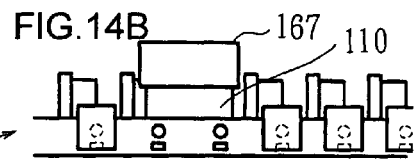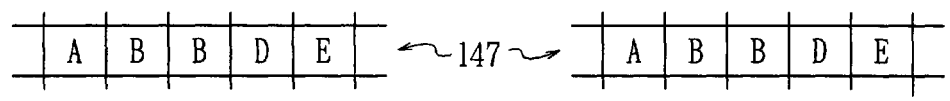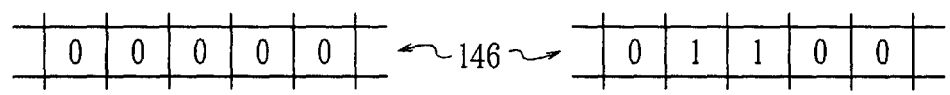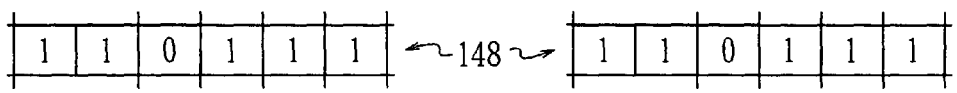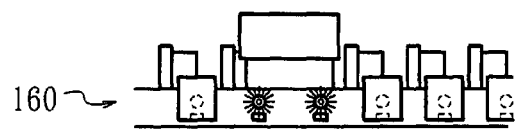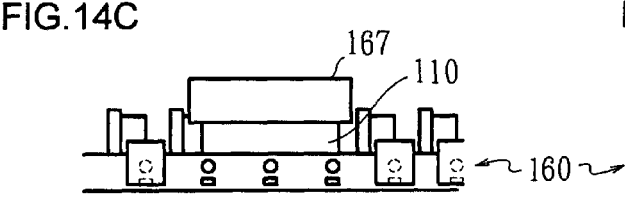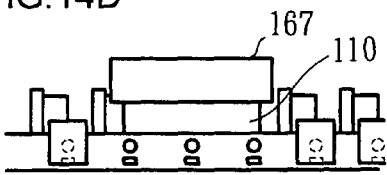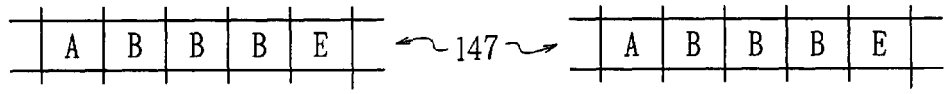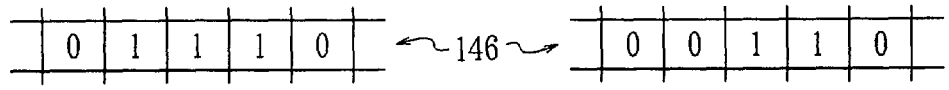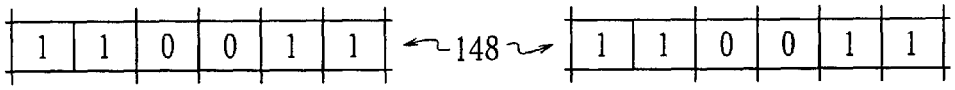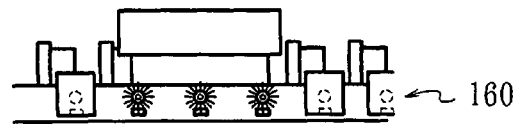

IN OPERATION  PATIENT INFORMATION  xxxxxxx
                                   0000000
DATE AND TIME 2004.8.26            ******

No.  MEDICAL        NO. OF    DATE AND TIME
     RESOURCE NAME  ITEMS
*  *FILTER      ONE PACKET  2004.8.26 15:00

139a

[CONFIGURE] [REGISTER] [CONFIRM] [TALLY] [REPLENISH]—139b

INFORMATION ON
REPLENISHMENT       OPERATOR       xxxxxxx
                  REPLENISHING     0000000
DATE AND TIME 2004.8.26            ******

139c—[REGISTERED]  [NEW REGISTRATION]   [RETURN]

REGISTERED                    LOCATION AVAILABILITY
DATE AND TIME 2004.8.26   [OCCUPIED] [EMPTY]—139e

MEDICAL         NO. OF EMPTY
ADDRESS No. RESOURCE NAME   LOCATIONS
*     * ***FILTER       ONE PACKET    ▲ —139f
139d—* * ***FILTER      THREE PACKETS
 :       :    :              :            ▼ —139f

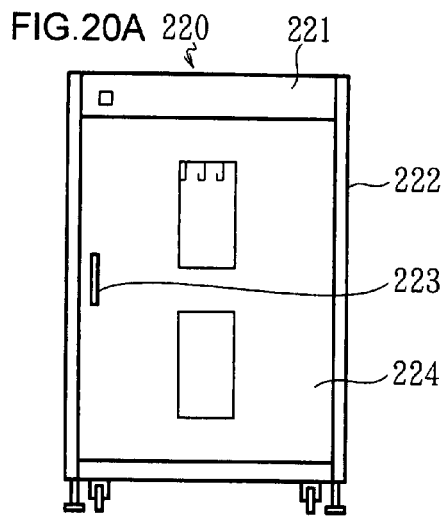
FIG.20A
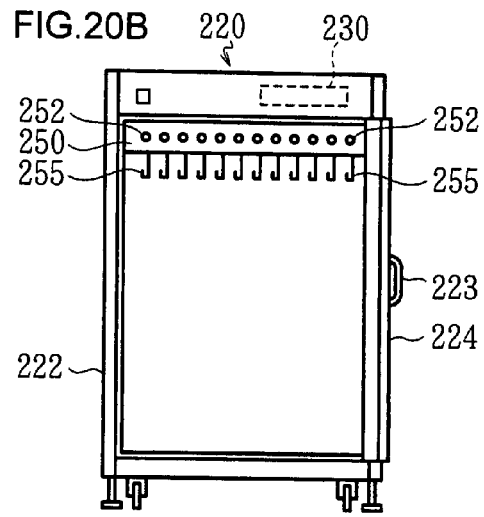
FIG.20B
FIG.20C
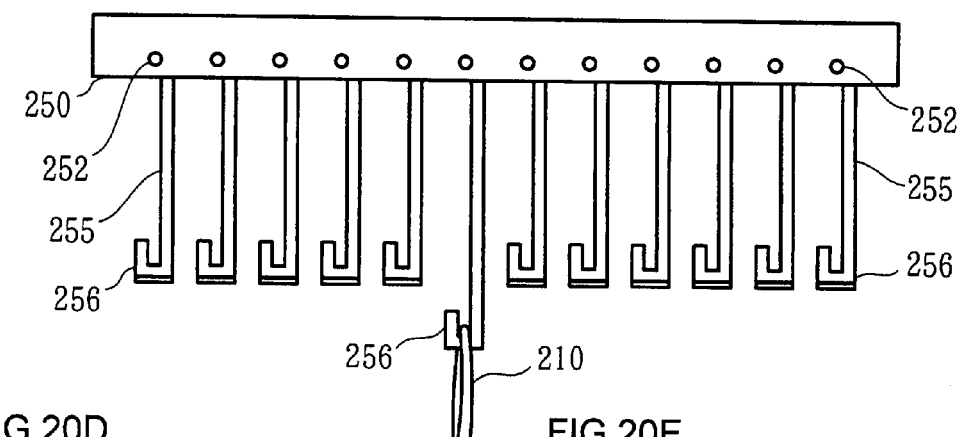
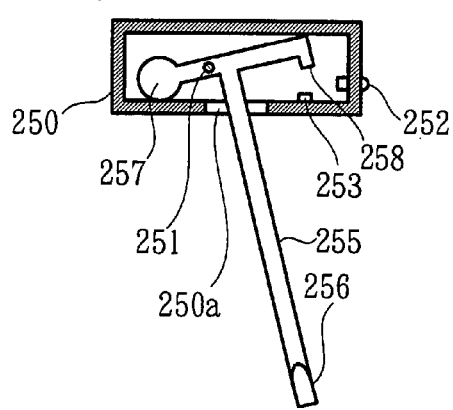
FIG.20D
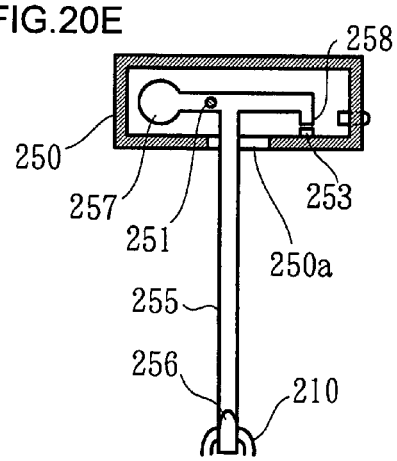
FIG.20E 255a
251  255

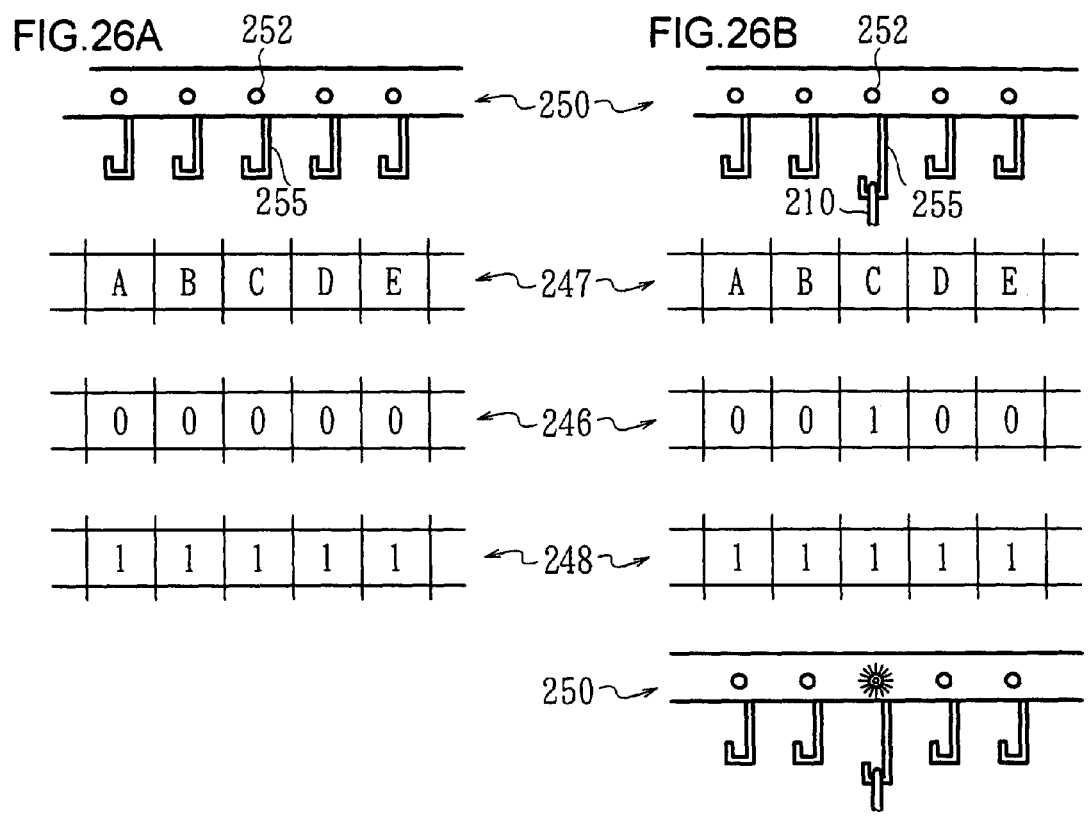

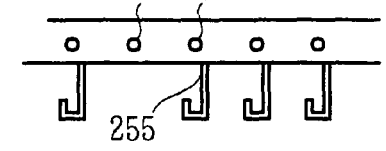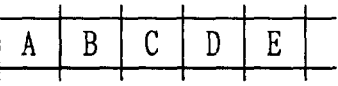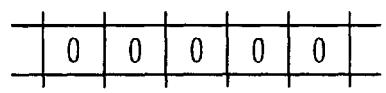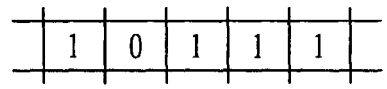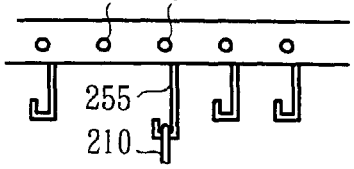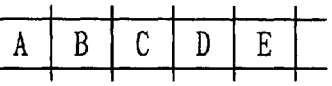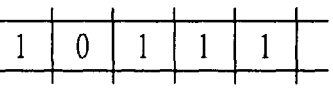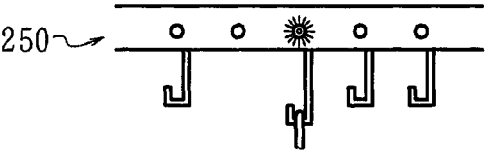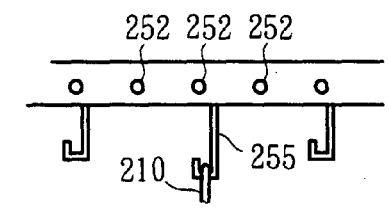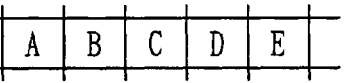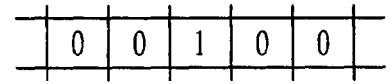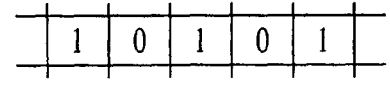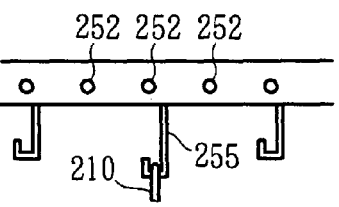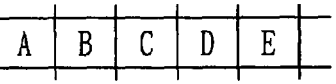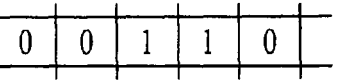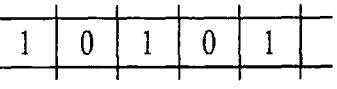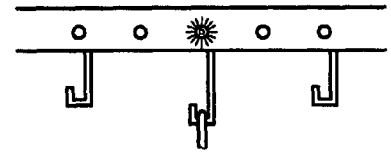

FIG.30A
FIG.30B
FIG.30C
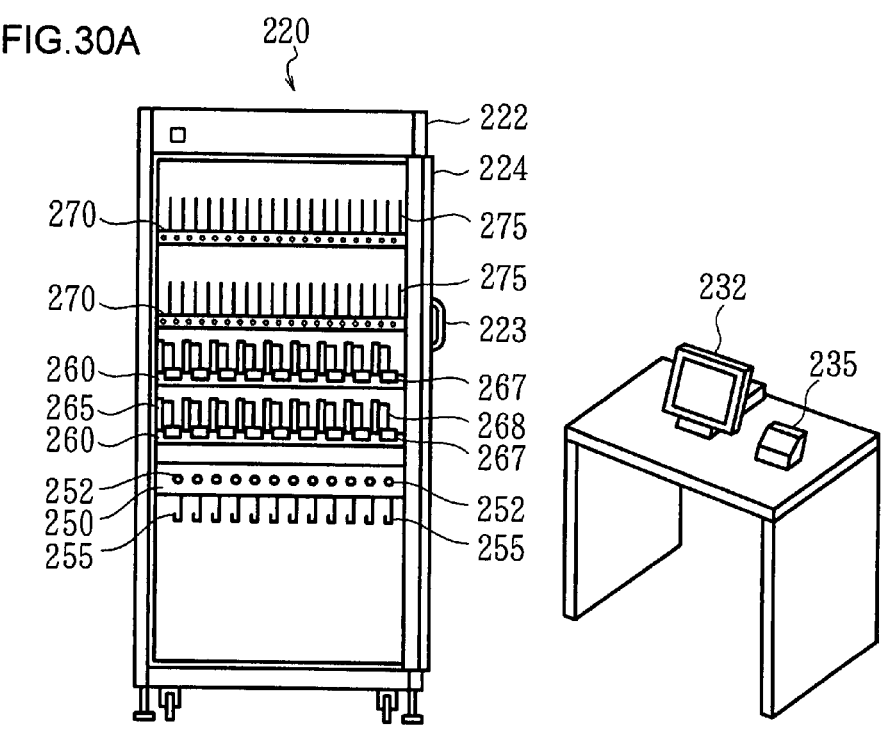
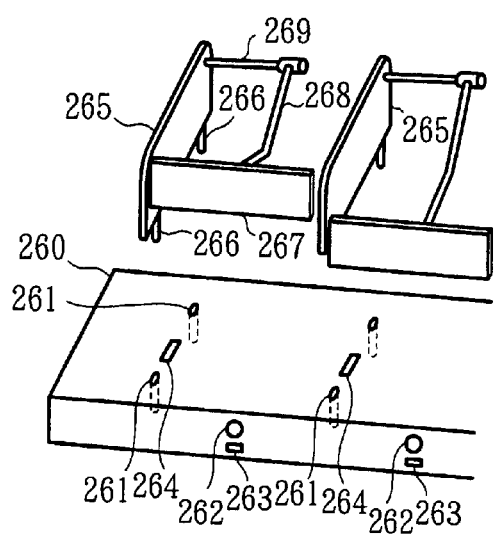
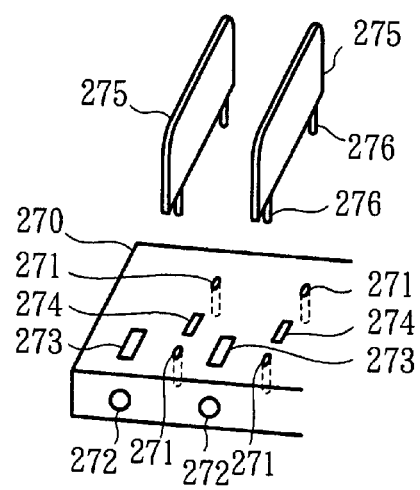

FIG.33A 239 (232+233+ 234)

IN OPERATION  PATIENT INFORMATION   xxxxxxx
                                    0000000
DATE AND TIME 2004.8.26              ******

MEDICAL         NO. OF
No.   RESOURCE NAME      ITEMS       DATE AND TIME
*   * CATHETER       ONE         2004.8.26 15:00

239a

| CONFIGURE | REGISTER | CONFIRM | TALLY | REPLENISH | — 239b

INFORMATION ON
REPLENISHMENT           OPERATOR       XXXXXXX
                       REPLENISHING    0000000
DATE AND TIME 2004.8.26                ******

239c —  | REGISTERED |   | NEW REGISTRATION |    | RETURN |

REGISTERED                    LOCATION AVAILABILITY
DATE AND TIME 2004.8.26   | OCCUPIED |  | EMPTY |   — 239e

MEDICAL         NO. OF EMPTY
         ADDRESS   No.   RESOURCE NAME   LOCATIONS
239d —   *       *   *** CATHETER    ONE        ▲ — 239f
         *       *   *** CATHETER    THREE
                                                    ▼ — 239f

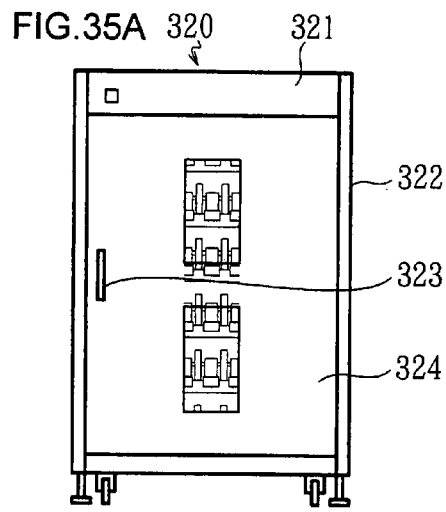
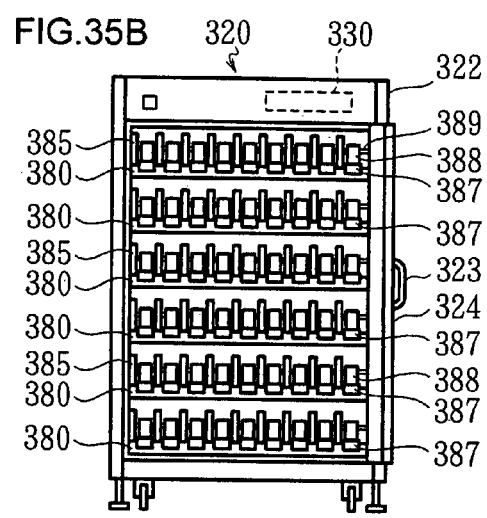
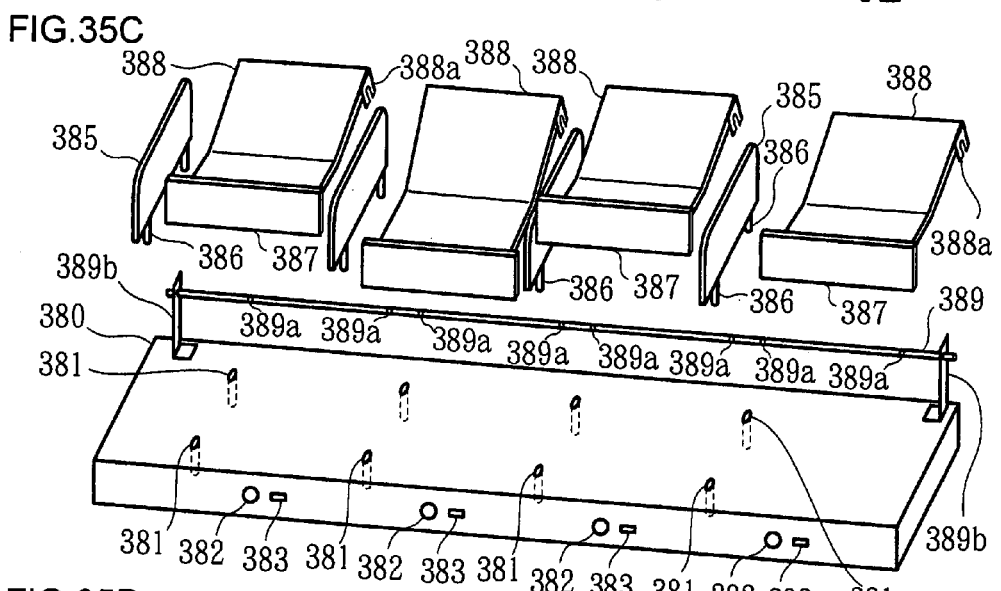
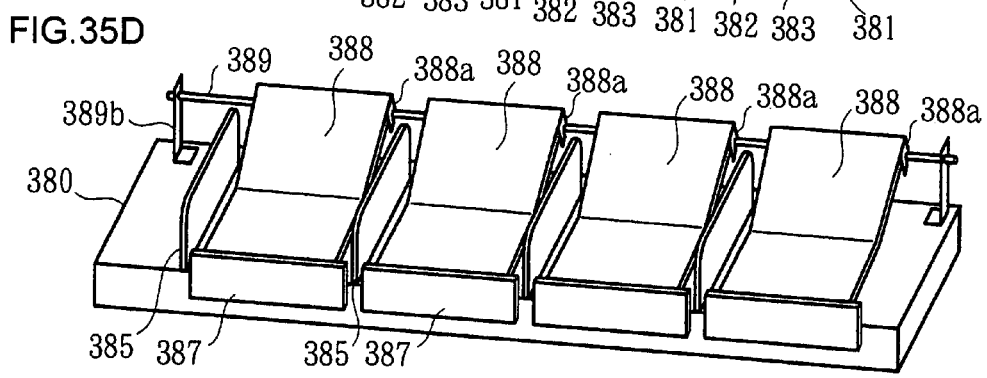

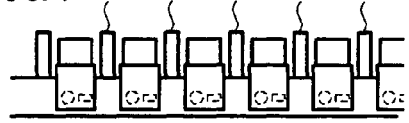
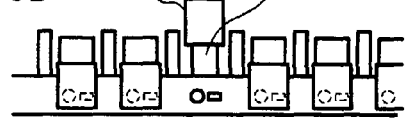
FIG.38A 385 385 385 385 385    FIG.38B 387  310
← 380 →
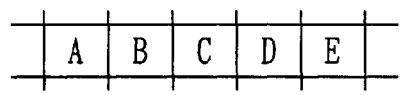
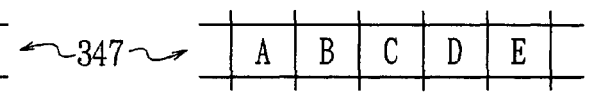
← 347 →
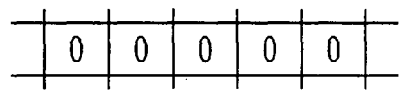
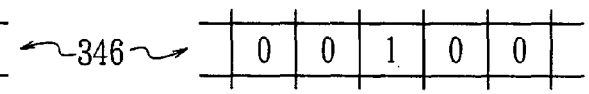
← 346 →
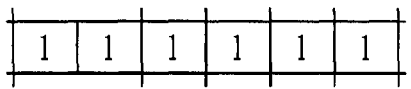
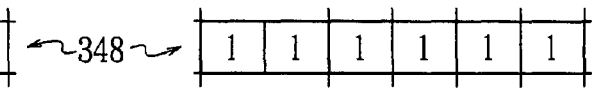
← 348 →
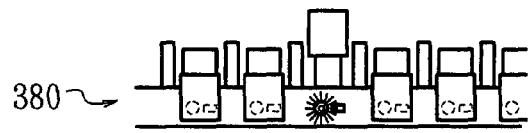
380 →

FIG.39A 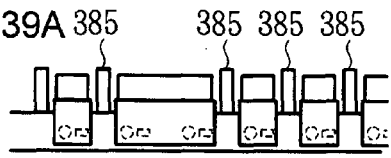  FIG.39B 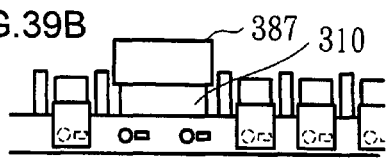
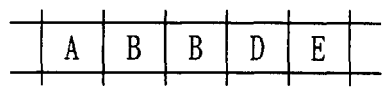 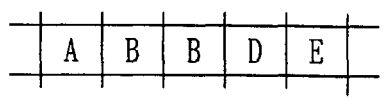
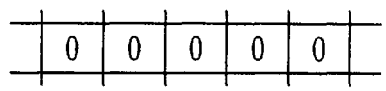 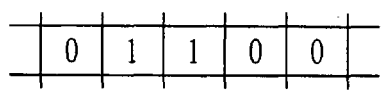
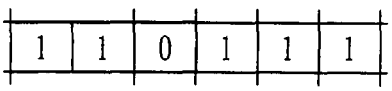 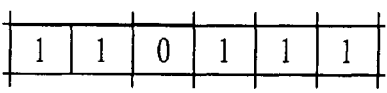
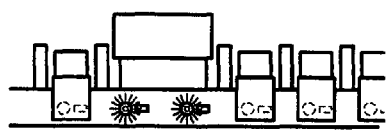
FIG.39C 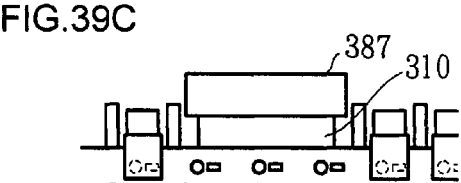  FIG.39D 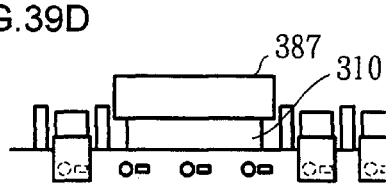
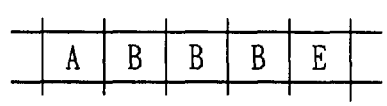 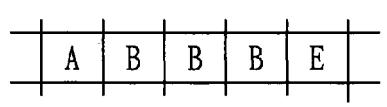
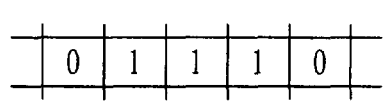 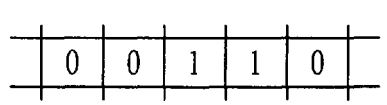
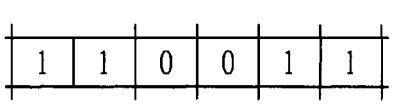 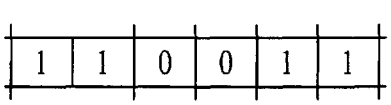
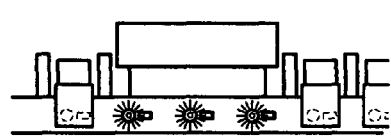

```
IN OPERATION  PATIENT INFORMATION   xxxxxxx
                                    0000000
DATE AND TIME 2004.8.26             *******

MEDICAL      NO. OF
No.  RESOURCE NAME  ITEMS    DATE AND TIME
***   ***FILTER  ONE PACKET  2004.8.26 15:00
 :       :           :             :
 :       :           :             :

[CONFIGURE] [REGISTER] [CONFIRM] [TALLY] [REPLENISH]
```

339a — left list area; 339b — buttons row

```
                   INFORMATION ON
REPLENISHMENT        OPERATOR       xxxxxxx
                   REPLENISHING     0000000
DATE AND TIME 2004.8.26             *******

NEW
         [REGISTERED]   [REGISTRATION]      [RETURN]
```

339c — REGISTERED button

```
REGISTERED              LOCATION AVAILABILITY
DATE AND TIME 2004.8.26  [OCCUPIED]  [EMPTY]

MEDICAL      NO. OF EMPTY
ADDRESS   No.   RESOURCE NAME    LOCATIONS
 ***      ***    ***FILTER       ONE PACKET     [▲]
 ***      ***    ***FILTER       THREE PACKETS
  :        :         :                :         [▼]
```

339d — list; 339e — OCCUPIED/EMPTY; 339f — scroll arrows

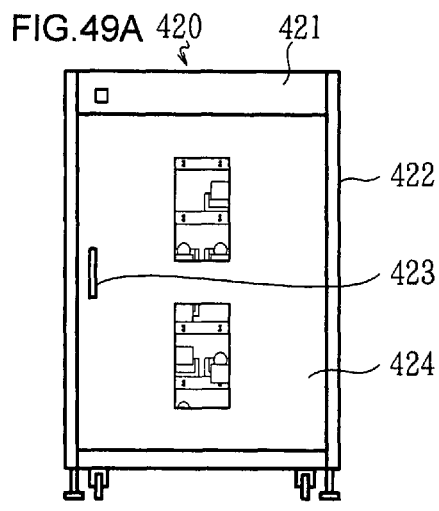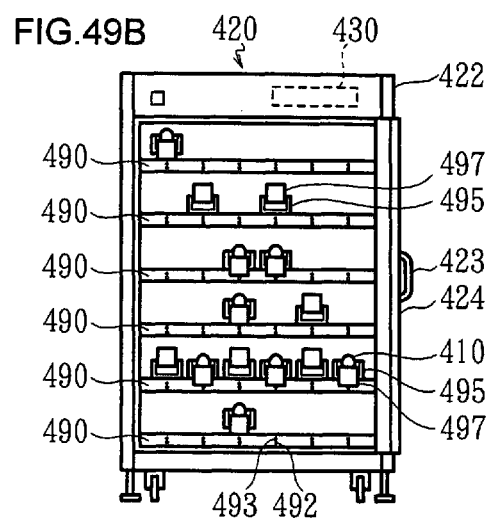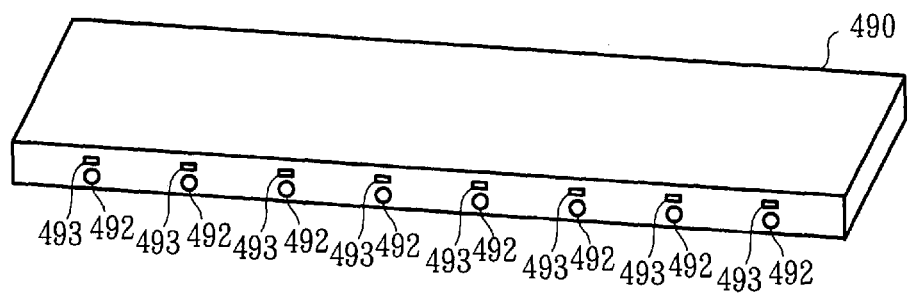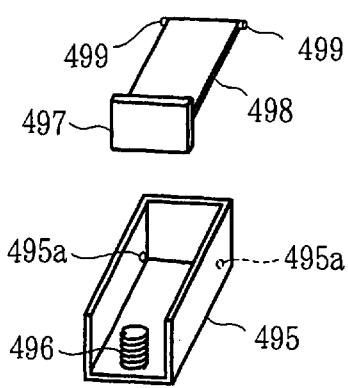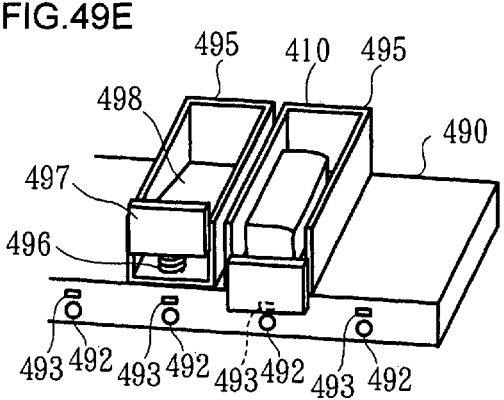

FIG.52A  FIG.52B 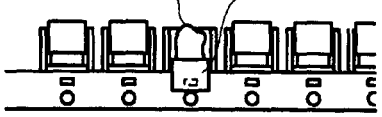
←~490~→
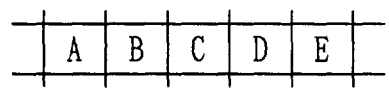 ←~447~→ 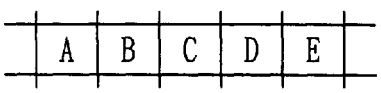
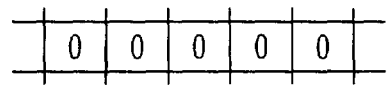 ←~446~→ 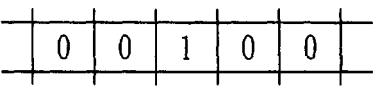
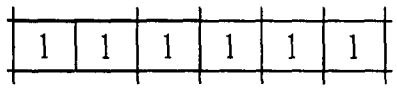 ←~448~→ 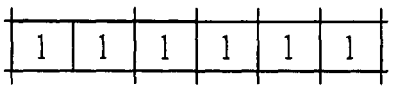
490~→ 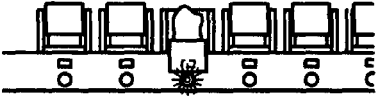

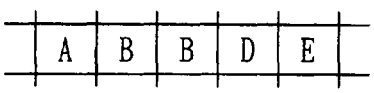 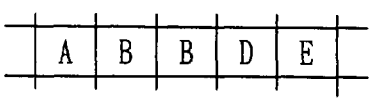
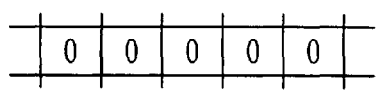 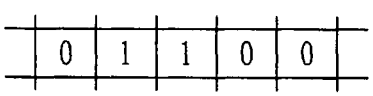
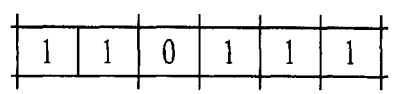 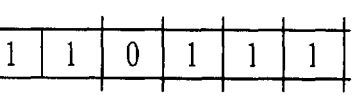
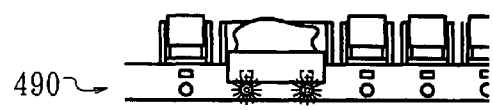

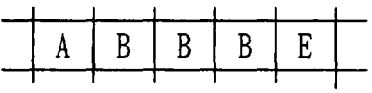 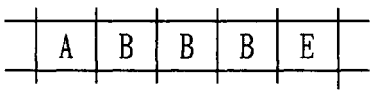
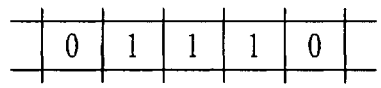 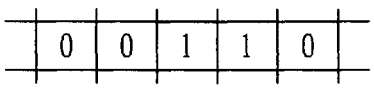
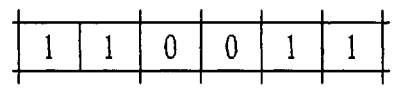 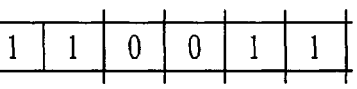
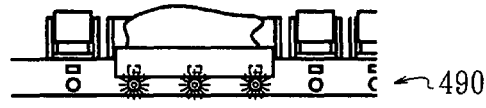

```
┌─────────────────────────────────────────────┐
│ ┌──────────────┐                            │
│ │IN OPERATION │ PATIENT INFORMATION  xxxxxxx│
│ └──────────────┘                     0000000│
│ DATE AND TIME 2004.8.26              ******│
│          MEDICAL      NO. OF                │
│   No.  RESOURCE NAME  ITEMS    DATE AND TIME│
│   ***   ***FILTER  ONE PACKET 2004.8.26 15:00│
│    :        :          :           :        │
│                                             │
│ [CONFIGURE][REGISTER][CONFIRM][TALLY][REPLENISH]│
└─────────────────────────────────────────────┘
```
439a (left); 439b (right)

```
┌─────────────────────────────────────────────┐
│ ┌──────────────┐   INFORMATION ON           │
│ │REPLENISHMENT │      OPERATOR       xxxxxxx│
│ └──────────────┘    REPLENISHING    0000000 │
│ DATE AND TIME 2004.8.26              ******│
│                                             │
│                       NEW                   │
│        [REGISTERED] [REGISTRATION] [RETURN] │
│                                             │
└─────────────────────────────────────────────┘
```
439c

```
┌─────────────────────────────────────────────┐
│ ┌──────────┐           ┌──────────────────┐│
│ │REGISTERED│           │LOCATION AVAILABILITY││
│ └──────────┘           └──────────────────┘│
│ DATE AND TIME 2004.8.26 [OCCUPIED] [EMPTY] │
│                    MEDICAL    NO. OF EMPTY │
│       ADDRESS  No. RESOURCE NAME LOCATIONS │
│        ***     *** ***FILTER  ONE PACKET  ▲│
│        ***     *** ***FILTER  THREE PACKETS│
│         :       :      :         :        ▼│
└─────────────────────────────────────────────┘
```
439e; 439d; 439f (×2)

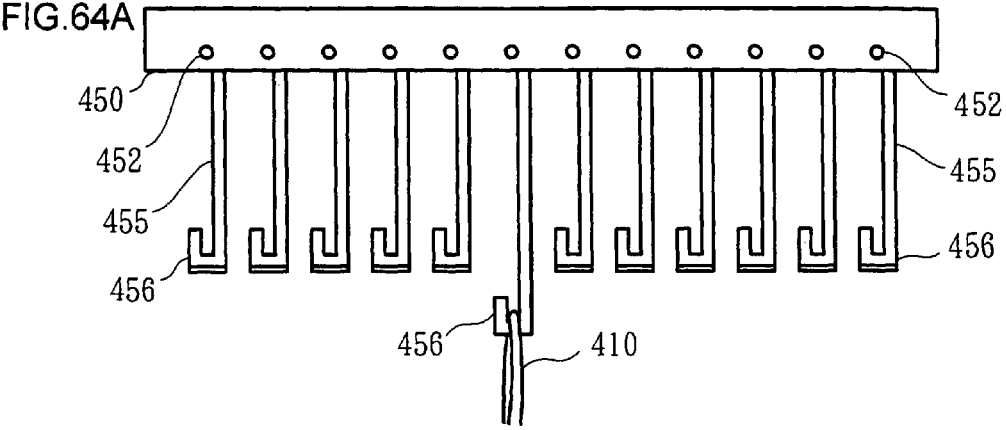
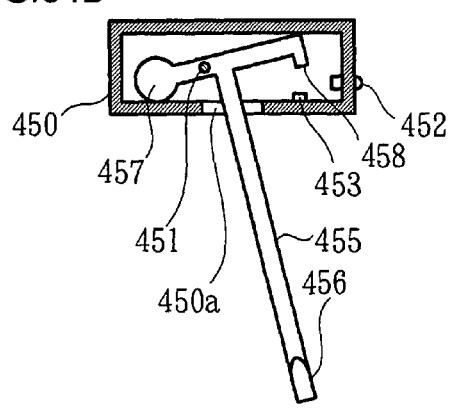
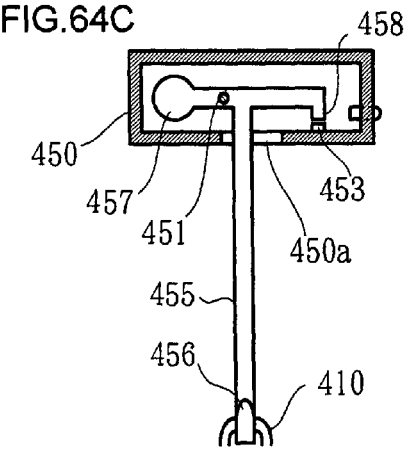
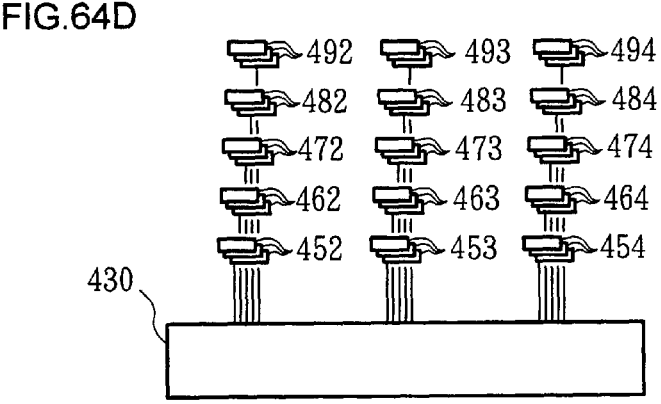

FIG.69

[CORRESPONDENCE INFORMATION FILE] 1021

| MEDICAL SUPPLY STORAGE PART CODE | MEDICAL SUPPLY CODE |
|---|---|
| 1 | ○○○○ |
| 2 | △△△△ |
| ⋮ | ⋮ |
| N | □□□□ |

FIG.70

[MANAGEMENT INFORMATION]

| WHETHER MEDICAL SUPPLY IS STORED |
|---|
| TYPE AND AMOUNT OF MEDICAL SUPPLIES STORED |
| TYPE AND AMOUNT OF MEDICAL SUPPLIES TAKEN OUT |
| TYPE AND AMOUNT OF MEDICAL SUPPLIES ACCEPTED |

FIG.87

[TYPE-BY-TYPE MEDICAL SUPPLY STOCK FILE]   1092

| TYPE OF MEDICAL SUPPLY | WHOLE INSTITUTION | MEDICAL OPERATION UNIT | DISPENSARY | MEDICAL WARD | ... |
|---|---|---|---|---|---|
| MEDICAL SUPPLY 1 | ○○○ | ○○○ | ○○○ | ○○○ | |
| MEDICAL SUPPLY 2 | ○○○ | ○○○ | ○○○ | ○○○ | |
| MEDICAL SUPPLY 3 | ○○○ | ○○○ | ○○○ | ○○○ | |
| ⋮ | ⋮ | ⋮ | ⋮ | ⋮ | |
| MEDICAL SUPPLY N | ○○○ | ○○○ | ○○○ | ○○○ | |
| ⋮ | ⋮ | ⋮ | ⋮ | ⋮ | |

FIG.88

[MEDICAL SUPPLY N]

| EXPIRATION DATE | AMOUNT |
|---|---|
| H16.11. 1~10 | ○○○○ |
| H16.11.11~20 | ○○○○ |
| H16.11.21~30 | ○○○○ |
| ⋮ | ⋮ |
| H○○.○○.○○~○○ | ○○○○ |
| ⋮ | ⋮ |

FIG.91

[TYPE-BY-TYPE TARGET MEDICAL SUPPLY STOCK FILE]    1093

| TYPE OF MEDICAL SUPPLY | WHOLE INSTITUTION | MEDICAL OPERATION UNIT | DISPENSARY | MEDICAL WARD | ... |
|---|---|---|---|---|---|
| MEDICAL SUPPLY 1 | ○○○ | ○○○ | ○○○ | ○○○ | |
| MEDICAL SUPPLY 2 | ○○○ | ○○○ | ○○○ | ○○○ | |
| MEDICAL SUPPLY 3 | ○○○ | ○○○ | ○○○ | ○○○ | |
| ⋮ | ⋮ | ⋮ | ⋮ | ⋮ | |
| MEDICAL SUPPLY N | ○○○ | ○○○ | ○○○ | ○○○ | |
| ⋮ | ⋮ | ⋮ | ⋮ | ⋮ | |

FIG.92

[TYPE-BY-TYPE MEDICAL SUPPLY ORDER FILE] 1094

| MEDICAL SUPPLY SUPPLIER | TYPE OF MEDICAL SUPPLY ORDERED | AMOUNT ORDERED |
|---|---|---|
| SUPPLIER A | MEDICAL SUPPLY 2 | ○○○○ |
| | MEDICAL SUPPLY 11 | ○○○○ |
| | MEDICAL SUPPLY 30 | ○○○○ |
| SUPPLIER B | — | — |
| SUPPLIER C | MEDICAL SUPPLY 5 | ○○○○ |
| | MEDICAL SUPPLY 9 | ○○○○ |
| ⋮ | ⋮ | ⋮ |

MEDICAL RESOURCE STORAGE AND MANAGEMENT APPARATUS AND MEDICAL SUPPLY MANAGEMENT SYSTEM

TECHNICAL FIELD

The present invention relates to a medical resource storage and management apparatus which stores and manages medical resources and a medical supply management system which manages medical supplies including medical resources and medicines.

BACKGROUND TECHNOLOGY

Medicine storage apparatuses, which allow retrieving medicines such as ampouled injection medicines in a single action, returning medicines without disturbing the arrangement, and keeping track of storage status properly, are being developed. The medicine storage apparatus is provided with a large number of cassettes each aligning and storing medicines, and a support means for arranging and holding the cassettes. A port is formed in each cassette to allow medicine to be pushed inside as well as retrieved from the cassette. The cassette is also provided with an urging means for urging the stored medicine toward the port. The support means is provided with a rack which holds the cassettes arranged in multiple tiers or multiple rows, while exposing the port, and with a counting means for determining the number of medicines stored in each cassette. For accurate medicine management providing a real-time output, the medicine storage apparatus is also provided with: an output means such as a printer, a storage medium and a communication device which outputs medicine management data in response to storage and retrieval of medicines in and out of the cassettes; and an information processing means which performs processes such as tallying, monitoring, reviewing and stock control, in accordance with the output data.

Before the medicine storage apparatuses of this type were developed and offered for use, people at a site of medical care such as an operating room tried to make a medical treatment easier by making available medicines such as injection medicines prior to a treatment such as an operation, i.e., by arranging and partitioning the medicines so as to be ready for use. To prevent medicines from running short during the treatment, extra supply of medicines were prepared. When the treatment is over, surplus medicines were returned to a dispensary and the medicines used in the treatment were counted. The task was primary undertaken by medical assistants or primary medical workers such as nurses. They had to rummage through a container such as a bucket for disposed articles. In many cases, they were also assigned the task of entering the number of medicines used in a form for management of medicines or in a computer system for stock control of medicines. Thus, those who completed a stressful task of attending a medical practice at a site of medical care such as an operating room had to continue to be responsible for extra management operations even after the main job is done. Consequently, they had hard time freeing themselves of strain and suffered heavy physical and mental burden. The task was made even more difficult and strenuous if, for example, an ampule of injection medicine is broken or a syringe was mixed in the disposed articles.

In addition to reduction in the burden of primary medical workers, provision of the aforementioned medicine storage apparatus for practical use offers the following additional advantages.

That is, the apparatus has made possible fair and impartial information management and information systems. Another advantage is that reproducibility is ensured easily. Computer-based management saves manpower expenses and labor cost, improves the quality of management and enhances reliability. Tallying the amount of use enables maintaining proper stock and reducing dead stock, thereby contributing to hospital management. As the flexibility in layout in the interior space is high, medicines are easy to handle, and work efficiency is improved. Since the apparatus also enables automated inputting and tallying of management data, input errors are reduced and the manpower expenses needed for operation are also reduced. The apparatus is of a simple configuration adapted for a mode of operation involving just as many people as are needed at a site of medical care. As such, the maintenance cost is low. The usage of the apparatus is easy to learn, not requiring in-depth system knowledge or understanding, or high-level proficiency. As a result, there would be only few operation mistakes.

When an action of retrieving a medicine is performed, it is determined that the medicine is set. When an action of returning a medicine is performed, it is determined that the setting action is revoked and made to remain uncompleted. In this process, not only the retrieval action but also the return action doe snot require entry of data, preventing input errors and human failures. The whole operation of retrieval, return, inspection, and replenishment can be done promptly. Since the sequence of taking out medicines and the combination of the medicines taken out can be checked in real time, the apparatus contributes also to mishaps-in-medical-practice prevention, prevention of mistakes, risk management, and prevention of near accidents. Since medicines are partitioned and stored into the cassettes, check and review can be performed easily when inspecting a refill at the time of replenishment and inspecting a returned article. Since the medicines are tallied in real time without time lag, a series of actions in setting a medicine can be reviewed without a data entry. Check of the expiration date of medicines, preparation of medication history lists of patients, etc. can be performed automatically.

[Patent Document No. 1]
JP 2001-198194
[Patent Document No. 2]
JP 2002-259778
[Patent Document No. 3]
JP 2002-11072

As such an excellent medicine storage apparatus becomes widely accepted, expectation arose that an apparatus having the same advantage could be used for accurate storage and management of medical resources other than medicines. This has led to a demand for medical resource storage and management apparatuses which are capable of easily and properly storing and retrieving medical resources and automatically keeping track of storage status.

It should then be noted that medical resources include consumable items and sterilized resources. An extensive variety would be encompassed even excluding drugs, medical implements and medical equipment. It is therefore improper to use the conventional scheme of aligning and storing them in cassettes.

Illustrative examples of such resources include catheters, tubes, plates to reconstruct osseous defect, artificial joints, pacemakers, which are all expensive. They come in a variety of forms. For example, they are boxed, packed, provided as a single article or packaged into a kit. The amount of medical resources used is also diversified. For example, the same resource may be used in a large amount or a large variety of resources may be used each in a small amount. Further, medicines are variously handled in a Class 1000 operating room, a central treatment room, an emergency treatment room or in a less-equipped medical ward. Another fact of note is that medical resources are expected to be sanitary and safe to use. Particularly, sterilized resources are cleansed in a pre-operation room, using various methods of sterilization such as EO gas sterilization, ultraviolet irradiation sterilization, sterilization by boiling and wet sterilization. It is also to be noted that the effect of sterilization derived from any sterilization method expires after a certain period of time, which differs from one method to another.

Accordingly, an important task would be to arrange and store an extensive variety of medical resources without accommodating them in cassettes, while still allowing easy retrieval. An additional task would be to employ measures to prevent disarrangement of the medical resources stored and resultant disorganization, in order to ensure that, even in cassetteless storage, availability of each medical resource can be properly detected for automatic management and that, for smooth retrieval, a user is properly guided to a location of storage of a medical resource to be taken out. A technical task to implement such measures would be to simplify the structure of the apparatus in view of the characteristics of medical resources and to work out a way to store as much variety as possible of medical resources in the simple apparatus.

DISCLOSURE OF THE INVENTION

An embodiment of the present invention relates to a medical resource storage and management apparatus. The apparatus comprises: a rack in which a series of depressions for insertion of partition members are formed so that a large number of medical resources are retrievably placed in respective partitions; partition members which are removably inserted into the depressions; medical resource detecting members which are arranged on the rack so as to alternate with the depressions in a direction in which the depressions are arranged, and each of which detects whether or not a medical resource is placed; retrieval guidance members for visual guidance which are arranged on the rack so as to alternate with the depressions in a direction in which the depressions are arranged; and a control unit which manages the storage status of the medical resources, based on the detection by the medical resource detecting members and which operates one of the retrieval guidance members in response to an input designating retrieval, wherein the control unit allows providing an input for configuration to designate whether or not the partition member is inserted into the depression, and the control unit collectively processes a block of medical resource detecting members and retrieval guidance members identified as being located on both sides of the depression from which the partition member is removed, based on the input for configuration.

Another embodiment of the present invention also relates to a medical resource storage and management apparatus. The apparatus may comprise: a rack in which a series of depressions for insertion of partition members are formed so that a large number of medical resources are retrievably placed in respective partitions; partition members which are removably inserted into the depressions; medical resource detecting members which are arranged on the rack so as to alternate with the depressions in a direction in which the depressions are arranged, and each of which detects whether or not a medical resource is placed; retrieval guidance members for visual guidance which are arranged on the rack so as to alternate with the depressions in a direction in which the depressions are arranged; a control unit which manages the storage status of the medical resources, based on the detection by the medical resource detecting members and which operates one of the retrieval guidance members in response to an input designating retrieval; and partition detecting members each of which detects whether the partition member is inserted into the depression, wherein the control unit may collectively process a block of medical resource detecting members and retrieval guidance members identified as being located on both sides of the depression from which the partition member is removed, based on the detection by the partition detecting member.

Still another embodiment of the present invention also relates to a medical resource storage and management apparatus. The apparatus may comprise: a rack in which a series of depressions for insertion of partition members are formed so that a large number of medical resources are retrievably placed in respective partitions; partition members which are removably inserted into the depressions; medical resource detecting members which are arranged on the rack so as to alternate with the depressions in a direction in which the depressions are arranged, and each of which detects whether or not a medical resource is placed; retrieval guidance members for visual guidance which are arranged on the rack so as to alternate with the depressions in a direction in which the depressions are arranged; and a control unit which manages the storage status of the medical resources, based on the detection by the medical resource detecting members and which operates one of the retrieval guidance members in response to an input designating retrieval, wherein a medical resource name plate for visual guidance may be attached to a partition member via a connecting member such that the connecting member is moved up and down depending on whether a medical resource is placed and as a result of interference between the connecting member and the medical resource, and that the medical resource name plate is located in a space where retrieval of a medical resource takes place, and is moved in association with the connecting member, and wherein the medical resource detecting member may indirectly detect whether or not a medical resource is placed by detecting whether the medical resource name plate is raised or lowered.

The medical resource name plate, when elevated in association with the placement of a medical resource in the associated location, may be located above the retrieval guidance member in the associated location, and the medical resource name plate, when lowered in response to the retrieval of the medical resource from the associated location, shields the retrieval guidance member in the associated location from view.

Yet another embodiment of the present invention also relates to a medical resource storage and management apparatus. The apparatus may comprise: a horizontal-bridging member which is provided with a series of hanger member fitting parts operable to hang and arrange a large number of medical resources, a hanger member which is fitted to the hanger member fitting part and is pivotally moved depending on whether a medical resource is hung; a medical resource detecting member which is provided in each of the hanger member fitting parts so as to detect whether a medical resource is hung in an associated location in accordance with the pivotal movement of the associated hanger member; a retrieval guidance member for visual confirmation provided in each of the hanger member fitting parts; and a control unit which manages the storage status of the medical resources, based on the detection by the medical resource detecting member, and which operates the retrieval guidance member in response to an input designating retrieval, wherein, at the time of hanging a medical resource, the pivotal movement of the hanger member may cause the engaging part engaged with the medical resource to be lowered, and, at the time of retrieving a medical resource, the pivotal movement may cause the engaging part to be elevated and moved toward an operator.

The pivotal movement of the hanger member may be based on the displacement between the center of gravitation and the pivot center.

Another embodiment of the present invention also relates to a medical resource storage and management apparatus. The apparatus may comprise: a rack in which a series of depressions for insertion of partition members are formed so that a large number of medical resources are retrievably placed in respective partitions; partition members which are removably inserted into the depressions; medical resource detecting members which are arranged on the rack so as to alternate with the depressions in a direction in which the depressions are arranged, and each of which detects whether or not a medical resource is placed; retrieval guidance members for visual guidance which are arranged on the rack so as to alternate with the depressions in a direction in which the depressions are arranged; and a control unit which manages the storage status of the medical resources, based on the detection by the medical resource detecting members and which operates one of the retrieval guidance members in response to an input designating retrieval, wherein a name plate support member may be provided so as to be in parallel to the rack and behind the partition members, and a medical resource name plate for visual guidance may be attached to the name plate support member via a detachable connecting member such that the connecting member is moved up and down depending on whether a medical resource is placed and as a result of interference between the connecting member and the medical resource, and that the medical resource name plate is moved in association with the connecting member in a space where retrieval of a medical resource takes place, and wherein the medical resource detecting member may indirectly detect whether or not a medical resource is placed by detecting whether the medical resource name plate is raised or lowered.

The medical resource name plate, when elevated in association with the placement of a medical resource in the associated location, may be located above the retrieval guidance member in the associated location, and the medical resource name plate, when lowered in response to the retrieval of the medical resource from the associated location, may shield the retrieval guidance member in the associated location from view.

Still another embodiment of the present invention also relates to a medical resource storage and management apparatus. The apparatus may comprise: a rack plate in which are provided a series of medical resource detecting members for detecting whether or not a medical resource is placed on the rack plate and a series of retrieval guidance members for visual guidance; a control unit which manages the storage status of the medical resources, based on the detection by the medical resource detecting members and which operates one of the retrieval guidance members in response to an input designating retrieval; a storage case which is bounded at the bottom, sides and back thereof by a fixed plate, in which a movable medical resource name plate is provided in front of the case, and in which a connecting member extending backward from the medical resource name plate is adapted to make a vertical pivotal movement about the rear end thereof, wherein the medical resource name plate may be moved up and down as a result of interference between the medical resource stored in the storage case and the connecting member, and whether the medical resource is placed or not may be indirectly detected by detecting the up and down movement of the medical resource name plate, based on the fact that the up and down movement of the medical resource name plate causes the plate to enter or leave a range of detection by the medical resource detecting member in a state in which the storage case is placed on the rack plate.

The storage case may store the medical resource on the connecting member, and the up and down movement of the medical resource name plate may be associated with the nonavailability and availability of the medical resource, respectively.

Yet another embodiment of the present invention also relates to a medical resource storage and management apparatus. The apparatus is for storing a plurality of medical resources at locations of storage reserved for respective types of medical resources and may comprise: a pivotal member which assumes different statuses of pivotal movement depending on whether the medical resource is stored in the location of storage or taken out therefrom; a medical resource detecting member which detects whether the medical resource is stored in the location of storage, in accordance with the status of pivotal movement of the pivotal member; a retrieval guidance member which is provided in the neighborhood of the location of storage so as to allow visual inspection of the location of storage as the medical resource is taken out from the location of storage; and a control unit which manages the storage status of the medical resource, based on the detection by the medical resource detecting member and operates the retrieval guidance member in response to an input designating retrieval.

Another embodiment of the present invention relates to a medical supply management system. The system is for managing medical supplies in a medical institution and comprises a plurality of storage and management apparatuses, wherein each of the plurality of storage and management apparatuses comprises: a plurality medical supply storage parts capable of storing a plurality of types of medical supplies; medical supply detecting means which detects whether a medical supply is stored in each of the medical supply storage parts; computer means which creates management information pertaining to the medical supplies in the plurality of medical supply storage parts on the basis of information detected by the medical supply detecting means; and retrieval guidance means which is controlled by the computer means so as to guide a user to the medical supply to be taken out, wherein the computer means in each storage and management apparatus is operable to control the retrieval guidance means on the basis of information on the medical supply to be taken out, and to create and output consumed medical supply information related to the type and amount of medical supplies consumed, the system further comprising stock control means which is communicably connected to the plurality of storage and management apparatuses, and which calculates and stores the amount of respective types of medical supplies in stock, on the basis of the latest amount of respective types of medical supplies in stock stored in the stock control means, and on the basis of the consumed medical supply information received from the storage and management apparatuses.

The stock control means may receive the amount of respective types of medical supplies delivered to the medical institution from an external source, and calculate and store the amount of respective types of medical supplies in stock on the basis of the delivered amount.

Effects of the Invention

According to the present invention, medical resources can be managed efficiently. The present invention also provides a medical supply management system capable of managing medical supplies efficiently.

BRIEF DESCRIPTION OF THE DRAWINGS

FIGS. 1A-1D show the mechanical structure of a medical resource storage and management apparatus according to an illustrative embodiment 1-1 of a first embodiment of the present invention.

FIG. 1A is a front view showing a door closed.

FIG. 1B is a front view showing the door opened.

FIG. 1C is a perspective view of a rack and partition members.

FIG. 1D is a perspective view showing the appearance of the rack in which the partition members are fitted.

FIG. 2A is a schematic block diagram showing the connection between the control unit and retrieval guidance members.

FIG. 2B is a functional block diagram of the control unit.

FIG. 3A relates to a medical resource information table.

FIG. 3B relates to medical resource availability data.

FIG. 3C relates to partition availability data.

FIGS. 4A-4B illustrate the operation of a medical resource storage and management apparatus according to the first embodiment.

FIG. 4A shows an empty condition.

FIG. 4B shows a condition in which a small medical resource is stored.

FIGS. 5A-5D illustrate the operation of the medical resource storage and management apparatus according to the first embodiment.

FIG. 5A shows a condition in which one partition member is removed from a rack while a partition is empty.

FIG. 5B shows a condition in which a medium-sized medical resource is stored.

FIG. 5C shows a condition in which a large medical resource is stored where two partition members are removed.

FIG. 5D shows a condition in which detection results from medical resource detecting members do not match.

FIG. 6A is an expanded perspective view of the rack and the partition members.

FIG. 6B is a functional block diagram of the control unit.

FIGS. 7A-7C are all perspective views of the partition member and the rack.

FIGS. 8A-8C show conditions of replenishment of medical resources according to an illustrative embodiment 1-4 of the first embodiment.

FIGS. 8A-8C are screen shots.

FIG. 9A is a perspective view of the rack fitted with partition members.

FIG. 9B is a perspective view showing how identification information is read from a medical resource.

FIG. 9C is a perspective view of the rack storing a medical resource.

FIG. 10A is a front view showing a door closed.

FIG. 10B is a front view showing the door opened.

FIG. 10C is a perspective view of a rack and partition members.

FIG. 10D is a perspective view showing the appearance of the rack in which the partition members are fitted.

FIG. 11A is a schematic block diagram showing the connection between the control unit and retrieval guidance members.

FIG. 11B is a functional block diagram of the control unit.

FIG. 12A relates to a medical resource information table.

FIG. 12B relates to medical resource availability data.

FIG. 12C relates to partition availability data.

FIGS. 13A-13B illustrate the operation of the medical resource storage and management apparatus according to the second embodiment.

FIG. 13A shows an empty condition.

FIG. 13B shows a condition in which a small medical resource is stored.

FIGS. 14A-14D also illustrate the operation of the medical resource storage and management apparatus according to the second embodiment.

FIG. 14A shows a condition in which one partition member is removed from the rack while the partition is empty.

FIG. 14B shows a condition in which a medium-sized medical resource is stored.

FIG. 14C shows a condition in which a large medical resource is stored where two partition members are removed.

FIG. 14D shows a condition in which detection results from medical resource detecting members do not match.

FIG. 15A is an expanded perspective view of the rack and the partition members.

FIG. 15B is a functional block diagram of the control unit.

FIGS. 16A-16C are all perspective views of the partition member and the rack.

FIG. 17A is a front view showing the door opened.

FIG. 17B is an expanded perspective view of the rack and the partition members.

FIG. 17C is a functional block diagram of the control unit.

FIGS. 18A-18C show conditions of replenishment of medical resources according to an illustrative embodiment 2-5 of the second embodiment.

FIGS. 18A-18C are screen shots.

FIG. 19A is a perspective view of the rack fitted with partition members.

FIG. 19B is a perspective view showing how identification information is read from a medical resource.

FIG. 19C is a perspective view of the rack storing a medical resource.

FIGS. 20A-20E show the mechanical structure of a medical resource storage and management apparatus according to an illustrative embodiment 3-1 of a third embodiment.

FIG. 20A is a front view showing a door closed.

FIG. 20B is a front view showing the door opened.

FIG. 20C is a front view showing a horizontal-bridging case and hanger members.

FIGS. 20D and 20E are left side views of a horizontal-bridging member and the hanger member showing a cross section of the horizontal-bridging member.

FIG. 21A is a schematic block diagram showing the connection between the control unit and retrieval guidance members.

FIG. 21B is a functional block diagram of the control unit.

FIG. 22C shows an empty condition.

FIG. 22D shows a condition in which a small medical resource is stored.

FIG. 23A shows a condition before the hanger member is fitted to the horizontal-bridging bar.

FIG. 23B shows a condition occurring immediately after the fitting.

FIG. 23C shows a condition in which the hanger member is pivotally moved after the fitting.

FIG. 24A is a schematic block diagram showing the connection between the control unit and the retrieval guidance members.

FIG. 24B is a functional block diagram of the control unit.

FIG. 25A relates to a medical resource information table.

FIG. 25B relates to medical resource availability data.

FIG. 25C relates to hanger availability data.

FIGS. 26A-26B illustrate the operation of the medical resource storage and management apparatus according to the illustrative embodiment 3-2.

FIG. 26A shows an empty condition.

FIG. 26B shows a condition in which a small medical resource is stored.

FIGS. 27A-27D illustrate the operation of the medical resource storage and management apparatus according to the illustrative embodiment 3-2.

FIG. 27A shows a condition in which one hanger member is removed from the horizontal-bridging case while the case is empty.

FIG. 27B shows a condition in which a medium-sized medical resource is stored.

FIG. 27C shows a condition in which a large medical resource is stored where two hanger members are removed.

FIG. 27D shows a condition in which incompatibility occurs between a result of detection by a medical resource detecting member and the configuration in the hanger availability data.

FIG. 28A is a side view of the horizontal-bridging bar and the hanger member.

FIG. 28B is a front view of the horizontal-bridging bar and the hanger member.

FIG. 28C is a functional block diagram of the control unit.

FIGS. 29A-29C are all perspective views of the medical resource storage and management apparatus.

FIGS. 30A-30C show the mechanical structure of the medical resource storage and management apparatus according to an illustrative embodiment 3-5 of the third embodiment.

FIG. 30A shows the appearance of the apparatus.

FIGS. 30B and 30C are expanded perspective views of a rack and a partition member.

FIGS. 33A-33C show conditions of replenishment of medical resources according to an illustrative embodiment 3-7 of the third embodiment.

FIGS. 33A-33C are screen shots.

FIG. 34A is a perspective view of the rack fitted with partition members.

FIG. 34B is a perspective view showing how identification information is read from a medical resource.

FIG. 34C is a perspective view of the rack storing a medical resource.

FIGS. 35A-35D show the mechanical structure of a medical resource storage and management apparatus according to an illustrative embodiment 4-1 of a fourth embodiment.

FIG. 35A is a front view showing a door closed.

FIG. 35B is a front view showing the door opened.

FIG. 35C is a perspective view of a rack and partition members.

FIG. 35D is a perspective view showing the appearance of the rack in which the partition members are fitted.

FIGS. 36A and 36B show the schematic structure of a control unit according to the illustrative embodiment 4-1.

FIG. 36A is a schematic block diagram showing the connection between the control unit and retrieval guidance members.

FIG. 36B is a functional block diagram of the control unit.

FIGS. 37A-37C show the data structure of the control unit according to the illustrative embodiment 4-1.

Figure 37A:
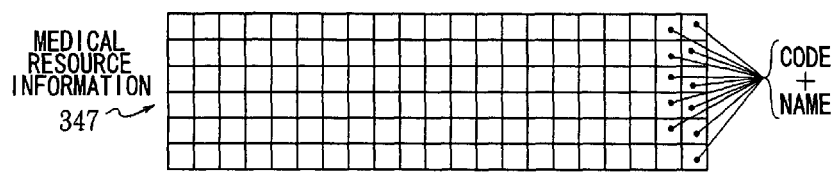

FIG. 37A relates to a medical resource information table.

Figure 37B:
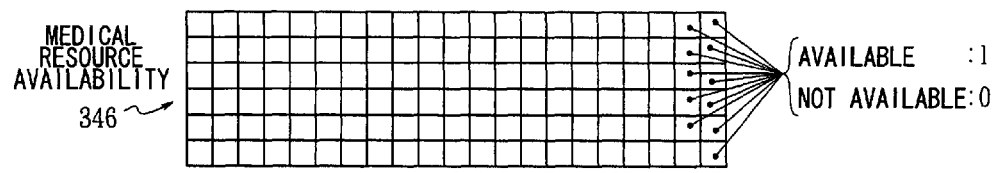

FIG. 37B relates to medical resource availability data.

Figure 37C:
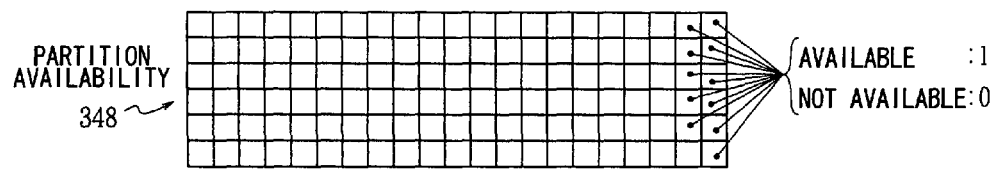

FIG. 37C relates to partition availability data.

FIGS. 38A-38B illustrate the operation of the medical resource storage and management apparatus according to the illustrative embodiment 4-1.

FIG. 38A shows an empty condition.

FIG. 38B shows a condition in which a small medical resource is stored.

FIGS. 39A-39D illustrate the operation of the medical resource storage and management apparatus according to the illustrative embodiment 4-1.

FIG. 39A shows a condition in which one partition member is removed from the rack while the partition is empty.

FIG. 39B shows a condition in which a medium-sized medical resource is stored.

FIG. 39C shows a condition in which a large medical resource is stored where two partition members are removed.

FIG. 39D shows a condition in which detection results from medical resource detecting members do not match.

Figure 40A:
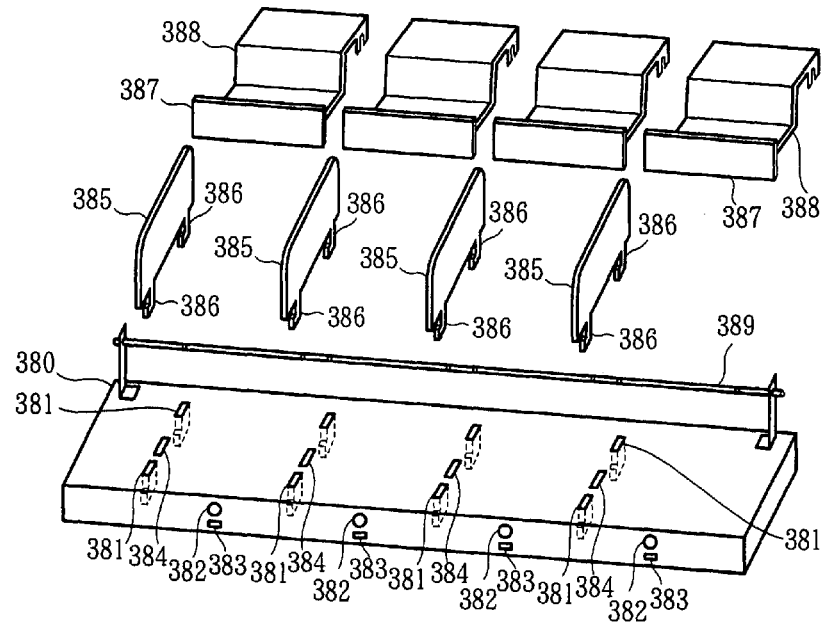
Figure 40B:
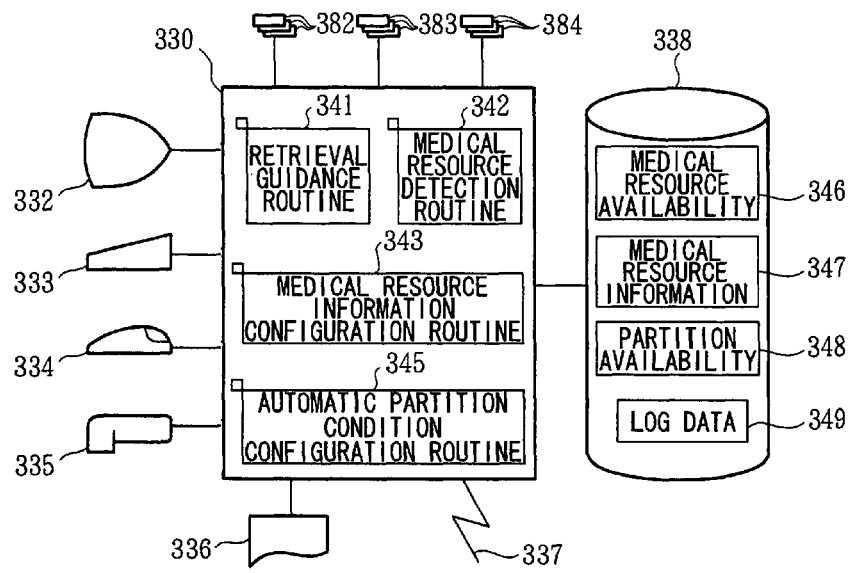

FIGS. 40A and 40B show the structure of the medical resource storage and management apparatus according to an illustrative embodiment 4-2 of the fourth embodiment.

FIG. 40A is an expanded perspective view of the rack and the partition members.

FIG. 40B is a functional block diagram of the control unit.

Figure 41A:
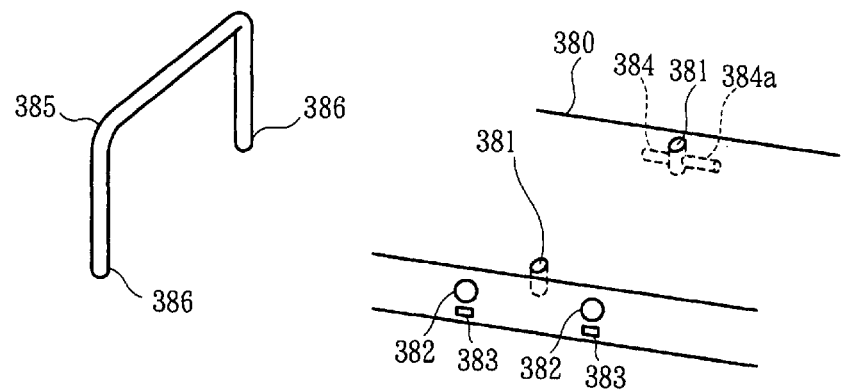
Figure 41B:
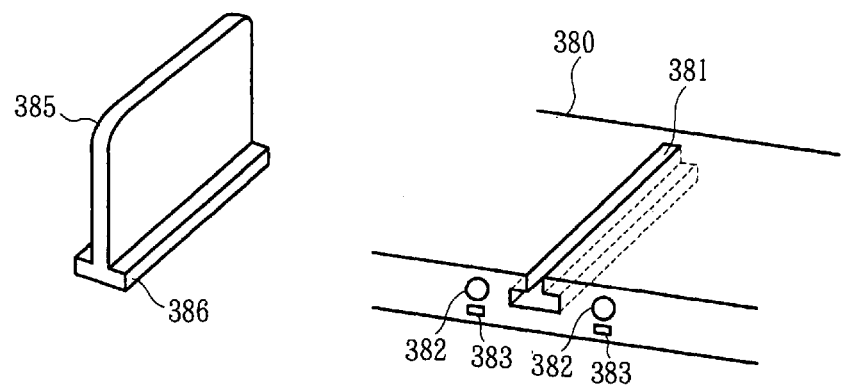
Figure 41C:
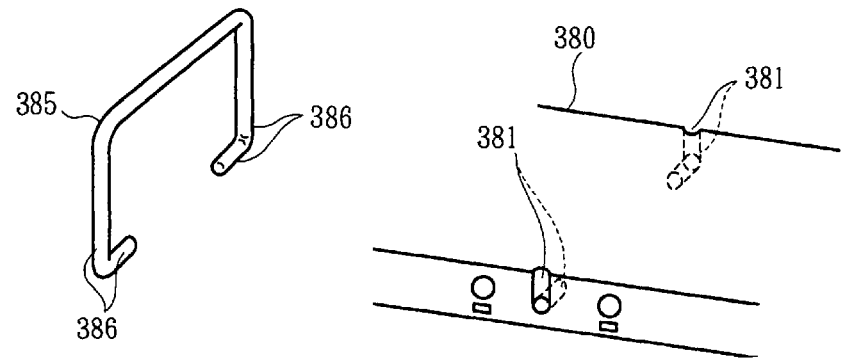

FIGS. 41A-41C show three variations to the structure according to an illustrative embodiment 4-3 of the fourth embodiment.

FIGS. 41A-41C are all perspective views of the partition member and the rack.

Figure 42A:
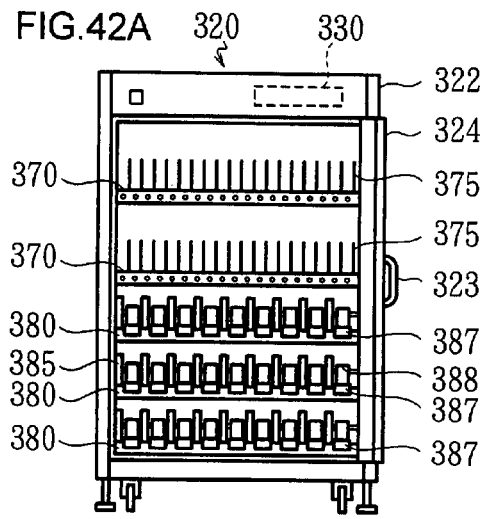
Figure 42B:
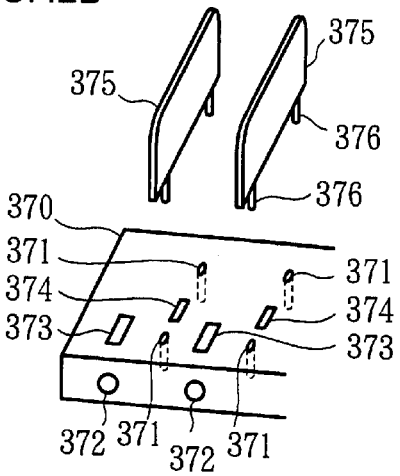
Figure 42C:
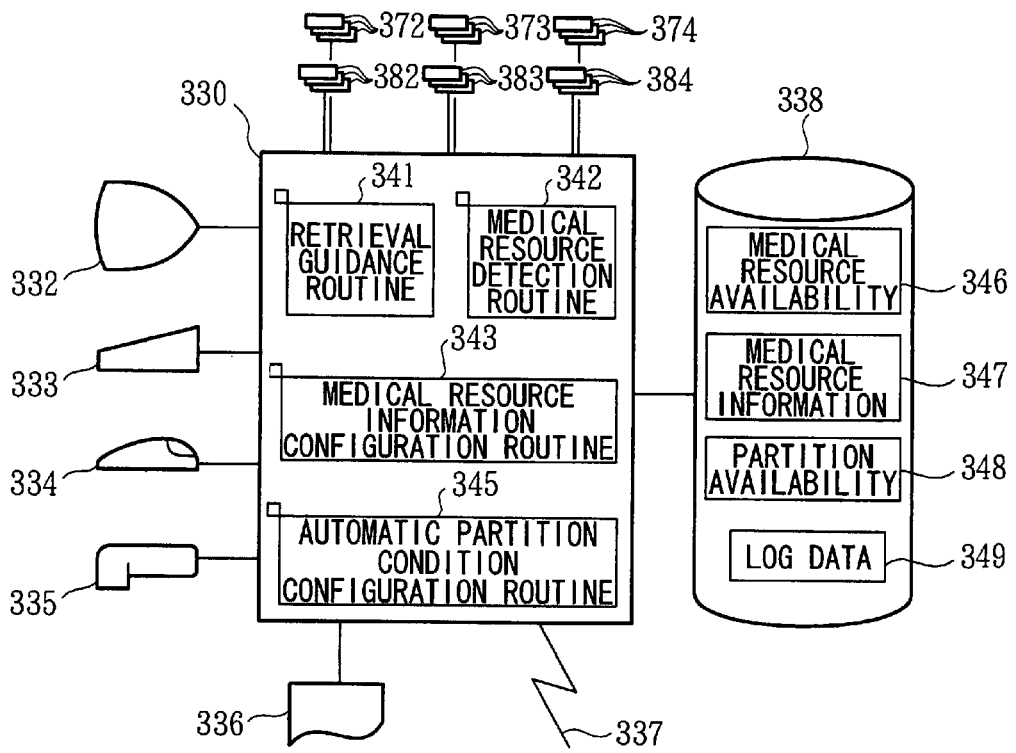

FIGS. 42A-42C show the structure of the medical resource storage and management apparatus according to an illustrative embodiment 4-4 of the fourth embodiment.

FIG. 42A is a front view showing the door opened.

FIG. 42B is an expanded perspective view of the rack and the partition members.

FIG. 42C is a functional block diagram of the control unit.

FIGS. 43A-43C show conditions of replenishment of medical resources according to an illustrative embodiment 4-5 of the fourth embodiment.

FIGS. 43A-43C are screen shots.

Figure 44A:
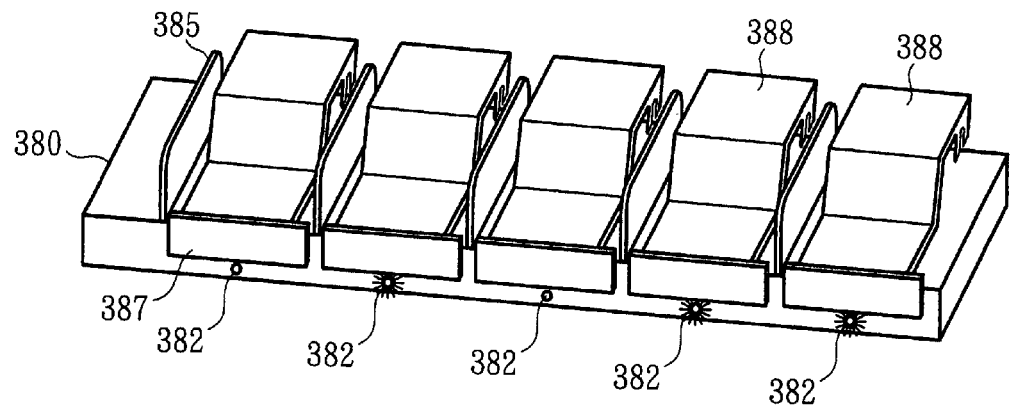
Figure 44B:
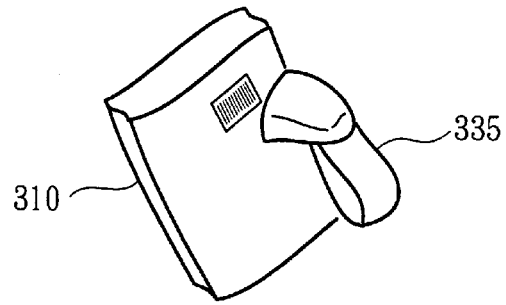
Figure 44C:
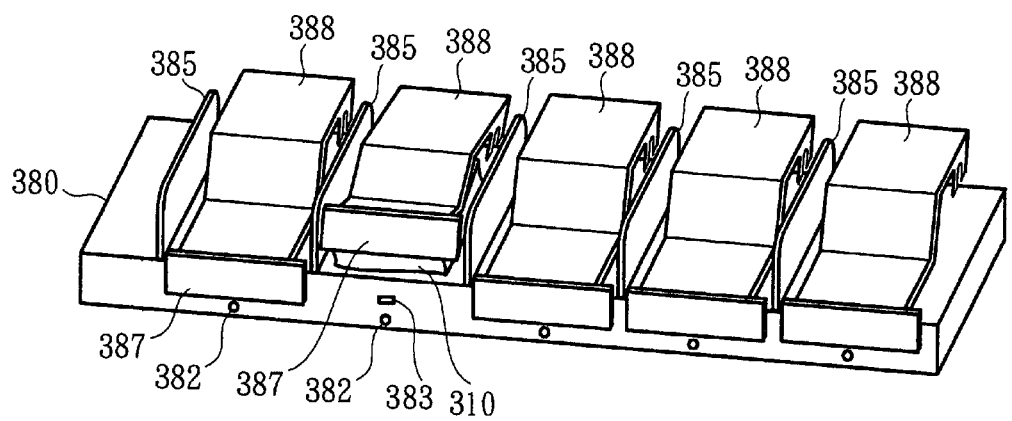

FIGS. 44A-44C also show conditions of replenishment of medical resources according to the illustrative embodiment 4-5.

FIG. 44A is a perspective view of the rack fitted with partition members.

FIG. 44B is a perspective view showing how identification information is read from a medical resource.

FIG. 44C is a perspective view of the rack storing a medical resource.

Figure 45A:
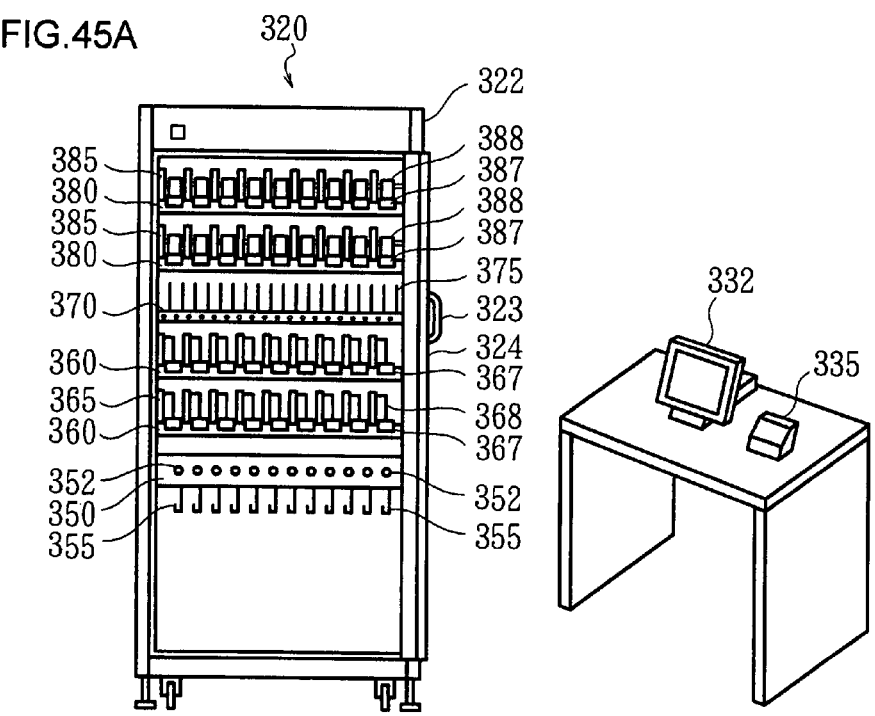
Figure 45B:
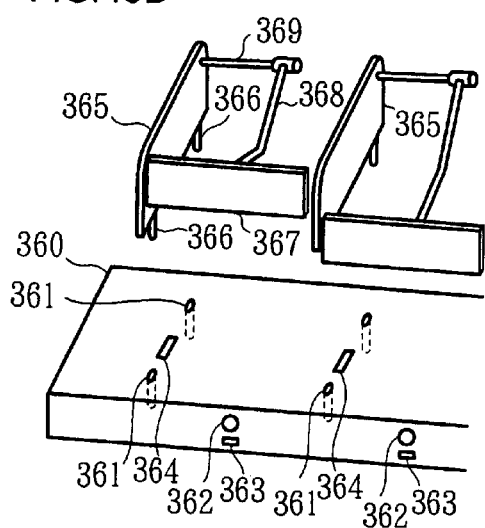
Figure 45C:
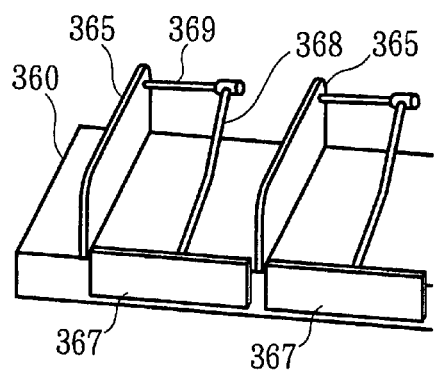

FIGS. 45A-45C show the mechanical structure of the medical resource storage and management apparatus according to an illustrative embodiment 4-6 of the fourth embodiment.

FIG. 45A is a front view showing a door opened.

FIG. 45B is a perspective view of a rack and partition members.

FIG. 45C is a perspective view showing the appearance of the rack in which the partition members are fitted.

FIGS. 46A-46D show the mechanical structure of a part of the medical resource storage and management apparatus according to the illustrative embodiment 4-6.

Figure 46A:
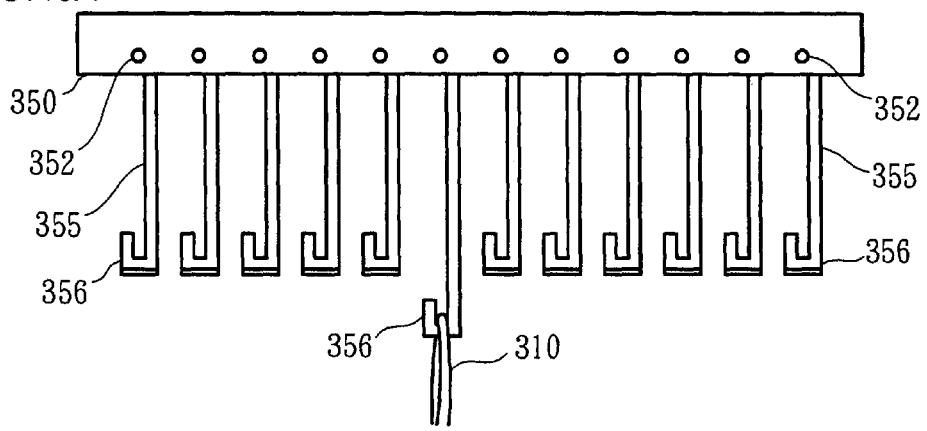

FIG. 46A is a front view of the horizontal-bridging case and the hanger member.

Figure 46B:
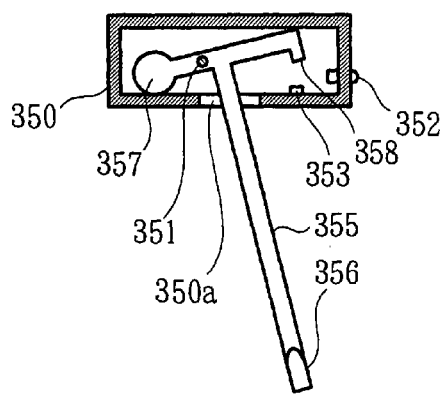
Figure 46C:
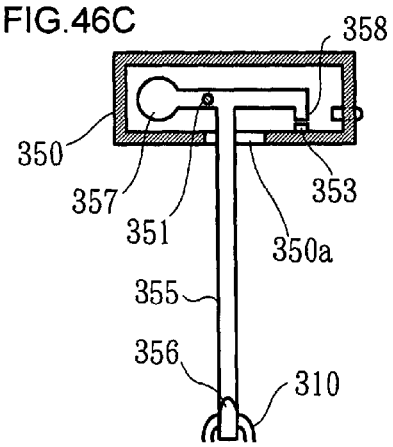

FIGS. 46B and 46C are left side views of the horizontal-bridging case and the hanger member showing the cross section of the horizontal-bridging member.

Figure 46D:
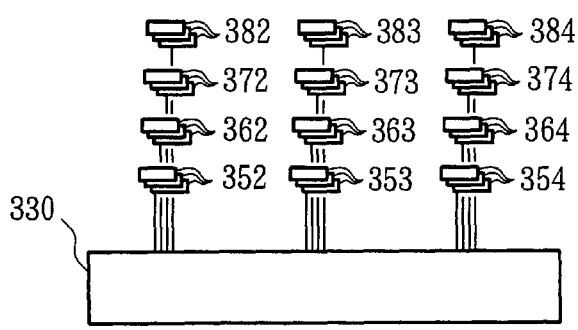

FIG. 46D is a schematic functional block diagram of the control unit.

Figure 47A:
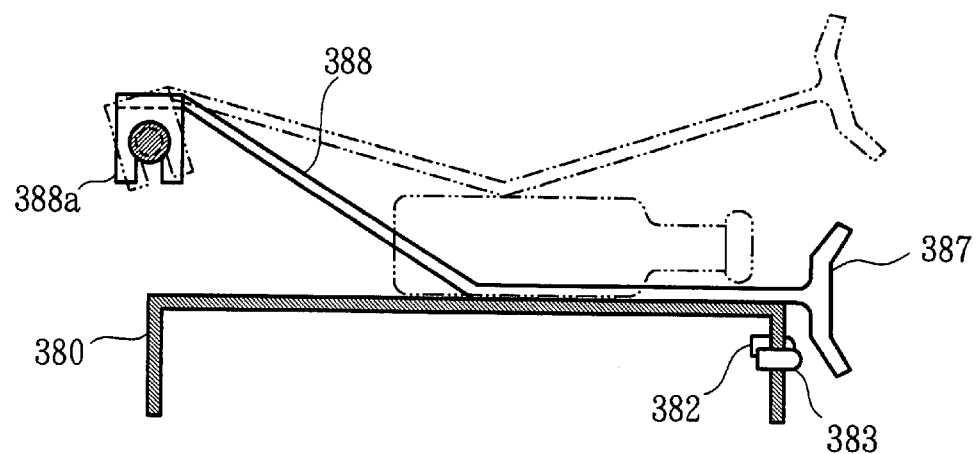
Figure 47B:
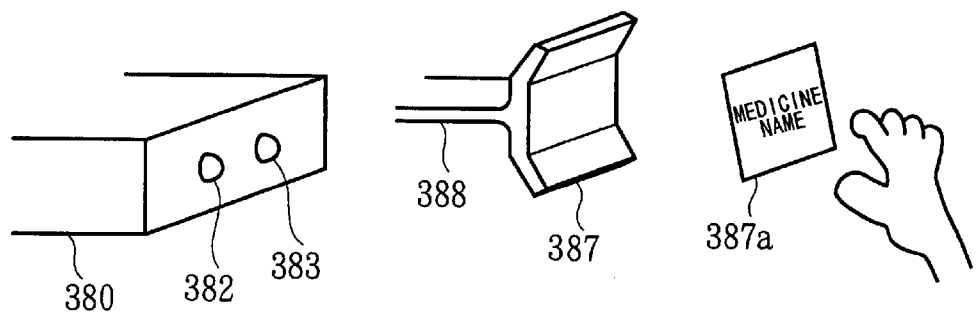

FIGS. 47A and 47B show the structure of the medical resource storage and management apparatus according to an illustrative embodiment 4-7 of the fourth embodiment.

FIG. 47A is a left side view showing a partial cross section of the rack, a medical resource name plate and a connecting member.

FIG. 47B is a perspective view showing an essential part of the rack, the medical resource name plate and the connecting member.

Figure 48:
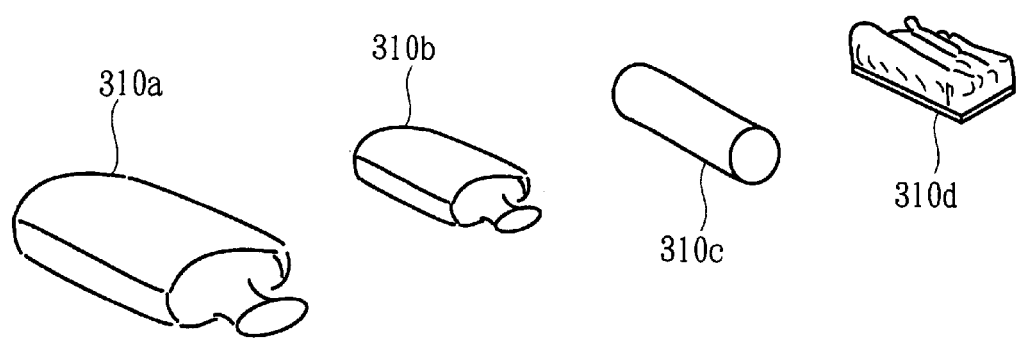

FIG. 48 shows perspective views of some of the medical resources suitable for storage.

FIGS. 49A-49E show a mechanical structure of the medical resource storage and management apparatus according to an illustrative embodiment 5-1 of a fifth embodiment.

FIG. 49A is a front view showing a door closed.

FIG. 49B is a front view showing the door opened.

FIG. 49C is a perspective view showing the appearance of a rack.

FIG. 49D is an expanded perspective view of a storage case.

FIG. 49E is a perspective view showing the appearance of the rack on which the storage case and a medical resource are placed.

Figure 50A:
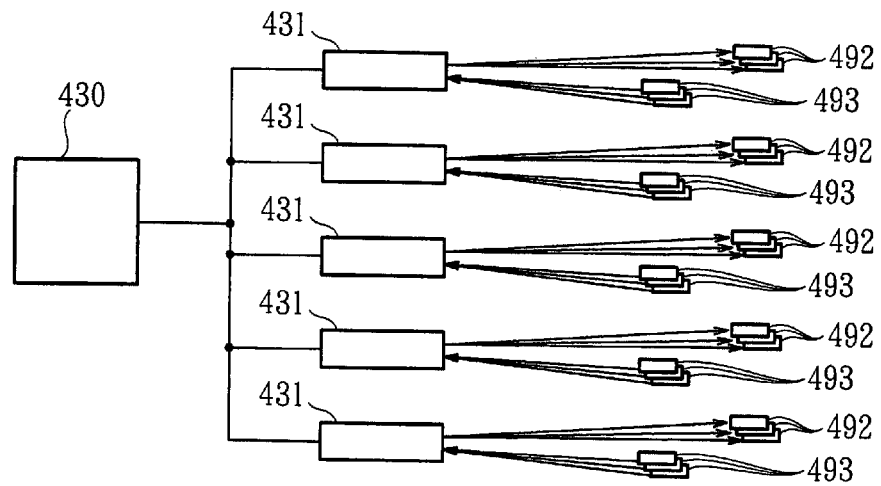
Figure 50B:
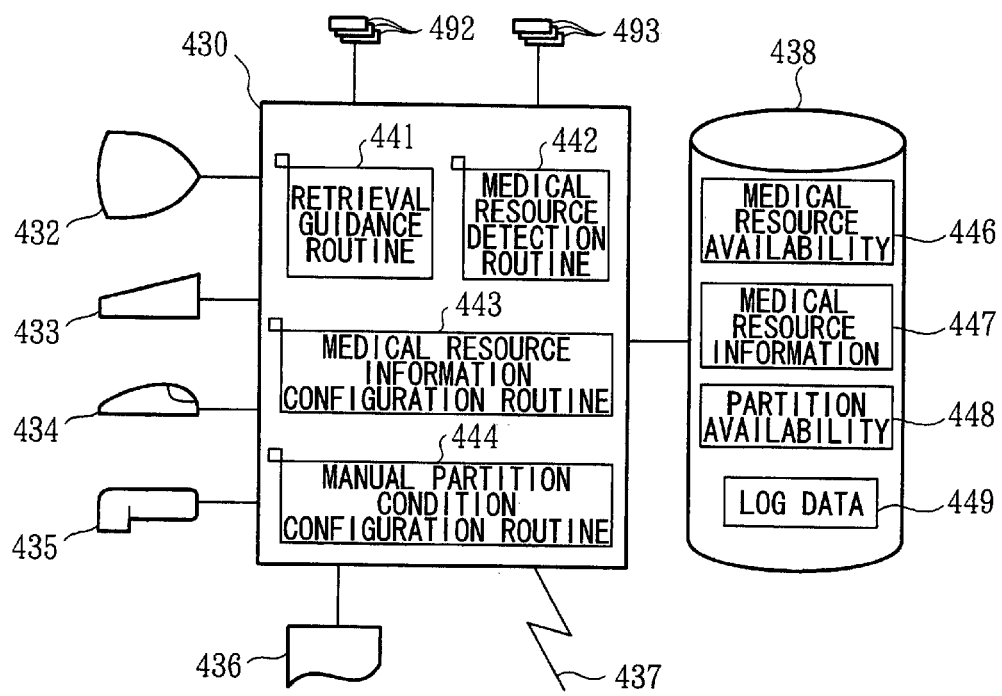

FIGS. 50A and 50B show the schematic structure of a control unit according to the illustrative embodiment 5-1.

FIG. 50A is a schematic block diagram showing the connection between the control unit and retrieval guidance members.

FIG. 50B is a functional block diagram of the control unit.

Figure 51A:
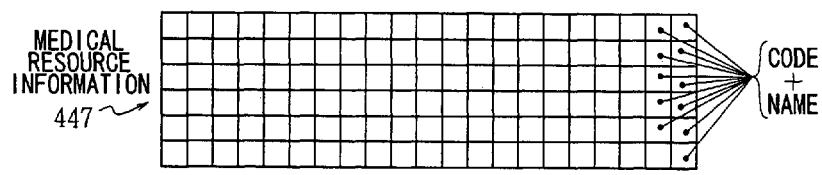
Figure 51B:
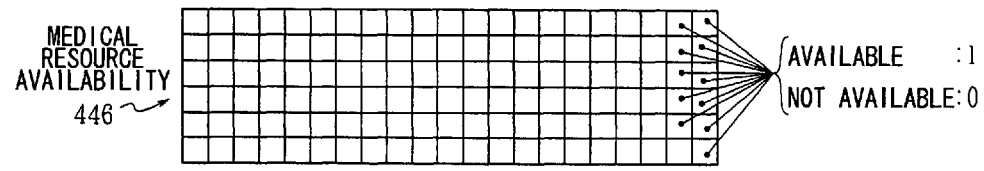
Figure 51C:
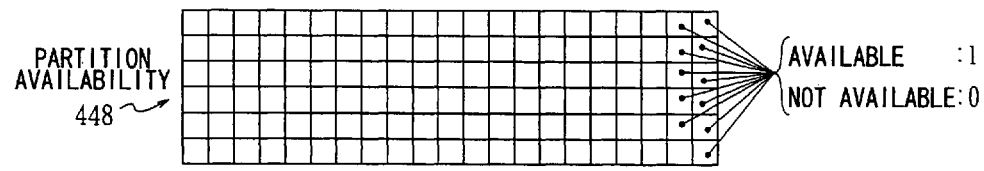

FIGS. 51A-51C show the data structure of the control unit according to the illustrative embodiment 5-1.

FIG. 51A relates to a medical resource information table.

FIG. 51B relates to medical resource availability data.

FIG. 51C relates to partition availability data.

FIGS. 52A-52B illustrate the operation of the medical resource storage and management apparatus according to the illustrative embodiment 5-1.

FIG. 52A shows small empty storage cases are arranged on the rack.

FIG. 52B shows a condition in which a medical resource is stored in one of them.

FIGS. 53A-53D also illustrate the operation of the medical resource storage and management apparatus according to the illustrative embodiment 5-1.

Figure 53A:

FIG. 53A shows a condition in which an empty medium-sized storage case is included.

Figure 53B:

FIG. 53B shows a condition in which a medical resource is stored in the medium-sized case.

Figure 53C:
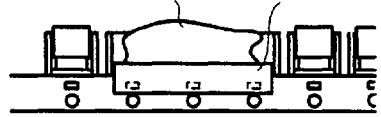

FIG. 53C shows a condition in which a large-sized storage case is included and a medical resource is stored therein.

Figure 53D:
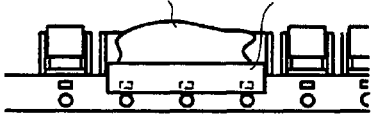

FIG. 53D shows a condition in which detection results from medical resource detecting members do not match.

Figure 54A:
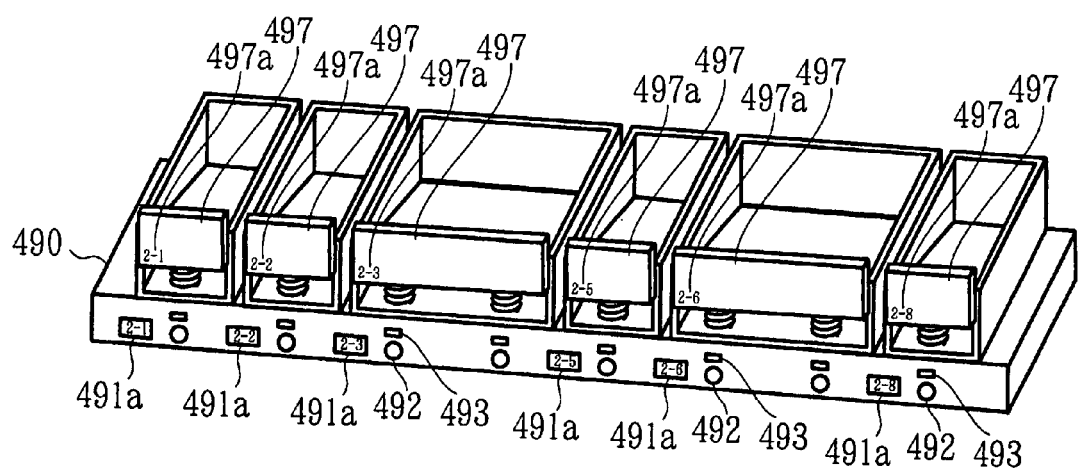
Figure 54B:
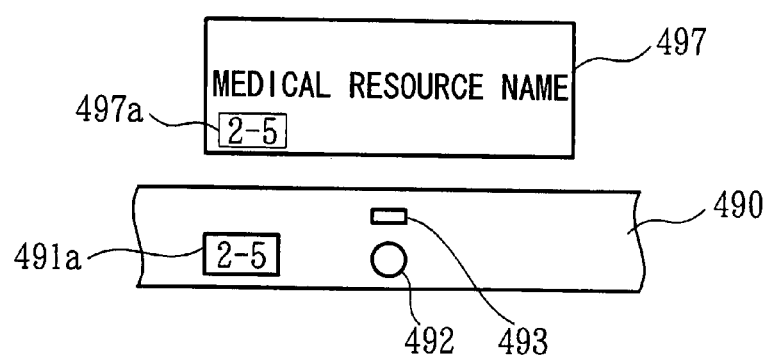

FIGS. 54A-54B show the mechanical structure of the medical resource storage and management apparatus according to an illustrative embodiment 5-2 of the fifth embodiment.

FIG. 54A is a perspective view showing the appearance of the rack in which the empty storage cases are arranged.

FIG. 54B is an expanded front view showing an essential part.

Figure 55A:
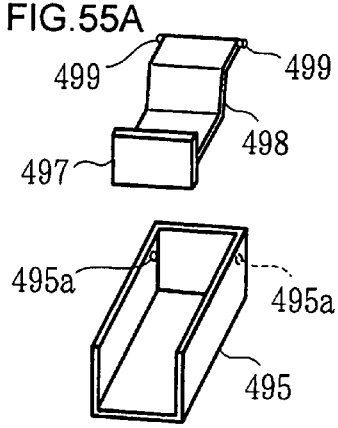
Figure 55B:
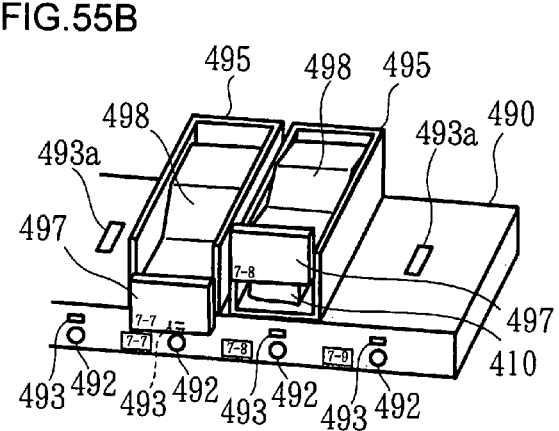

FIGS. 55A-55B show the mechanical structure of the medical resource storage and management apparatus according to an illustrative embodiment 5-3 of the fifth embodiment.

FIG. 55A is an expanded perspective of the storage case.

FIG. 55B is a perspective view showing the appearance of the rack on which the storage case or the medical resource is placed.

Figure 56A:
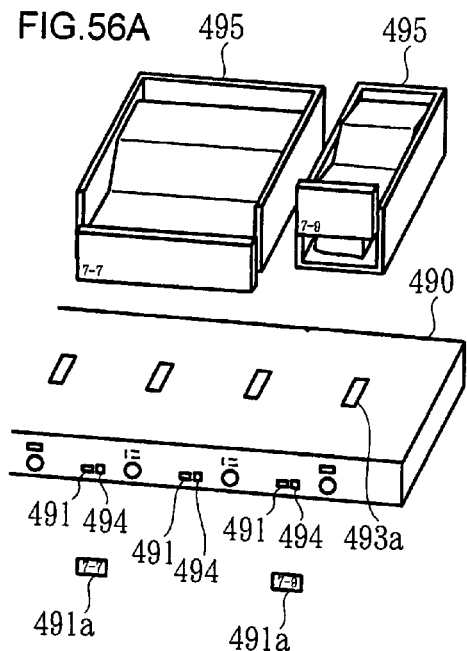
Figure 56B:
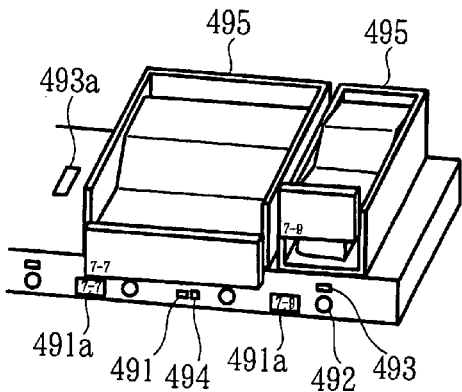
Figure 56C:
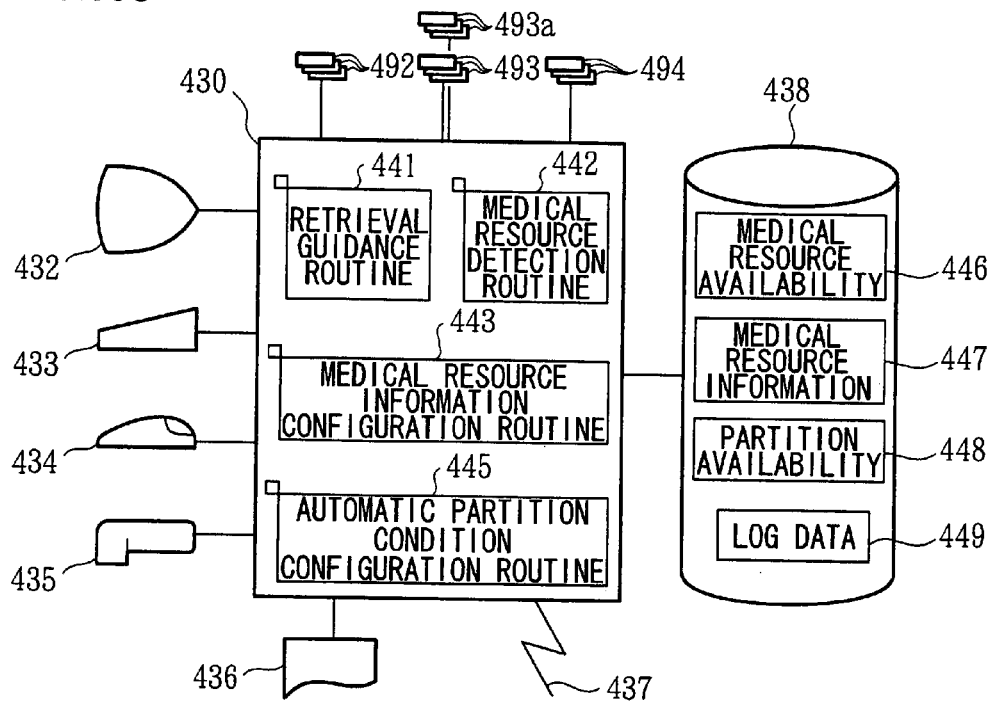

FIGS. 56A-56C show the structure of the medical resource storage and management apparatus according to an illustrative embodiment 5-4 of the fifth embodiment.

FIG. 56A is an expanded perspective view of the storage case and the rack.

FIG. 56B is a perspective view showing the appearance of the rack on which the storage case and the medical resource are placed.

FIG. 56C is a functional block diagram of the control unit.

FIGS. 57A-57C show conditions of replenishment of medical resources according to an illustrative embodiment 5-5 of the fifth embodiment.

FIGS. 57A-57C are screen shots.

Figure 58A:
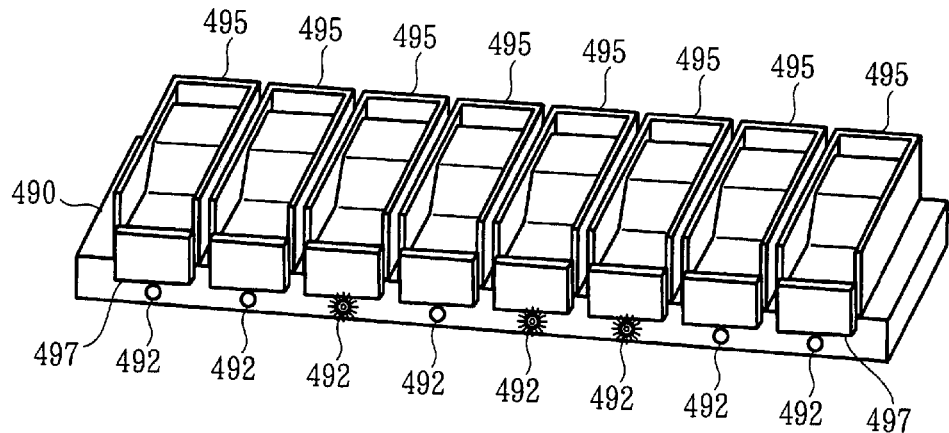
Figure 58B:
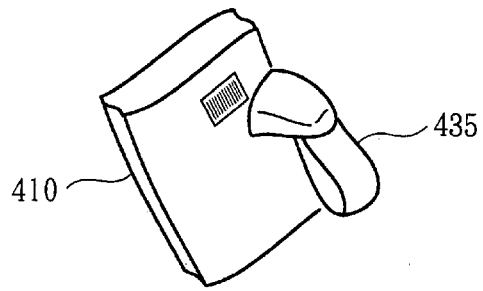
Figure 58C:
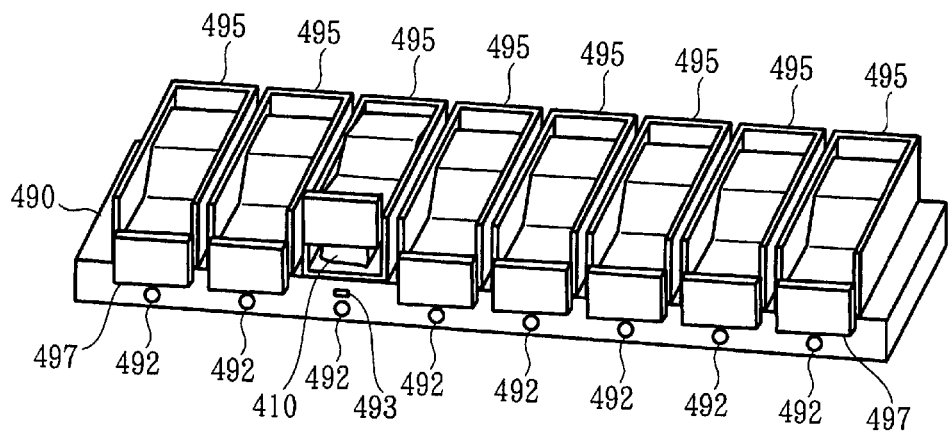

FIGS. 58A-58C also show conditions of replenishment of medical resources according to the illustrative embodiment 5-5.

FIG. 58A is a perspective view of the rack on which the empty storage cases are arranged.

FIG. 58B is a perspective view showing how identification information is read from the medical resource.

FIG. 58C is a perspective view of the rack storing the medical resource.

Figure 59A:
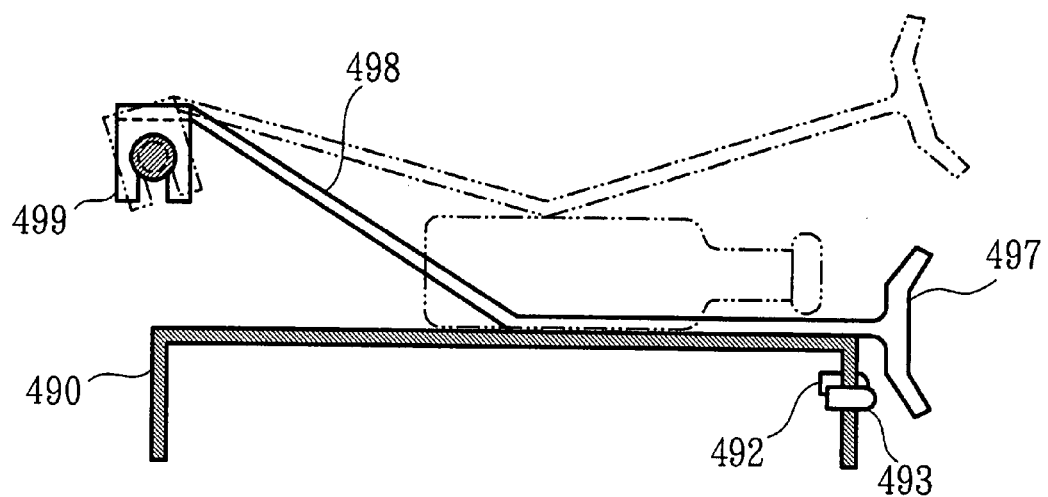
Figure 59B:
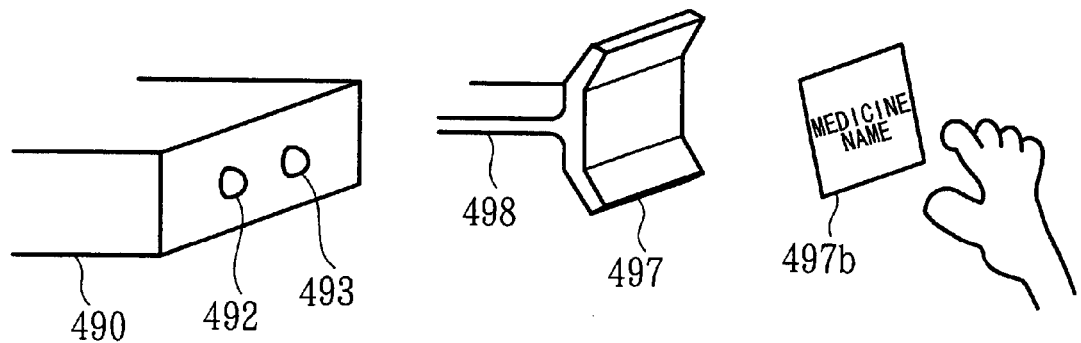

FIGS. 59A and 59B show the structure of an essential part of the medical resource storage and management apparatus according to an illustrative embodiment 5-6 of the fifth embodiment.

FIG. 59A is a left side view showing a partial cross section of the rack, a medical resource name plate and a connecting member.

FIG. 59B is a perspective view showing an essential part of the rack, the medical resource name plate and the connecting member.

Figure 60:
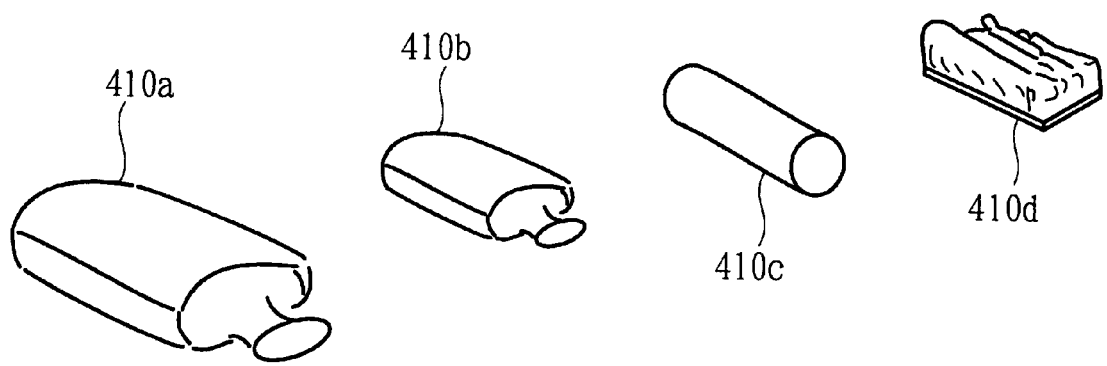

FIG. 60 shows perspective views of some of the medical resources suitable for storage.

Figure 61A:
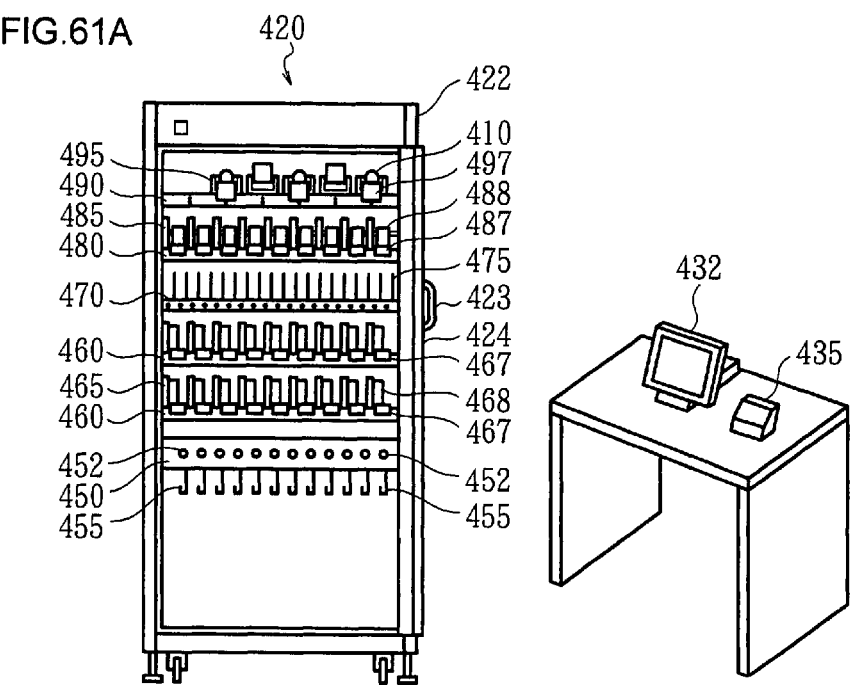
Figure 61B:
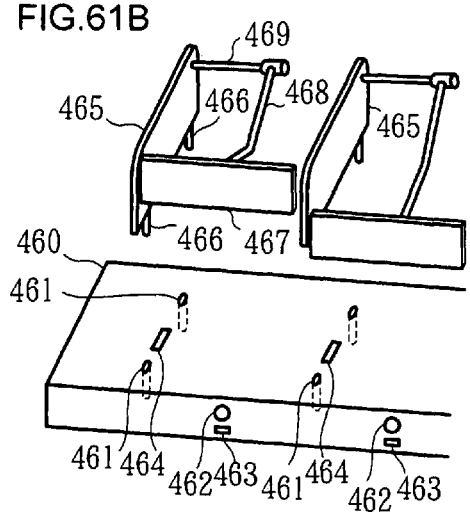
Figure 61C:
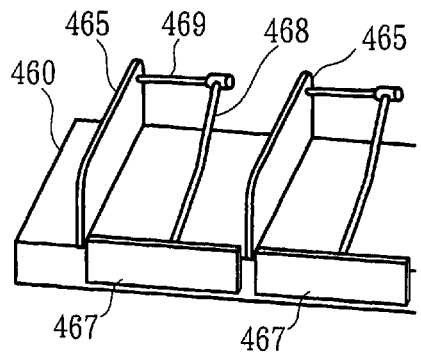

FIGS. 61A-61C show the mechanical structure of the medical resource storage and management apparatus according to an illustrative embodiment 5-7 of the fifth embodiment.

FIG. 61A is a front view showing the door opened.

FIG. 61B is an expanded perspective view of the rack and the partition members.

FIG. 61C is a perspective view showing the appearance of the rack to which the partition members are fitted.

Figure 62A:
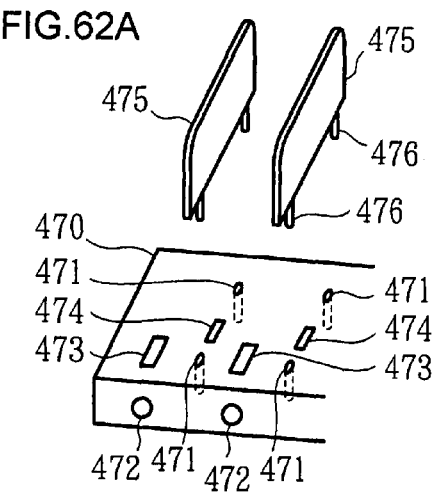
Figure 62B:
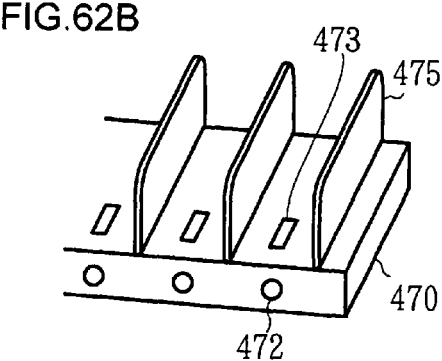

FIGS. 62A and 62B show the mechanical structure of a part of the medical resource storage and management apparatus according to the illustrative embodiment 5-7.

FIG. 62A is an expanded perspective view of the rack and the partition members.

FIG. 62B is a perspective view showing the appearance of the rack to which the partition members are fitted.

Figure 63:
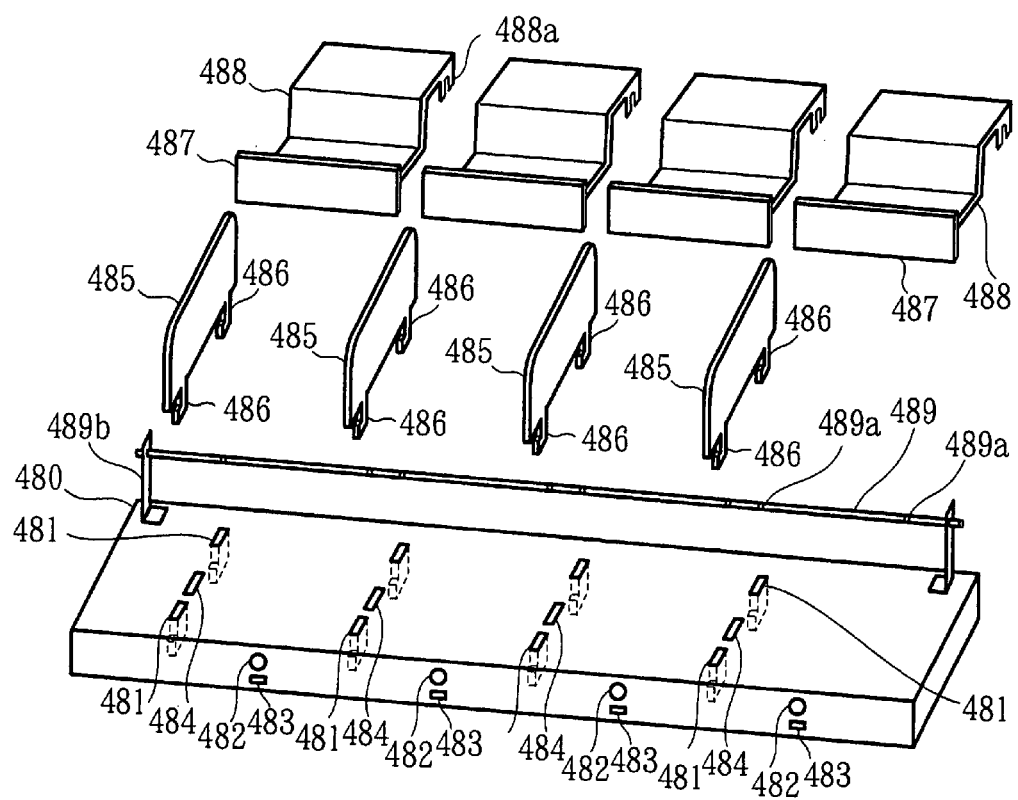

FIG. 63 shows the mechanical structure of another part of the medical resource storage and management apparatus according to the illustrative embodiment 6-3 and is an expanded perspective view of the rack and the partition members.

FIGS. 64A-64D show the structure of the medical resource storage and management apparatus according to the illustrative embodiment 5-7.

FIG. 64A is a front view of a horizontal-bridging case and hanger members.

FIGS. 64B and 64C are left side views of the horizontal-bridging member and the hanging member showing the longitudinal cross section of the horizontal-bridging member.

FIG. 64D is a schematic functional block diagram of the control unit.

Figure 65:
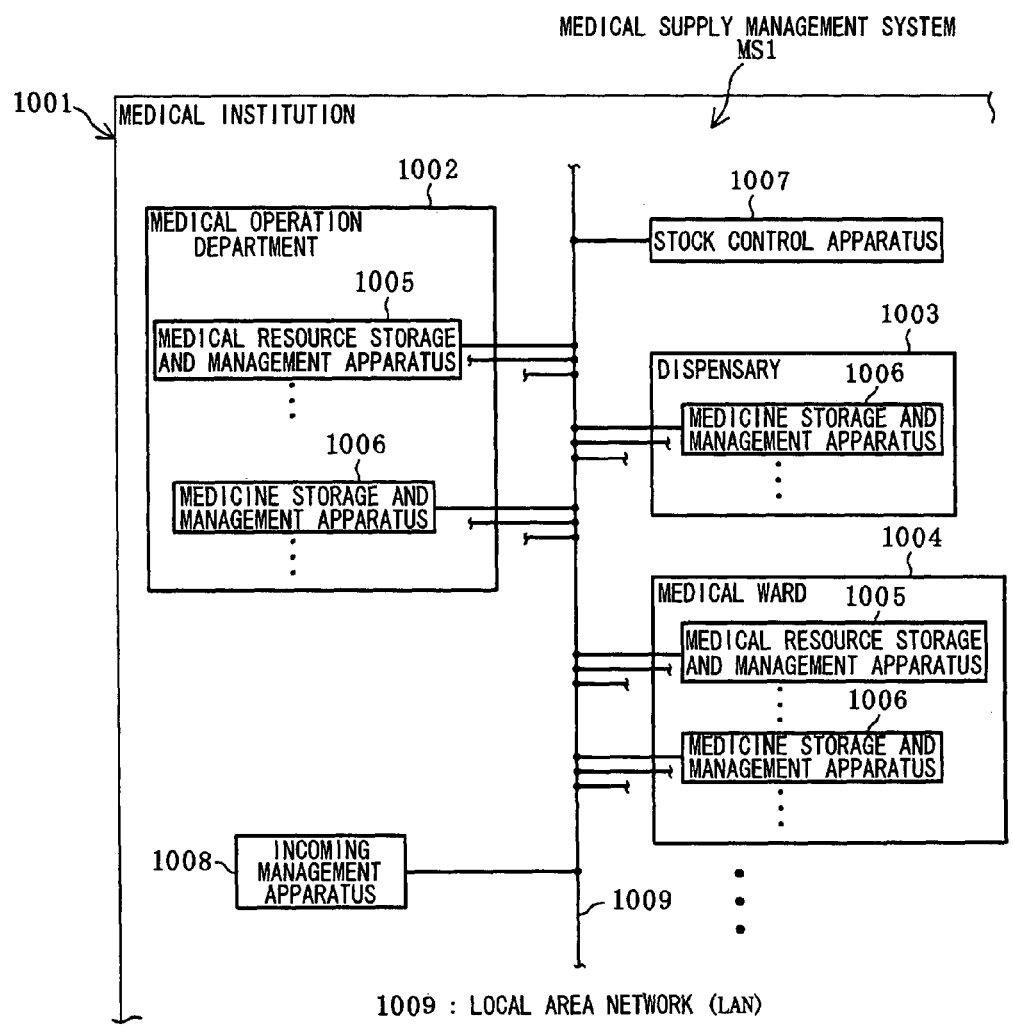

FIG. 65 shows the structure of a medical management system according to an illustrative embodiment 6-1 of a sixth embodiment.

Figure 66:
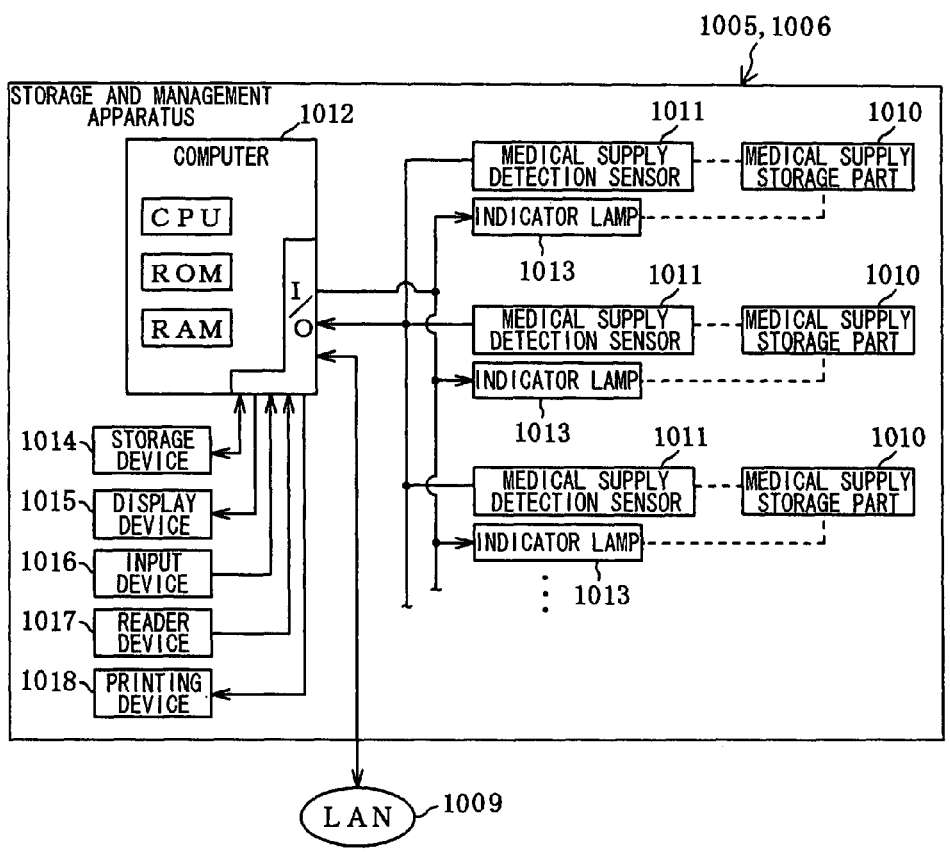

FIG. 66 is a block diagram of equipment in a storage and management apparatus according to the illustrative embodiment 6-1.

Figure 67:
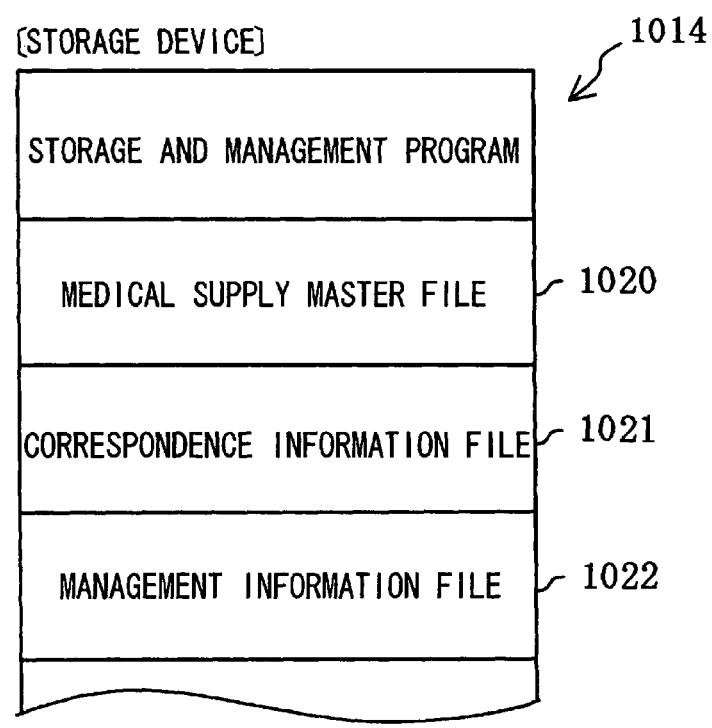

FIG. 67 shows information stored in a storage device in the storage and management apparatus according to the illustrative embodiment 6-1.

Figure 68:
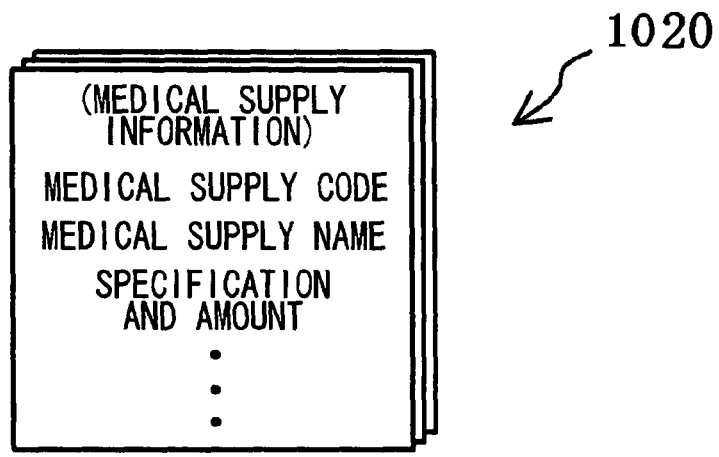

FIG. 68 shows medical supply information stored in a medical supply master file according to the illustrative embodiment 6-1.

FIG. 69 shows correspondence information table stored in a correspondence information file according to the illustrative embodiment 6-1.

FIG. 70 shows management information according to the illustrative embodiment 6-1.

Figure 71:
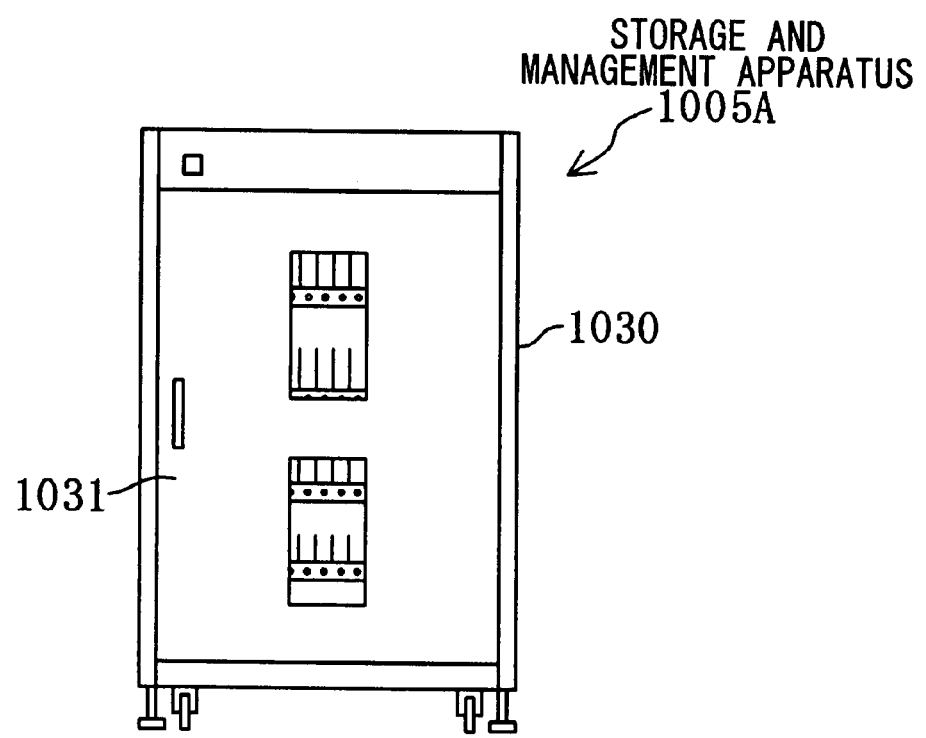

FIG. 71 is a front view showing a door of a medical resource storage and management apparatus according to illustrative embodiment 6-1 closed.

Figure 72:
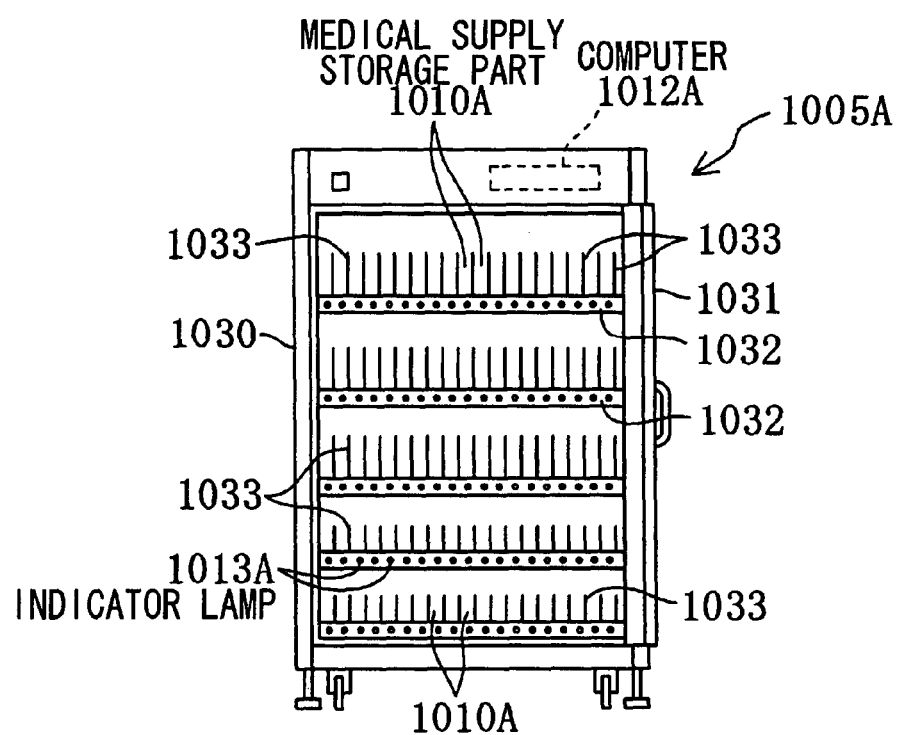

FIG. 72 is a front view showing the door of the medical resource storage and management apparatus according to illustrative embodiment 6-1 opened.

Figure 73:
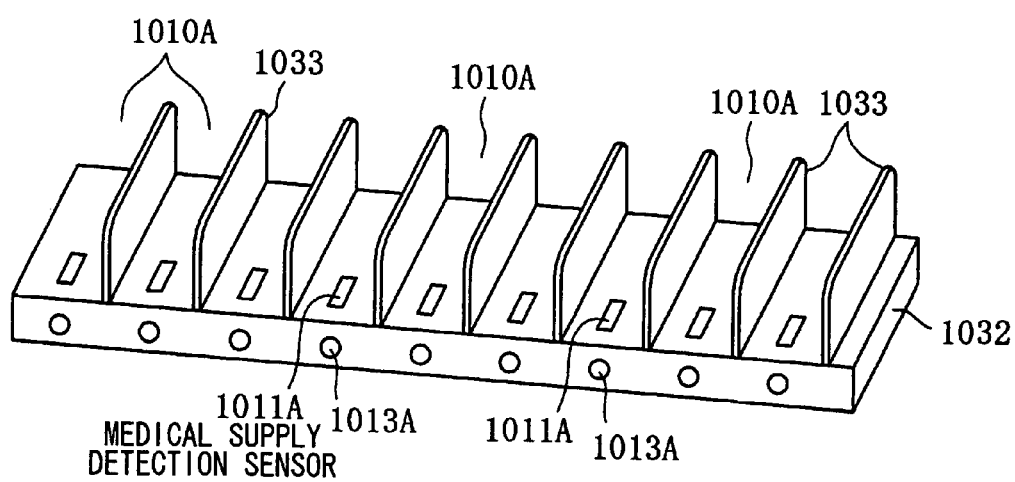

FIG. 73 is a perspective view showing an essential part of the medical resource storage and management apparatus according to illustrative embodiment 6-1.

Figure 74:
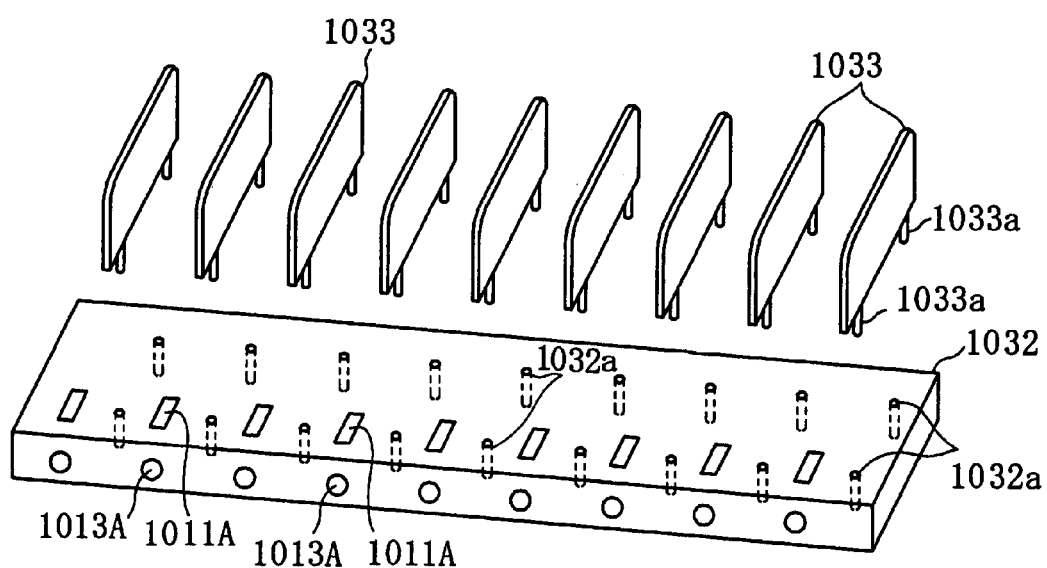

FIG. 74 is an exploded perspective view showing an essential part of the medical resource storage and management apparatus according to illustrative embodiment 6-1.

Figure 75:
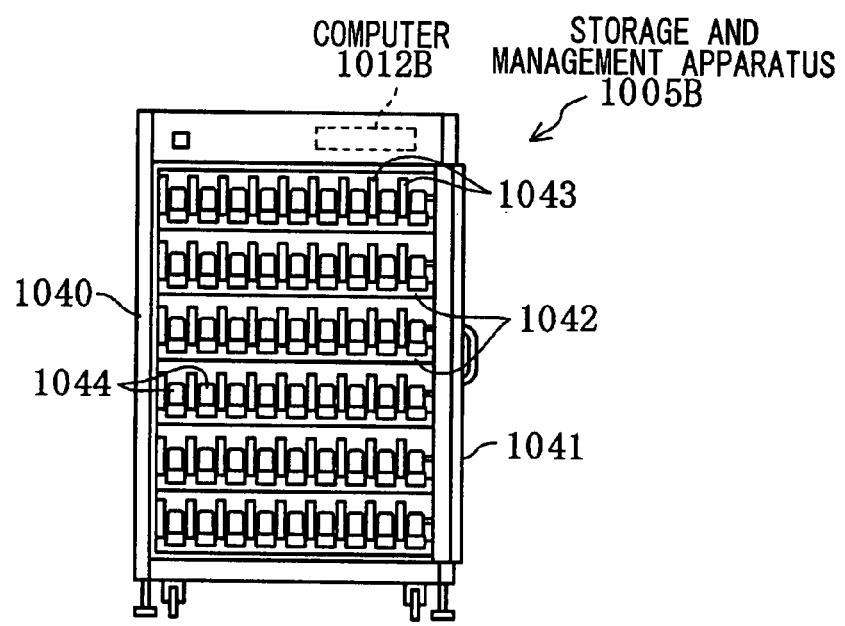

FIG. 75 is a front view showing the door of the medical resource storage and management apparatus according to illustrative embodiment 6-1 opened.

Figure 76:
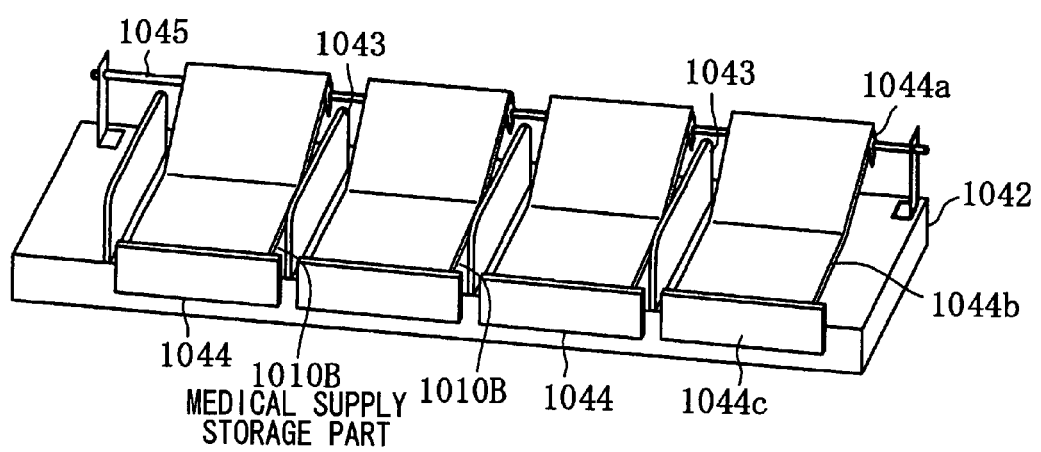

FIG. 76 is a perspective view showing an essential part of the medical resource storage and management apparatus according to illustrative embodiment 6-1.

Figure 77:
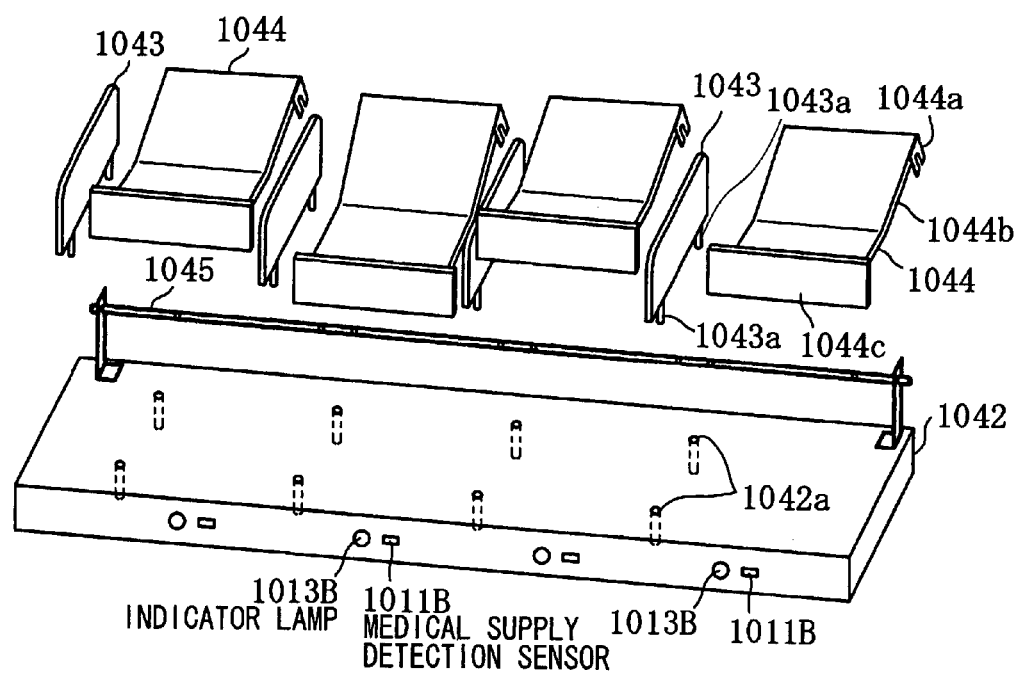

FIG. 77 is an exploded perspective view showing an essential part of the medical resource storage and management apparatus according to illustrative embodiment 6-1.

Figure 78:
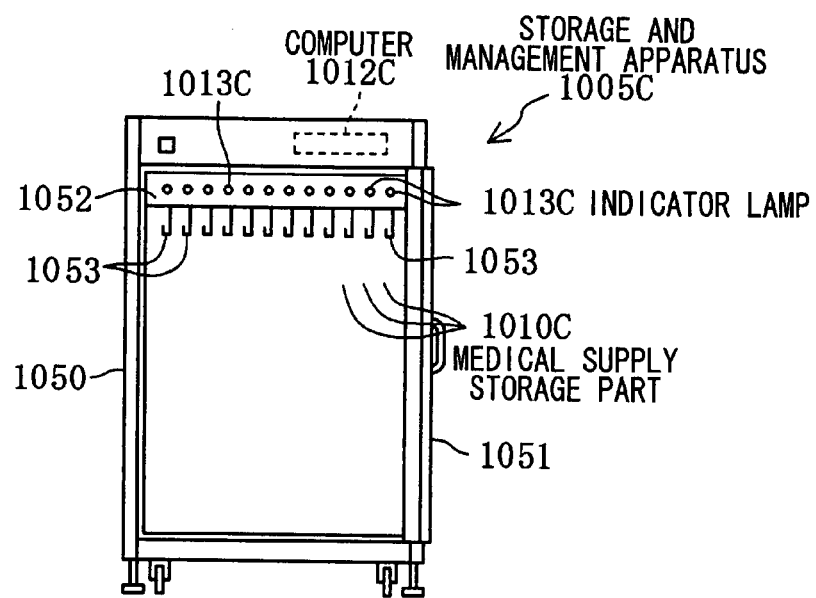

FIG. 78 is a front view showing the door of the medical resource storage and management apparatus according to illustrative embodiment 6-1 opened.

Figure 79:
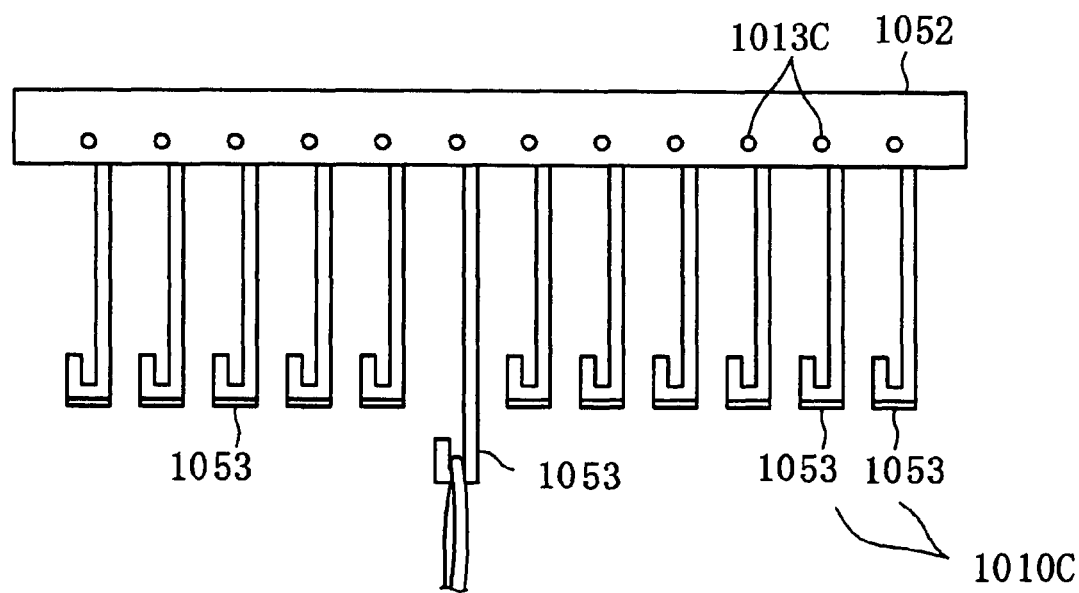

FIG. 79 is a front view showing an essential part of the medical resource storage and management apparatus according to illustrative embodiment 6-1.

Figure 80:
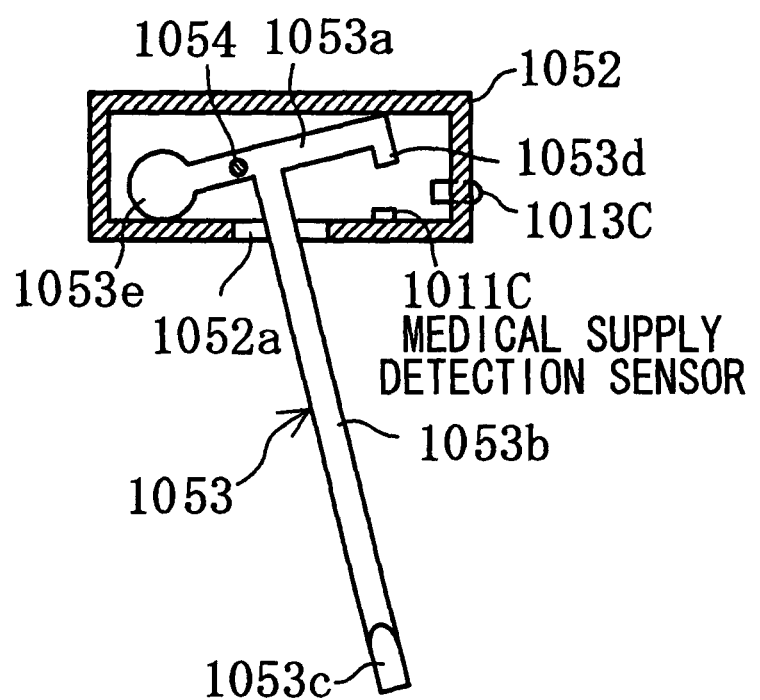

FIG. 80 is a longitudinal sectional view of an essential part of the medical resource storage and management apparatus according to illustrative embodiment 6-1 showing that a medical resource is not stored.

Figure 81:
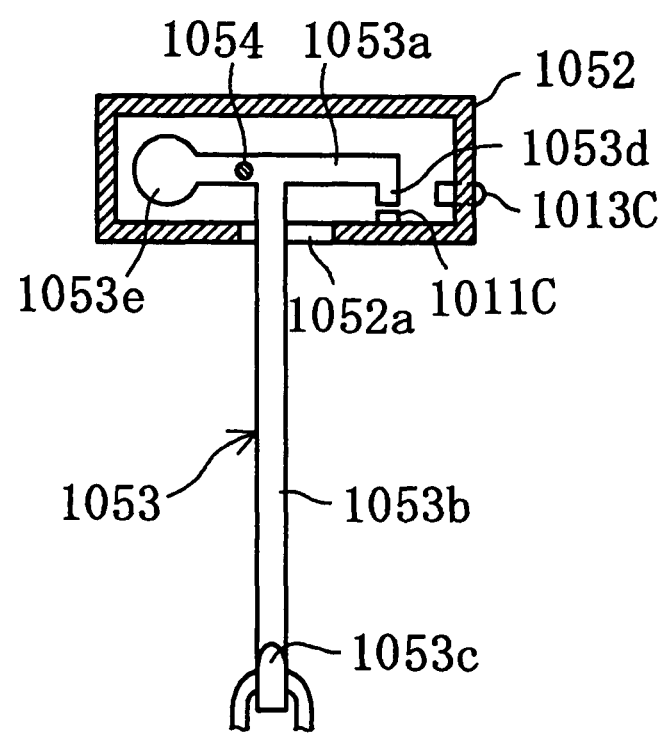

FIG. 81 is a longitudinal sectional view of an essential part of the medical resource storage and management apparatus according to illustrative embodiment 6-1 showing that a medical resource is stored.

Figure 82:
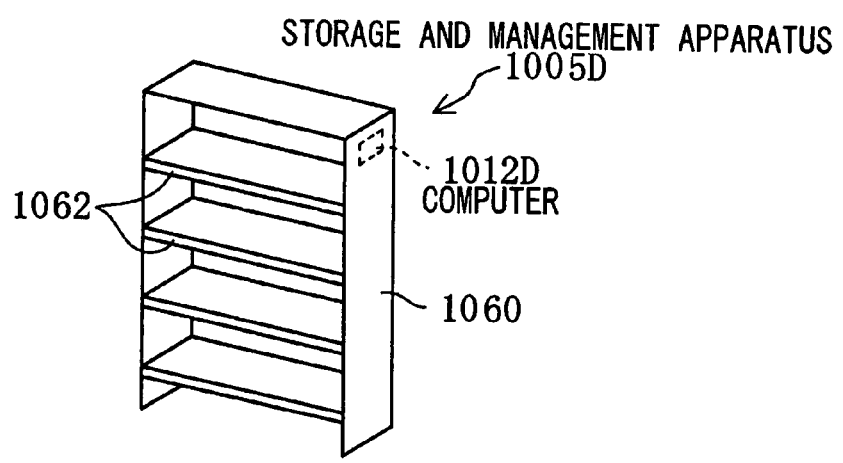

FIG. 82 is a perspective view showing the medical resource storage and management apparatus according to illustrative embodiment 6-1.

Figure 83:
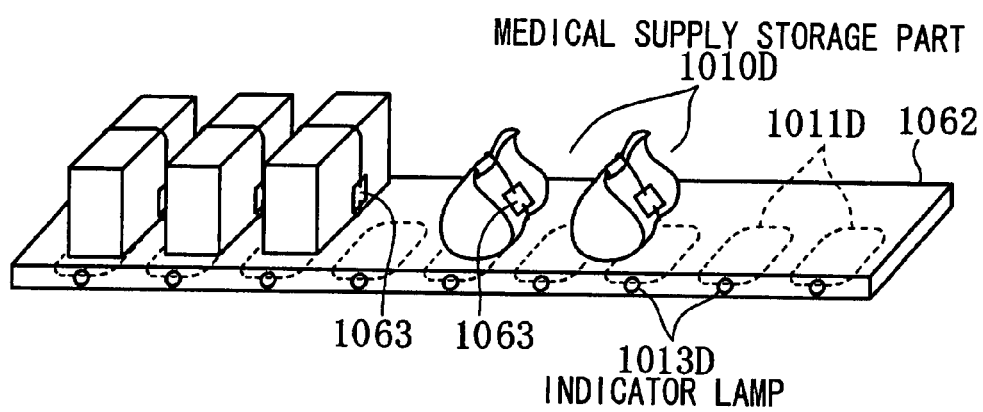

FIG. 83 is a perspective view showing an essential part of the medical resource storage and management apparatus according to illustrative embodiment 6-1.

Figure 84:
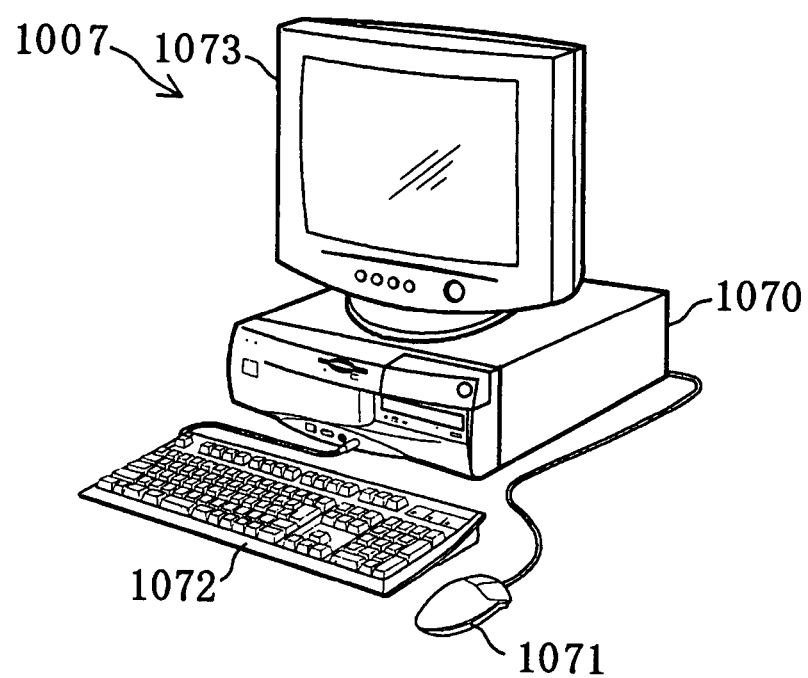

FIG. 84 is a perspective view of a stock control apparatus according to the illustrative embodiment 6-1.

Figure 85:
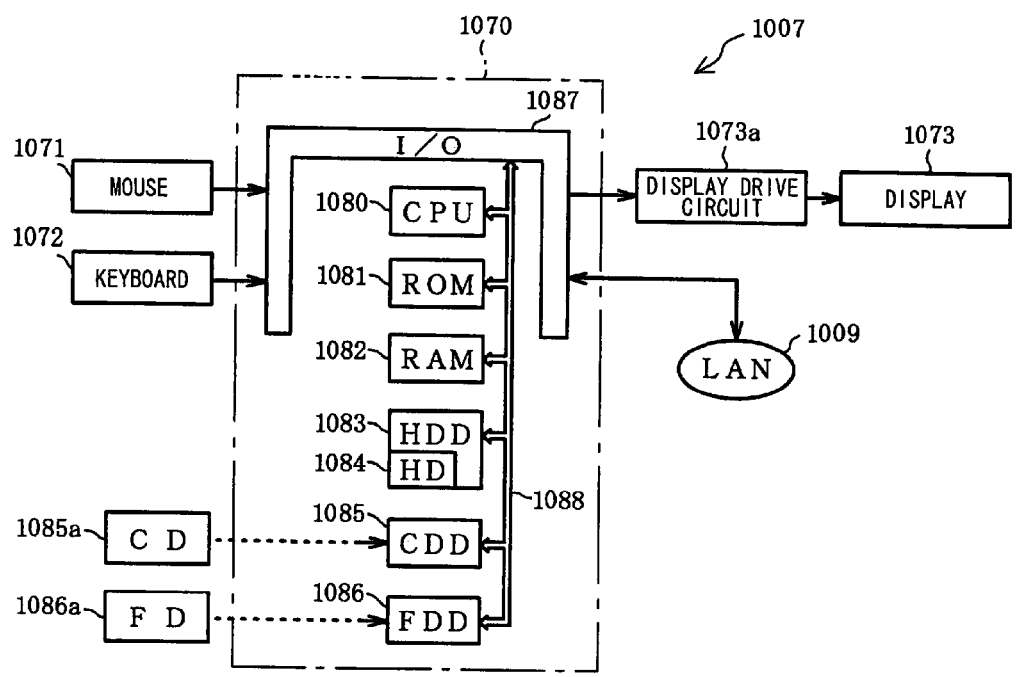

FIG. 85 is a functional block diagram of the stock control apparatus according to the illustrative embodiment 6-1.

Figure 86:
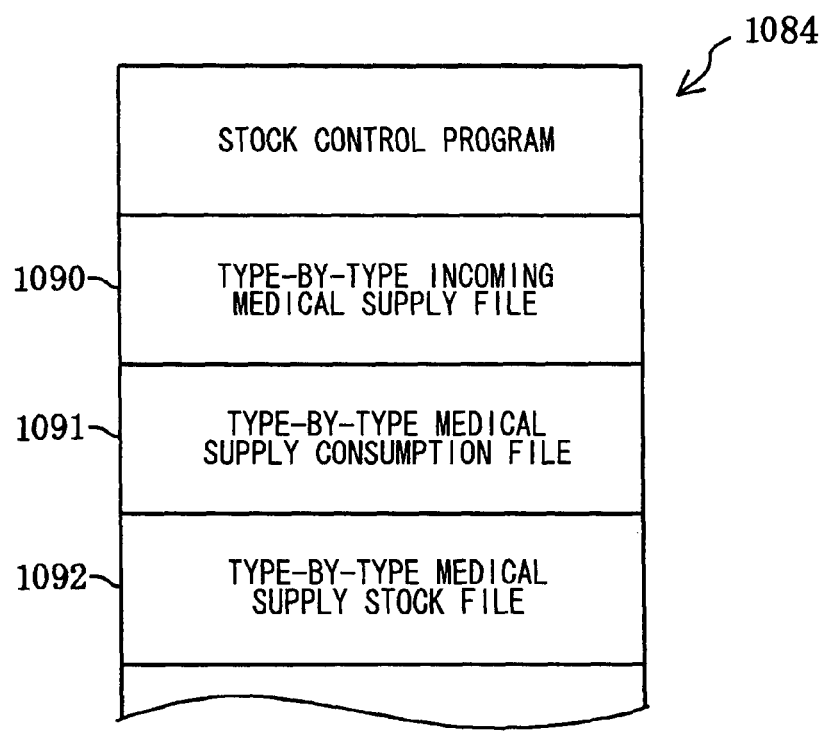

FIG. 86 shows information stored in a storage unit of the stock control apparatus according to the illustrative embodiment 6-1.

FIG. 87 shows information in a type-by-type medical supply stock file according to the illustrative embodiment 6-1.

FIG. 88 shows information on expiration dates of medical supplies according to the illustrative embodiment 6-1.

Figure 89:
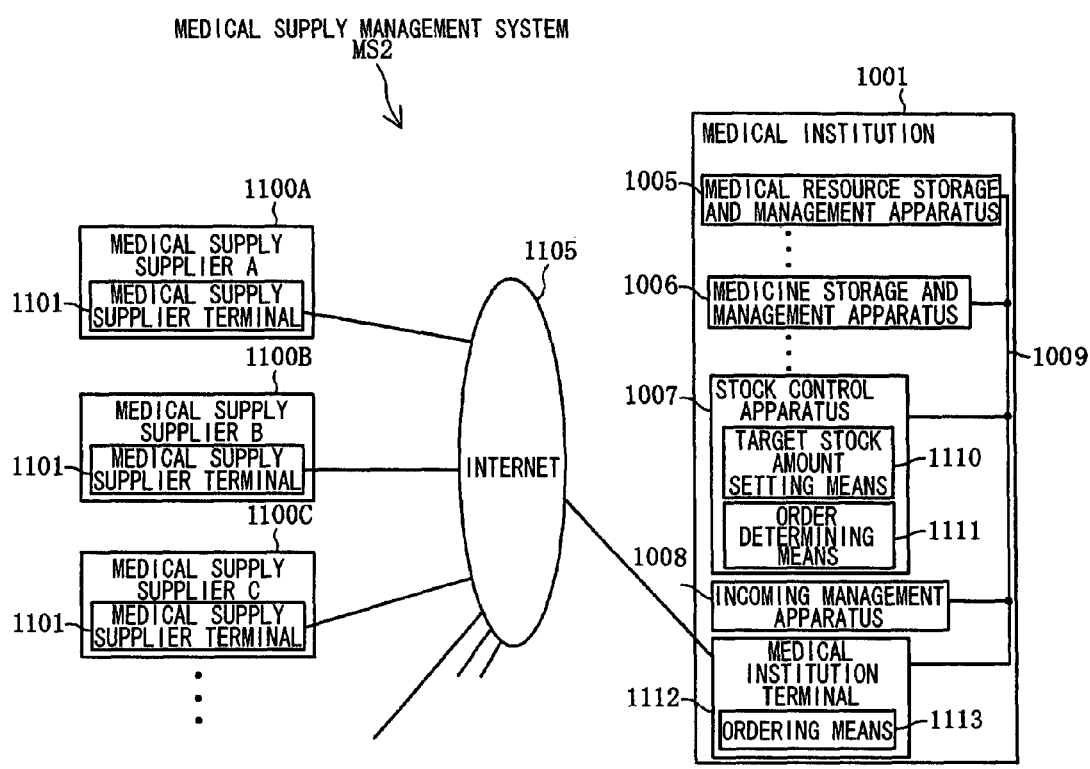

FIG. 89 shows the structure of the medical management system according to an illustrative embodiment 6-2 of the sixth embodiment.

Figure 90:
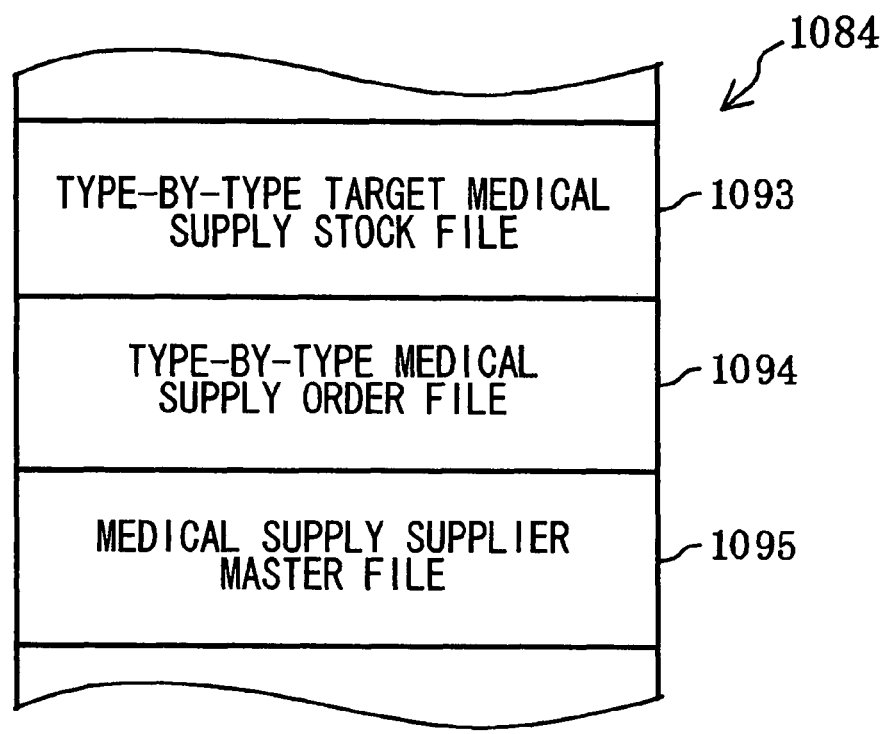

FIG. 90 shows information stored in the storage unit of the stock control apparatus according to the illustrative embodiment 6-2.

FIG. 91 shows information in a type-by-type medical supply stock file according to the illustrative embodiment 6-2.

FIG. 92 shows type-by-type medical supply order file according to the illustrative embodiment 6-2.

Figure 93:
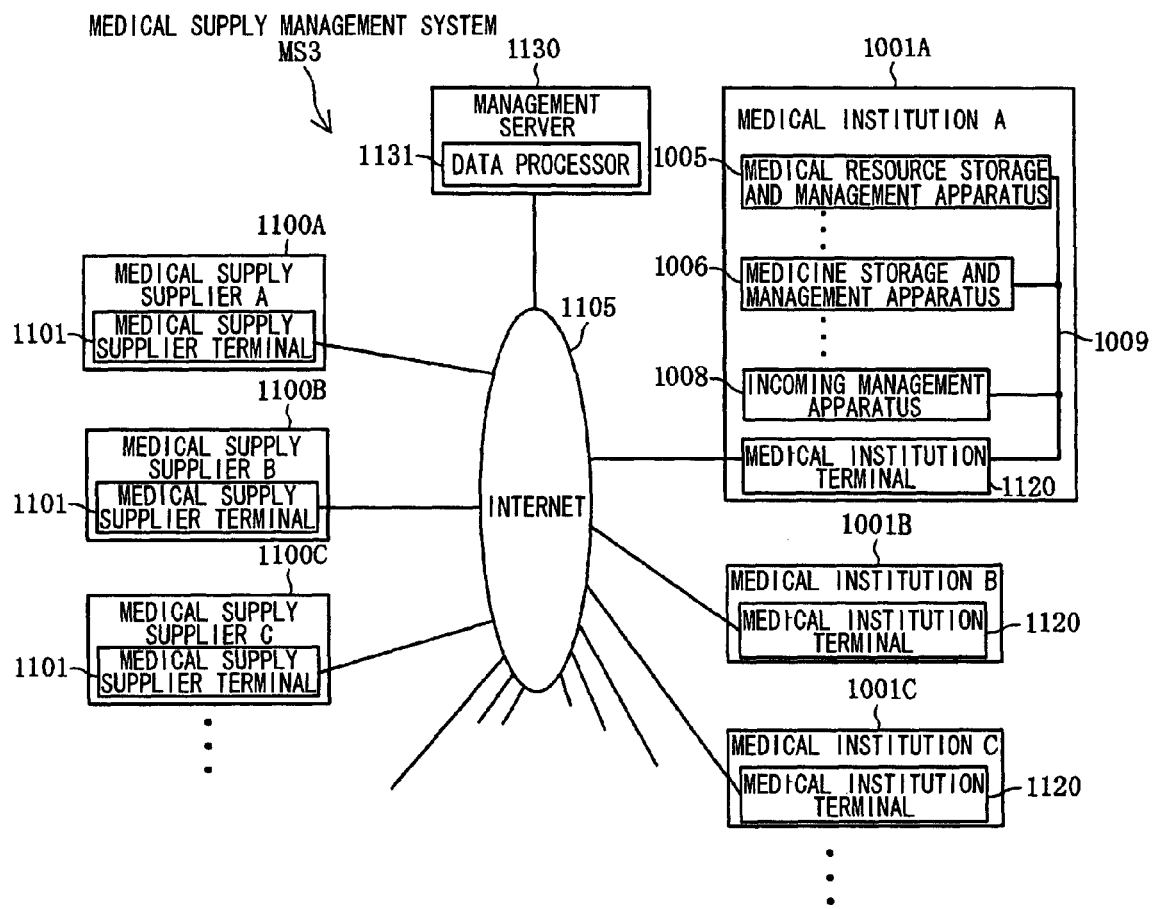

FIG. 93 shows the structure of the medical management system according to an illustrative embodiment 6-3 of the sixth embodiment.

Figure 94:
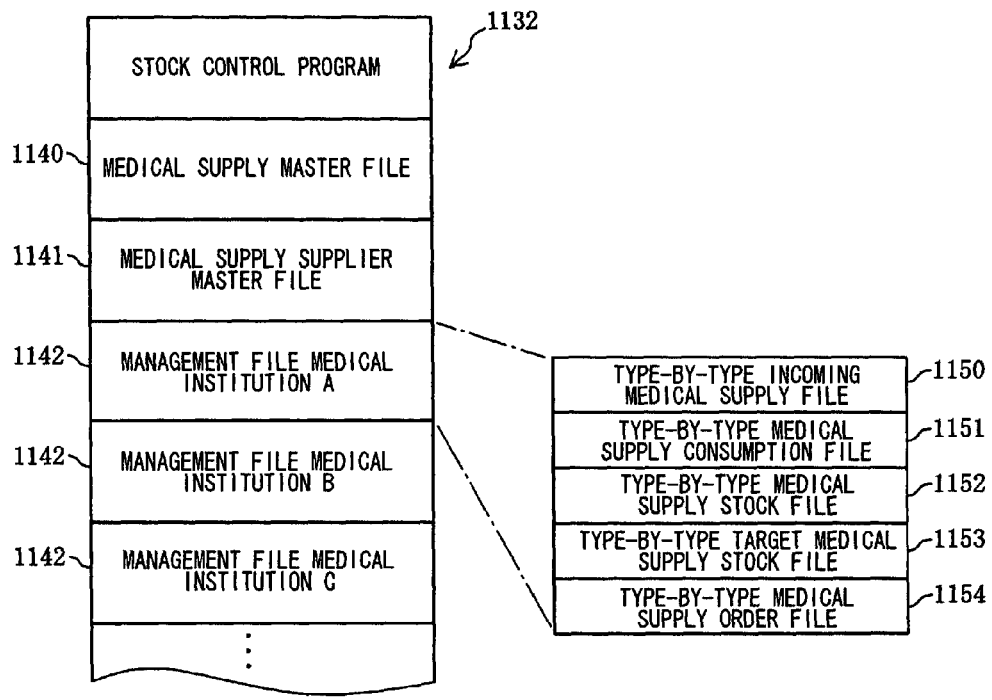

FIG. 94 shows information stored in the storage unit of the stock control apparatus according to the illustrative embodiment 6-3.

Figure 95:
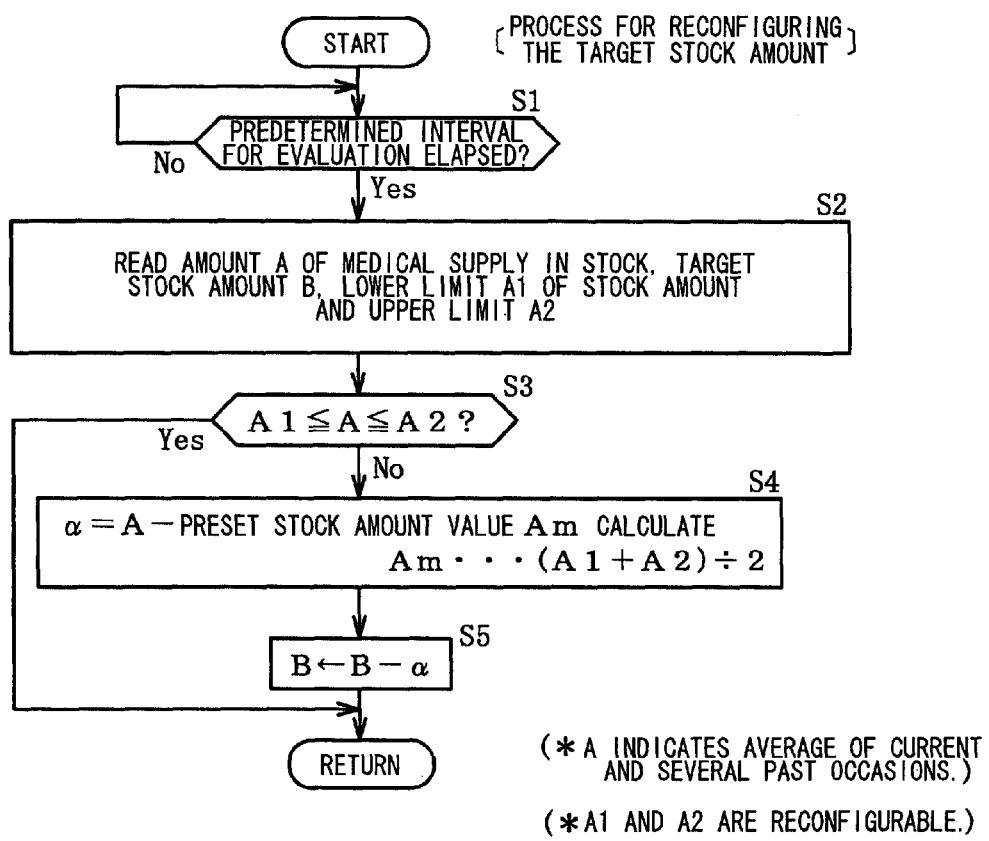

FIG. 95 is a flowchart showing a process for reconfiguration of a target stock amount according to an illustrative embodiment 6-4 of the sixth embodiment.

Figure 96:
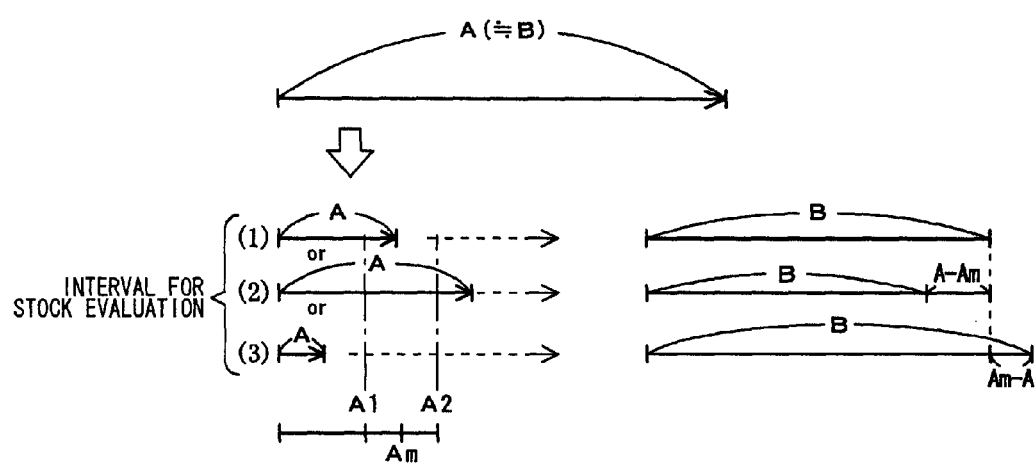

FIG. 96 shows how the target stock amount is reconfigured according to the process of FIG. 95.

Figure 97:
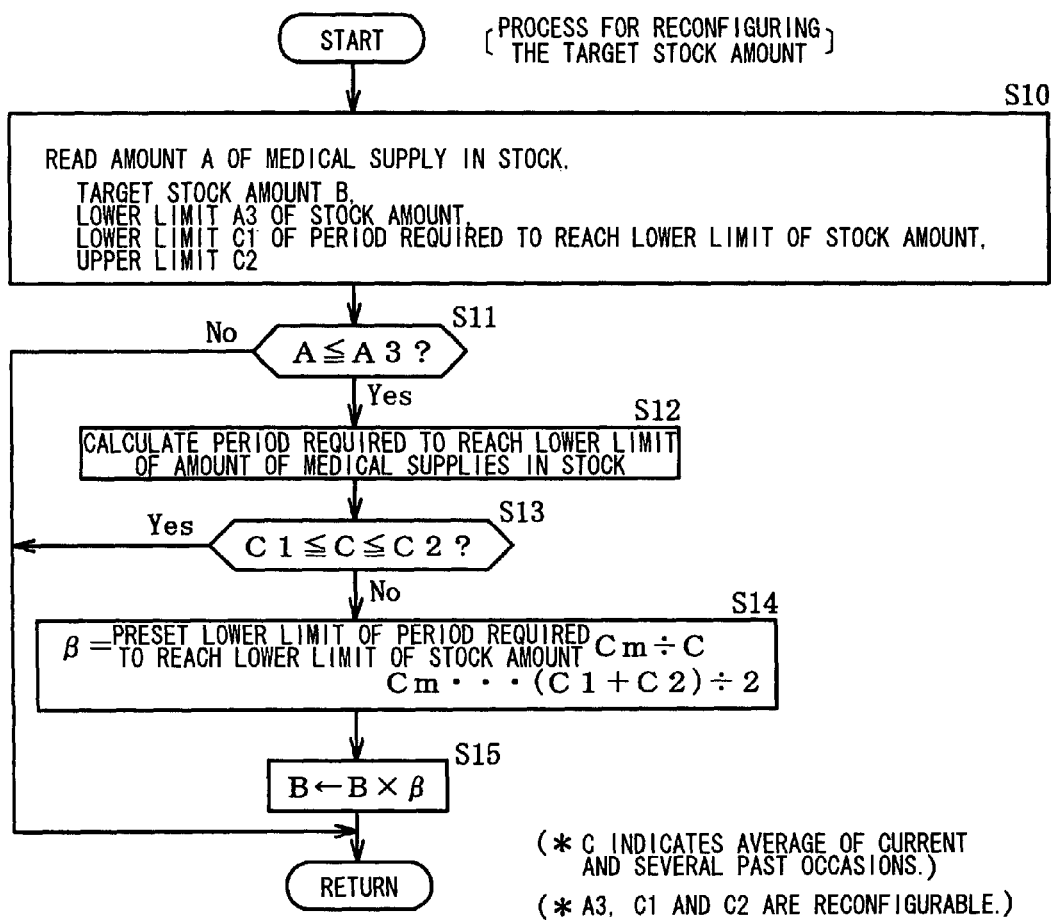

FIG. 97 is a flowchart for the process of reconfiguring according to a variation of the illustrative embodiment 6-4 of the sixth embodiment.

Figure 98:
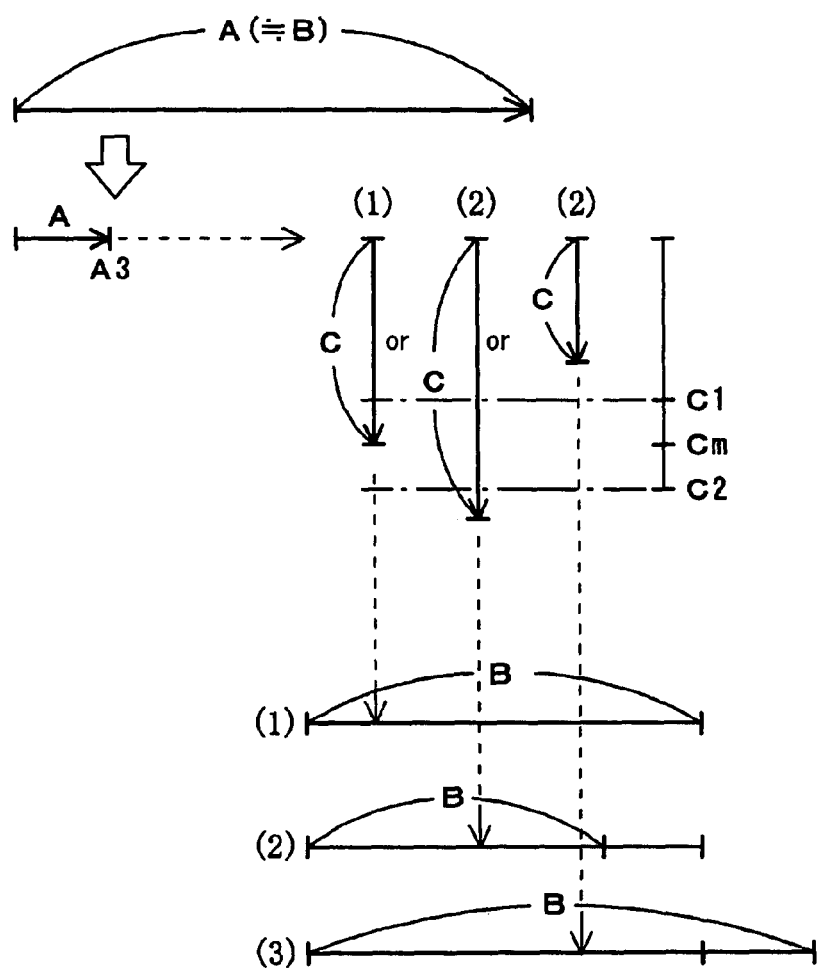

FIG. 98 shows how the target stock amount is reconfigured according to the process of FIG. 97.

EXPLANATION OF THE REFERENCE SYMBOLS 10 medical resource, 20 medical resource storage and management apparatus, 21 electric equipment, 22 housing, 23 handle, 24 door, 30 control unit, 31 rack controller, 32 display, 33 keyboard, 34 mouse, 35 barcode reader, 36 printer, 37 LAN (local area network), 38 hard disk, 41 retrieval guidance routine, 42 medical resource detection routine, 43 medical resource information configuration routine, 44 manual partition condition configuration routine, 45 automatic partition condition configuration routine, 46 medical resource availability data, 47 medical resource information table, 48 partition availability data, 49 log data, 70 rack, 71 depression (for insertion of partition), 72 retrieval guidance member, 73 medical resource detecting member, 74 partition detecting member, 74a light-emitting device, 75 partition member, 76 fitting, 110 medical resource, 120 medical resource storage and management apparatus, 121 electric equipment, 122 housing, 123 handle, 124 door, 130 control unit, 131 rack controller, 132 display, 133 keyboard, 134 mouse, 135 barcode reader, 136 printer, 137 LAN (Local Area Network), 138 hard disk, 141 retrieval guidance member, 142 medical resource detection routine, 143 medical resource information configuration routine, 144 manual partition condition configuration routine, 145 automatic partition condition configuration routine, 146 medical resource availability data, 147 medical resource information table, 148 partition availability data, 149 log data, 160 rack, 161 depression (for insertion of partition), 162 retrieval guidance member, 163 medical resource detecting member, 164 partition detecting member, 164a light-emitting device, 165 partition member, 166 fitting, 167 medical resource name plate, 168 connecting member, 169 pivot shaft, 170 rack, 171 depression (for insertion of partition), 172 retrieval guidance member, 173 medical resource detecting member, 174 partition detecting member, 175 partition member, 176 fitting, 210 medical resource, 220 medical resource storage and management apparatus, 225 drawer unit, 226 space with an open front, 227 shutter, 230 control unit, 231 low-level controller, 232 display, 233 keyboard, 234 mouse, 235 barcode reader, 236 printer, 237 LAN (Local Area Network), 238 hard disk, 241 retrieval guidance routine, 242 medical resource detection routine, 243 medical resource information configuration routine, 244 manual hanger condition configuration routine, 245 automatic hanger condition configuration routine, 246 medical resource availability data, 247 medical resource information table, 248 partition availability data, 249 log data, 250 horizontal-bridging case (horizontal-bridging member), 250a oblong hole (hanger member fitting part), 251 horizontal-bridging bar (horizontal-bridging member), 252 retrieval guidance member, 253 medical resource detecting member, 254 hanger detecting member, 254a light-emitting device, 256 hanger member, 255a pivot center, 256 engaging part, 257 weight part, 258 detected part, 260 rack, 261 depression (for insertion of partition), 262 retrieval guidance member, 263 medical resource detecting member, 264 partition detecting member, 264a light-emitting device, 265 partition member, 266 fitting, 267 medical resource name plate, 268 connecting member, 269 pivot shaft, 270 rack, 271 depression (for insertion of partition), 272 retrieval guidance member, 273 medical resource detecting member, 274 partition detecting member, 275 partition member, 276 fitting, 310 medical resource, 320 medical resource storage and management apparatus, 321 electric equipment, 322 housing, 323 handle, 324 door, 330 control unit, 331 rack controller, 332 display, 333 keyboard, 334 mouse, 335 barcode reader, 336 printer, 337 LAN (Local Area Network), 338 hard disk, 341 retrieval guidance routine, 342 medical resource detection routine, 343 medical resource information configuration routine, 344 manual partition condition configuration routine, 345 automatic partition condition configuration routine, 346 medical resource availability data, 347 medical resource information table, 348 partition availability data, 349 log data, 350 horizontal-bridging case (horizontal-bridging member), 350a oblong hole (hanger member fitting part), 351 horizontal-bridging bar (horizontal-bridging member), 352 retrieval guidance member, 353 medical resource detecting member, 354 hanger detecting member, 354a light-emitting device, 355 hanger member, 355a pivot center, 356 engaging part, 357 weight part, 358 detected part, 360 rack, 361 depression (for insertion of partition), 362 retrieval guidance member, 363 medical resource detecting member, 364 partition detecting member, 364a light-emitting device, 365 partition member, 366 fitting, 367 medical resource name plate, 368 connecting member, 369 pivot shaft, 370 rack, 371 depression (for insertion of partition), 372 retrieval guidance member, 373 medical resource detecting member, 374 partition detecting member, 375 partition member, 376 fitting, 380 rack, 381 depression (for insertion of partition), 382 retrieval guidance member, 383 medical resource detecting member, 384 partition detecting member, 384a light-emitting device, 385 partition member, 386 fitting, 387 medical resource name plate, 388 connecting member, 389 name plate support member, 410 medical resource, 420 medical resource storage and management apparatus, 421 electric equipment, 422 housing, 423 handle, 424 door, 430 control unit, 431 rack controller, 432 display, 433 keyboard, 434 mouse, 435 barcode reader, 436 printer, 437 LAN (Local Area Network), 438 hard disk, 441 retrieval guidance routine, 442 medical resource detection routine, 443 medical resource information configuration routine, 444 manual partition condition configuration routine, 445 automatic partition condition configuration routine, 446 medical resource availability data, 447 medical resource information table, 448 partition availability data, 449 log data, 450 horizontal-bridging case (horizontal-bridging member), 450a oblong hole (hanger member fitting part), 451 horizontal-bridging bar (horizontal-bridging member), 452 retrieval guidance member, 453 medical resource detecting member, 454 hanger detecting member, 455 hanger member, 456 engaging part, 457 weight part, 458 detected part, 460 rack, 461 depression (for insertion of partition), 462 retrieval guidance member, 463 medical resource detecting member, 464 partition detecting member, 465 partition member, 466 fitting, 467 medical resource name plate, 468 connecting member, 469 pivot shaft, 470 rack, 471 depression (for insertion of partition), 472 retrieval guidance member, 473 medical resource detecting member, 474 partition detecting member, 475 partition member, 476 fitting, 480 rack, 481 depression (for insertion of partition), 482 retrieval guidance member, 483 medical resource detecting member, 484 partition detecting member, 485 partition member, 486 fitting, 487 medical resource name plate, 488 connecting member, 489 name plate support member, 490 rack, 491 depression (for insertion of partition), 491*a* storage location indicator (partition configuration member), 492 retrieval guidance member, 493 medical resource detecting member, 493*a* case detecting member, 494 partition detecting member, 495 storage case, 495*a* engaging part, 496 biasing member, 497 medical resource name plate, 497*a* storage location indicator, 498 connecting member, 499 engaging part (pivot shaft), MS1, MS2, MS3 medical supply management system, 1001, 1001A-1001C medical institution, 1005, 1005A-1005D, 1006 storage and management apparatus, 1007 stock control apparatus, 1008 incoming management apparatus, 1009 Local Area Network (LAN), 1010, 1010A-1010D medical supply storage part, 1011, 1011A-1011C medical supply detection sensor, 1011D antenna, 1012, 1012A-1012D computer, 1013, 1013A-1013D indicator lamp, 1100A-1100C medical supply supplier, 1101 medical supply supplier terminal, 1105 Internet, 1110 target stock amount setting means, 1111 order determining means, 1112, 1120 medical institution terminal, 1113 ordering means, 1130 management server, 1131 data processor

BEST MODE FOR CARRYING OUT THE INVENTION

A description of the best mode of carrying out the present invention will be given by highlighting first through sixth embodiments.

FIRST EMBODIMENT

A first embodiment of the present invention relates to a medical resource storage and management apparatus which arranges and stores medical resources and also performs management of storage status, and, more particularly, to a medical resource storage and management apparatus which automatically manages availability of medical resources at each location of storage and also guides a user for retrieval.

A summary of the first embodiment will be given.

A first medical resource storage and management apparatus according to the first embodiment comprises: a rack in which a series of depressions for insertion of partition members are formed so that a large number of medical resources are retrievably placed in respective partitions; partition members which are removably inserted into the depressions; medical resource detecting members which are arranged on the rack so as to alternate with the depressions in a direction in which the depressions are arranged, and each of which detects whether or not a medical resource is placed; retrieval guidance members for visual guidance which are arranged on the rack so as to alternate with the depressions in a direction in which the depressions are arranged; and a control unit which manages the storage status of the medical resources, based on the detection by the medical resource detecting members and which operates one of the retrieval guidance members in response to an input designating retrieval, wherein the control unit allows providing an input for configuration to designate whether or not the partition member is inserted into the depression, and the control unit collectively processes a block of medical resource detecting members and retrieval guidance members identified as being located on both sides of the depression from which the partition member is removed, based on the input for configuration.

A second medical resource storage and management apparatus according to the first embodiment comprises: a rack in which a series of depressions for insertion of partition members are formed so that a large number of medical resources are retrievably placed in respective partitions; partition members which are removably inserted into the depressions; medical resource detecting members which are arranged on the rack so as to alternate with the depressions in a direction in which the depressions are arranged, and each of which detects whether or not a medical resource is placed; retrieval guidance members for visual guidance which are arranged on the rack so as to alternate with the depressions in a direction in which the depressions are arranged; a control unit which manages the storage status of the medical resources, based on the detection by the medical resource detecting members and which operates one of the retrieval guidance members in response to an input designating retrieval; and partition detecting members each of which detects whether the partition member is inserted into the depression, wherein the control unit collectively process a block of medical resource detecting members and retrieval guidance members identified as being located on both sides of the depression from which the partition member is removed, based on the detection by the partition detecting member.

A third medical resource storage and management apparatus according to the first embodiment is a modification to the first medical resource storage and management apparatus or the second medical resource storage and management apparatus, wherein the control unit issues an alarm if the results of detection by the medical resource detecting members in a block to be processed collectively continue to fail to match beyond a predetermined period of time.

In the first medical resource storage and management apparatus, the medical resources are arranged on the rack such that the locations of storage are partitioned by the partition members. Therefore, it is easy to retrievably align and store medical resources without accommodating them in cassettes and to prevent disarrangement of the medical resources stored and resultant disorganization.

Since the medical resource detecting member and the retrieval guidance member are placed in respective partitions on the rack, it is possible to detect whether each medical resource is stored for automatic management and to properly guide a user to the location of storage of the medical resource to be retrieved.

Since the partition member can be removed from the rack and the location of insertion is formed as a depression, a relatively large medical resource can be placed where the partition member is removed.

In this case, whether or not the partition member is inserted is designated by providing an input for configuration in the control unit. In this way, the control unit can collectively process medical resource detecting members and retrieval guidance members. Therefore, a user will not be at a loss or face any inconvenience in handling and management even if there are multiple medical resource detecting members or retrieval guidance members where a single, large medical resource resides.

Thus, even with a simple apparatus in which racks are partitioned and medical resources are arranged, a large variety of large and small medical resources can be easily stored for automatic management by means of attachment and detachment of partition members and by an input of associated information for configuration.

Thus, the first medical resource storage and management apparatus provides capability for easily and properly storing and retrieving medical resources, and automatically and accurately keeping track of storage status.

According to the second medical resource storage and management apparatus, convenience is enhanced by additionally ensuring that whether or not the partition member is inserted is automatically detected and reflected in the control.

Thus, the second medical resource storage and management apparatus provides capability for easily and properly storing and retrieving medical resources, and accurately and automatically keeping track of partition status as well as storage status.

According to the third medical resource storage and management apparatus, reliability is enhanced while avoiding an increase in hardware cost, by exploiting the redundancy of results of detection by multiple medical resource detecting members in a single block and detecting an error accordingly.

Specific embodiments of the medical resource storage and management apparatus according to the first embodiment will be described using illustrative embodiments 1-1 through 1-4.

Figure 6A:
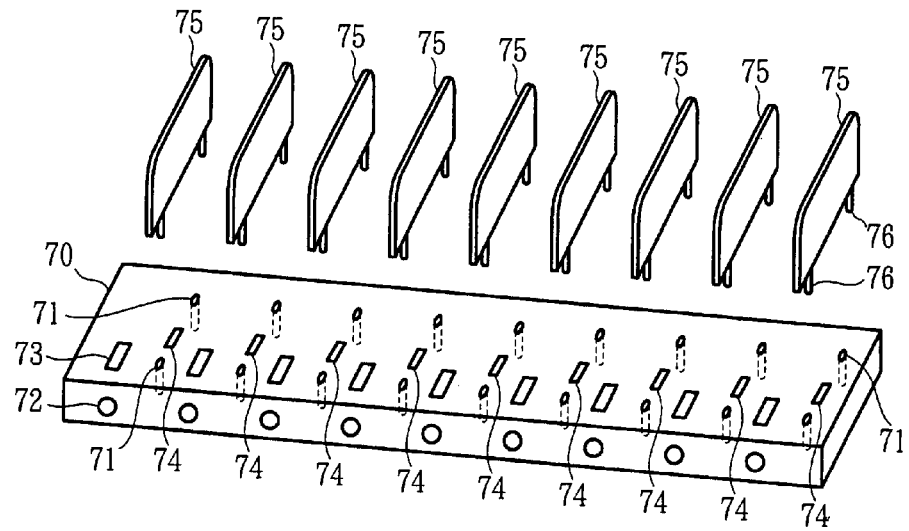
FIGS. 6A and 6B show the structure of the medical resource storage and management apparatus according to an illustrative embodiment 1-2 of the first embodiment.
Figure 6B:
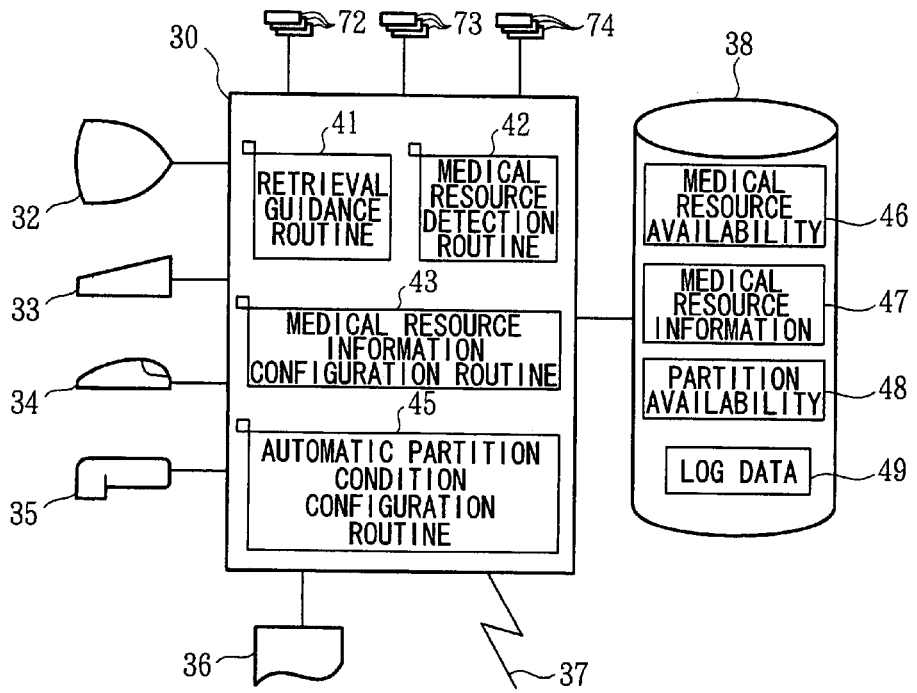

The illustrative embodiment 1-1 shown in FIGS. 1A-5D is an embodiment of the first medical resource storage and management apparatus and the third medical resource storage and management apparatus mentioned above. The illustrative embodiment 1-2 shown in FIGS. 6A-6B is an embodiment of the second medical resource storage and management apparatus mentioned above. The illustrative embodiment 1-3 shown in FIGS. 7A-7C and the illustrative embodiment 1-4 shown in FIGS. 8-9 are variations.

In the illustration, fasteners such as bolts, connectors such as hinges, electronic circuits such as drivers are omitted for brevity, highlighting those elements necessary to explain the embodiment and related elements.

Illustrative Embodiment 1-1

Figure 2A:
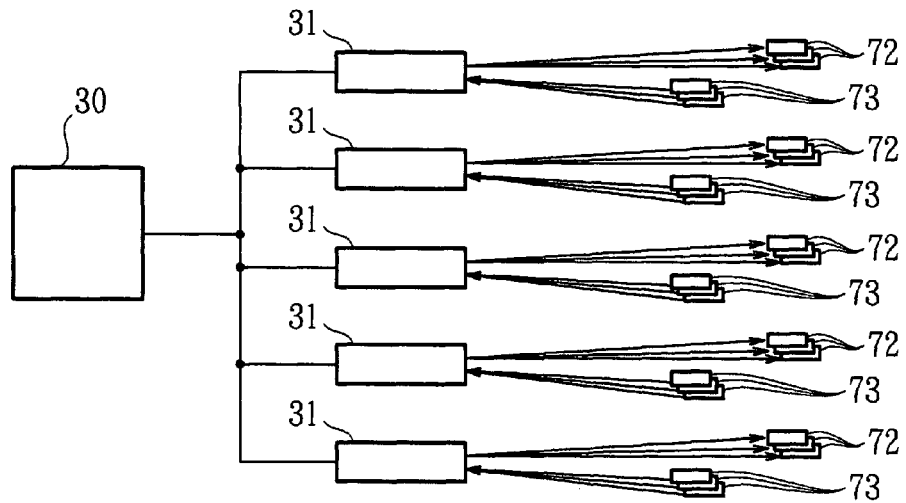
FIGS. 2A and 2B show the schematic structure of a control unit according to the first embodiment.
Figure 2B:
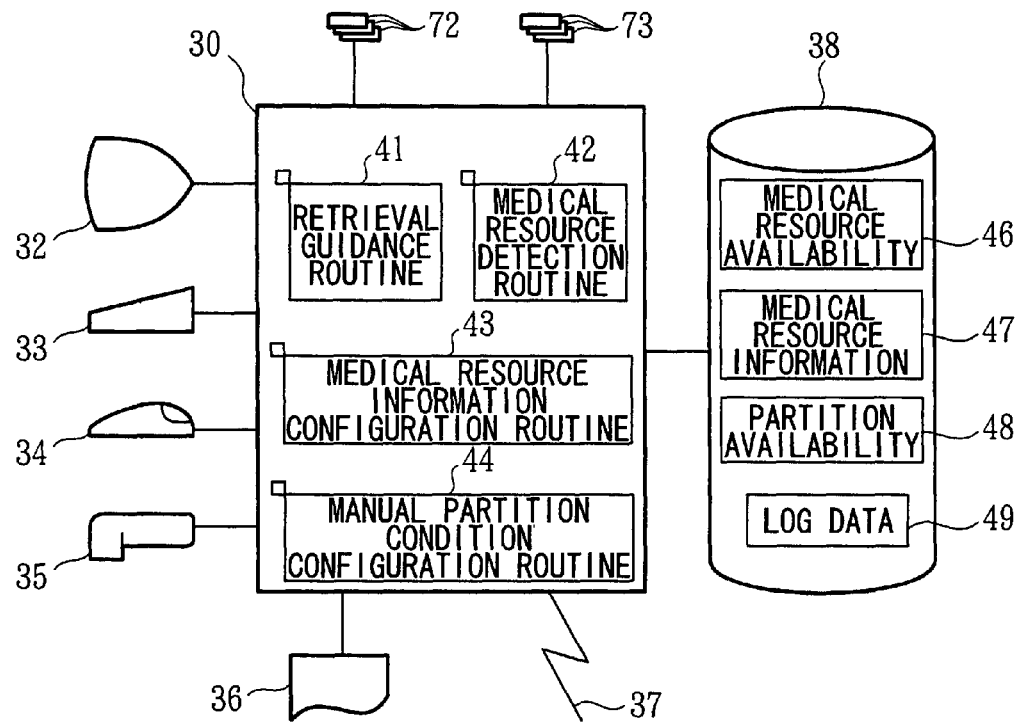
Figure 3A:
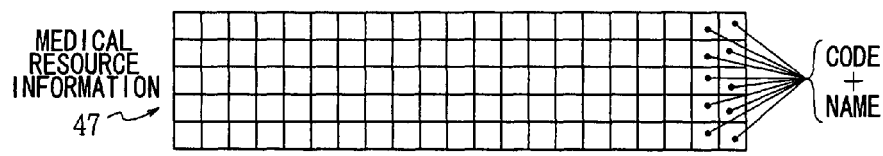
FIGS. 3A-3C show the data structure of the control unit according to the first embodiment.
Figure 3B:
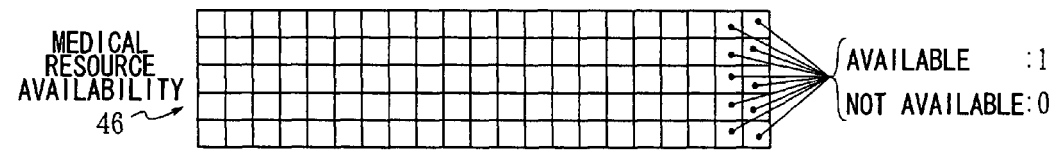
Figure 3C:
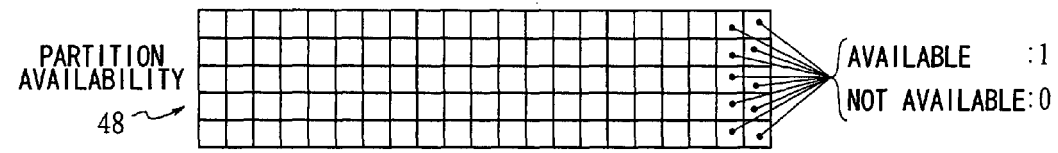

A specific structure of the illustrative embodiment 1-1 of the medical resource storage and management apparatus according to the first embodiment will be described with reference to the associated drawings. FIGS. 1A-1D show the mechanical structure of the medical resource storage and management apparatus. FIG. 1A is a front view showing a door closed; FIG. 1B is a front view showing the door opened; FIG. 1C is a perspective view of a rack and partition members; and FIG. 1D is a perspective view showing the appearance of the rack in which the partition members are fitted. FIGS. 2A and 2B show the schematic structure of a control unit. FIG. 2A is a schematic block diagram showing the connection between the control unit and retrieval guidance members; and FIG. 2B is a functional block diagram of the control unit. FIGS. 3A-3C show the data structure of the control unit. FIG. 3A relates to a medical resource information table; FIG. 3B relates to medical resource availability data; and FIG. 3C relates to partition availability data.

A medical resource storage and management apparatus 20 is provided with a housing 22 a large portion of which is for storage and a part of which comprises electric equipment 21. The electric equipment 21 stores a control unit 30 and a power supply unit etc. (not shown). The front of the storage part of the housing 22 is provided with an openable door 24 with a handle 23. The door 24 may be implemented by a shutter or the like, or may be omitted. Inside the storage part exposed when the door 24 is opened is provided a rack 70. Although there may be only one rack 70, an orthodox apparatus would comprise multiple tiers. The pitch between the racks 70 may be selectable. The rack 70 is implemented by a horizontally extending plate with a flat top face. Partition members 75 formed as thin plates are fitted to the top face thereof at regular or irregular pitches in a longitudinal direction (in the figure, sideways) in order to place a large number of medical resources in respective partitions retrievably.

Two rows of depressions 71 to fit partition members are formed on the top face of the rack 70 (see FIGS. 1C and 1D) at regular or irregular pitches in a longitudinal direction (in the figures, sideways). Two fittings 76 are formed to protrude from the bottom of each of the partition members 75. In this example, the fitting 76 is a small round bar and the depression 71 is a through hole. By inserting the fitting 76 into the depression 71, the partition member 75 is removably fitted to the depression 71 in the rack 70. The front of the rack 70 exposed when the door 24 is opened is equipped with retrieval guidance members 72, and the top face of the rack 70 which carries medical resources 10 is equipped with medical resource detecting members 73. The retrieval guidance members 72 and the medical resource detecting members 73 are arranged in the rack 70 so as to alternate with the depressions 71 in a direction in which the depressions 71 are arranged, i.e., in the longitudinal direction of the rack 70.

In order to detect whether the medical resource 10 is placed in its location partitioned by the partition member 75, each of the medical resource detecting members 73 is implemented by a mechanical switch, a reflective photosensor, a capacity sensor or the like which senses the bottom of the medical resource 10, so as to output a binary signal which turns on and off according to whether the medical resource 10 is detected.

In order to visually guide a user to the location of placement of the medical resource 10 to be retrieved, a miniature bulb, a light-emitting diode or the like that can be turned on and off is used as the retrieval guidance member 72.

The control unit 30 (see FIG. 2A) comprises a programmable controller such as a personal computer and a sequencer. A local area network (LAN) connects the control unit 30 to the retrieval guidance members 72 and the medical resource detecting members 73 via, for example, a rack controller 31. Alternatively, the control unit 30, the retrieval guidance members 72 and the medical resource detecting members 73 are in direct star connection (not shown). The connection enables retrieving detection results of the medical resource detecting members 73 and controlling the lighting of the retrieval guidance members 72.

The control unit 30 (see FIG. 2B) is provided with a display 32 for screen display, a keyboard 33 for key entry, a mouse 34 for inputting instructions etc. on a screen, a bar code reader 35 for reading identification information, a printer 36 for delivering printouts, an interface for a local area network (LAN) 37 which is responsible for communication with a prescription order-entry system etc., and a hard disk 38 as a secondary storage.

A retrieval guidance routine 41, a medical resource detection routine 42, a medical resource information configuration routine 43, and a manual partition condition configuration routine 44 are installed in the control unit 30, as programs for managing the storage status of the medical resources, based on the detection by the medical resource detecting members 73, and for operating selected retrieval guidance members 72 in response to an input designating retrieval. The hard disk 38 stores medical resource availability data 46, a medical resource information table 47, partition availability data 48, and log data 49, which are divided into individual files or are unified in an appropriate database. The figures show (see FIGS. 3A-3B) the data 46, the table 47 and the data 48 maintained in a table format. Each table comprises a 5×21 matrix, in association with the fact that the racks 70 form five tiers and the maximum number of partitions in each rack 70 (i.e., the maximum number of the partition members 75, the retrieval guidance members 72 and the medical resource detecting members 73) is twenty one.

Each field in the medical resource information table 47 (see FIG. 3A) contains an identification code and a name displayed on a screen for the medical resource 10 which is stored or can be stored in an associated location. "1" or "0" is written in the medical resource availability data 46 (see FIG. 3B), "1", indicating that the medical resource 10 is stored in the associated location, and "0", indicating that no medical resources 10 are stored. "1" or "0" is written in the partition availability data 48 (see FIG. 3C), "1", indicating that the partition member 75 is inserted, and "0", indicating that the partition member 75 is removed from the associated location. The medical resource information table 47 should be configured at least once before operating the apparatus for the first time since its installation. Therefore, the table is usually initialized upon starting the apparatus and updated when the operation is stopped. The partition availability data 48 is also initialized so that the insertion condition of the partition member 75 is reflected before the initial operation. Configuration inputs for update are also provided when the partition member 75 is attached or detached. The medical resource availability data 46 is all cleared by initialization before the initial operation, and is subsequently updated with each storage or retrieval of the medical resource 10.

The medical resource information configuration routine 43 is started by the keyboard 33 or mouse 34 operation. When dumping from a medicine master file located on a host computer via the LAN 37 is dictated in an environment where such an action is possible, the medical resource information configuration routine 43 dumps the data. The routine 43 also allows the user to set the code or name of the medical resource 10 in the medical resource information table 47 by selecting an item using the mouse 34 or entering data using the keyboard 33, while viewing screen display on the display 32.

The manual partition condition configuration routine 44 is also started by the keyboard 33 or mouse 34 operation. The routine 44 allows the user to provide an input for configuration to designate in the partition availability data 48 whether the partition member 75 is inserted into the depression 71 in the rack 70, by selecting an item or toggling using the mouse 34 or the keyboard 33, while viewing screen display on the display 32.

The medical resource detection routine 42 is started periodically and automatically by a timer, etc. or irregularly and automatically started by an interruption initiated in the event of a change in a detection signal from the medical resource detecting member 73. The medical resource detection routine 42 manages the storage status of the medical resources 10 based on the detection by the medical resource detecting members 73. More specifically, each time the medical resource detection routine 42 is started, it imports the detection results from all medical resource detecting members 73 or those results changed since its last import, and writes "1" or "0" in the medical resource availability data 46 in association with the on-off condition. When the detection result from the medical resource detecting member 73 undergoes an on/off change and the storage or retrieval of the medical resource 10 is detected accordingly, the medical resource detection routine 42 appends information indicating the detection to the log data 49 with a time stamp, causes the printer 36 to deliver a printout which carries the name listed in the associated field in the medical resource information table 47, and submits a report to a host medical management computer via the LAN 37.

The retrieval guidance routine 41 is started when the code of the medical resource 10 or a prescription ID number is entered by allowing the barcode reader 35 to scan the code or the ID, or by using the keyboard 33 or the mouse 34, in order to operate one of the retrieval guidance members 72 in response to an input designating retrieval. The retrieval guidance routine 41 searches the medical resource information table 47 to determine the location of storage of the medical resource 10 designated to be retrieved via the reading or via the mouse or keyboard operation, and lights the medical resource detecting member 73 at the associated location. The medical resource detection routine 42 is responsible for turning the medical resource detecting member 73 off when the retrieval of the medical resource 10 at the associated location is detected.

The retrieval guidance routine 41 and the medical resource detection routine 42 learn whether or not the partition member 75 is inserted, and collectively process the medical resource detecting members 73 and the retrieval guidance members 72 identified as being located on both sides of the depression 71 from which the partition member 75 is removed. If the results of detection by the medical resource detecting members 73 in the block to be processed collectively continue to fail to match beyond a predetermined period of time, an alarm is issued.

More specifically, the retrieval guidance routine 41 refers to the medical resource availability data 46 to check whether the partition member 75 is inserted to the left or right of a location of storage, before lighting the medical resource detecting member 73. If "0" is entered to the left or right, indicating that the partition member 75 there is removed, the associated, adjacent retrieval guidance member 72 is also lighted. In association with this, the medical resource detection routine 42 performs a similar check by referring to the medical resource availability data 46 in turning off the retrieval guidance member 72, and turns off the retrieval guidance members 72 in the block at a time.

The medical resource detection routine 42 also performs, upon detecting the storage or retrieval of the medical resource 10, a similar check by referring to the medical resource availability data 46 before changing the value of the medical resource availability data 46. If a series of adjacent partitions are to be processed collectively as a single block, the medical resource detection routine 42 examines whether the values from the medical resource detecting members 73 in the single block match. If the values match, the routine 42 terminates the process normally; if the values do not match, the routine 42 continues the monitoring. If the values from the medical resource detecting members 73 in a block continue to fail to match beyond a maximum period of time required for storage or retrieval of the medical resource 10 while the monitoring is proceeding, the medical resource detection routine 42 displays an alarm on the display 32 or sounds an alarm buzzer (not shown).

In order to help the routines 41 and 42 to collectively process a block where the partition member 75 is removed, the manual partition condition configuration routine 44 configures, in designating in the partition availability data 48 that the partition member 75 is removed, the associated fields in the medical resource information table 47 such that field values (i.e., codes and names maintained) corresponding to the locations of storage identified as being located on both sides of the depression 71 from which the partition member 75 is removed, match. The manual partition condition configuration routine 44 returns the field values to their original values in designating in the partition availability data 48 that the partition member 75 is inserted.

In addition, the control unit 30 acquires operator identification information by requesting an operator to input operator identification information each time an operation is carried out. Alternatively, the control unit 30 acquires operator identification information input by an operator in advance of an operation. The control unit 30 also stores, in the log data 49, related information then collected by automatic detection etc. together with a time stamp. The data stored is also output via the LAN 37. The process is performed in the manual partition condition configuration routine 44 as well as in the retrieval guidance routine 41.

The mode of using the medical resource storage and management apparatus according to the illustrative embodiment 1-1 and its operation will be described with reference to the drawings. FIGS. 4A-4B illustrate the operation of the medical resource storage and management apparatus. FIG. 4A shows an empty condition; and FIG. 4B shows a condition in which a small medical resource is stored. FIGS. 5A-5D also illustrate the operation of the medical resource storage and management apparatus. FIG. 5A shows a condition in which one partition member is removed from the rack while the partition is empty; FIG. 5B shows a condition in which a medium-sized medical resource is stored; FIG. 5C shows a condition in which a large medical resource is stored where two partition members are removed; and FIG. 5D shows a condition in which detection results from medical resource detecting members do not match.

Prior to the operation of the medical resource storage and management apparatus 20, a desired number of racks 70 are set in the storage part of the housing 22, and the partition members 75 are inserted into the depressions 71 in each rack 70. The medical resource information configuration routine 43 in the control unit 30 is started by an operation using the keyboard 33 or the mouse 34 so as to set the identification code and the displayed name of the medical resources 10 in the respective fields in the medical resource information table 47. The manual partition condition configuration routine 44 in the control unit 30 is started by an operation using the keyboard 33 or the mouse 34 so as to designate whether the partition members 75 are inserted into the depressions 71 in the rack 70, in the respective fields in the partition availability data 48. The medical resource availability data 46 and the log data 49 are cleared by a suitable initialization routine (not shown).

This completes preparation for operation. The operating conditions of the medical resource storage and management apparatus 20 will be described specifically. The operation for storage (replenishment or return) and associated updating of data, and the operation for retrieval and associated updating of data will now be described in the cases where: the partition members 75 are inserted into all of the depressions 71 (FIGS. 4A and 4B); a partition member 75 is removed from one of the depressions 71 (see FIGS. 5A and 5B); and two partition members 75 are removed from two adjacent depressions 71 (FIGS. 5C and 5D).

When the partition members 75 are inserted into all of the depressions 71 (see FIGS. 4A and 4B) and when the medical resources 10 are not stored yet (see the top row of FIG. 4A), the fields in the medical resource information table 47 contain individual values (see A-E in the second row from top in FIG. 4A, where A-E denote different codes and names). The fields in the medical resource availability data 46 all contain "0", indicating the absence of medical resources (see the third row from top in FIG. 4A), and the fields in the partition availability data 48 all contain "1", indicating that the presence of the partition members (see the fourth row from top in FIG. 4A).

When a medical resource 10 is stored on the rack 70 (see the top row of FIG. 4B), the medical resource information table 47 and the partition availability data 48 remain unchanged (see the second and fourth rows from top in FIG. 4B). Meanwhile, the associated field in the medical resource availability data 46 is updated by the medical resource detection routine 42 to "1", indicating the presence of a medical resource (see the third row from top in FIG. 4B). The medical resource detection routine 42 retrieves the code and name of the medical resource 10 (in the illustrated embodiment, "C") from the medical resource information table 47. The medical resource detection routine 42 further requests the input of operator identification information. These items of information are appended to the log data 49, printed by the printer 36 and reported to the host medical management computer via the LAN 37.

For retrieval of the medical resource 10 thus stored from the medical resource storage and management apparatus 20, a retrieval instruction including the code "C" and the operator identification information are input to the control unit 30 by an operation using the barcode reader 35 or the like. This prompts the retrieval guidance routine 41 in the control unit 30 to search the medical resource information table 47 and check the associated field in the medical resource availability data 46. In this case, the value "1" is found in the field, showing that the medical resource is available, whereupon the retrieval guidance member 72 at the associated location is lighted (see the bottom row of FIG. 4B). The operator viewing this can take out the target medical resource 10 without fail.

When the medical resource 10 is taken out, the medical resource detection routine 42 updates the value entered in the associated field in the medical resource availability data 46 to "0", indicating the absence of medical resources. The information is combined with the code and name (in the illustrated embodiment, "C") supplied from the retrieval guidance routine 41, and with operator identification information. The combined information is appended to the log date 49, printed by the printer 36 and reported to the host medical management computer via the LAN 37. When the retrieval guidance member 72 of the associated location is turned off, the operating condition returns to a pre-storage state (see FIG. 4A).

When a partition member is removed from one of the depressions 71 (see FIGS. 5A and 5B), the manual partition condition configuration routine 44 is started by an operation using the keyboard 33 or the mouse 34, before storing a medical resource 10 therein (see the top row of FIG. 5A). An instruction for update is entered so as to change the value in the associated field in the partition availability data 48 to "0", indicating the absence of the partition member (see the fourth row from top in FIG. 5A). This prompts the manual partition condition configuration routine 44 to automatically update the medical resource information table 47 so that the values in the fields, corresponding to the locations of storage identified as being located on both sides of the recess 71 from which the partition member 75 is removed, match (see "BB" in the second row from top in FIG. 5A). All the fields in the medical resource availability data 46 contain "0" (see the third row from top in FIG. 5A).

When a medical resource 10 twice as wide is stored in a part on the rack from which the partition member 75 is removed (see the top row of FIG. 5B), the medical resource information table 47 and the partition availability data 48 remain unchanged (see the second and fourth rows from top in FIG. 5B). Meanwhile, the values in the two associated fields in the medical resource availability data 46 are changed by the medical resource detection routine 42 to "1", indicating the presence of the medical resource (see the third row from top in FIG. 5B). The medical resource detection routine 42 retrieves the code and name of the medical resource 10 (in the illustrated embodiment, "B") from the medical resource information table 47. The medical resource detection routine 42 further requests the input of operator identification information. These items of information are appended to the log data 49, printed by the printer 36 and reported to the host medical management computer via the LAN 37.

For retrieval of the medical resource 10 thus stored from the medical resource storage and management apparatus 20, a retrieval instruction including the code "B" and the operator identification information are input to the control unit 30 by an operation using the barcode reader 35 or the like. This prompts the retrieval guidance routine 41 in the control unit 30 to search the medical resource information table 47 and select the two adjacent fields (see "BB" in the second row from top in FIG. 5B), and then to check the two associated fields in the medical resource availability data 46. In this case, the two fields contain "1", indicating that the medical resource is available, whereupon the two adjacent retrieval guidance members 72 at the associated locations are lighted at a time (see the bottom row of FIG. 5B). The operator viewing this will not find any difficulty in taking out the target medical resource 10.

When the wide medical resource 10 is taken out, the medical resource detection routine 42 updates the values entered in the two associated fields in the medical resource availability data 46 to "0", indicating the absence of medical resources. The information is combined with the code and name (in the illustrated embodiment, "B") supplied from the retrieval guidance routine 41, and with operator identification information. The combined information is appended to the log date 49, printed by the printer 36 and reported to the host medical management computer via the LAN 37. When the retrieval guidance members 72 at the associated locations are turned off at a time, the operating condition returns to a pre-storage state (see FIG. 5A).

In the case where the two partition members 75 are removed from the adjacent two depressions 71 (see FIG. 5C), the operation will easily be surmised from the above explanation so that a detailed explanation will not be repeated. It will be noted that a medical resource 10 three times as wide can be stored (see the top row of FIG. 5C). When the manual partition condition configuration routine 44 is started so as to update the values in the two associated fields in the partition availability data 48 to "0", indicating the absence of a partition member (see the fourth row from top in FIG. 5C), the values in the three associated fields in the medical resource information table 47 are made to match (see "BBB" in the second row from top in FIG. 5C).

When a medical resource 10 three times as wide is stored (see the top row of FIG. 5C), each of the three associated fields in the medical resource availability data 46 is updated to contain "1" (see the third row from top in FIG. 5C), and relevant information is appended to the log data 49.

When a retrieval instruction including the code "B" is input to the control unit 30, the three associated fields in the medical resource information table 47 (see "BBB" in the second row from top in FIG. 5C) are selected, and then the three associated fields in the medical resource availability data 46 are checked. In this case, the three fields contain "1", showing a match. Thereupon, the three adjacent retrieval guidance members 72 at the associated locations are lighted at a time (see the bottom row of FIG. 5C). The operator viewing this will not find difficulty in taking out the target medical resource 10.

When a medical resource 10 smaller than the location of storage three times as wide (e.g., a medical resource 10 twice as large) is stored (see FIG. 5D), two of the three associated fields in the medical resource availability data 46 are changed to "1", while one field continues to store "0" (see the third row from top in FIG. 5D). This results in incompatibility between the medical resource availability data 46 and the partition availability data 48 as checked by the medical resource detection routine 42, in respect of the three fields to be collectively processed. If the condition of incompatibility (failure to match) continues beyond a maximum period of time required for storage or retrieval of the medical resource 10, the medical resource detection routine 42 issues an alarm.

When the medical resource 10 twice as wide is taken out, the three retrieval guidance members 72 at the associated locations are lighted by the retrieval guidance routine 41 (see the bottom row of FIG. 5D). This makes it obvious that the medical resource 10 is inordinately smaller than the width of the location of storage and that an improper medical resource 10 was stored. Therefore, incorrect storage or misuse can be prevented.

When the medical resource detecting member 73 goes out of order, incompatibility as described above continues to occur, and the alarm continues to be issued. In this case, however, the breadth of the medical resource 10 is larger than the range of retrieval guidance members 72 being lighted so that abnormality of the device is known.

Illustrative Embodiment 1-2

A specific structure of the illustrative embodiment 1-2 of the medical resource storage and management apparatus according to the first embodiment will be described with reference to the associated drawings. FIGS. 6A and 6B show the structure of the medical resource storage and management apparatus 20. FIG. 6A is an expanded perspective view of the rack 70 and the partition members 75; and FIG. 6B is a functional block diagram of the control unit 30.

The medical resource storage and management apparatus 20 according to this embodiment differs from that of the illustrative embodiment 1-1 in that partition detecting members 74 are added and the manual partition condition configuration routine 44 is replaced by an automatic partition condition configuration routine 45.

The partition detecting member 74 (see FIG. 6A) is implemented by a mechanical switch, a reflective photosensor, a capacity sensor or the like. The partition detecting member 74 is embedded in the top face of the rack 70 to face upward so as to sense the lower end face of the partition member 75 inserted into the depression 71 on the top face of the rack 70, and is placed at respective locations of insertion of the partition members 75 in the rack 70. In this example, the partition detecting member 74 is provided between a pair of depressions 71 arranged in a width direction in order to detect whether the partition member 75 is inserted in its location. The partition member 74 outputs a binary signal which turns on and off according to whether the partition member 75 is available.

The automatic partition condition configuration routine 45 (see FIG. 6B) is started periodically and automatically by a timer, etc. or irregularly and automatically started by an interruption initiated in the event of a change in a detection signal from the partition detecting member 74. The automatic partition condition configuration routine 45 updates the partition availability data 48 based on the detection by the partition detecting member 74. More specifically, each time the automatic partition condition configuration routine 45 is started, it imports the detection results from all partition detecting members 74 or those results changed since its last import, and writes "1" or "0" in the partition availability data 48 in association with the on-off condition. The other functions (e.g., automatic updating of the medical resource information table 47) are the same as those of the manual partition condition configuration routine 44. This arrangement allows the control unit 30 to collectively process a block of medical resource detecting members 73 and retrieval guidance members 72 identified as being located on both sides of the depression 71 from which the partition member 75 is removed, in accordance with the detection by the partition detecting members 74.

In this case, removal of the partition member 75 from the depression 71 in the rack 70 or insertion of the partition member 75 into the depression 71 on the rack 70 need not be designated by manual input for configuration. The removal or insertion is detected by the partition detecting member 74, and the partition availability data 48 is automatically configured by the automatic partition condition configuration routine 45. This will prevent incompatibility between the insertion condition of the partition member 75 and the partition availability data 48 from occurring due to a failure to provide an input for configuration.

The other usage modes and operations are the same as those of the illustrative embodiment 1-1 described above.

Illustrative Embodiment 1-3

Figure 7A:
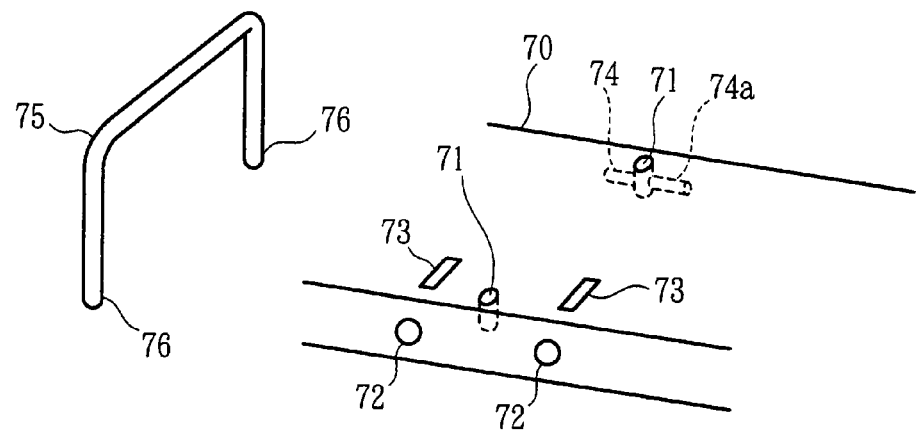
FIGS. 7A-7C show three variations to the structure according to an illustrative embodiment 1-3 of the first embodiment.

The partition member 75 and the rack 70 shown in a perspective view of FIG. 7A differ from those of the illustrative embodiments 1-1 and 1-2 in that the partition member 75 is formed by bending a round bar instead of as a plate, and that the depression 71 is a bottomed hole instead of a through hole. The partition detecting member 74 is embedded in the rack 70 so as to face a light-emitting device 74a across the depression 71. Whether or not the partition member 75 is inserted is detected depending on whether light emitted from the light-emitting device 74a is shielded by the fitting 76 at the end of the partition member 75 or received by the partition detecting member 74.

Figure 7B:
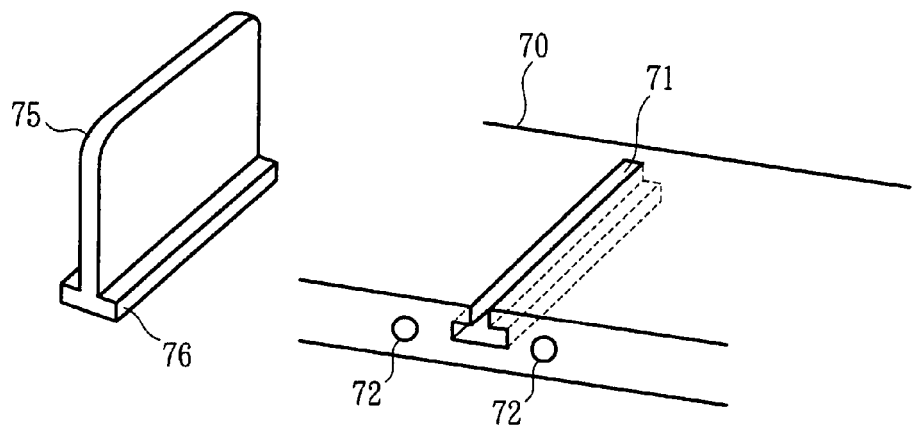

The partition member 75 and the rack 70 shown in a perspective view of FIG. 7B differ from those of the illustrative embodiments 1-1 and 1-2 in that the longitudinal cross section of the partition member 75 is of an inverted T shape, and that the depression 71 is formed as a groove. In this case, the partition member 75 is inserted into the depression 71 by slipping the fitting 76 at the lower end of the partition member 75 into the depression 71.

Figure 7C:
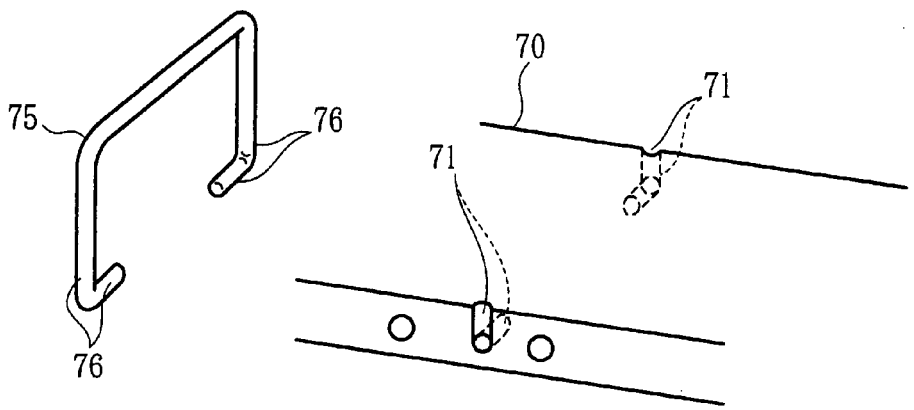

The partition member 75 and the rack 70 shown in a perspective view of FIG. 7C differ from those of the illustrative embodiments 1-1 and 1-2 in that the partition member 75 is formed by bending a round bar instead of as a plate, and that the depression 71 is formed as a notch or bore formed at the front and back of the rack 70 instead of on the top face thereof. In this case, the partition member 75 is inserted into the depression 71 and secured and stabilized therein by a snapping force, by extending the fittings 76 at both ends of the partition member 75 before inserting them in the depression 71.

Illustrative Embodiment 1-4

Figure 9A:
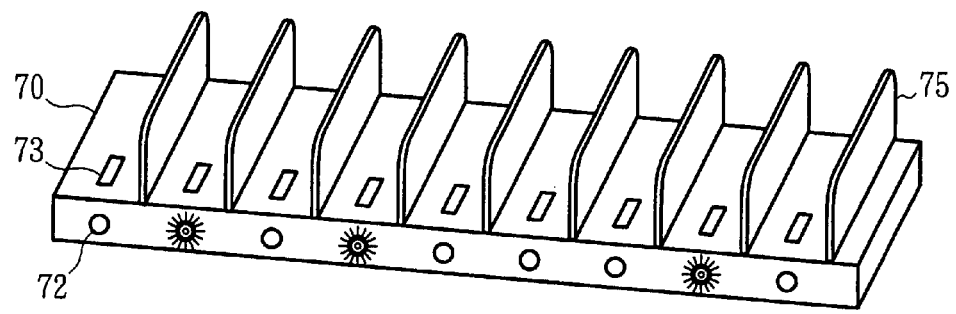
FIGS. 9A-9C also show conditions of replenishment of medical resources according to the illustrative embodiment 1-4.
Figure 9B:
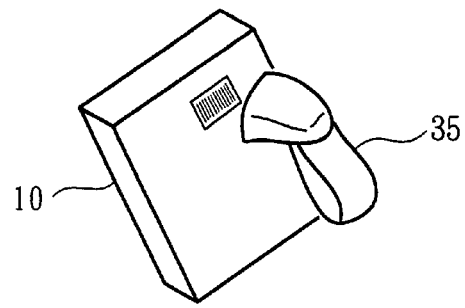
Figure 9C:
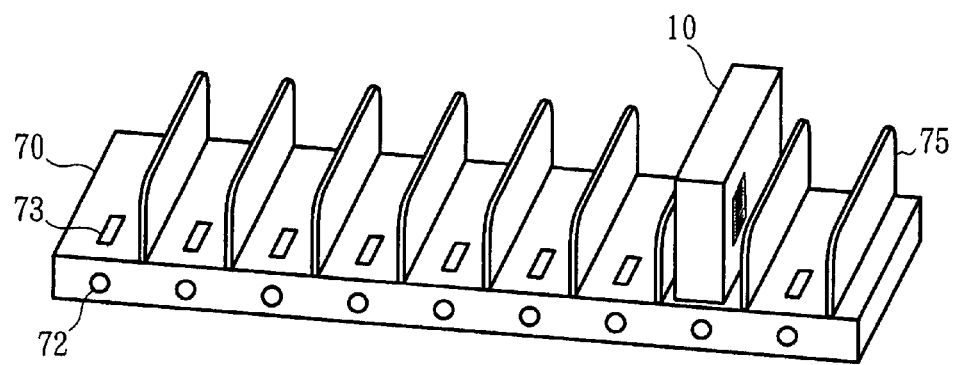

An illustrative embodiment 1-4 of the medical resource storage and management apparatus according to the first embodiment will be described with reference to the associated drawings. FIGS. 8A-8C show conditions of replenishment of medical resources. FIGS. 8A-8C are screen shots. FIGS. 9A-9C also show conditions of replenishment of medical resources. FIG. 9A is a perspective view of the rack fitted with partition members; FIG. 9B is a perspective view showing how identification information is read from a medical resource; and FIG. 9C is a perspective view of the rack storing a medical resource.

This medical resource storage and management apparatus differs from the aforementioned embodiments of the apparatus in that guidance is displayed in replenishing as well as in retrieving a medical resource, and that the display 32, the keyboard 33 and the mouse 34 are implemented as a touch panel 39.

In a normal operation (see FIG. 8A), information on the medical resource 10 retrieved from the medical resource storage and management apparatus is arranged chronologically and displayed on the touch panel 39 on a real time basis. A direct finger-touch selection of any the items 39a displayed on the screen causes relevant details to be displayed for review. Guidance for replenishment is also displayed in accordance with a specific operation for selection.

More specifically, selecting a replenishment button 39b displayed on the screen while in a normal operation (see FIG. 8A) switches the display of the touch panel 39 to a replenishment mode selection screen (see FIG. 8B). By entering information on an operator who replenishes a medical resource, selection of a "registered" button 39c and/or a "new registration" button is available. By selecting the "new registration" button, the operator can register the code (code No.) identifying the medical resource 10 that can be stored in a location of storage (address) and the name for screen display (medical resource name). If the registration is complete, selection of the "registered" button 39c is enabled. The "registered" button 39c is selected when the display of guidance for replenishment is desired.

The selection switches to the screen of the touch panel 39 showing a list of registered resources (see FIG. 8C). After confirming that a location for storage is shown as being empty, the operator scrolls the screen as necessary by using a scroll button 39f so as to directly select a field 39d for a relevant medical resource 10 with the finger.

If the number of empty locations 39e designated as capable of storing the medical resource (e.g., a tube in a case) is three (i.e., three tubes can be stored), the three retrieval guidance members 72 in the empty locations are all lighted because, in this example, the retrieval guidance member 72 also serves as a replenishment destination guidance member (see FIG. 9A).

The operator proceeds to scan the barcode (identification information) assigned to the medical resource 10 about to be stored, by using the barcode reader 35 (see FIG. 9B) for checking, before storing the medical resource 10 in one of the locations on the rack 70 lighted by the guidance member. This turns off all of the guidance members (see FIG. 9C), and the log data, indicating the identity of the operator who replenished the resource, the identify of the resource replenished and the location of replenishment, is recorded with a time stamp.

Thus, guidance display is provided properly and a job record is maintained properly for replenishment. In this example, the selection of the field 39*d* on the screen showing a list of registered resources, and the scanning of the identification information assigned to the medical resource 10 by using the barcode reader 35 are both performed to reinforce checking. However, only one of the tasks may be performed since it serves the purpose of identifying a medical resource 10. In another alternative, the operator may be allowed to complete both tasks, but guidance display guiding the operator to the destination of replenishment may not require completion of both tasks but may be immediately provided upon completion of one of the tasks.

[Other Points of Note]

The medical resource 10 may be packaged, bundled or contained in a case or a container. Suitable for storage in the medical resource storage and management apparatus 20 according to the first embodiment of the present invention are those relatively stable in form that can stand on its own while in storage (for example, those contained in a container with the shape of a CD case or a rectangular box). Examples of such medical resources are tube sets for injection/infusion, small and short-length catheters and sets of articles including the same.

In the first embodiment, the control unit 30 is accommodated in the electric equipment 21. Alternatively, the control unit 30 may be placed outside the housing 22. The input and output means of the control unit 30 may not be restricted to the display 32, the keyboard 33 and the like mentioned above and may be implemented by a touch panel or a mobile information terminal.

In the first embodiment, the medical resource detection routine 42 is designed to associate the on and off states of the result of detection by the medical resource detecting member 73 with the storage and retrieval of the medical resource 10, respectively. It is easy to expand the capabilities to automatically manage the return of a medical resource 10 once taken out and not used. For example, a determination may be made that a resource is not replenished but returned, if retrieval and storage are conducted successively in a short time span, or if a resource is stored in one of the modes of operation introduced in the control unit 30 in which mode an action of retrieval is restricted. In this case, information indicating the return may suitably be appended to the log data 49 or other output data. In addition to data storage and output, provisions may also be made for management of expiration dates, stock control, preparation of drug history and inspection.

SECOND EMBODIMENT

A second embodiment of the present invention relates to a medical resource storage and management apparatus which arranges and stores medical resources and also performs management of storage status, and, more particularly, to a medical resource storage and management apparatus which automatically manages availability of medical resources at each location of storage and also guides a user for retrieval.

A summary of the second embodiment will be given.

A first medical resource storage and management apparatus according to the second embodiment comprises: a rack in which a series of depressions for insertion of partition members are formed so that a large number of medical resources are retrievably placed in respective partitions; partition members which are removably inserted into the depressions; medical resource detecting members which are arranged on the rack so as to alternate with the depressions in a direction in which the depressions are arranged, and each of which detects whether or not a medical resource is placed; retrieval guidance members for visual guidance which are arranged on the rack so as to alternate with the depressions in a direction in which the depressions are arranged; and a control unit which manages the storage status of the medical resources, based on the detection by the medical resource detecting members and which operates one of the retrieval guidance members in response to an input designating retrieval, wherein a medical resource name plate for visual guidance is attached to a partition member via a connecting member such that the connecting member is moved up and down depending on whether a medical resource is placed and as a result of interference between the connecting member and the medical resource, and that the medical resource name plate is located in a space where retrieval of a medical resource takes place, and is moved in association with the connecting member, and wherein the medical resource detecting member indirectly detects whether or not a medical resource is placed by detecting whether the medical resource name plate is raised or lowered.

A second medical resource storage and management apparatus according to the second embodiment is a modification to the first medical resource storage and management apparatus, wherein the medical resource name plate, when elevated in association with the placement of a medical resource in the associated location, is located above the retrieval guidance member in the associated location. The medical resource name plate, when lowered in response to the retrieval of the medical resource from the associated location, shields the retrieval guidance member in the associated location from view.

A third medical resource storage and management apparatus according to the second embodiment is a modification to the first medical resource storage and management apparatus or the second medical resource storage and management apparatus, wherein the control unit allows providing an input for configuration to designate whether the partition member is inserted into the depression, and, based on the configuration, the control unit collectively processes the medical resource detecting members and the retrieval guidance members identified as being located on both sides of the depression from which the partition member is removed.

A fourth medical resource storage and management apparatus according to the second embodiment is a modification to the first medical resource storage and management apparatus or the second medical resource storage and management apparatus and comprises a partition detecting member which detects whether the partition member is inserted into the depression, wherein, based on the detection by the partition, the control unit collectively processes the medical resource detecting members and the retrieval guidance members identified as being located on both sides of the depression from which the partition member is removed.

A fifth medical resource storage and management apparatus according to the second embodiment is a modification to the third medical resource storage and management apparatus or the fourth medical resource storage and management apparatus, wherein the control unit issues an alarm if the results of detection by the medical resource detecting members in a block to be processed collectively continue to fail to match beyond a predetermined period of time.

In the first medical resource storage and management apparatus, the medical resources are arranged on the rack such that the locations of storage are partitioned by the partition members. Therefore, it is easy to retrievably align and store medical resources without accommodating them in cassettes and to prevent disarrangement of the medical resources stored and resultant disorganization.

Since the medical resource detecting member and the retrieval guidance member are placed in respective partitions on the rack, it is possible to detect whether each medical resource is stored for automatic management and to properly guide a user to the location of storage of the medical resource to be retrieved.

Since the partition member can be removed from the rack and the location of insertion is formed as a depression, a relatively large medical resource can be placed where the partition member is removed.

Since the medical resource name plate is attached to the partition member in an easy-to-view space where retrieval of a medical resource takes place, not only the product name or the like of the medical resource to be stored can be identified at a glance but also the replacement of a medical resource name plate can be performed readily in association with a size change effected by attachment or detachment of a partition member.

As a medical resource is stored or taken out, the medical resource name plate is moved up or down in association with the connecting member. The medical resource detecting member indirectly and automatically detects whether or not the medical resource is placed by detecting whether the medical resource name plate is raised or lowered. Accordingly, availability of the medical resource is visually confirmed even if the medical resource name plate is in front of the medical resource. This makes it possible to indirectly detect a medical resource even when it is difficult to detect, for example, the bottom thereof due to the form or material of the medical resource.

Thus, even with a simple apparatus in which racks are partitioned and medical resources are arranged, a large variety of large and small medical resources can be stored in the least confusing manner. Even those resources that are not suitable for direct detection can also be detected properly for automatic management.

Thus, the first medical resource storage and management apparatus provides capability for easily and properly storing and retrieving medical resources, and automatically and accurately keeping track of storage status.

In the second medical resource storage and management apparatus, the retrieval guidance member is viewable when the medical resource is stored, and is shielded from view when the medical resource is taken out. With this, the availability of the medical resource can be visually identified not only by viewing the up and down movement of the medial resource name plate but also by seeing whether or not the retrieval guidance member is shielded from view. Moreover, the likelihood of misidentifying the operating status of the retrieval guidance member is reduced.

In the third medical resource storage and management apparatus, not only the partition members are removably attached but also whether or not the partition member is inserted is designated by providing an input for configuration in the control unit, allowing the control unit to collectively process medical resource detecting members and retrieval guidance members in a block. Therefore, a user will not be at a loss or face any inconvenience in handling and management even if there are multiple medical resource detecting members or retrieval guidance members where a single, large medical resource resides.

Thus, even with a simple apparatus in which racks are partitioned and medical resources are arranged, a large variety of large and small medical resources can be easily stored for automatic management by means of attachment and detachment of partition members and by an input of associated information for configuration.

According to the fourth medical resource storage and management apparatus, convenience is enhanced by additionally ensuring that whether or not the partition member is inserted is automatically detected and reflected in the control.

According to the firth medical resource storage and management apparatus, reliability is enhanced while avoiding an increase in hardware cost, by exploiting the redundancy of results of detection by multiple medical resource detecting members in a single block and detecting an error accordingly.

Specific embodiments of the medical resource storage and management apparatus according to the second embodiment will be described below using illustrative embodiments 2-1 through 2-5.

Figure 15A:
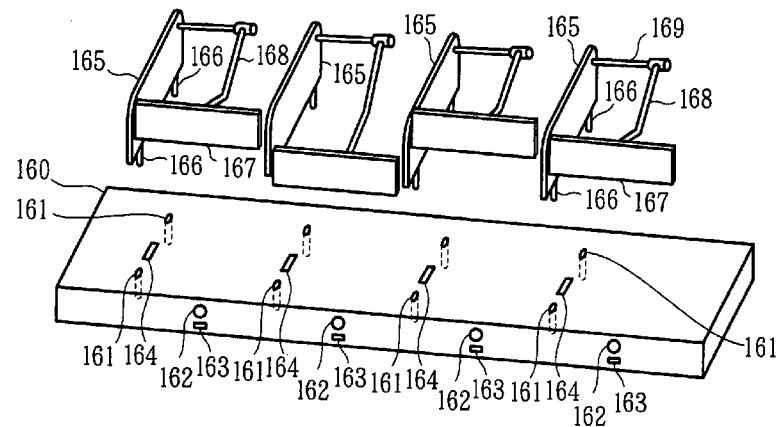
FIGS. 15A-15B show the structure of medical resource storage and management apparatus according to an illustrative embodiment 2-2 of the second embodiment.
Figure 15B:
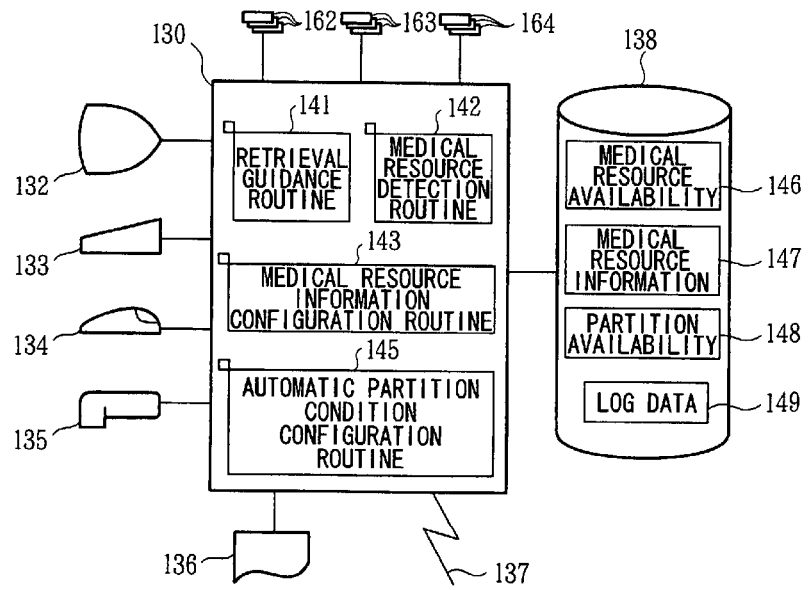

The illustrative embodiment 2-1 shown in FIGS. 10A-14D is an embodiment of the first through third and the fifth medical resource storage and management apparatuses mentioned above. The illustrative embodiment 2-2 shown in FIGS. 15A-15B is an embodiment of the fourth medical resource storage and management apparatus mentioned above. The illustrative embodiment 2-3 shown in FIGS. 16A-16C, the illustrative embodiment 2-4 shown in FIGS. 17A-17C and the illustrative embodiment 2-5 shown in 18A-19C are variations.

In the illustration, fasteners such as bolts, connectors such as hinges, electronic circuits such as drivers are omitted for brevity, highlighting those elements necessary to explain the embodiment and related elements.

Illustrative Embodiment 2-1

Figure 10A:
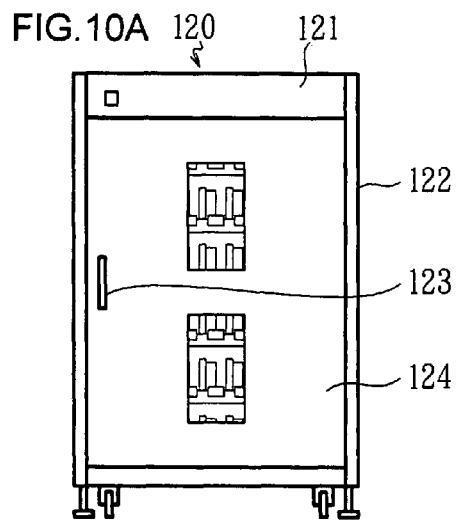
FIGS. 10A-10D show the mechanical structure of a medical resource storage and management apparatus according to an illustrative embodiment 2-1 of a second embodiment of the present invention.
Figure 10B:
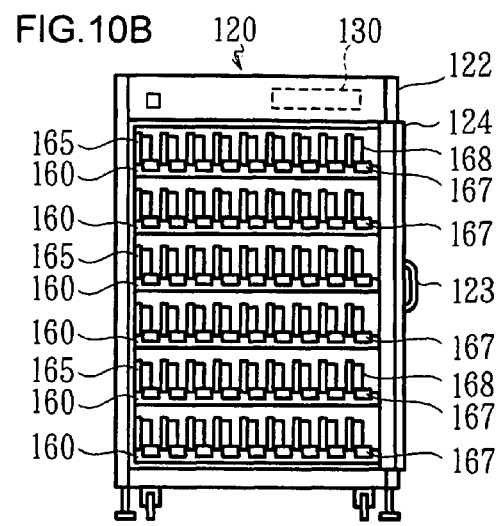
Figure 10C:
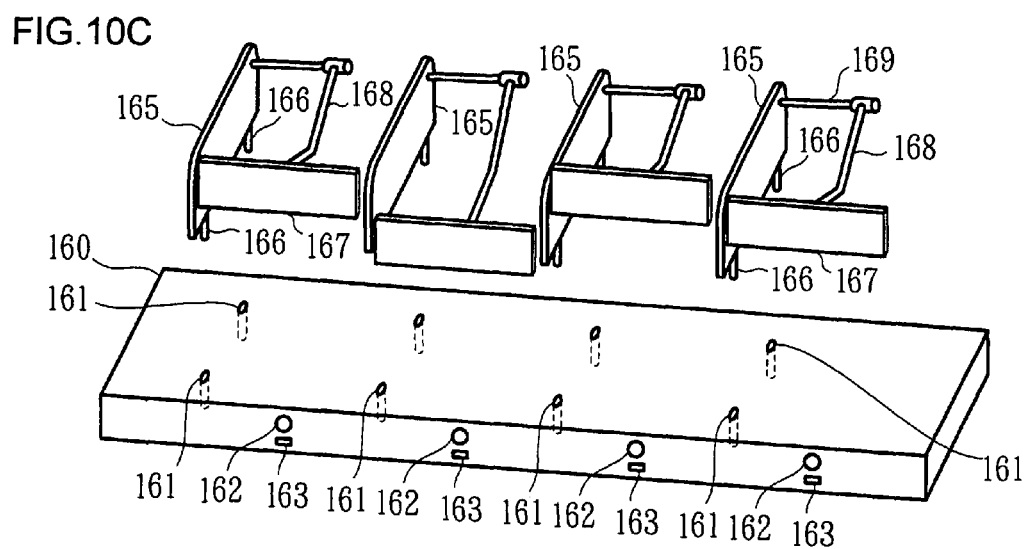
Figure 10D:
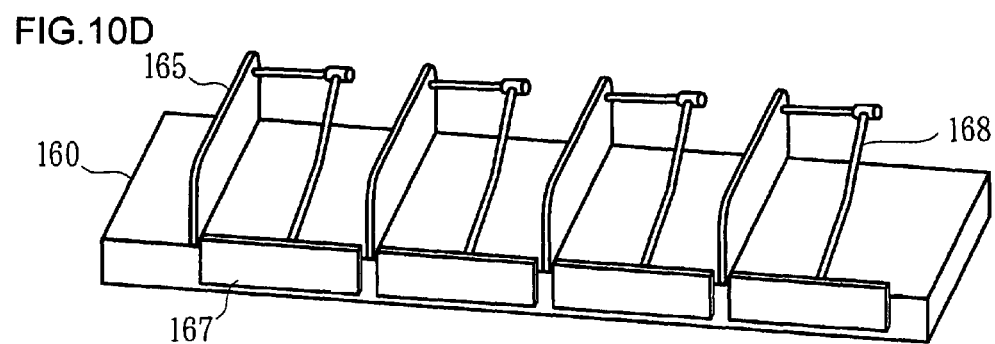
Figure 11A:
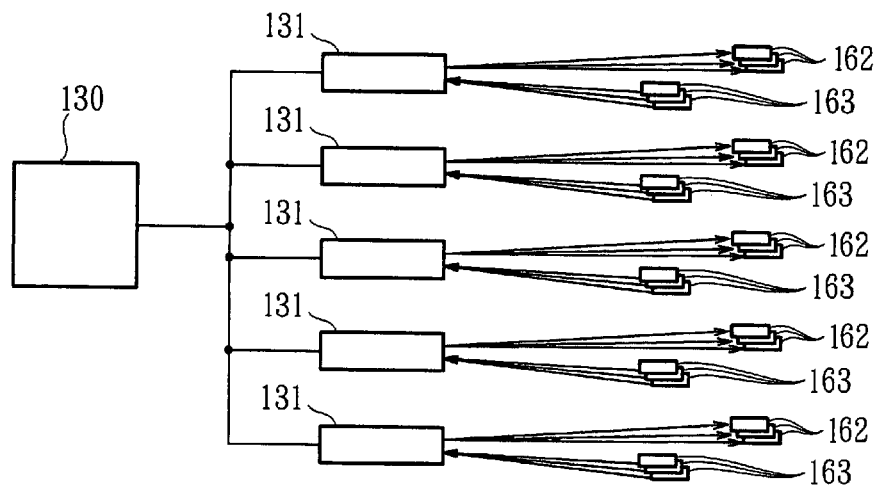
FIGS. 11A and 11B show the schematic structure of a control unit according to the second embodiment.
Figure 11B:
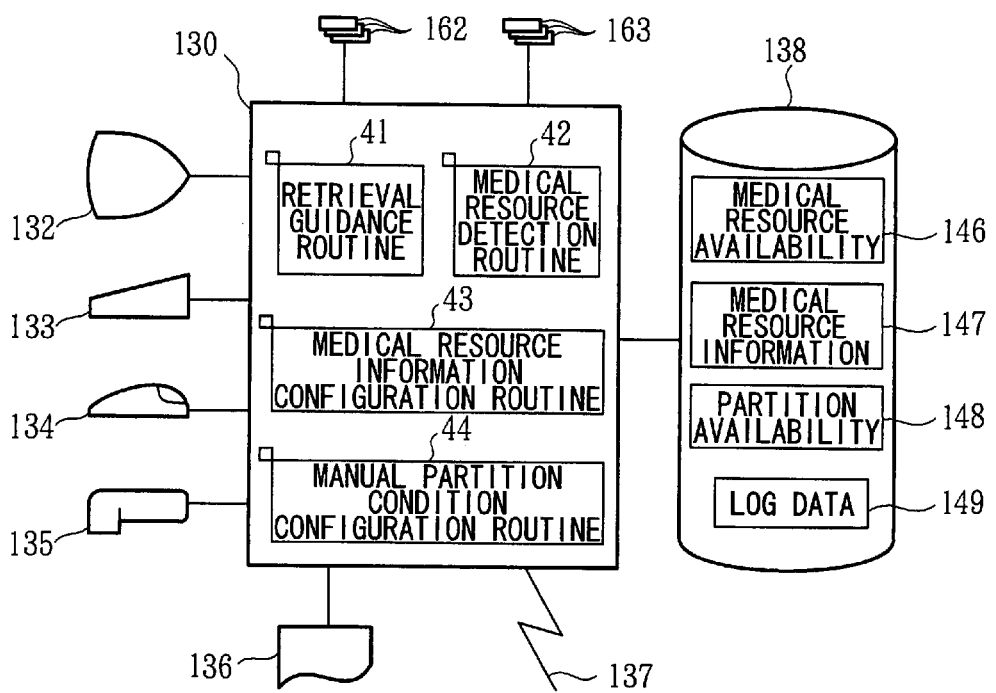
Figure 12A:
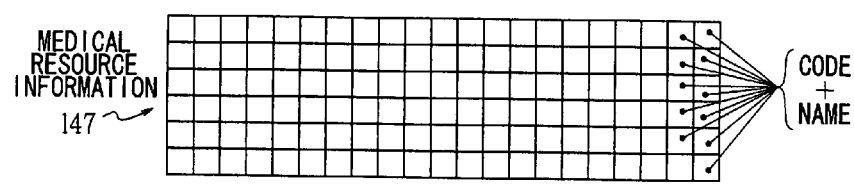
FIGS. 12A-12C show the data structure of the control unit according to the second embodiment.
Figure 12B:
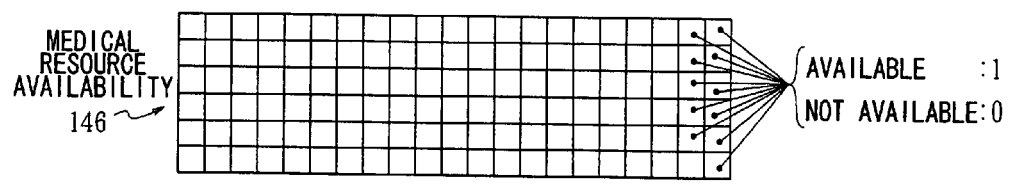
Figure 12C:
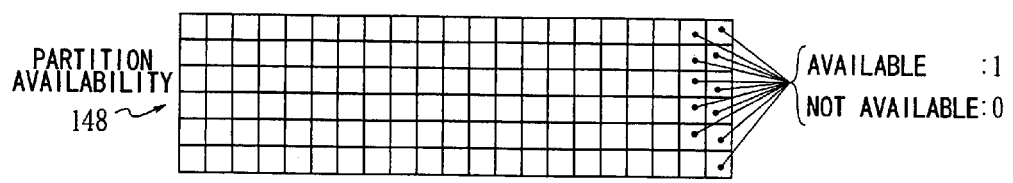

A specific structure of the illustrative embodiment 2-1 of the medical resource storage and management apparatus according to the second embodiment will be described with reference to the associated drawings. FIGS. 10A-10D show the mechanical structure of the medical resource storage and management apparatus. FIG. 10A is a front view showing a door closed; FIG. 10B is a front view showing the door opened; FIG. 10C is a perspective view of a rack and partition members; and FIG. 10D is a perspective view showing the appearance of the rack in which the partition members are fitted. FIGS. 11A and 11B show the schematic structure of a control unit. FIG. 11A is a schematic block diagram showing the connection between the control unit and retrieval guidance members; and FIG. 11B is a functional block diagram of the control unit. FIGS. 12A-12C show the data structure of the control unit. FIG. 12A relates to a medical resource information table; FIG. 12B relates to medical resource availability data; and FIG. 12C relates to partition availability data.

A medical resource storage and management apparatus 120 (see FIGS. 10A and 10B) is provided with a housing 122 a large portion of which is for storage and a part of which comprises electric equipment 121. The electric equipment 121 stores a control unit 130 and a power supply unit etc. (not shown). The front of the storage part of the housing 122 is provided with an openable door 124 with a handle 123. The door 124 may be implemented by a shutter or the like, or may be omitted. Inside the storage part exposed when the door 124 is opened is provided a rack 160. Although there may be only one rack 160, an orthodox apparatus would comprise multiple tiers. The pitch between the racks 160 may be selectable. The rack 160 is implemented by a horizontally extending plate with a flat top face. Partition members 165 formed as thin plates are fitted to the top face thereof at regular or irregular pitches in a longitudinal direction (in the figure, sideways) in order to place a large number of medical resources in respective partitions retrievably.

Two rows of depressions 161 to fit partition members are formed on the top face of the rack 70 (see FIGS. 10C and 10D) at regular or irregular pitches in a longitudinal direction (in the figures, sideways). Two fittings 166 are formed at the lower end of each of the partition members 165. In this example, the fitting 166 is a small round bar and the depression 161 is a through hole. By inserting the fitting 166 into the depression 161, the partition member 165 is removably fitted to the depression 161 in the rack 160. A medical resource name plate 167, a connecting member 168, and a pivot shaft 169 are attached to one side (in the illustrated example. the right side) of the partition member 165.

One end of the pivot shaft 169 is secured to the partition member 165 toward the back thereof; one end of the connecting member 168 is pivotally connected to the other end of the pivot shaft 169; and the medical resource name plate 167 is secured to the other end of the connecting member 168 extending to the front. Thus, by pivotally moving the connecting member 168, the medical resource name plate 167 is moved up and down in association with the connecting member 168 in an easy-to-view space where retrieval of a medical resource takes place (more specifically, slightly in front of the front of the rack 160).

The front of the rack 160 exposed when the door 124 is opened is equipped with retrieval guidance members 162 and medical resource detecting members 163 in close proximity with each other. The retrieval guidance members 162 and the medical resource detecting members 163 are arranged in the rack 160 so as to alternate with the depressions 161 in a direction in which the depressions 161 are arranged, i.e., in the longitudinal direction of the rack 160.

When the partition member 165 is inserted into the depression 161 on the top face of the rack 160 and when the connecting member 168 and the medical resource name plate 167 are allowed to make a pivotal movement freely, the member 168 and the plate 167 are lowered under their own weight until the connecting member 168 comes into contact with the top face of the rack 160 and the medical resource name plate 167 in front thereof is lowered to the front of the rack 160. This shields the retrieval guidance member 162 and the medical resource detecting member 163 at the front of the rack 160 from view (see FIG. 10D). The medical resource name plate 167, as it is lowered in response to the retrieval of the medical resource from the associated location, shields the associated retrieval guidance member 162 from view.

When the medical resource name plate 167 is raised so as to store a medical resource 110 on the rack 160, the connecting member 168 rests on the medical resource 110 instead of on the rack 160, causing the medical resource name plate 167 to remain at an elevated position. The medical resource name plate 167 is located above the associated retrieval guidance member 162, revealing the retrieval guidance member 162 and the medical resource detecting member 163 at the front of the rack 160 for view. The medical resource detecting member 163 provided at the front of the rack 160 does not sense the medical resource 110 placed on the rack 160 but senses the medical resource name plate 167 immediately in front of the rack 160. Due to this and the fact that the medical resource name plate 167 is moved up and down in response to the storage/retrieval of the medical resource 110 as a result of interference between the connecting member 168 and the medical resource 110, the medical resource detecting member 163 indirectly detects whether or not the medical resource 110 is placed by detecting whether the medical resource name plate 167 is raised or lowered.

In order to detect the medical resource name plate 167 for indirect detection of the medical resource 110, each of the medical resource detecting members 73 is implemented by a mechanical switch, a reflective photosensor, a capacity sensor or the like, so as to output a binary signal which turns on and off according to whether the medical resource name plate 167 is raised or lowered.

In order to visually guide a user to the location of placement of the medical resource 110 to be retrieved, a miniature bulb, a light-emitting diode or the like that can be turned on and off is used as the retrieval guidance member 162.

The control unit 130 (see FIG. 11A) comprises a programmable controller such as a personal computer and a sequencer. A local area network (LAN) connects the control unit 130 to the retrieval guidance members 162 and the medical resource detecting members 163 via, for example, a rack controller 131. Alternatively, the control unit 130, the retrieval guidance members 162 and the medical resource detecting members 163 are in direct star connection (not shown). The connection enables retrieving detection results of the medical resource detecting members 163 and controlling the lighting of the retrieval guidance member 162.

The control unit 130 (see FIG. 11B) is provided with a display 132 for screen display, a keyboard 133 for key entry, a mouse 134 for inputting instructions etc. on a screen, a bar code reader 135 for reading identification information, a printer 136 for delivering printouts, an interface for a local area network (LAN) 137 which is responsible for communication with a prescription order-entry system etc., and a hard disk 138 as a secondary storage.

A retrieval guidance routine 141, a medical resource detection routine 142, a medical resource information configuration routine 143, and a manual partition condition configuration routine 144 are installed in the control unit 130, as programs for managing the storage status of medical resources, based on the detection by the medical resource detecting members 163, and for operating selected retrieval guidance members 162 in response to an input designating retrieval. The hard disk 138 stores medical resource availability data 146, a medical resource information table 147, partition availability data 148, and log data 149, which are divided into individual files or are unified in an appropriate database. The figures show (see FIGS. 12A-12C) the data 146, 147 and 148 maintained in a table format. Each table comprises a 6×21 matrix, in association with the fact that the racks 160 form six tiers and the maximum number of partitions in each rack 160 (i.e., the maximum number of the partition members 165, the retrieval guidance members 162 and the medical resource detecting members 163) is twenty one.

Each field in the medical resource information table 147 (see FIG. 12A) contains an identification code and a name displayed on a screen for the medical resource 110 which is stored or can be stored in an associated location. "1" or "0" is written in the medical resource availability data 146 (see FIG. 12B), "1", indicating that the medical resource 110 is stored in the associated location, and "0", indicating that no medical resources 110 are stored. "1" or "0" is written in the partition availability data 148 (see FIG. 12C), "1", indicating that the partition member 165 is inserted, and "0", indicating that the partition member 165 is removed from the associated location. The medical resource information table 147 should be configured at least once before operating the apparatus for the first time since its installation. Therefore, the table is usually initialized upon starting the apparatus and updated when the operation is stopped. The partition availability data 148 is also initialized so that the insertion condition of the partition member 165 is reflected before the initial operation. Configuration inputs for update are also provided when the partition member 165 is attached or detached. The medical resource availability data 146 is all cleared by initialization before the initial operation, and is subsequently updated with each storage or retrieval of the medical resource 110.

The medical resource information configuration routine 143 is started by the keyboard 133 or mouse 134 operation. When dumping from a medicine master file located on a host computer via the LAN 137 is dictated in an environment where such an action is possible, the medical resource information configuration routine 143 dumps the data. The routine 143 also allows the user to set the code or name of the medical resource 110 in the medical resource information table 147 by selecting an item using the mouse 134 or entering data using the keyboard 133, while viewing screen display on the display 132.

The manual partition condition configuration routine 144 is also started by the keyboard 133 or mouse 134 operation. The routine 144 allows the user to provide an input for configuration to designate in the partition availability data 148 whether the partition member 165 is inserted in the depression 161 in the rack 160, by selecting an item or toggling using the mouse 134 or the keyboard 133, while viewing screen display on the display 132.

The medical resource detection routine 142 is started periodically and automatically by a timer etc. or irregularly and automatically started by an interruption initiated in the event of a change in a detection signal from the medical resource detecting member 163. The medical resource detection routine 142 manages the storage status of the medical resources 110 based on the detection by the medical resource detecting members 163. More specifically, each time the medical resource detection routine 142 is started, it imports the detection results from all medical resource detecting members 163 or those results changed since its last import, and writes "1" or "0" in the medical resource availability data 146 in association with the on-off condition. When the detection result from the medical resource detecting member 163 undergoes an on/off change and the storage or retrieval of the medical resource 110 is detected accordingly, the medical resource detection routine 142 appends information indicating the detection to the log data 149 with a time stamp, causes the printer 136 to deliver a printout which carries the name listed in the associated field in the medical resource information table 147, and submits a report to a host medical management computer via the LAN 137.

The retrieval guidance routine 141 is started when the code of the medical resource 110 or a prescription ID number is entered by allowing the barcode reader 135 to read the code or the ID, or by using the keyboard 133 or the mouse 134, in order to operate one of the retrieval guidance members 162 in response to an input designating retrieval. The retrieval guidance routine 141 searches the medical resource information table 147 to determine the location of storage of the medical resource 110 designated to be retrieved via the reading or via the mouse or keyboard operation, and lights the medical resource detecting member 163 at the associated location. The medical resource detection routine 142 is responsible for turning the medical resource detecting member 163 off when the retrieval of the medical resource 110 at the associated location is detected.

The retrieval guidance routine 141 and the medical resource detection routine 142 learn whether or not the partition member 165 is inserted, and collectively process the medical resource detecting members 163 and the retrieval guidance members 162 identified as being located on both sides of the depression 161 from which the partition member 165 is removed. The retrieval guidance routine 141 and the medical resource detection routine 142 issue an alarm if the results of detection by the medical resource detecting members 163 in a block to be processed collectively continue to fail to match beyond a predetermined period of time.

More specifically, the retrieval guidance routine 141 refers to the medical resource availability data 146 to check whether the partition member 165 is inserted to the left or right of a location of storage, before lighting the medical resource detecting member 163. If "0" is entered to the left or right, indicating that the partition member 165 there is removed, the associated, adjacent retrieval guidance member 162 is also lighted. In association with this, the medical resource detection routine 142 performs a similar check by referring to the medical resource availability data 146 in turning off the retrieval guidance member 162, and turns off the retrieval guidance members 162 in the block at a time.

The medical resource detection routine 142 also performs, upon detecting the storage or retrieval of the medical resource 110, a similar check by referring to the medical resource availability data 146 before changing the value of the medical resource availability data 146. If a series of adjacent partitions are to be processed as a single block, the medical resource detection routine 142 examines whether the values from the medical resource detecting members 163 in the single block match. If the values match, the routine 142 terminates the process normally; if the values do not match, the routine 142 continues the monitoring. If the values from the medical resource detecting members 163 in the block continue to fail to match beyond a maximum period of time required for storage or retrieval of the medical resource 110 while the monitoring is proceeding, the medical resource detection routine 142 displays an alarm on the display 132 or sounds an alarm buzzer (not shown).

In order to help the routines 141 and 142 to collectively process a block where the partition member 165 is removed, the manual partition condition configuration routine 144 configures, in designating in the partition availability data 148 that the partition member 165 is removed, the associated fields in the medical resource information table 147 such that field values (i.e., codes and names maintained) corresponding to the locations of storage identified as being located on both sides of the depression 161 from which the partition member 165 is removed, match. The manual partition condition configuration routine 144 returns the field values to their original values in designating in the partition availability data 148 that the partition member 165 is inserted.

In addition, the control unit 130 acquires operator identification information by requesting an operator to input operator identification information each time an operation is carried out. Alternatively, the control unit 130 acquires operator identification information input by an operator in advance of an operation. The control unit 130 also stores, in the log data 149, related information then collected by automatic detection etc. together with a time stamp. The data stored is also output via the LAN 137. The process is performed in the manual partition condition configuration routine 144 as well as in the retrieval guidance routine 141.

The mode of using the medical resource storage and management apparatus according to the illustrative embodiment 2-1 and its operation will be described with reference to the drawings. FIGS. 13A-13B illustrate the operation of the medical resource storage and management apparatus. FIG. 13A shows an empty condition; and FIG. 13B shows a condition in which a small medical resource is stored. FIGS. 14A-14b also illustrate the operation of the medical resource storage and management apparatus. FIG. 14A shows a condition in which one partition member is removed from the rack while the partition is empty; FIG. 14B shows a condition in which a medium-sized medical resource is stored; FIG. 14C shows a condition in which a large medical resource is stored where two partition members are removed; and FIG. 14D shows a condition in which detection results from medical resource detecting members do not match.

Prior to the operation of the medical resource storage and management apparatus 120, a desired number of racks 160 are set in the storage part of the housing 122, and the partition members 165 are inserted into the depressions 161 in each rack 160. The medical resource information configuration routine 143 in the control unit 30 is started by an operation using the keyboard 133 or the mouse 134 so as to set the identification code and the displayed name of the medical resources 110 in the respective fields in the medical resource information table 147. In this process, it is also favorable to perform a comparison check with the product name of the medical resource currently written in the medical resource name plate 167. The manual partition condition configuration routine 144 in the control unit 130 is started by an operation using the keyboard 133 or the mouse 134 so as to designate whether the partition members 165 are inserted into the depressions 161 in the rack 160, in the respective fields in the partition availability data 148. The medical resource availability data 146 and the log data 149 are cleared by a suitable initialization routine (not shown).

This completes preparation for operation. The operating conditions of the medical resource storage and management apparatus 120 will be described specifically. The operation for storage (replenishment or return) and associated updating of data, and the operation for retrieval and associated updating of data will now be described in the cases where: the partition members 165 are inserted into all of the depressions 161 (FIGS. 13A and 13B); a partition member 165 is removed from one of the depressions 161 (see FIGS. 14A and 14B); and two partition members 165 are removed from two adjacent depressions 161 (FIGS. 14C and 14D).

When the partition members 165 are inserted into all of the depressions 161 (see FIGS. 13A and 13B) and when the medical resources 110 are not stored yet (see the top row of FIG. 13A), the fields in the medical resource information table 147 contain individual values (see A-E in the second row from top in FIG. 13A, where A-E denote different codes and names). The fields in the medical resource availability data 146 all contain "0", indicating the absence of medical resources (see the third row from top in FIG. 13A), and the fields in the partition availability data 148 all contain "1", indicating that the presence of the partition members (see the fourth row from top in FIG. 13A).

When the medical resource 110 is stored on the rack 160 in this condition (see the top row of FIG. 13B), only the medical resource name plate 167 at the location of storage of the medical resource 110 is elevated above the rack 160, revealing the retrieval guidance member 162 for view. In this condition, the medical resource information table 147 and the partition availability data 148 remain unchanged (see the second and fourth rows from top in FIG. 13B). Meanwhile, the associated field in the medical resource availability data 146 is updated by the medical resource detection routine 142 to "1", indicating the presence of a medical resource (see the third row from top in FIG. 13B). The medical resource detection routine 142 retrieves the code and name of the medical resource 110 (in the illustrated example, "C") from the medical resource information table 147. The medical resource detection routine 142 further requests the input of operator identification information. These items of information are appended to the log data 149, printed by the printer 136 and reported to the host medical management computer via the LAN 137.

For retrieval of the medical resource 110 thus stored from the medical resource storage and management apparatus 120, a retrieval instruction including the code "C" and the operator identification information are input to the control unit 130 by an operation using the barcode reader 135 or the like. This prompts the retrieval guidance routine 141 in the control unit 130 to search the medical resource information table 147 and check the associated field in the medical resource availability data 146. In this case, the value "1" is found in the field, showing that the medical resource is available, whereupon the retrieval guidance member 162 at the associated location is lighted (see the bottom row of FIG. 13B). The operator viewing this can take out the target medical resource 110 without fail.

When the medical resource 110 is taken out, the medical resource name plate 167 at the associated location is lowered to the front of the rack 160, shielding the retrieval guidance member 162 and the medical resource detecting member 163 from view. In this process, the medical resource detection routine 142 updates the value entered in the associated field in the medical resource availability data 146 to "0", indicating the absence of medical resources. The information is combined with the code and name (in the illustrated example, "C") supplied from the retrieval guidance routine 141, and with operator identification information. The combined information is appended to the log date 149, printed by the printer 136 and reported to the host medical management computer via the LAN 137. When the retrieval guidance member 162 of the associated location is turned off, the operating condition returns to a pre-storage state (see FIG. 13A).

When a partition member 165 is removed from one of the depressions 161, (see FIGS. 14A and 14B), the adjacent partition member 165 is changed, or the medical resource name plate 167 is changed, whereupon the medical resource name plate 167 twice as wide is set there. The manual partition condition configuration routine 144 is started by an operation using the keyboard 133 or the mouse 134, before storing a medical resource 110 therein (see the top row of FIG. 14A). An instruction for update is entered so as to change the value in the associated field in the partition availability data 148 to "0", indicating the absence of the partition member (see the fourth row from top in FIG. 14A). This prompts the manual partition condition configuration routine 144 to automatically update the medical resource information table 147 so that the values in the fields, corresponding to the locations of storage located on both sides of the recess 161 from which the partition member 165 is removed, match (see "BB" in the second row from top in FIG. 14A). All the fields in the medical resource availability data 146 contain "0" (see the third row from top in FIG. 14A).

When a medical resource 110 not more than twice as wide is stored in a part on the rack from which the partition member 165 is removed (see the top row of FIG. 14B), the medical resource information table 147 and the partition availability data 148 remain unchanged (see the second and fourth rows from top in FIG. 14B). Meanwhile, the values in the two associated fields in the medical resource availability data 146 are changed by the medical resource detection routine 142 to "1", indicating the presence of the medical resource (see the third row from top in FIG. 14B). The medical resource detection routine 142 retrieves the code and name of the medical resource 110 (in the illustrated example, "B") from the medical resource information table 147. The medical resource detection routine 142 further requests the input of operator identification information. These items of information are appended to the log data 149, printed by the printer 136 and reported to the host medical management computer via the LAN 137.

For retrieval of the medical resource 110 thus stored from the medical resource storage and management apparatus 120, a retrieval instruction including the code "B" and the operator identification information are input to the control unit 130 by an operation using the barcode reader 135 or the like. This prompts the retrieval guidance routine 141 in the control unit 130 to search the medical resource information table 147 and select the two adjacent fields (see "BB" in the second row from top in FIG. 14B), and then to check the two associated fields in the medical resource availability data 146. In this case, the two fields contain "1", indicating that the medical resource is available, whereupon the two adjacent retrieval guidance members 162 at the associated locations are lighted at a time (see the bottom row of FIG. 14B). The operator viewing this will not find any difficulty in taking out the target medical resource 110.

As the wide medical resource 110 is taken out, the wide medical resource name plate 167 at the associated location is lowered to the front of the rack 160, shielding two pairs of retrieval guidance members 162 and medical resource detecting member 163 from view. In this process, the medical resource detection routine 142 updates the values entered in the two associated field in the medical resource availability data 146 to "0", indicating the absence of medical resources. The information is combined with the code and name (in the illustrated example, "B") supplied from the retrieval guidance routine 141, and with operator identification information. The combined information is appended to the log date 149, printed by the printer 136 and reported to the host medical management computer via the LAN 137. When the retrieval guidance members 162 at the associated locations are turned off at a time, the operating condition returns to a pre-storage state (see FIG. 14A).

In the case where the two partition members 165 are removed from the adjacent two depressions 161 (see FIG. 14C), the operation will easily be surmised from the above explanation so that a detailed explanation will not be repeated. It will be noted that a medical resource 110 three times as wide can be stored (see the top row of FIG. 14C). When the medical resource name plate 167 three times as wide is set, and the manual partition condition configuration routine 144 is started so as to update the values in the two associated fields in the partition availability data 148 to "0", indicating the absence of a partition member (see the fourth row from top in FIG. 14C), the values in the three associated fields in the medical resource information table 147 are made to match (see "BBB" in the second row from top in FIG. 14C).

When a medical resource 110 not more than three times as wide is stored (see the top row of FIG. 14C), each of the three associated fields in the medical resource availability data 146 is updated to contain "1" (see the third row from top in FIG. 14C), and relevant information is appended to the log data 149.

When a retrieval instruction including the code "B" is input to the control unit 130, the three associated fields in the medical resource information table 147 (see "BBB" in the second row from top in FIG. 14C) are selected, and then the three associated fields in the medical resource availability data 146 are checked. In this case, the three fields contain "1", showing a match. Thereupon, the three adjacent retrieval guidance members 162 at the associated locations are lighted at a time (see the bottom row of FIG. 14C). The operator viewing this will not find difficulty in taking out the target medical resource 110.

If one of the three medical resource detecting members 163 expected to detect the medical resource name plate 167 three times as wide at a time fails (see FIG. 14D), two of the three associated fields in the medical resource availability data 146 are changed to "1", while one field continues to store "0" (see the third row from top in FIG. 14D). This results in incompatibility between the medical resource availability data 146 and the partition availability data 148 as checked by the medical resource detection routine 142, in respect of the three fields to be collectively processed. If the condition of incompatibility (failure to match) continues beyond a maximum period of time required for storage or retrieval of the medical resource 110, the medical resource detection routine 142 issues an alarm, revealing abnormality.

Illustrative Embodiment 2-2

A specific structure of the illustrative embodiment 2-2 of the medical resource storage and management apparatus according to the second embodiment will be described with reference to the associated drawings. FIGS. 15A-15B show the structure of medical resource storage and management apparatus 120. FIG. 15A is an expanded perspective view of the rack 160 and the partition members 165; FIG. 15B is a functional block diagram of the control unit 130.

The medical resource storage and management apparatus 120 according to this embodiment differs from that of the illustrative embodiment 2-1 in that partition detecting members 164 are added and the manual partition condition configuration routine 144 is replaced by an automatic partition condition configuration routine 145.

The partition detecting member 164 (see FIG. 15A) is implemented by a mechanical switch, a reflective photosensor, a capacity sensor or the like. The partition detecting member 164 is embedded in the top face of the rack 160 to face upward so as to sense the lower end face of the partition member 165 inserted into the depression 161 on the top face of the rack 160, and is placed at respective locations of insertion of the partition members 165 in the rack 160. In this example, the partition detecting member 164 is provided between a pair of depressions 161 arranged in a width direction in order to detect whether the partition member 165 is inserted in its location. The partition member 164 outputs a binary signal which turns on and off according to whether the partition member 165 is available.

The automatic partition condition configuration routine 145 (see FIG. 15B) is started periodically and automatically by a timer, etc. or irregularly and automatically started by an interruption initiated in the event of a change in a detection signal from the partition detecting member 164. The automatic partition condition configuration routine 145 updates the partition availability data 148 based on the detection by the partition detecting member 164. More specifically, each time the automatic partition condition configuration routine 145 is started, it imports the detection results from all partition detecting members 164 or those results changed since its last import, and writes "1" or "0" in the partition availability data 148 in association with the on-off condition. The other functions (e.g., automatic updating of the medical resource information table 147) are the same as those of the manual partition condition configuration routine 144. This arrangement allows the control unit 130 to collectively process a block of medical resource detecting members 163 and retrieval guidance members 162 identified as being located on both sides of the depression 161 from which the partition member 165 is removed, in accordance with the detection by the partition detecting members 164.

In this case, removal of the partition member 165 from the depression 161 in the rack 160 or insertion of the partition member 165 into the depression 161 on the rack 160 need not be designated by manual input for configuration. The removal or insertion is detected by the partition detecting member 164, and the partition availability data 148 is automatically configured by the automatic partition condition configuration routine 145. This will prevent incompatibility between the insertion condition of the partition member 165 and the partition availability data 148 from occurring due to a failure to provide an input for configuration.

The other usage modes and operations are the same as those of the illustrative embodiment 2-1 described above.

Illustrative Embodiment 2-3

Figure 16A:
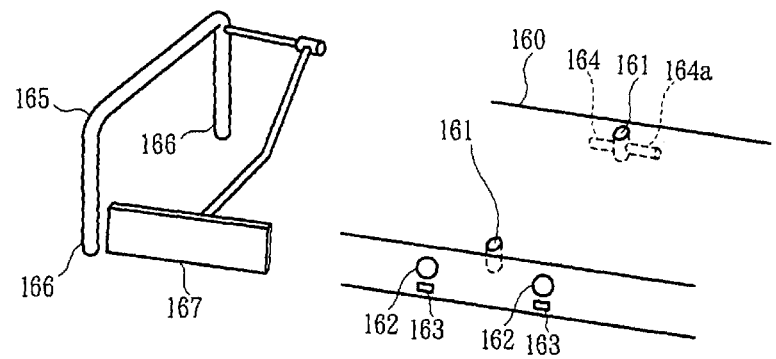
FIGS. 16A-16C show three variations to the structure according to an illustrative embodiment 2-3 of the second embodiment.

The partition member 165 and the rack 160 shown in a perspective view of FIG. 16A differ from those of the illustrative embodiments 2-1 and 2-2 in that the partition member 165 is formed by bending a round bar instead of as a plate, and that the depression 161 is a bottomed hole instead of a through hole. The partition detecting member 164 is embedded in the rack 160 so as to face a light-emitting device 164a across the depression 161. Whether or not the partition member 165 is inserted is detected depending on whether light emitted from the light-emitting device 164a is shielded by the fitting 166 at the end of the partition member 165 or received by the partition detecting member 164.

Figure 16B:
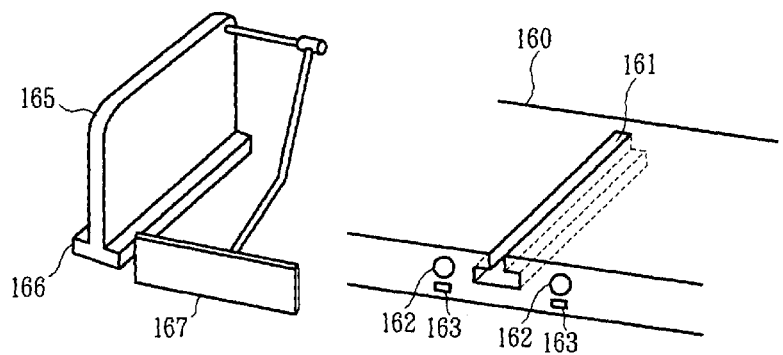

The partition member 165 and the rack 160 shown in a perspective view of FIG. 16B differ from those of the illustrative embodiments 2-1 and 2-2 in that the longitudinal cross section of the partition member 165 is of an inverted T shape, and that the depression 161 is formed as a groove. In this case, the partition member 165 is inserted into the depression 161 by slipping the fitting 166 at the lower end of the partition member 165 into the depression 161.

Figure 16C:
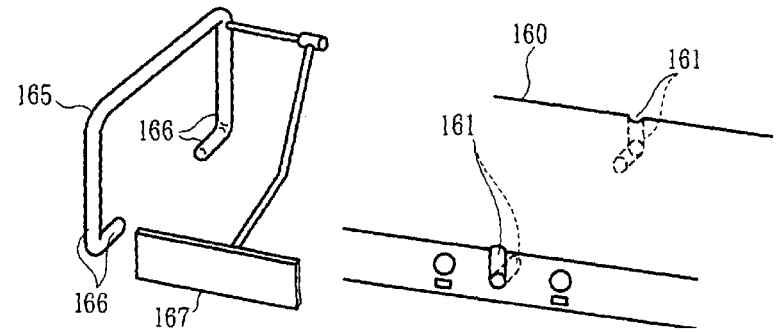

The partition member 165 and the rack 160 shown in a perspective view of FIG. 16C differ from those of the illustrative embodiments 2-1 and 2-2 in that the partition member 165 is formed by bending a round bar instead of as a plate, and that the depression 161 is formed as a notch or bore formed at the front and back of the rack 160 instead of on the top face thereof. In this case, the partition member 165 is inserted into the depression 161 and secured and stabilized therein by a snapping force, by extending the fittings 166 at both ends of the partition member 165 before inserting them in the depression 161.

Illustrative Embodiment 2-4

Figure 17A:
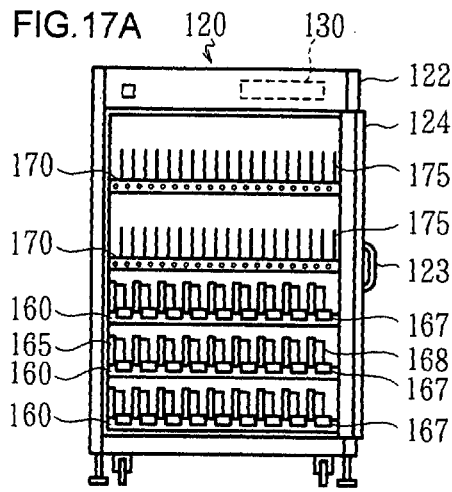
FIGS. 17A-17C show the structure of the medical resource storage and management apparatus according to an illustrative embodiment 2-4 of the second embodiment.
Figure 17B:
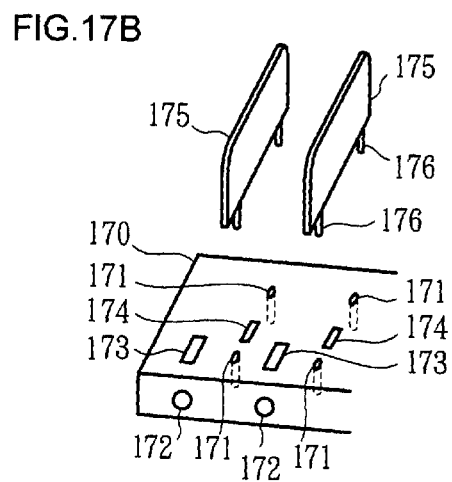
Figure 17C:
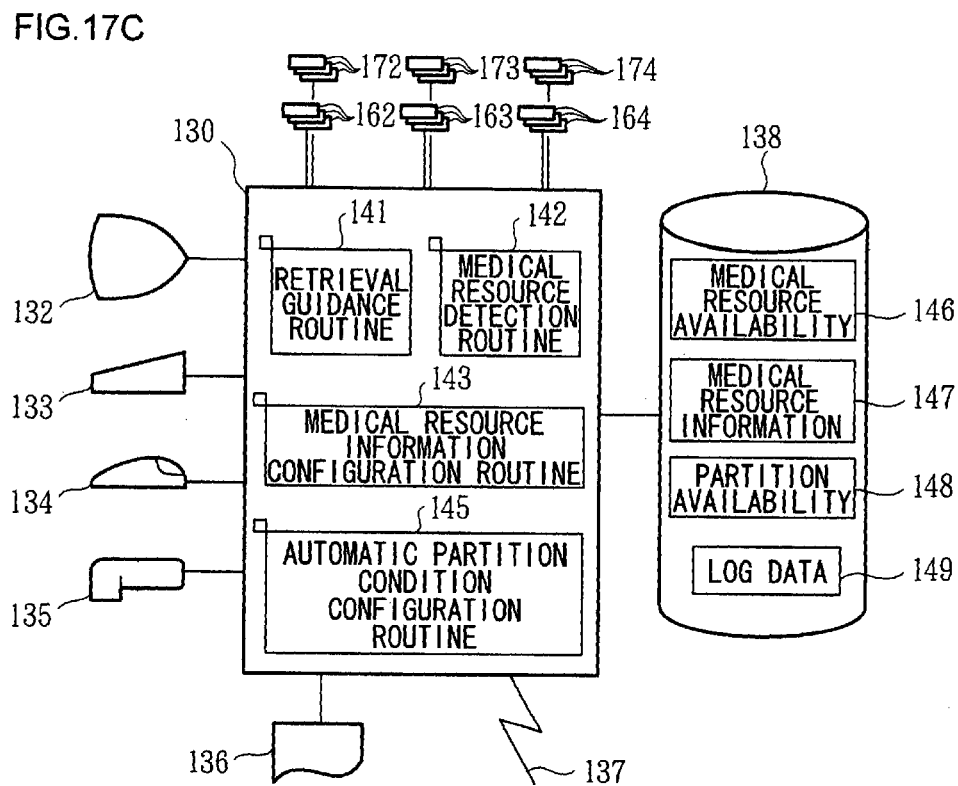

A specific structure of the illustrative embodiment 2-4 of the medical resource storage and management apparatus according to the second embodiment will be described with reference to the associated drawings. FIGS. 17A-17B show the structure of the medical resource storage and management apparatus 120. FIG. 17A is a front view showing the door 124 opened; FIG. 17B is an expanded perspective view of a rack 170 and partition members 175; and FIG. 17C is a functional block diagram of the control unit 130.

The medical resource storage and management apparatus 120 according to this embodiment differs from those of the illustrative embodiments 2-1 through 2-3 in that racks 170, instead of the racks 160, are placed in an area in the storage part (see FIG. 17A).

The rack 170 is for inserting the partition member 175. The partition member 175 is configured such that the medical resource name plate 167, the connecting member 168 and the pivot shaft 169 are omitted from the partition member 165 (see FIG. 17B). Therefore, instead of the medical resource detecting members 163, medical resource detecting members 173 are provided on the top face of the rack 170 to directly detect whether the medical resource 110 is placed by sensing the bottom of the medical resource 110. A depression 171, a retrieval guidance member 172, a partition detecting member 174 and a fitting 176 are of the same structure or function as the depression 161, the retrieval guidance member 162, the partition detecting member 164 and the fitting 166, respectively, although they differ in the destination of installation.

The control unit 130 is expanded in its capabilities so that access to the retrieval guidance member 172, the medical resource detecting member 173 and the partition detecting member 174, as well as to the retrieval guidance member 162, the medical resource detecting member 163 and the partition detecting member 164, is enabled. The routines 141-145 and the data 145-149 of the control unit 130 are also altered to reflect the structure by, for example, fine-tuning the definition of addresses storing the components or the size of tables.

The basic usage mode and operation are the same as those in the illustrative embodiments already described. For detection of the medical resource 110, the rack 170 is designed for direct detection, while the rack 160 is designed for indirect detection. As a mixture of two types is provided in the storage part of the medical resource storage and management apparatus 120, medical resources 110 of different types can be stored for accurate and automatic management.

The medical resource 10 may be packaged, bundled or contained in a case or a container. Suitable for storage on the rack 170 of direct detection type are those relatively stable in form that can stand on its own while in storage (for example, those contained in a container with the shape of a CD case or a rectangular box). Examples of such medical resources are tube sets for injection/infusion, small and short-length catheters and sets of articles including the same.

Suitable for storage on the rack 160 of indirect detection type are those relatively thick and unstable in form that do not stand on its own while in storage (for example, those contained in a round, hard case, those in a blister package or those in a soft package). Examples of such medical resources are those for respirator medicine such as filters, resources for medical operations, and resources for artificial replacement.

Illustrative Embodiment 2-5

Figure 19A:
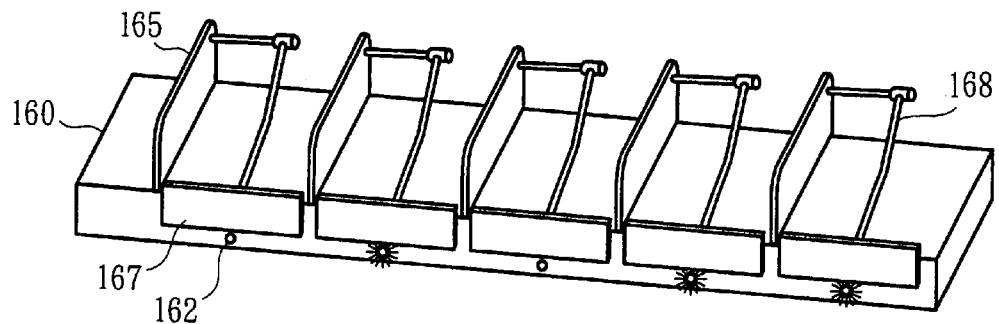
FIGS. 19A-19C also show conditions of replenishment of medical resources according to the illustrative embodiment 2-5.
Figure 19B:
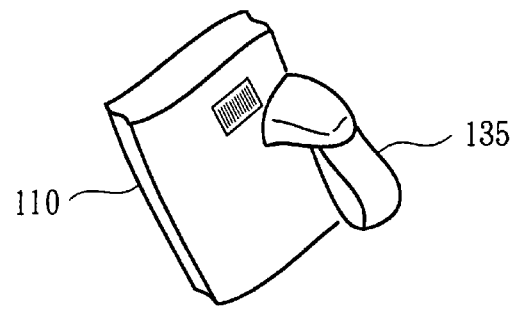
Figure 19C:
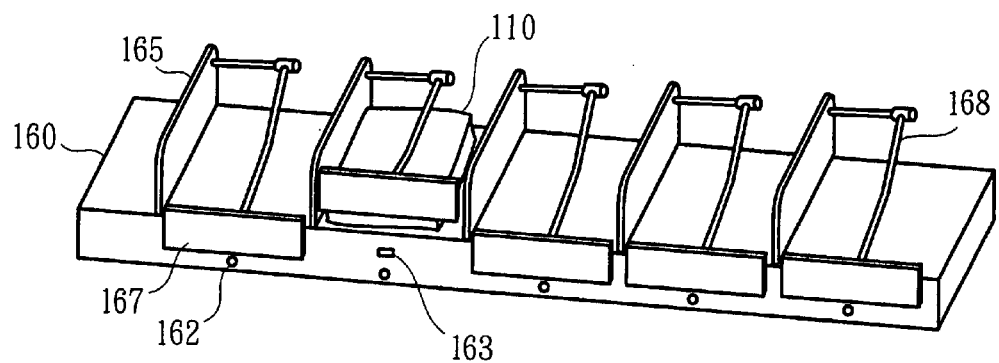

An illustrative embodiment 2-5 of the medical resource storage and management apparatus according to the second embodiment will be described with reference to the associated drawings. FIGS. 18A-18C show conditions of replenishment of medical resources. FIGS. 18A-18C are screen shots. FIGS. 19A-19C also show conditions of replenishment of medical resources. FIG. 19A is a perspective view of the rack fitted with partition members; FIG. 19B is a perspective view showing how identification information is read from a medical resource; and FIG. 19C is a perspective view of the rack storing a medical resource.

This medical resource storage and management apparatus differs from the aforementioned embodiments of the apparatus in that guidance is displayed in replenishing as well as in retrieving a medical resource, that the display 132, the keyboard 133 and the mouse 134 are implemented as a touch panel 139, and that, even in an empty condition, the retrieval guidance member 162 is viewable and not shielded from view by the medical resource name plate 167.

In a normal operation (see FIG. 18A), information on the medical resource 110 retrieved from the medical resource storage and management apparatus is arranged chronologically and displayed on the touch panel 139 on a real time basis. A direct finger-touch selection of any the items 139a displayed on the screen causes relevant details to be displayed for review. Guidance for replenishment is also displayed in accordance with a specific operation for selection.

More specifically, selecting a replenishment button 139b displayed on the screen while in a normal operation (see FIG. 18A) switches the display of the touch panel 139 to a replenishment mode selection screen (see FIG. 18B). By entering information on an operator who replenishes a medical resource, selection of a "registered" button 139c and/or a "new registration" button is available. By selecting the "new registration" button, the operator can register the code (code No.) identifying the medical resource 110 that can be stored in a location of storage (address) and the name for screen display (medical resource name). If the registration is complete, selection of the "registered" button 139c is enabled. The "registered" button 139c is selected when the display of guidance for replenishment is desired.

The selection switches to the screen of the touch panel 139 showing a list of registered resources (see FIG. 18C). After confirming that a location for storage is shown as being empty, the operator scrolls the screen as necessary by using a scroll button 139f so as to directly select a field 139d for a relevant medical resource 110 with the finger.

If the number of empty locations 139e designated as capable of storing the medical resource (e.g., a filter in a bag) is three (i.e., three bags can be stored), the three retrieval guidance members 162 in the empty locations are all lighted because, in this example, the retrieval guidance member 162 also serves as a replenishment destination guidance member (see FIG. 19A).

The operator proceeds to scan the barcode (identification information) assigned to the medical resource 110 about to be stored, by using the barcode reader 135 (see FIG. 19B) for checking, before storing the medical resource 110 in one of the locations on the rack 160 lighted by the guidance member. This turns off all of the guidance members (see FIG. 19C), and the log data, indicating the identity of the operator who replenished the resource, the identity of the resource replenished and the location of replenishment, is recorded with a time stamp.

Thus, guidance display is provided properly and a job record is maintained properly for replenishment. In this example, the selection of the field 139d on the screen showing a list of registered resources, and the scanning of the identification information assigned to the medical resource 110 by using the barcode reader 135 are both performed to reinforce checking. However, only one of the tasks may be performed since it serves the purpose of identifying a medical resource 110. In another alternative, the operator may be allowed to complete both tasks, but guidance display guiding the operator to the destination of replenishment may not require completion of both tasks but may be immediately provided upon completion of one of the tasks.

Other Points of Note

In the second embodiment, the control unit 130 is accommodated in the electric equipment 121. Alternatively, the control unit 130 may be placed outside the housing 122. The input and output means of the control unit 130 may not be restricted to the display 132, the keyboard 133 and the like mentioned above and may be implemented by a touch panel or a mobile information terminal.

In the second embodiment, the medical resource detection routine 142 is designed to associate the on and off states of the result of detection by the medical resource detecting member 163 with the storage and retrieval of the medical resource 110, respectively. It is easy to expand the capabilities to automatically manage the return of a medical resource 110 once taken out and not used. For example, a determination may be made that a resource is not replenished but returned, if retrieval and storage are conducted successively in a short time span, or if a resource is stored in one of the modes of operation introduced in the control unit 130 in which mode an action of retrieval is restricted. In this case, information indicating the return may suitably be appended to the log data 149 or other output data. In addition to data storage and output, provisions may also be made for management of expiration dates, stock control, preparation of drug history and inspection.

Some forms of medical resources require that the medical resource be contained in an atypical package with irregular surfaces. Some medical resources do not fit into a soft package, while other medical resources need be contained in a container due, for example, to their lightness or small size. All of these types of resources may be stored in the rack provided with the above-described function, using a detachable lid (case with a name plate).

THIRD EMBODIMENT

A third embodiment of the present invention relates to a medical resource storage and management apparatus which arranges and stores medical resources and also performs management of storage status, and, more particularly, to a medical resource storage and management apparatus which automatically manages availability of medical resources at each location of storage and also guides a user for retrieval.

A summary of a third embodiment will be given.

A first medical resource storage and management apparatus according to the third embodiment comprises: a horizontal-bridging member which is provided with a series of hanger member fitting parts operable to hang and arrange a large number of medical resources, a hanger member which is fitted to the hanger member fitting part and is pivotally moved depending on whether a medical resource is hung; a medical resource detecting member which is provided in each of the hanger member fitting parts so as to detect whether a medical resource is hung in an associated location in accordance with the pivotal movement of the associated hanger member; a retrieval guidance member for visual confirmation provided in each of the hanger member fitting parts; and a control unit which manages the storage status of the medical resources, based on the detection by the medical resource detecting member, and which operates the retrieval guidance member in response to an input designating retrieval, wherein, at the time of hanging a medical resource, the pivotal movement of the hanger member causes the engaging part engaged with the medical resource to be lowered, and, at the time of retrieving a medical resource, the pivotal movement causes the engaging part to be elevated and moved toward an operator.

A second medical resource storage and management apparatus according to the third embodiment is a modification to the first medical resource storage and management apparatus, wherein the pivotal movement of the hanger member is based on the displacement between the center of gravitation and the pivot center.

A third medical resource storage and management apparatus according to the third embodiment is a modification to the first medical resource storage and management apparatus or the second medical resource storage and management apparatus, wherein the control unit allows providing an input for configuration to designate whether the hanger member is fitted to the hanger member fitting part, and, based on the configuration, the control unit terminates the operation of the retrieval guidance member if it is determined that the hanger member is removed from the associated hanger member fitting part.

A fourth medical resource storage and management apparatus according to the third embodiment is a modification to the first medical resource storage and management apparatus or the second medical resource storage and management apparatus, wherein the hanger member is detachable, the apparatus further comprising a hanger detecting member which detects whether the hanger member is fitted to the hanger member fitting part, wherein the control unit terminates the operation of the retrieval guidance member if it is determined that the hanger member is removed from the associated hanger member fitting part.

A fifth medical resource storage and management apparatus according to the third embodiment is a modification to the third medical resource storage and management apparatus or the fourth medical resource storage and management apparatus, wherein the control unit issues an alarm if informed, by the medical resource detecting member of the hanger member fitting part in which it is determined that the hanger member is removed, that a medical resource is hung.

In the first medical resource storage and management apparatus, the medical resources are stored by being hung from the hanger members. Since a series of hanger members are fitted to the horizontal-bridging member so that the locations of storage are partitioned, it is easy to retrievably align and store medical resources without accommodating them in cassettes and to prevent disarrangement of the medical resources stored and resultant disorganization.

Since the medical resource detecting member and the retrieval guidance member are provided in each location of hanging, i.e. each block, it is possible to detect the availability of each medical resource for automatic management and to properly guide an operator to the location of storage of the medical resource to be taken out.

By exploiting the pivotal movement of the hanger member that depends on whether a medical resource is hung, and accordingly allowing the medical resource detecting member to indirectly detect whether a medical resource is hung, the apparatus is prevented from becoming complex. This is because the detection of availability takes place in the horizontal-bridging member even if there are a variety of types of medical resources or even if the medical resources are hung below the horizontal-bridging member.

Further, the location of the engaging part engaged with the medical resource is moved back and forth as well as up and down in accordance with the availability of the medical resource, by ensuring that, at the time of hanging a medical resource, the pivotal movement of the hanger member, which depends on the availability of a medical resource, causes the engaging part engaged with the medical resource to be lowered, and, at the time of retrieving a medical resource, the pivotal movement causes the engaging part to be elevated and moved toward an operator. Accordingly, both the task of hanging and the task of retrieving can be performed with ease.

Thus, even with a simple apparatus in which hanger members are arranged and medical resources are hung therefrom, a large variety of medical resources can be stored in the least confusing manner. Even those resources that are not suitable for direct detection can also be detected properly for automatic management.

Thus, the first medical resource storage and management apparatus provides capability for easily and properly storing and retrieving medical resources, and automatically and accurately keeping track of storage status.

In the second medical resource storage and management apparatus, the pivotal movement of the hanger member is based on the displacement between the center of gravitation and the pivot center. As a result, there is no need to build driving members such as motors or urging members such as springs in the apparatus. Accordingly, the number of parts is reduced, the number of causes of trouble is reduced, and the production cost is reduced.

In the third medical resource storage and management apparatus, the activation of the retrieval guidance member is avoided if it is determined that the hanger member is removed from the associated hanger member fitting part, by providing an input for configuration designating whether the hanger member is fitted. Therefore, a user will not be at a loss or face any inconvenience in handling and management even if there are multiple medical resource detecting members or retrieval guidance members where a single, large medical resource resides.

Thus, even with a simple apparatus in which a series of hanger members fitted to a horizontal-bridging member hang medical resources, a large variety of large and small medical resources can be stored for automatic management by means of attachment and detachment of hanger members and by an input of associated information for configuration.

In the fourth medical resource storage and management apparatus, convenience is enhanced by additionally ensuring that whether or not the hanger member is fitted is automatically detected and reflected in the control, in addition to ensuring that the hanger members are detachable from the horizontal-bridging member.

According to the firth medical resource storage and management apparatus, reliability is enhanced while avoiding an increase in hardware cost, by taking advantage of redundancy of results of detection by multiple medical resource detecting members located where a single large medical resource resides and detecting an error or abnormal condition accordingly.

Specific embodiments of the medical resource storage and management apparatus according to the third embodiment will be described below using illustrative embodiments 3-1 through 3-7.

The illustrative embodiment 3-1 shown in FIGS. 20A-22D is an embodiment of the first medical resource storage and management apparatus and the second medical resource storage and management apparatus mentioned above.

Figure 28A:
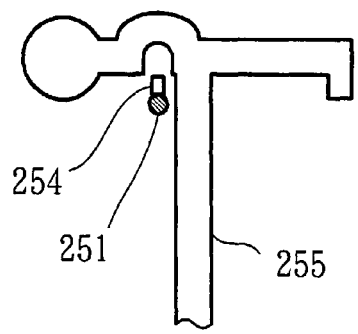
FIGS. 28A-28C show the structure of the medical resource storage and management apparatus according to an illustrative embodiment 3-3 of the third embodiment.
Figure 28B:
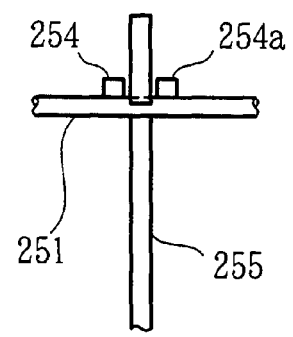
Figure 28C:
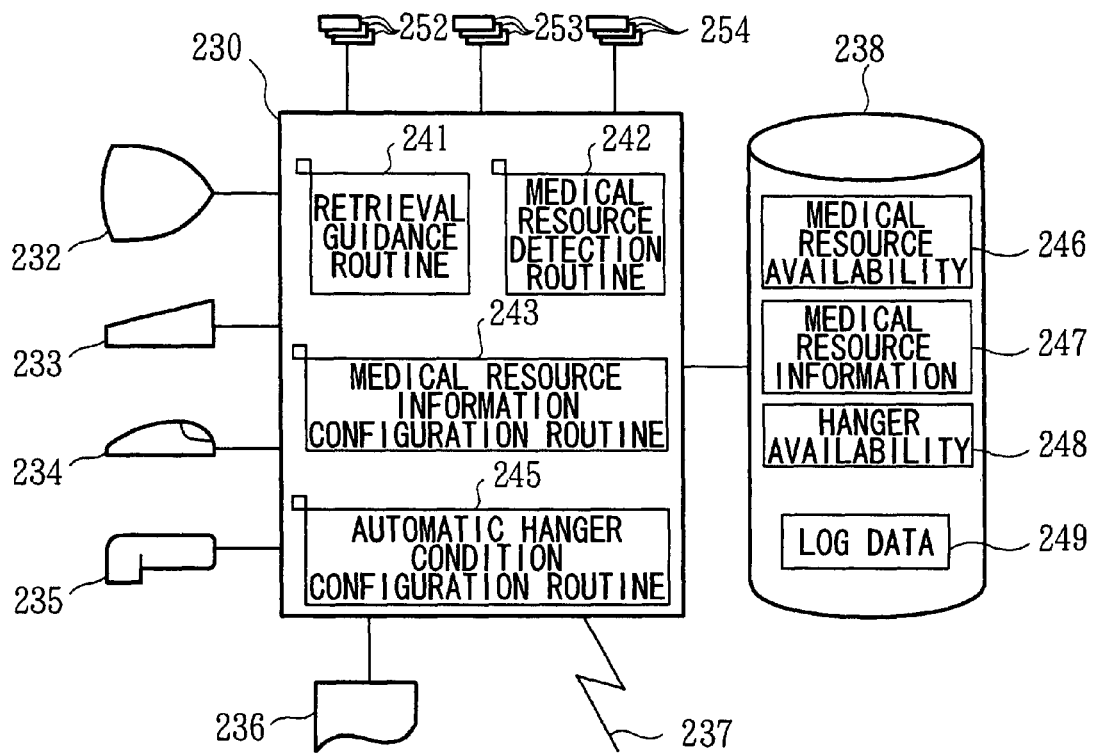

The illustrative embodiment 3-2 shown in FIGS. 23A-27D is an embodiment of the third and fifth medical resource storage and management apparatuses mentioned above. The illustrative embodiment 3-3 shown in FIGS. 28A-28C is an embodiment of the fourth medical resource storage and management apparatus mentioned above. The illustrative embodiment 3-4 shown in FIGS. 29A-29C, the illustrative embodiment 3-5 shown in FIGS. 30A-31, the illustrative embodiment 3-6 shown in FIG. 32, and the illustrative embodiment 3-7 shown in FIGS. 33A-34C are variations.

In the illustration, fasteners such as bolts, connectors such as hinges, electronic circuits such as drivers are omitted for brevity, highlighting those elements necessary to explain the embodiment and related elements.

Illustrative Embodiment 3-1

Figure 21A:
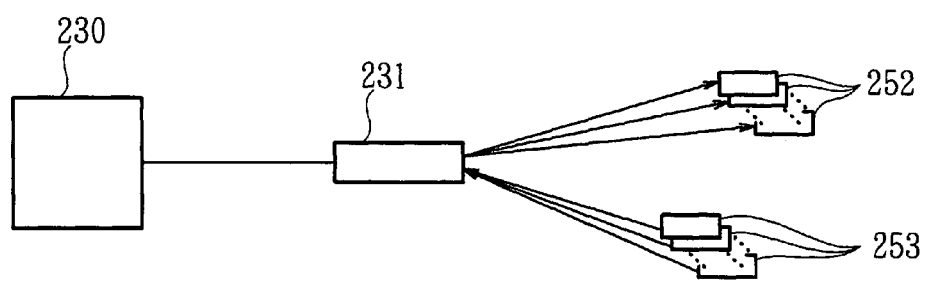
FIGS. 21A and 21B show the schematic structure of a control unit according to the illustrative embodiment 3-1 of the third embodiment.
Figure 21B:
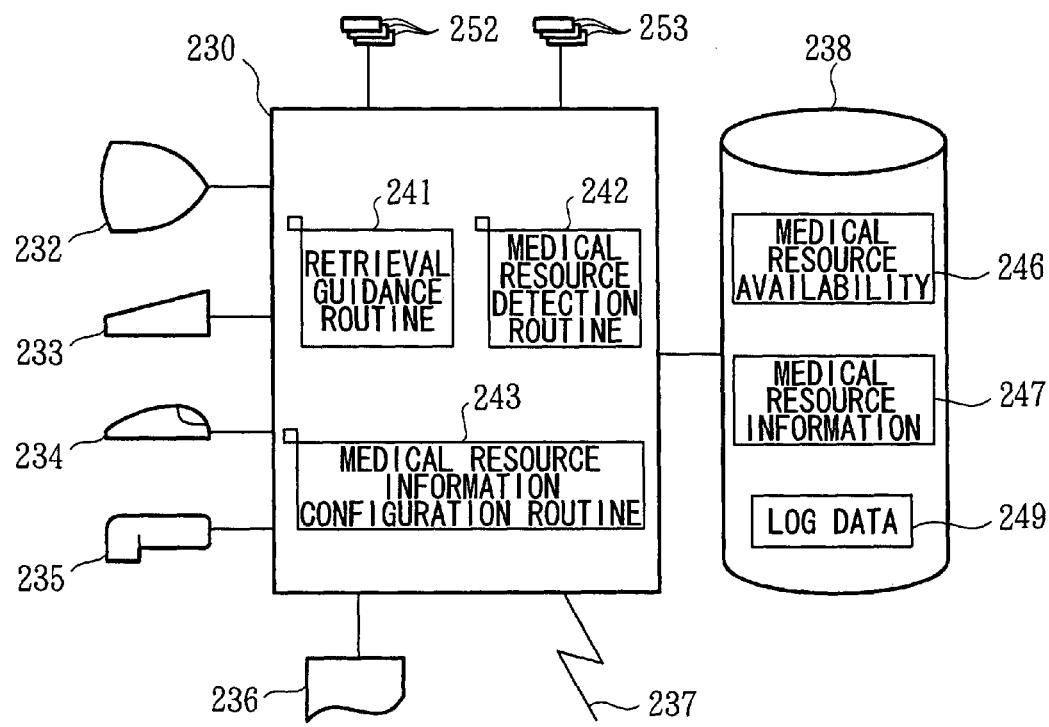
Figure 22A:
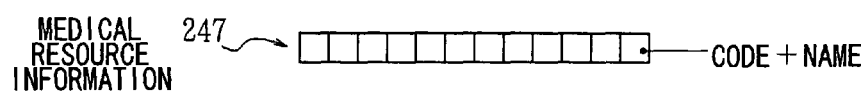
FIG. 22A shows the structure of a medical resource information table of the control unit according to the illustrative embodiment 3-1 of the third embodiment.
Figure 22B:
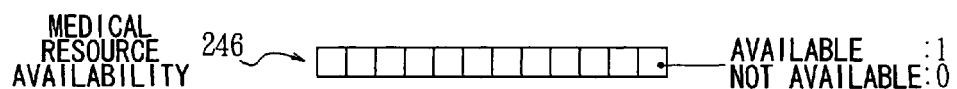
FIG. 22B shows the data structure of medical resource availability data of the control unit.

A specific structure of the illustrative embodiment 3-1 of the medical resource storage and management apparatus according to the third embodiment will be described with reference to the associated drawings. FIGS. 20A-20E show the mechanical structure of the medical resource storage and management apparatus. FIG. 20A is a front view showing a door closed; FIG. 20B is a front view showing the door opened; FIG. 20C is a front view showing a horizontal-bridging case and hanger members; FIGS. 20D and 20E are left side views of a horizontal-bridging member and the hanger member showing a cross section of the horizontal-bridging member. FIGS. 21A and 21B show the schematic structure of a control unit. FIG. 21A is a schematic block diagram showing the connection between the control unit and retrieval guidance members; and FIG. 21B is a functional block diagram of the control unit. FIGS. 22A-22D show the data structure of the control unit. FIG. 22A relates to a medical resource information table; and FIG. 22B relates to medical resource availability data.

A medical resource storage and management apparatus 220 is provided with a housing 222 a large portion of which is for storage and a part of which comprises electric equipment 221. The electric equipment 221 stores a control unit 230 and a power supply unit etc. (not shown). The front of the storage part of the housing 222 is provided with an openable door 224 with a handle 223. The door 224 may be implemented by a shutter or the like, or may be omitted. Inside the storage part exposed when the door 224 is opened is provided a horizontal-bridging case 250 (horizontal-bridging member). In the illustrated example, only one horizontal-bridging case 250 is provided so as to extend horizontally toward the top of the storage part. The horizontal-bridging case 250 comprises a rectangular cylinder. A series of arm-shaped hanger members 255 are hung from the lower part or the bottom of the case 250 in a longitudinal direction (in the figure, sideways) at regular or irregular pitches so as to arrange a large number of medical resources by retrievably hanging them.

In the hollow interior of the horizontal-bridging case 250 (see FIGS. 20C-20E) is housed a horizontal-bridging bar 251 (horizontal-bridging member) extending in a longitudinal direction. The series of hanger members 255 are fitted to the horizontal-bridging bar 251. More specifically, the hanger member 255 comprises a bar member substantially T-shaped in side view. The lower end of an vertical bar is bent into a hook, forming an engaging part 256. One end of a top side bar is formed into a weight part 257 by bulging or by being provided with a weight. The other end of the top side bar is provided with a permanent magnet and is formed into a target of detection 258.

A through hole through which the horizontal-bridging bar 251 can be movably inserted is formed in the middle of the top side bar toward the weight part 257. Alternatively, a bearing is fitted thereto. By introducing the bar 251 through the hole or the bearing, the hanger member 255 is supported by the bar 251 so as to be pivotable around the bar 251. The center of gravitation of the hanger member 255 is displaced from the pivot center toward the weight part 257. Therefore, at the time of retrieving a medical resource, the pivotal movement of the hanger member 255 causes the engaging part 256 to be elevated and moved toward an operator (see FIG. 20D). At the time of hanging a medical resource, the pivotal movement causes the engaging part 256 engaged with a medical resource 210 to be lowered and moved toward the back (see FIG. 20E).

On the underside of the horizontal-bridging case 250, a series of oblong holes 250a (hanger member fitting parts) are formed in a longitudinal direction at regular or irregular pitches. As the hanger member 255 is movably introduced into the oblong hole 250a, the hanger member 255 is allowed to move back and forth freely, while substantially being prevented from moving sideways in a front view (see FIG. 20C). The provision maintains the hanger members 255 in an aligned state (lined up in a longitudinal direction), without inhibiting the pivotal movement thereof.

Further (see FIGS. 20D and 20E), a medical resource detecting member 253 is provided on the interior face of the horizontal-bridging case 250 where the target of detection 258 leaves or comes into contact as a result of the pivotal movement of the hanger member 255. A retrieval guidance member 252 is provided on the front of the horizontal-bridging case 250 which becomes viewable when the door 224 is opened. The retrieval guidance member 252 and the medical resource detecting member 253 are provided in the horizontal-bridging case 250 so as to be alignment with the oblong hole 250a and are provided for each hanger member 255, i.e., at each location of storage.

In this example, the medical resource detecting member 253 is implemented by a sensor using a Hall device that senses the magnetic field in the magnet of the target of detection 258, in order to detect whether the medical resource 210 is hung in accordance with the pivotal movement of the hanger member 255. The hanger member 255 is pivotally moved as the medical resource 210 is hung or removed therefrom. As the target of detection 258 leaves or comes into contact with the medical resource detecting member 253 as a result of the pivotal movement, the medical resource detecting member 253 outputs a binary signal which turns on and off. The medical resource detecting member 253 may be implemented by other devices so long as detection in association with the pivotal movement is enabled. For example, the medical resource detecting member 253 may be implemented by a mechanical switch, a reflective photosensor, a capacity sensor.

In order to visually guide a user to the location of placement of the medical resource 210 to be retrieved, a miniature bulb, a light-emitting diode or the like that can be turned on and off is used as the retrieval guidance member 252.

The control unit 230 (see FIG. 21A) comprises a programmable controller such as a personal computer and a sequencer. A local area network (LAN) connects the control unit 230 to the retrieval guidance members 252 and the medical resource detecting members 253 via, for example, a low-level controller 231. Alternatively, the control unit 230, the retrieval guidance members 252 and the medical resource detecting members 253 are in direct star connection (not shown). The connection enables retrieving detection results of the medical resource detecting members 253 and controlling the lighting of the retrieval guidance members 252.

The control unit 230 (see FIG. 21B) is provided with a display 232 for screen display, a keyboard 233 for key entry, a mouse 234 for inputting instructions etc. on a screen, a bar code reader 235 for reading identification information, a printer 236 for delivering printouts, an interface for a local area network (LAN) 237 which is responsible for communication with a prescription order-entry system etc., and a hard disk 238 as a secondary storage.

A retrieval guidance routine 241, a medical resource detection routine 242 and a medical resource information configuration routine 243 are installed in the control unit 230, as programs for managing the storage status of the medical resources, based on the detection by the medical resource detecting members 253, and for operating selected retrieval guidance members 252 in response to an input designating retrieval. The hard disk 238 stores medical resource availability data 246, a medical resource information table 247, and log data 249, which are divided into individual files or are unified in an appropriate database. The figures show (see FIGS. 22A-22B) the data 246 and the table 247 maintained in a table format. Each table comprises a 1×21 matrix, in association with the fact that there is one horizontal-bridging case 250 and the number of hanger members 255, retrieval guidance members 252 and medical resource detecting members 253 accommodated in the horizontal-bridging case 250 is "12".

Each field in the medical resource information table 247 (see FIG. 22A) contains an identification code and a name displayed on a screen for the medical resource 210 which is stored or can be stored in an associated location. "1" or "0" is written in the medical resource availability data 246 (see FIG. 22B), "1", indicating that the medical resource 210 is stored in the associated location, and "0", indicating that no medical resources 210 are stored. The medical resource information table 247 should be configured at least once before operating the apparatus for the first time since its installation. Therefore, the table is usually initialized upon starting the apparatus and updated when the operation is stopped. The medical resource availability data 246 is all cleared by initialization before the initial operation, and are subsequently updated with each storage or retrieval of the medical resource 210.

The medical resource information configuration routine 243 is started by the keyboard 233 or mouse 234 operation. When dumping from a medicine master file located on a host computer (not shown) via the LAN 237 is dictated in an environment where such an action is possible, the medical resource information configuration routine 243 dumps the data. The routine 243 also allows the user to set the code or name of the medical resource 210 in the medical resource information table 247 by selecting an item using the mouse 234 or entering data using the keyboard 233, while viewing screen display on the display 232.

The medical resource detection routine 242 is started periodically and automatically by a timer, etc. or irregularly and automatically started by an interruption initiated in the event of a change in a detection signal from the medical resource detecting member 253. The medical resource detection routine 242 manages the storage status of the medical resources 210 based on the detection by the medical resource detecting members 253. More specifically, each time the medical resource detection routine 242 is started, it imports the detection results from all medical resource detecting members 253 or those results changed since its last import, and writes "1" or "0" in the medical resource availability data 246 in association with the on-off condition. When the detection result from the medical resource detecting member 253 undergoes an on/off change and the storage or retrieval of the medical resource 210 is detected accordingly, the medical resource detection routine 242 appends information indicating the detection to the log data 249 with a time stamp, causes the printer 236 to deliver a printout which carries the name listed in the associated field in the medical resource information table 247, and submits a report to a host medical management computer via the LAN 237.

The retrieval guidance routine 241 is started when the code of the medical resource 210 or a prescription ID number is entered by allowing the barcode reader 235 to scan the code or the ID, or by using the keyboard 233 or the mouse 234, in order to operate one of the retrieval guidance members 252 in response to an input designating retrieval. The retrieval guidance routine 241 searches the medical resource information table 247 to determine the location of storage of the medical resource 210 designated to be retrieved via the reading or via the mouse or keyboard operation, and lights the medical resource detecting member 253 at the associated location. The medical resource detection routine 242 is responsible for turning the medical resource detecting member 253 off when the retrieval of the medical resource 210 at the associated location is detected.

In addition, the control unit 230 acquires operator identification information by requesting an operator to input operator identification information each time an operation is carried out. Alternatively, the control unit 230 acquires operator identification information input by an operator in advance of an operation. The control unit 230 also stores, in the log data 249, related information then collected by automatic detection etc. together with a time stamp. The data stored is also output via the LAN 237. The above process is performed also in the retrieval guidance routine 241.

Figures 22C, 22D:
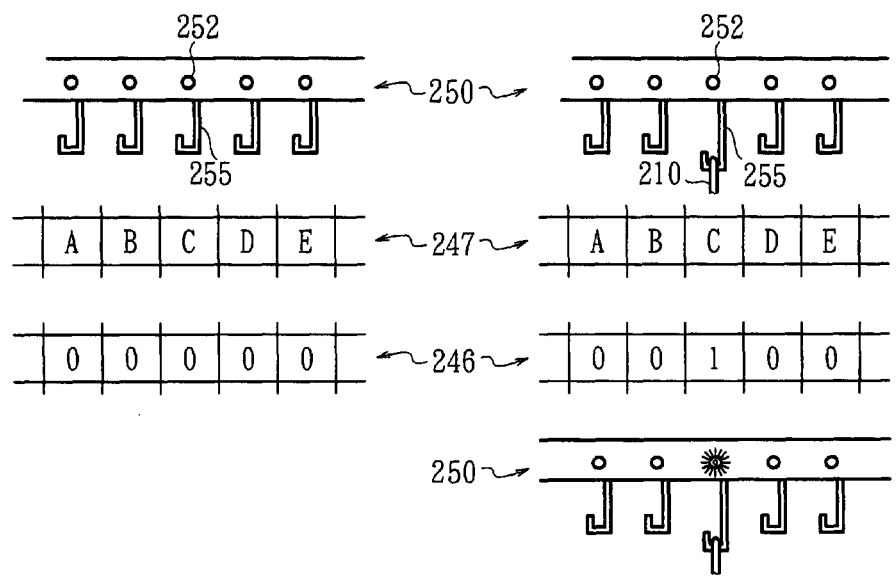
FIGS. 22C-22D illustrate the operation of the medical resource storage and management apparatus according to the illustrative embodiment 3-1.

The mode of using the medical resource storage and management apparatus according to the illustrative embodiment 3-1 and its operation will be described with reference to the drawings. FIGS. 22C-22D illustrate the operation of the medical resource storage and management apparatus. FIG. 22C shows an empty condition; and FIG. 22D shows a condition in which a small medical resource is stored.

Prior to the operation of the medical resource storage and management apparatus 220, the medical resource information configuration routine 243 in the control unit 230 is started by an operation using the keyboard 233 or the mouse 234 so as to set the identification code and the displayed name of the medical resources 210 in the respective fields in the medical resource information table 247. The medical resource availability data 246 and the log data 249 are cleared by a suitable initialization routine (not shown). This completes preparation for operation. The operating conditions of the medical resource storage and management apparatus 220 will be described specifically.

When the medical resources 210 are not hung and stored yet (see the top row of FIG. 22C), the fields in the medical resource information table 247 contain individual values (see A-E in the second row from top in FIG. 22C where A-E denote different codes and names). The fields in the medical resource availability data 246 all contain "0", indicating the absence of medical resources (see the third row from top in FIG. 22C).

When the medical resource 210 is hung from the hanger member 255 in this condition (see the top row of FIG. 22D), the weight of the medical resource 210 pivotally moves the hanger member 255 at the location of storage, causing the engaging part 256 to be lowered away from the operator (see the top row of FIG. 22D). In this process, the medical resource information table 247 in the control unit 230 remains unchanged (see the second row from top in FIG. 22D). Meanwhile, the associated field in the medical resource availability data 246 is updated by the medical resource detection routine 242 to "1", indicating the presence of a medical resource (see the third row from top in FIG. 22D). The medical resource detection routine 242 retrieves the code and name of the medical resource 210 (in the illustrated example, "C") from the medical resource information table 247. The medical resource detection routine 242 further requests the input of operator identification information. These items of information are appended to the log data 249, printed by the printer 236 and reported to the host medical (not shown) management computer via the LAN 237.

For retrieval of the medical resource 210 thus stored from the medical resource storage and management apparatus 220, a retrieval instruction including the code "C" and the operator identification information are input to the control unit 230 by an operation using the barcode reader 235 or the like. This prompts the retrieval guidance routine 241 in the control unit 230 to search the medical resource information table 247 and check the associated field in the medical resource availability data 246. In this case, the value "1" is found in the field, showing that the medical resource is available, whereupon the retrieval guidance member 252 at the associated location is lighted (see the bottom row of FIG. 22D). The operator viewing this can take out the target medical resource 210 without fail. The target engaging part 256 is somewhat further away from the operator than those of the other hanger members 255, but it is easy to remove the medical resource 210 because the target engaging part 256 is lower than those of the other hanger members 255.

When the medical resource 210 is taken out, the associated hanger member 255 is raised toward the operator in a reverse pivotal movement. The medical resource detection routine 242 in the control unit 230 updates the value entered in the associated field in the medical resource availability data 246 to "0", indicating the absence of medical resources. The information is combined with the code and name (in the illustrated example, "C") supplied from the retrieval guidance routine 41, and with operator identification information. The combined information is appended to the log date 249, printed by the printer 236 and reported to the host medical management computer via the LAN 237. When the retrieval guidance member 252 of the associated location is turned off, the operating condition returns to a pre-storage state (see FIG. 22C).

Illustrative Embodiment 3-2

Figure 23A:
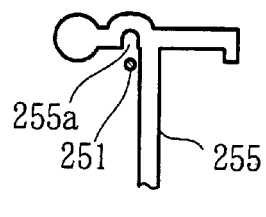
FIGS. 23A-23C are side views of a horizontal-bridging bar and the hanger member according to an illustrative embodiment 3-2 of the third embodiment.
Figure 23B:
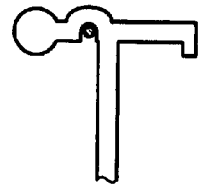
Figure 23C:
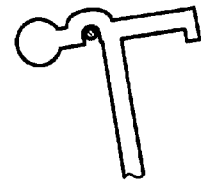
Figure 24A:
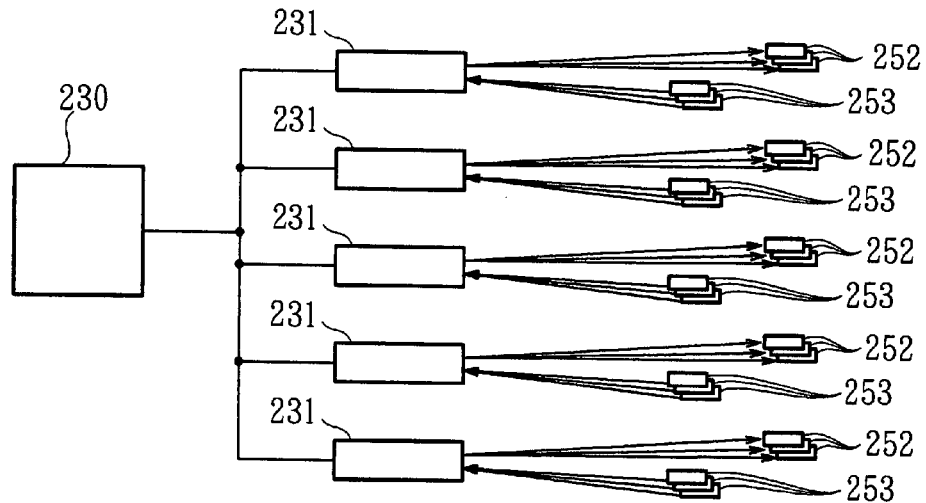
FIGS. 24A and 24B show the schematic structure of the control unit according to the illustrative embodiment 3-2 of the third embodiment.
Figure 24B:
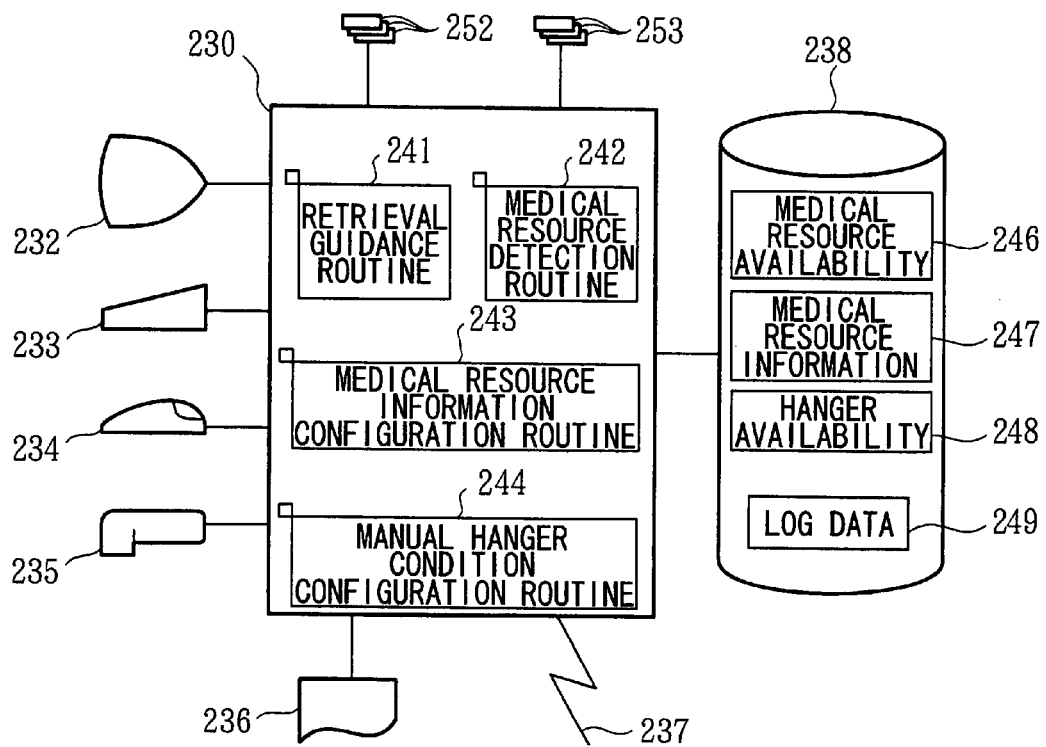
Figure 25A:
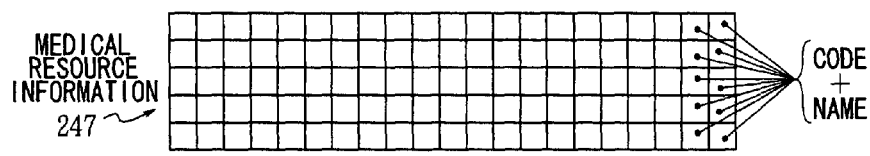
FIGS. 25A-25C show the data structure of the control unit according to the illustrative embodiment 3-2.
Figure 25B:
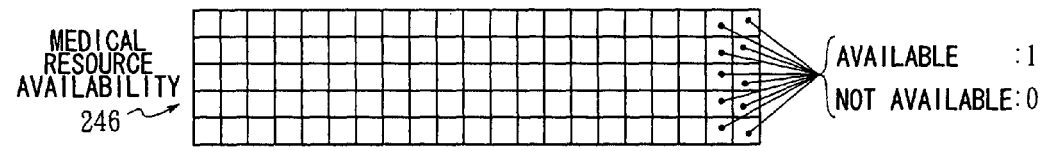
Figure 25C:
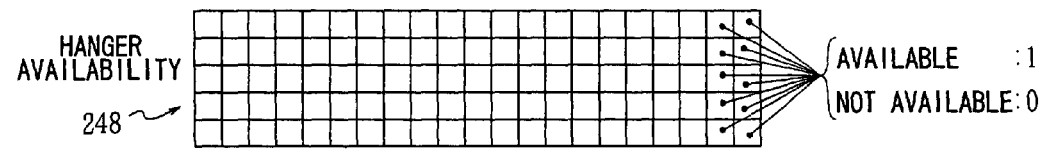

A specific structure of the illustrative embodiment 3-2 of the medical resource storage and management apparatus according to the third embodiment will be described with reference to the associated drawings. FIGS. 23A-23C are side views of the horizontal-bridging bar 251 and the hanger member 255. FIG. 23A shows a condition before the hanger member 255 is fitted to the horizontal-bridging bar 251; FIG. 23B shows a condition occurring immediately after the fitting; and FIG. 23C shows a condition in which the hanger member 255 is pivotally moved after the fitting. FIGS. 24A and 24B show the schematic structure of the control unit 230. FIG. 24A is a schematic block diagram showing the connection between the control unit 230 and the retrieval guidance members 252; and FIG. 24B is a functional block diagram of the control unit 230. FIGS. 25A-25C show the data structure of the control unit 230. FIG. 25A relates to a medical resource information table 247; FIG. 25B relates to medical resource availability data; and FIG. 25C relates to hanger availability data 248.

The medical resource management and storage apparatus 220 according to this embodiment differs from that of the illustrative embodiment 3-1 in that the hanger member 255 is removable (see FIGS. 23A-23C), that multiple (in this example, five) storage units are provided in the storage part of the medical resource storage and management unit 220, each storage unit comprising the horizontal-bridging case 250 and the low-level controller 231, and that a manual hanger condition configuration routine 244 is additionally installed.

A pivot center 255a of the hanger member 255 directly in contact with the horizontal-bridging bar 251 is formed as an indentation by notching or bending (see FIG. 23A) so that the hanger member 255 is removable and detachable from the horizontal-bridging bar 251. The indentation is deeper than the diameter of the horizontal-bridging bar 251. The hanger member 255, once hung from the horizontal-bridging bar 251 such that the bar 251 is engaged with the pivot center 255a, is suspended from the horizontal-bridging bar 251 (see FIG. 23B). The hanger member 2505 is not removed undesirably even if the member 255 is inclined due to the pivotal movement (see FIG. 23C).

Associated with the fact that the hanger member 255 is removable, the manual hanger condition configuration routine 244 is additionally installed in the control unit 230. The hanger availability data 248 is additionally maintained in the hard disk 238 (see FIG. 24B). "1" or "0" is written in the hanger availability data 248 (see FIG. 25C), "1", indicating that the hanger member 255 is stored in an associated area, and "0", indicating that the hanger member 255 is removed. The hanger availability data 248 is also initialized so that the condition (fitted or removed condition) of the hanger member 255 is reflected before the initial operation. Configuration inputs for update are also provided when the hanger member 255 is fitted or removed. The manual hanger condition configuration routine 244 responsible for the configuration is started by the keyboard 233 or mouse 234 operation. The routine 244 allows the user to provide an input for configuration to designate in the hanger availability data 248 whether the hanger member 255 is fitted to the horizontal-bridging bar 251 of the horizontal-bridging case 250, by selecting an item or toggling using the mouse 234 or the keyboard 233, while viewing screen display on the display 232.

Associated with the fact that the number of storage units is increased to five, the number of low-level controllers 231 in the medical resource storage and management apparatus 220 is increased to five (see FIG. 24A). The figures show (see FIGS. 25A-25C) the data 246, the table 247 and the data 248 are maintained in a table format. Each table comprises a 5×21 matrix, in association with the fact that there are five storage units and the maximum number of hanger members 255, retrieval guidance members 252 and medical resource detecting members 253 accommodated in the horizontal-bridging case 250 in each unit is "21". The range of access by the routines 241-244 in the control unit 230 is extended accordingly.

Further (see FIG. 24B), the retrieval guidance routine 241 operates one of the retrieval guidance members 252 in response to an input designating retrieval, based upon the condition of the hanger member 255 configured in the hanger availability data 248. More specifically, the value entered in the associated field in the hanger availability data 248 is referred to so as to determine whether "1" or "0" is stored, "1" indicating that the hanger member 255 is fitted, and "0" indicating that it is removed. If the member 255 is fitted, the routine 241 lights the retrieval guidance member 252. If the member 255 is removed, the routine 241 does not light the retrieval guidance member 252.

The medical resource detection routine 242, upon detecting the storage of the medical resource 210 by the medical resource detecting member 253 and changing the value in the medical resource availability data 246 to "1" to indicate the presence of the medical resource, also performs a similar check by referring to the associated field in the hanger availability data 248. If the value contained therein is "1", indicating that the member 255 is fitted, the routine 242 terminates the process normally; if the value is "0", indicating that the member 255 is removed, the routine 242 continues the monitoring. If the result of detection by the medical resource detecting member 253 and the value in the associated field in the medical resource availability data 246 remain unchanged beyond a maximum period of time required for storage or retrieval of the medical resource 210 while the monitoring is proceeding, the medical resource detection routine 242 displays an alarm on the display 232 or sounds an alarm buzzer (not shown).

The mode of using the medical resource storage and management apparatus according to the illustrative embodiment 3-2 and its operation will be described with reference to the drawings. FIGS. 26A-26B illustrate the operation of the medical resource storage and management apparatus. FIG. 26A shows an empty condition; and FIG. 26B shows a condition in which a small medical resource is stored. FIGS. 27A-27D also illustrate the operation of the medical resource storage and management apparatus. FIG. 27A shows a condition in which one hanger member is removed from the horizontal-bridging case while the case is empty; FIG. 27B shows a condition in which a medium-sized medical resource is stored; FIG. 27C shows a condition in which a large medical resource is stored where two hanger members are removed; and FIG. 27D shows a condition in which incompatibility occurs between a result of detection by a medical resource detecting member and the configuration in the hanger availability data.

A step-by-step description will be given below, reiterating some of the explanations already given as needed. Prior to the operation of the medical resource storage and management apparatus 220, the hanger members 255 are fitted to the horizontal-bridging bar 251 in the horizontal-bridging case 250 in each storage unit provided in the storage part of the housing 222. The medical resource information configuration routine 243 in the control unit 230 is started by an operation using the keyboard 233 or the mouse 234 so as to set the identification code and the displayed name of the medical resources 210 in the respective fields in the medical resource information table 247. The manual hanger condition configuration routine 244 in the control unit 230 is started by an operation using the keyboard 233 or the mouse 234 so as to designate whether the hanger members 255 are fitted to the horizontal-bridging bar 251 of the horizontal-bridging case 250, in the respective fields in the partition availability data 48. The medical resource availability data 246 and the log data 249 are cleared by a suitable initialization routine (not shown).

This completes preparation for operation. The operating conditions of the medical resource storage and management apparatus 220 will be described specifically. The operation for storage (replenishment or return) and associated updating of data, and the operation for retrieval and associated updating of data will now be described in the cases where: the hanger members 255 are fitted in all of the hanger member fitting parts of the horizontal-bridging case 250 (see FIGS. 26A and 26B); the hanger member 255 is removed from one of the hanging member fitting parts of the horizontal-bridging case 250 (see FIGS. 27A and 27B); and the hanger member 255 is removed from every second hanger member fitting part of the horizontal-bridging case 250 (see FIGS. 27C and 27D).

When the hanger members 255 are fitted in all of the hanger member fitting parts of the horizontal-bridging case 250 (see FIGS. 26A and 26B) and when the medical resources 210 are not stored yet (see the top row of FIG. 26A), the fields in the medical resource information table 247 contain individual values (see A-E in the second row from top in FIG. 26A). The fields in the medical resource availability data 246 all contain "0", indicating the absence of medical resources (see the third row from top in FIG. 26A), and the fields in the hanger availability data 248 all contain "1", indicating that the presence of the hanger members (see the fourth row from top in FIG. 26A).

When the medical resource 210 is hung from any of the hanger members 255 in this condition (see the top row of FIG. 26B), the weight of the medical resource 210 pivotally moves the hanger member 255, causing the engaging part 256 to be lowered away from the operator (see the top row of FIG. 26B). In this process, the medical resource information table 247 and the hanger availability data 248 in the control unit 230 remain unchanged (see the second and fourth rows from top in FIG. 26B). Meanwhile, the associated field in the medical resource availability data 246 is updated by the medical resource detection routine 242 to "1", indicating the presence of a medical resource (see the third row from top in FIG. 26B). The medical resource detection routine 242 retrieves the code and name of the medical resource 210 (in the illustrated example, "C") from the medical resource information table 247. The medical resource detection routine 242 further requests the input of operator identification information. These items of information are appended to the log data 249, printed by the printer 236 and reported to the host medical management computer via the LAN 237.

For retrieval of the medical resource 210 thus stored from the medical resource storage and management apparatus 220, a retrieval instruction including the code "C" and the operator identification information are input to the control unit 230 by an operation using the barcode reader 235 or the like. This prompts the retrieval guidance routine 241 in the control unit 230 to search the medical resource information table 247 and check the associated field in the medical resource availability data 246. In this case, the value "1" is found in the field, showing that the medical resource is available, whereupon the retrieval guidance member 252 at the associated location is lighted (see the bottom row of FIG. 26B). The operator viewing this can take out the target medical resource 210 without fail.

When the medical resource 210 is taken out, the medical resource detection routine 242 updates the value entered in the associated field in the medical resource availability data 246 to "0", indicating the absence of medical resources. The information is combined with the code and name (in the illustrated example, "IC") supplied from the retrieval guidance routine 241, and with operator identification information. The combined information is appended to the log date 249, printed by the printer 236 and reported to the host medical management computer via the LAN 237. When the retrieval guidance member 252 of the associated location is turned off, the operating condition returns to a pre-storage state (see FIG. 26A).

When the hanger member 255 is removed from one of the hanger member fitting parts of the horizontal-bridging case 250 (see FIGS. 27A and 27B), the manual hanger condition configuration routine 244 is started by an operation using the keyboard 233 or the mouse 234, before storing a medical resource 210 therein (see the top row of FIG. 27A). An instruction for update is entered so as to change the value in the associated field in the hanger availability data 248 to "0" a, indicating the absence of the hanger member (see the fourth row from top in FIG. 27A). The medical resource information table 247 remains as initially configured (see the second row from top in FIG. 27A). All the fields in the medical resource availability data 246 contain "0" (see the third row from top in FIG. 27A).

In this condition, a medical resource 210 not more than twice as wide could be hung from the hanger member 255 adjacent to where the hanger member 255 is removed. When a medical resource 210 is hung from the hanger 255 (see the top row of FIG. 27B), the medical resource information table 247 and the hanger availability data 248 remain unchanged (see the second and fourth rows from top in FIG. 27B). Meanwhile, the values in the two associated fields in the medical resource availability data 246 are changed by the medical resource detection routine 242 to "1", indicating the presence of the medical resource (see the third row from top in FIG. 27B). The medical resource detection routine 242 retrieves the code and name of the medical resource 210 (in the illustrated example, "C") from the medical resource information table 247. The medical resource detection routine 242 further requests the input of operator identification information. These items of information are appended to the log data 249, printed by the printer 236 and reported to the host medical management computer via the LAN 237.

For retrieval of the medical resource 210 thus stored from the medical resource storage and management apparatus 220, a retrieval instruction including the code "C" and the operator identification information are input to the control unit 230 by an operation using the barcode reader 235 or the like. This prompts the retrieval guidance routine 241 in the control unit 230 to search the medical resource information table 247 and select the associated field (see "C" in the second row from top in FIG. 27B), and then to check the associated field in the medical resource availability data 246. In this case, the associated field contains "1", indicating that the medical resource is available, whereupon the retrieval guidance member 252 at the associated location is lighted (see the bottom row of FIG. 27B). The operator viewing this will not find any difficulty in taking out the target medical resource 210.

When the medical resource 210 is taken out, the medical resource detection routine 242 updates the value entered in the associated field in the medical resource availability data 246 to "0", indicating the absence of medical resources. The information is combined with the code and name (in the illustrated example, "C") supplied from the retrieval guidance routine 241, and with operator identification information. The combined information is appended to the log date 249, printed by the printer 236 and reported to the host medical management computer via the LAN 237. When the retrieval guidance member 252 at the associated location is turned off, the operating condition returns to a pre-storage state (see FIG. 27A).

In the case where the hanger member 255 is removed from every second hanger member fitting part of the horizontal-bridging case 250 (see FIG. 27C), the operation will easily be surmised from the above explanation so that a detailed explanation will not be repeated. It will be noted that a medical resource 210 not more than three times as wide can be stored (see the top row of FIG. 27C). In this case, the manual hanger condition configuration routine 244 is started so as to configure the values in the two associated fields in the hanger availability data 248 to "0", indicating the absence of hanger members (see the fourth row from top in FIG. 27C).

When a medical resource 210 not more than three times as wide is hung and stored (see the top row of FIG. 27C), the associated field in the medical resource availability data 246 is updated to contain "1" (see the third row from top in FIG. 27C), and relevant information is appended to the log data 249.

When a retrieval instruction including the code "C" is input to the control unit 230, the associated field in the medical resource information table 247 (see "C" in the second row from top in FIG. 27C) is selected, and then the associated field in the medical resource availability data 246 is checked. In this case, the checked field contains "1". Thereupon, the retrieval guidance member 252 at the associated location is lighted (see the bottom row of FIG. 27C). The operator viewing this will not find difficulty in taking out the target medical resource 210.

If any of the medical resource detecting members 253 provided at a location where the hanger member 255 is removed fails (see FIG. 27D), it will result in incompatibility such that the associated field in the medical resource availability data 246 contains "1" (see the third row from top in FIG. 27D), while the associated field in the hanger availability data 248 contains "0" (see the fourth row from top in FIG. 27D). If the condition of incompatibility continues beyond a maximum period of time required for storage or retrieval of the medical resource 210, the medical resource detection routine 242 issues an alarm. An alarm is also issued if the hanger member 255 is actually fitted but is indicated as being removed in error, and if the medical resource 210 is hung from that hanger member 255. This will reveal a failure or a mistake in configuration.

Illustrative Embodiment 3-3

A specific structure of the illustrative embodiment 3-3 of the medical resource storage and management apparatus according to the third embodiment will be described with reference to the associated drawings. FIGS. 28A and 28B show the structure of the medical resource storage and management apparatus. FIG. 28A is a side view of the horizontal-bridging bar and the hanger member; FIG. 28B is a front view of the horizontal-bridging bar and the hanger member; and FIG. 28C is a functional block diagram of the control unit.

The medical resource storage and management apparatus 220 according to this embodiment differs from that of the illustrative embodiments 3-1 and 3-2 in that hanger detecting members 254 are added (see FIGS. 28A and 28B) and the manual hanger condition configuration routine 244 is replaced by an automatic hanger condition configuration routine 245 (see FIG. 28C).

The hanger detecting member 254 (see FIGS. 28A and 28B) may be implemented by a mechanical switch, a reflective photosensor, a capacity sensor or the like. The hanger detecting member 254 in the illustrated example is implemented by a photosensor fitted to the horizontal-bridging bar 251 so as to face a light-emitting device 254a. As the hanger member 255 is fitted in the hanger member fitting part sandwiched between the light-emitting device 254a and the hanger detecting member 254, light emitted from the light-emitting device 254a is shielded by the hanger member 255, preventing the hanger detecting member 254 from receiving light. As the hanger member 255 is removed, the hanger detecting member 254 is capable of receiving light. The hanger detecting member 254 and the light-emitting device 254a are provided in each of the hanger member fitting parts of the horizontal-bridging case 250, so as to output a binary signal which turns on and off according to whether the hanger member 255 is fitted or removed.

The automatic hanger condition configuration routine 245 (see FIG. 28C) is started periodically and automatically by a timer, etc. or irregularly and automatically started by an interruption initiated in the event of a change in a detection signal from the hanger detecting member 254. The automatic hanger condition configuration routine 245 updates the hanger availability data 248 based on the detection by the partition hanger detecting member 254. More specifically, each time the automatic hanger condition configuration routine 245 is started, it imports the detection results from all hanger detecting members 254 or those results changed since its last import, and writes "1" or "0" in the hanger availability data 248 in association with the on-off condition.

In this case, removal of the hanger member 255 from the horizontal-bridging bar 251 of the horizontal-bridging case 250 or fitting of the hanger member 255 to the horizontal-bridging bar 251 of the horizontal-bridging case 250 need not be designated by manual input for configuration. The removal or fitting is detected by the hanger detection routine 254, and the hanger availability data 248 is automatically configured by the automatic hanger condition configuration routine 245. This will prevent incompatibility between the fitting condition of the hanger member 255 and the hanger availability data 248 from occurring due to a failure to provide an input for configuration.

The other usage modes and operations are the same as those of the illustrative embodiment 3-1 described above.

Illustrative Embodiment 3-4

Figure 29A:
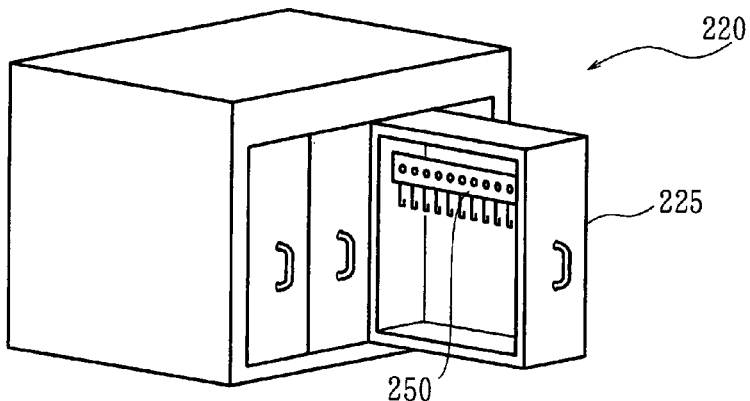
FIGS. 29A-29C show three variations to the structure according to an illustrative embodiment 3-4 of the third embodiment.
Figure 29B:
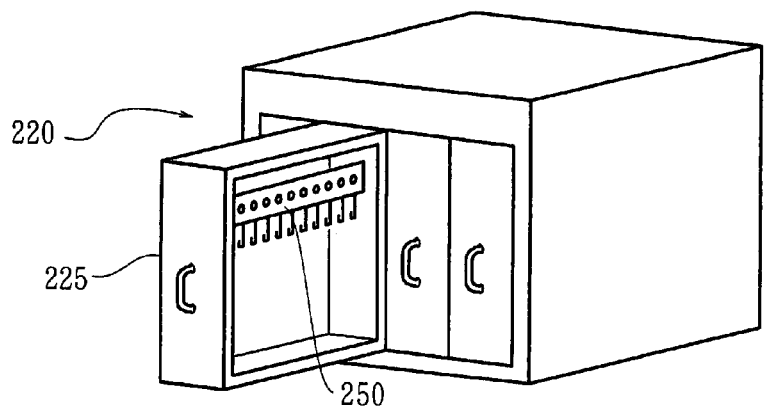
Figure 29C:
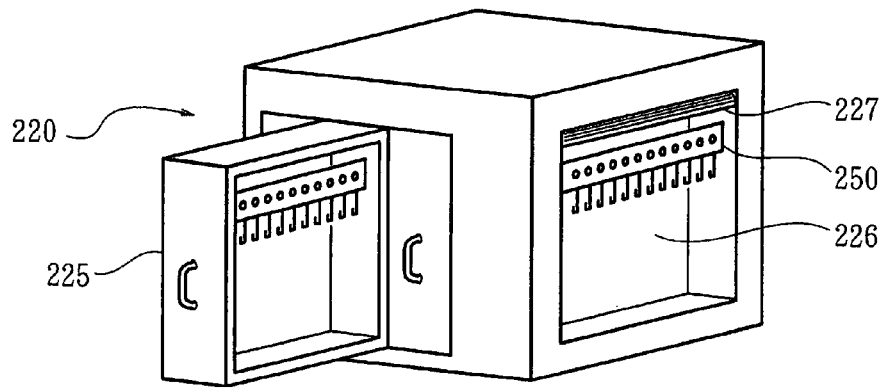

The medical resource storage and management apparatus 220 according to an illustrative embodiment 3-4 shown in perspective views of FIGS. 29A-29C differs from that of the illustrative embodiments 3-1 through 3-3 in that the storage unit is formed as a drawer unit 225 in order to accommodate the storage units, each of which is provided with the horizontal-bridging case 250, in such a manner that the space is efficiently used.

All four drawer units 225 of the medical resource storage and management apparatus 220 of FIG. 29A can be drawn toward the operator; and all four drawer units 225 of the medical resource storage and management apparatus 220 of FIG. 29B can be drawn to the left.

In the case of the of the medical resource storage and management apparatus 220 of FIG. 29C, the one unit at the front cannot be drawn. Since the horizontal-bridging box 250 is accommodated in a space 226 with an open front, which can be covered by a shutter 227, medical resources 210 that are frequently used may suitably be stored therein. The three rear units can be drawn to the left. Therefore, a large number of medical resources 210 comparable to those of the other configurations can be stored.

Illustrative Embodiment 3-5

Figure 31:
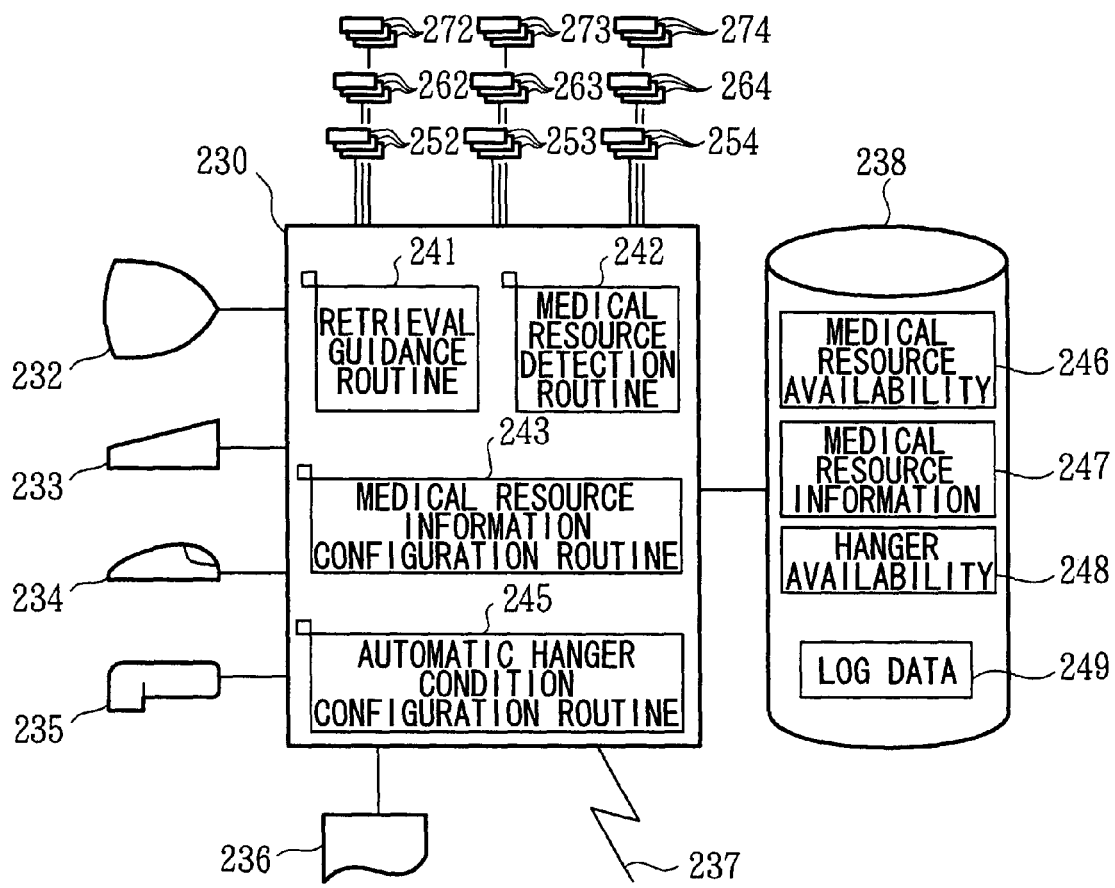
FIG. 31 is a functional block diagram of the control unit according to the illustrative embodiment 3-5.

A specific structure of the illustrative embodiment 3-5 of the medical resource storage and management apparatus according to the third embodiment will be described with reference to the associated drawings. FIGS. 30A-30C show the mechanical structure of the medical resource storage and management apparatus. FIG. 30A shows the appearance of the apparatus; FIGS. 30B and 30C are expanded perspective views of a rack and a partition member. FIG. 31 is a functional block diagram of a control unit.

The medical resource storage and management apparatus 220 according to this embodiment differs from those of the illustrative embodiments 3-1 through 3-4 in that racks 260 or racks 270, instead of the horizontal-bridging box 250, are placed in an area in the storage part (see FIG. 30A).

The rack 260 (see FIG. 30B) is implemented by a horizontally extending plate with a flat top face. Partition members 265 formed as thin plates are fitted to the top face thereof at regular or irregular pitches in a longitudinal direction (in the figure, sideways) in order to place a large number of medical resources 210 in respective partitions retrievably. Two rows of depressions 261 to fit partition members are formed on the top face of the rack 260 at regular or irregular pitches in a longitudinal direction. Two fittings 266 are formed to protrude from the bottom of each of the partition members 265. In this example, the fitting 266 is a small round bar and the depression 261 is a through hole. By inserting the fitting 266 into the depression 261, the partition member 265 is removably fitted to the depression 261 in the rack 260. A medical resource name plate 267, a connecting member 268, and a pivot shaft 269 are attached to one side (in the illustrated example. the right side) of the partition member 265.

One end of the pivot shaft 269 is secured to the partition member 265 toward the back thereof; one end of the connecting member 268 is pivotally connected to the other end of the pivot shaft 269; and the medical resource name plate 267 is secured to the other end of the connecting member 268 extending to the front. Thus, by pivotally moving the connecting member 268, the medical resource name plate 267 is moved up and down in association with the connecting member 268 in an easy-to-view space where retrieval of a medical resource takes place (more specifically, slightly in front of the front of the rack 260).

The front of the rack 260 exposed when the door 224 is opened is equipped with retrieval guidance members 262 and medical resource detecting members 263 in close proximity with each other. The retrieval guidance members 262 and the medical resource detecting members 263 are arranged in the rack 160 so as to alternate with the depressions 261 in a direction in which the depressions 261 are arranged, i.e., in the longitudinal direction of the rack 260.

When the partition member 265 is inserted into the depression 261 on the top face of the rack 260 and when the connecting member 268 and the medical resource name plate 267 are allowed to swing freely, the member 268 and the plate 267 are lowered under their own weight until the connecting member 268 comes into contact with the top face of the rack 260 and the medical resource name plate 267 in front thereof is lowered to the front of the rack 260. This shields the retrieval guidance member 262 and the medical resource detecting member 263 at the front of the rack 160 from view. The medical resource name plate 267, as it is lowered in response to the retrieval of the medical resource from the associated location, shields the associated retrieval guidance member 262 from view.

When the medical resource name plate 267 is raised so as to store a medical resource 210 on the rack 260, the connecting member 268 rests on the medical resource 210 instead of on the rack 260, causing the medical resource name plate 267 to remain at an elevated position. The medical resource name plate 267 is located above the associated retrieval guidance member 262, revealing the retrieval guidance member 262 and the medical resource detecting member 263 at the front of the rack 260 for view. The medical resource detecting member 263 provided at the front of the rack 260 does not sense the medical resource 210 placed on the rack 260 but senses the medical resource name plate 267 immediately in front of the rack 260. Due to this and the fact that the medical resource name plate 267 is moved up and down in response to the storage/retrieval of the medical resource 210 as a result of interference between the connecting member 268 and the medical resource 210, the medical resource detecting member 263 indirectly detects whether or not the medical resource 210 is placed by detecting whether the medical resource name plate 267 is raised or lowered.

In order to detect the medical resource name plate 267 for indirect detection of the medical resource 210, each of the medical resource detecting members 263 is implemented by a mechanical switch, a reflective photosensor, a capacity sensor or the like, so as to output a binary signal which turns on and off according to whether the medical resource name plate 267 is raised or lowered. Like the medical resource detecting member 253, the medical resource detecting member 263 may be implemented by a magnetic sensor.

In order to visually guide a user to the location of placement of the medical resource 210 to be retrieved, a miniature bulb, a light emitting diode or the like that can be turned on and off is used as the retrieval guidance member 262 as in the case of the retrieval guidance member 252.

The rack 270 (see FIG. 30C) is for inserting a partition member 275. The partition member 275 is configured such that the medical resource name plate 267, the connecting member 268 and the pivot shaft 269 are omitted from the partition member 265. Therefore, instead of the medical resource detecting members 263, medical resource detecting members 273 are provided on the top face of the rack 270 to directly detect whether the medical resource 210 is placed by sensing the bottom of the medical resource 210. A depression 271, a retrieval guidance member 272, a partition detecting member 274 and a fitting 276 are of the same structure or function as the depression 261, the retrieval guidance member 262, the partition detecting member 264 and the fitting 266, respectively, although they differ in the destination of installation.

The control unit 230 is expanded in its capabilities so that access to the retrieval guidance member 262, the medical resource detecting member 263, the partition detecting member 264, the retrieval guidance member 272 and the medical resource detecting member 273, as well as to the retrieval guidance member 252, the medical resource detecting member 253 and the hanger member detecting member 254, is enabled. The routines 241-245 and the data 246-249 of the control unit 230 are also altered to reflect the structure by, for example, fine-tuning the definition of addresses storing the components or the size of tables.

The basic usage mode and operation are the same as those in the illustrative embodiments already described. For detection of the medical resource 210, the rack 270 is designed for direct detection, while the rack 260 and the horizontal-bridging case 250 are designed for indirect detection. A difference in the scheme employed to store medical resources 210 is that the rack 270 and the rack 260 are designed so that medical resources 210 are placed thereon, while the horizontal-bridging case 250 is designed to hang medical resources 210. As a mixture of three types is provided in the storage part of the medical resource storage and management apparatus 220, medical resources 210 of different types can be stored for accurate and automatic management. The medical resource 210 may be packaged, bundled or contained in a case or a container. Suitable for storage on the rack 270 of direct detection type are those relatively stable in form that can stand on its own while in storage (for example, those contained in a container with the shape of a CD case or a rectangular box). Examples of such medical resources are tube sets for injection/infusion, small and short catheters and sets of articles including the same.

Suitable for storage on the rack 260 of indirect detection and placement type are those relatively thick and unstable in form that do not stand on its own while in storage (for example, those contained in a round, hard case, those in a blister package or those in a soft package). Examples of such medical resources are those for respirator medicine such as filters, resources for medical operations, and resources for artificial replacement.

Suitable for storage on the horizontal-bridging case 250 of indirect detection and hanger type are those that are long and relatively unstable in form, those that are light or thin but heavy enough to be detected by being hung. Examples of such medical resources are long sterilized catheters of not less than 0.5 cm, long tubes, or resources for medical operations that are light or thin.

Illustrative Embodiment 3-6

Figure 32:
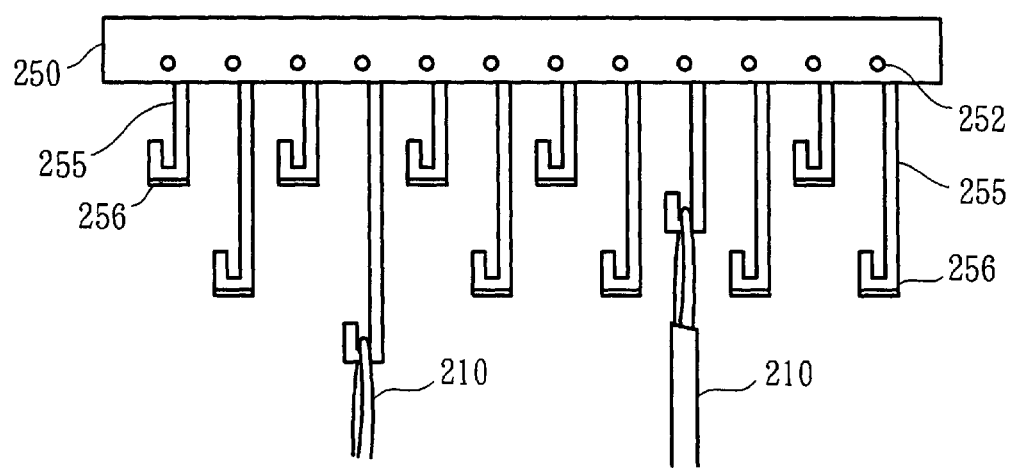
FIG. 32 is a front view of the horizontal-bridging case and the hanger member according to an illustrative embodiment 3-6 of the third embodiment.

The medical resource storage and management apparatus according to the illustrative embodiment 3-6 shown in the front view FIG. 32 of the horizontal-bridging case and the hanger member differs from those of the other embodiments in that hanger members 255 are not uniform in length such that the engaging parts 256 are alternately high and low. Alternatively, the hanger members 255 are of irregular length (not shown).

Weights may be appropriately attached to or detached from the weight part 257 to achieve proper balance so that extremely thin or extremely light objects (e.g., postcard-sized drug packing paper weighing 3 g/5 g/10 g per piece) can be detected when hung from the hanger member 255.

Illustrative Embodiment 3-7

Figure 34A:
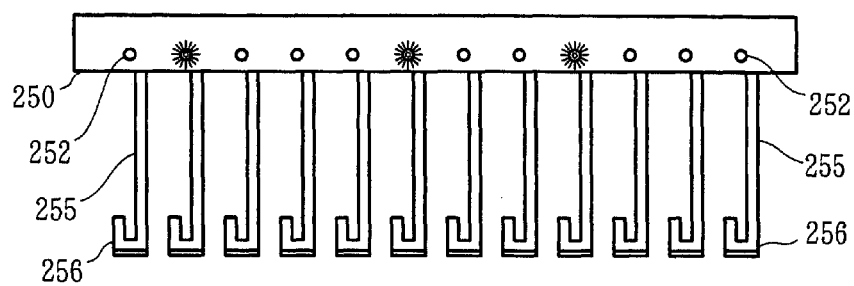
FIGS. 34A-34C also show conditions of replenishment of medical resources according to the illustrative embodiment 3-7.
Figure 34B:
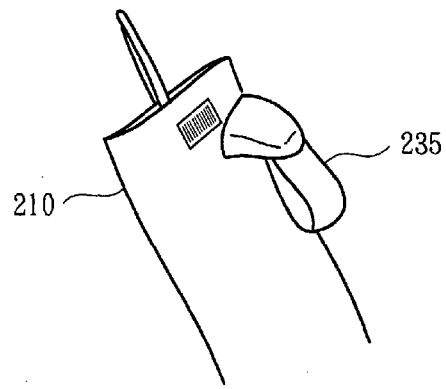
Figure 34C:
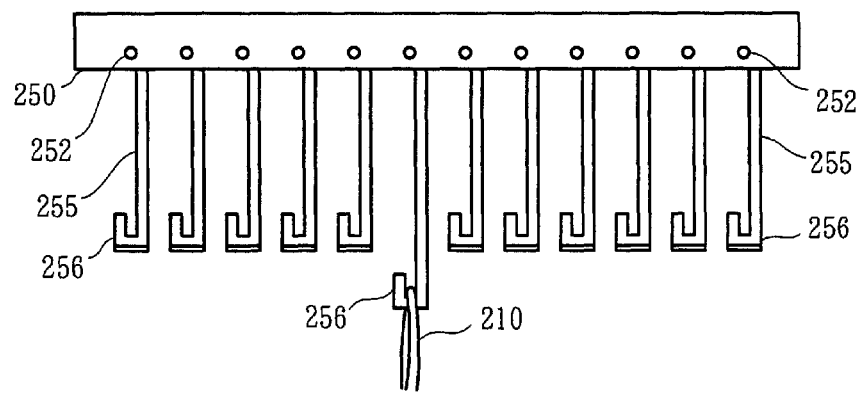

An illustrative embodiment 3-7 of the medical resource storage and management apparatus according to the third embodiment will be described with reference to the associated drawings. FIGS. 33A-33C show conditions of replenishment of medical resources. FIGS. 33A-33C are screen shots. FIGS. 34A-34C also show conditions of replenishment of medical resources. FIG. 34A is a perspective view of the rack fitted with partition members; FIG. 34B is a perspective view showing how identification information is read from a medical resource; and FIG. 34C is a perspective view of the rack storing a medical resource.

This medical resource storage and management apparatus differs from the aforementioned embodiments of the apparatus in that guidance is displayed in replenishing as well as in retrieving a medical resource, and that the display 232, the keyboard 233 and the mouse 234 are implemented as a touch panel 239.

In a normal operation (see FIG. 33A), information on the medical resource 210 retrieved from the medical resource storage and management apparatus is arranged chronologically and displayed on the touch panel 239 on a real time basis. A direct finger-touch selection of any the items 239a displayed on the screen causes relevant details to be displayed for review. Guidance for replenishment is also displayed in accordance with a specific operation for selection.

More specifically, selecting a replenishment button 239b displayed on the screen while in a normal operation (see FIG. 33A) switches the display of the touch panel 239 to a replenishment mode selection screen (see FIG. 33B). By entering information on an operator who replenishes a medical resource, selection of a "registered" button 239c and/or a "new registration" button is available. By selecting the "new registration" button, the operator can register the code (code No.) identifying the medical resource 210 that can be stored in a location of storage (address) and the name for screen display (medical resource name). If the registration is complete, selection of the "registered" button 239c is enabled. The "registered" button 239c is selected when the display of guidance for replenishment is desired.

The selection switches to the screen of the touch panel 239 showing a list of registered resources (see FIG. 33C). After confirming that a location for storage is shown as being empty, the operator scrolls the screen as necessary by using a scroll button 239f so as to directly select a field 239d for a relevant medical resource with the finger.

If the number of empty locations 239e designated as capable of storing the medical resource (e.g., catheter in an elongated hermetically sealed package) is three (i.e., three packages can be stored), the three retrieval guidance members 252 in the empty locations are all lighted because, in this example, the retrieval guidance member 252 also serves as a replenishment destination guidance member (see FIG. 34A).

The operator proceeds to scan the barcode (identification information) assigned to the medical resource 210 about to be stored, by using the barcode reader 235 (see FIG. 34B) for checking, before hanging the medical resource 210 from the hanger member 255 at one of the locations in the horizontal-bridging case 250 lighted by the guidance member. This turns off all of the guidance members (see FIG. 34C), and the log data, indicating the identity of the operator who replenished the resource, the identity of the resource replenished and the location of replenishment, is recorded with a time stamp.

Thus, guidance display is provided properly and a job record is maintained properly for replenishment. In this example, the selection of the field 239d on the screen showing a list of registered resources, and the scanning of the identification information assigned to the medical resource 210 by using the barcode reader 235 are both performed to reinforce checking. However, only one of the tasks may be performed since it serves the purpose of identifying a medical resource 210. In another alternative, the operator may be allowed to complete both tasks, but guidance display guiding the operator to the destination of replenishment may not require completion of both tasks but may be immediately provided upon completion of one of the tasks.

Other Points of Note

In the third embodiment, the hanger member fitting part is implemented by the oblong hole 250a. The hanger member fitting part may be formed in other manners so long as it is capable of defining the position of fitting the hanger member 255 in the longitudinal direction of the horizontal-bridging member, while allowing pivotal movement of the hanger. For example, the hanger member fitting part may be formed as a slit defined by partition bars provided on the underside of the horizontal-bridging case 250, bearings provided in series in the horizontal-bridging bar 251, spacers, or retainers.

In the third embodiment, the control unit 230 is accommodated in the electric equipment 221. Alternatively, the control unit 230 may be placed outside the housing 222. The input and output means of the control unit 230 may not be restricted to the display 232, the keyboard 233 and the like mentioned above and may be implemented by a touch panel or a mobile information terminal.

In the third embodiment, the medical resource detection routine 242 is designed to associate the on and off states of the result of detection by the medical resource detecting member 253 with the storage and retrieval of the medical resource 210, respectively. It is easy to expand the capabilities to automatically manage the return of a medical resource 210 once taken out and not used. For example, a determination may be made that a resource is not replenished but returned, if retrieval and storage are conducted successively in a short time span, or if a resource is stored in one of the modes of operation introduced in the control unit 230 in which mode an action of retrieval is restricted. In this case, information indicating the return may suitably be appended to the log data 249 or other output data. In addition to data storage and output, provisions may also be made for management of expiration dates, stock control, preparation of drug history and inspection.

FOURTH EMBODIMENT

A fourth embodiment of the present invention relates to a medical resource storage and management apparatus which arranges and stores medical resources and also performs management of storage status, and, more particularly, to a medical resource storage and management apparatus which automatically manages availability of medical resources at each location of storage and also guides a user for retrieval.

A summary of the fourth embodiment will be given.

A first medical resource storage and management apparatus according to the fourth embodiment comprises: a rack in which a series of depressions for insertion of partition members are formed so that a large number of medical resources are retrievably placed in respective partitions; partition members which are removably inserted into the depressions; medical resource detecting members which are arranged on the rack so as to alternate with the depressions in a direction in which the depressions are arranged, and each of which detects whether or not a medical resource is placed; retrieval guidance members for visual guidance which are arranged on the rack so as to alternate with the depressions in a direction in which the depressions are arranged; and a control unit which manages the storage status of the medical resources, based on the detection by the medical resource detecting members and which operates one of the retrieval guidance members in response to an input designating retrieval, wherein a name plate support member is provided so as to be in parallel to the rack and behind the partition members, and a medical resource name plate for visual guidance is attached to the name plate support member via a detachable connecting member such that the connecting member is moved up and down depending on whether a medical resource is placed and as a result of interference between the connecting member and the medical resource, and that the medical resource name plate is moved in association with the connecting member in a space where retrieval of a medical resource takes place, and wherein the medical resource detecting member indirectly detects whether or not a medical resource is placed by detecting whether the medical resource name plate is raised or lowered.

A second medical resource storage and management apparatus according to the fourth embodiment is a modification to the first medical resource storage and management apparatus, wherein the medical resource name plate, when elevated in association with the placement of a medical resource in the associated location, is located above the retrieval guidance member in the associated location, and the medical resource name plate, when lowered in response to the retrieval of the medical resource from the associated location, shields the retrieval guidance member in the associated location from view.

A third medical resource storage and management apparatus according to the fourth embodiment is a modification to the first medical resource storage and management apparatus or the second medical resource storage and management apparatus, wherein the control unit allows providing an input for configuration to designate whether the partition member is inserted into the depression, and, based on the configuration, the control unit collectively processes the medical resource detecting members and the retrieval guidance members identified as being located on both sides of the depression from which the partition member is removed.

A fourth medical resource storage and management apparatus according to the fourth embodiment is a modification to the first medical resource storage and management apparatus or the second medical resource storage and management apparatus and further comprises a partition detecting member which detects whether the partition member is inserted into the depression, wherein, based on detection by the partition, the control unit collectively processes the medical resource detecting members and the retrieval guidance members identified as being located on both sides of the depression from which the partition member is removed.

A fifth medical resource storage and management apparatus according to the fourth embodiment is a modification to the third medical resource storage and management apparatus or the fourth medical resource storage and management apparatus, wherein the control unit issues an alarm if the results of detection by the medical resource detecting members in a block to be processed collectively continue to fail to match beyond a predetermined period of time.

In the first medical resource storage and management apparatus, the medical resources are arranged on the rack such that the locations of storage are partitioned by the partition members. Therefore, it is easy to retrievably align and store medical resources without accommodating them in cassettes and to prevent disarrangement of the medical resources stored and resultant disorganization.

Since the medical resource detecting member and the retrieval guidance member are placed in respective partitions on the rack, it is possible to detect whether each medical resource is stored for automatic management and to properly guide a user to the location of storage of the medical resource to be retrieved.

Since the partition member can be removed from the rack and the location of insertion is formed as a depression, a relatively large medical resource can be placed where the partition member is removed.

Since the medical resource name plate is provided in each partitioned block, i.e., in each location of storage, and in an easy-to-view space where retrieval of a medical resource takes place, the product name or the like of the medical resource to be stored can be identified at a glance.

When the size of a location of storage is changed by attaching or detaching a partition member, the medical resource name plate has to be replaced by that of a proper size. Since the medical resource name plate is fitted to the name plate support member via the connecting member and the connecting member is detachable from the name plate support member, the medical resource name plate can be replaced easily.

Since the name plate support member is provided so as to be in parallel to the rack and behind the partition members and since the medical resource name plate is located where retrieval of a medical supply takes place, the connecting member which connects both automatically interferes with the medical supply above the rack.

As a medical resource is stored or taken out, the medical resource name plate is moved up or down in association with the connecting member. The medical resource detecting member indirectly and automatically detects whether or not the medical resource is placed by detecting whether the medical resource name plate is raised or lowered. Accordingly, availability of the medical resource is visually confirmed even if the medical resource name plate is in front of the medical resource. This makes it possible to indirectly detect a medical resource even when it is difficult to detect, for example, the bottom thereof due to the form or material of the medical resource.

Thus, even with a simple apparatus in which racks are partitioned and medical resources are arranged, a large variety of large and small medical resources can be stored in the least confusing manner. Even those resources that are not suitable for direct detection can also be detected properly for automatic management.

Thus, the first medical resource storage and management apparatus provides capability for easily and properly storing and retrieving medical resources, and automatically and accurately keeping track of storage status.

In the second medical resource storage and management apparatus, the retrieval guidance member is viewable when the medical resource is stored, and is shielded from view when the medical resource is taken out. With this, the availability of the medical resource can be visually identified not only by viewing the up and down movement of the medial resource name plate but also by seeing whether or not the retrieval guidance member is shielded from view. Moreover, the likelihood of misidentifying the operating status of the retrieval guidance member is reduced.

In the third medical resource storage and management apparatus, not only the partition member is detachable but also whether or not the partition member is inserted is designated by providing an input for configuration in the control unit. In this way, the control unit can collectively process medical resource detecting members and retrieval guidance members. Therefore, a user will not be at a loss or face any inconvenience in handling and management even if there are multiple medical resource detecting members or retrieval guidance members where a single, large medical resource resides.

Thus, even with a simple apparatus in which racks are partitioned and medical resources are arranged, a large variety of large and small medical resources can be easily stored for automatic management by means of attachment and detachment of partition members and by an input of associated information for configuration.

According to the fourth medical resource storage and management apparatus, convenience is enhanced by additionally ensuring that whether or not the partition member is inserted is automatically detected and reflected in the control.

According to the firth medical resource storage and management apparatus, reliability is enhanced while avoiding an increase in hardware cost, by taking advantage of redundancy of results of detection by multiple medical resource detecting members in a single block so as to detect an error accordingly.

Specific embodiments of the medical resource storage and management apparatus according to the fourth embodiment will be described using illustrative embodiments 4-1 through 4-7.

The illustrative embodiment 4-1 shown in FIGS. 35A-39D is an embodiment of the first, third and fifth medical resource storage and management apparatuses mentioned above. The illustrative embodiment 4-2 shown in FIGS. 40A-40B is an embodiment of the fourth medical resource storage and management apparatus mentioned above. The illustrative embodiment 4-3 shown in FIGS. 41A-41C, the illustrative embodiment 4-4 shown in FIGS. 42A-42C, the illustrative embodiment 4-5 shown in FIGS. 43A-44C, the illustrative embodiment 4-6 shown in FIGS. 45A-46D, and the illustrative embodiment 4-7 shown in FIGS. 47A-48 are variations.

In the illustration, fasteners such as bolts, connectors such as hinges, electronic circuits such as drivers are omitted for brevity, highlighting those elements necessary to explain the embodiment and related elements.

Illustrative Embodiment 4-1

Figure 36A:
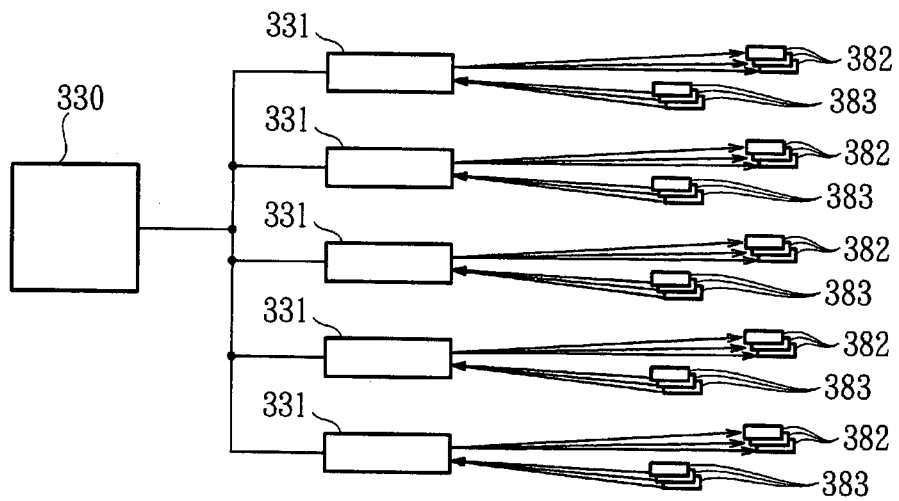
Figure 36B:
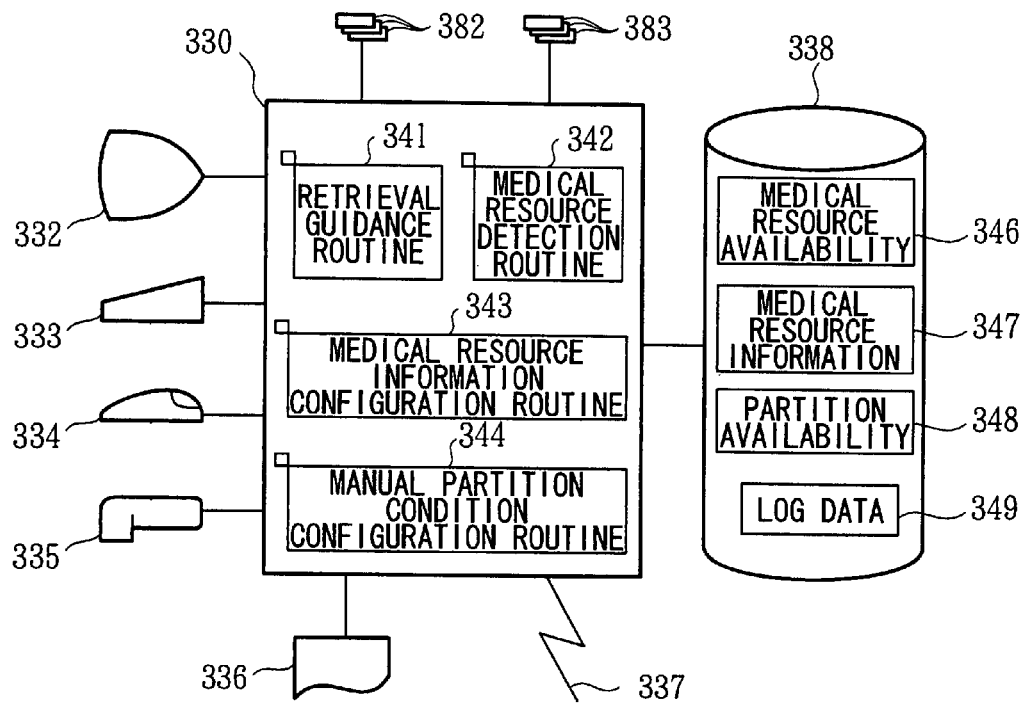

A specific structure of the illustrative embodiment 4-1 of the medical resource storage and management apparatus according to the fourth embodiment will be described with reference to the associated drawings. FIGS. 35A-35D show the mechanical structure of the medical resource storage and management apparatus. FIG. 35A is a front view showing a door closed; FIG. 35B is a front view showing the door opened; FIG. 35C is a perspective view of a rack and partition members; and FIG. 35D is a perspective view showing the appearance of the rack in which the partition members are fitted. FIGS. 36A and 36B show the schematic structure of a control unit. FIG. 36A is a schematic block diagram showing the connection between the control unit and retrieval guidance members; and FIG. 36B is a functional block diagram of the control unit. FIGS. 37A-37C show the data structure of the control unit. FIG. 37A relates to a medical resource information table; FIG. 37B relates to medical resource availability data; and FIG. 37C relates to partition availability data.

A medical resource storage and management apparatus 320 is provided with a housing 322 a large portion of which is for storage and a part of which comprises electric equipment 321. The electric equipment 321 stores a control unit 330 and a power supply unit etc. (not shown). The front of the storage part of the housing 322 is provided with an openable door 324 with a handle 323. The door 324 may be implemented by a shutter or the like, or may be omitted. Inside the storage part exposed when the door 324 is opened is provided a rack 380. Although there may be only one rack 380, an orthodox apparatus would comprise multiple tiers. The pitch between the racks 380 may be selectable. The rack 380 is implemented by a horizontally extending plate with a flat top face. Partition members 385 formed as thin plates are fitted to the top face thereof at regular or irregular pitches in a longitudinal direction (in the figure, sideways) in order to place a large number of medical resources in respective partitions retrievably.

Two rows of depressions 381 to fit partition members are formed on the top face of the rack 380 (see FIGS. 35C and 35D) at regular or irregular pitches in a longitudinal direction (in the figures, sideways). Two fittings 386 are formed at the lower end of each of the partition members 385. In this example, the fitting 386 is a small round bar and the depression 381 is a through hole. By inserting the fitting 386 into the depression 381, the partition member 385 is removably fitted to the depression 381 in the rack 380.

A name plate support member 389 is provided above the rack 380 so as to be in parallel to the rack 380 and behind the partition member 385 as it is fitted to the rack 380. In the illustrated example, the name plate support member 389 is a round bar or shaft extending straight. The ends of the member 389 is supported by support posts 389b provided to stand on the rack 380 so that the member 389 can be accommodated in or removed from the housing 322 along with the rack 380. Locking groove 389a are formed at appropriate locations in the name plate support member 389 at a fine pitch, or at least at a pitch determined by the pitch at which the depressions 381 are provided. Each of the locking groove 389a is formed by engraving the entire circumference of the name plate support member 389 to a regular width and depth.

A connecting member 388 is removably fitted to the name plate support member 388. More specifically, the connecting member 388 is of a form that would be made by bending a plate of a width slightly smaller than the pitch at which the depressions 381 are provided. A locking piece 388a lockable with the locking groove 389a of the name plate support member 389 is provided at the rear end of the connecting member 388. A medical resource name plate 387 is secured to the other end of the connecting member 388 extending forward. As the locking piece 388a is engaged with the locking groove 389a, slight play therebetween allows the connecting member 388 to rotate in both directions around the name plate support member 389 as a pivot axis or an axis of rotation. Meanwhile, travel of the connecting member 388 in the longitudinal direction of the name plate support member 389 is restricted. Thus, by pivotally moving the connecting member 388, the medical resource name plate 387 is moved up and down in association with the connecting member 388 in an easy-to-view space where retrieval of a medical resource takes place (more specifically, slightly in front of the front of the rack 380).

The front of the rack 380 exposed when the door 324 is opened is equipped with retrieval guidance members 382 and medical resource detecting members 383 in close proximity with each other. The retrieval guidance members 382 and the medical resource detecting members 383 are arranged in the rack 380 so as to alternate with the depressions 381 in a direction in which the depressions 381 are arranged, i.e., in the longitudinal direction of the rack 380. When the partition member 385 is inserted into the depression 381 on the top face of the rack 380, when the connecting member 388, with a width adapted to the interval between adjacent partition members 385, is fitted to the name plate support member 389, and when the connecting member 388 and the medical resource name plate 387 are allowed to swing freely, the member 388 and the plate 387 are lowered under their own weight until the connecting member 388 comes into contact with the top face of the rack 380 and the medical resource name plate 387 in front thereof is lowered to the front of the rack 380. This shields the retrieval guidance member 382 and the medical resource detecting member 383 at the front of the rack 380 from view (see FIG. 35D). The medical resource name plate 387, as it is lowered in response to the retrieval of the medical resource from the associated location, shields the associated retrieval guidance member 382 from view.

When the medical resource name plate 387 is raised so as to store a medical resource 310 on the rack 380, the connecting member 388 rests on the medical resource 310 instead of on the rack 380, causing the medical resource name plate 387 to remain at an elevated position. The medical resource name plate 387 is located above the associated retrieval guidance member 382, revealing the retrieval guidance member 382 and the medical resource detecting member 383 at the front of the rack 380 for view. The medical resource detecting member 383 provided at the front of the rack 380 does not sense the medical resource 310 placed on the rack 380 but senses the medical resource name plate 387 immediately in front of the rack 380. Due to this and the fact that the medical resource name plate 387 is moved up and down in response to the storage/retrieval of the medical resource 310 as a result of interference between the connecting member 388 and the medical resource 310, the medical resource detecting member 383 indirectly detects whether or not the medical resource 310 is placed by detecting whether the medical resource name plate 387 is raised or lowered.

In order to detect the medical resource name plate 387 for indirect detection of the medical resource 310, each of the medical resource detecting members 383 is implemented by a mechanical switch, a reflective photosensor, a capacity sensor or the like, so as to output a binary signal which turns on and off according to whether the medical resource name plate 387 is raised or lowered.

In order to visually guide a user to the location of placement of the medical resource 310 to be retrieved, a miniature bulb, a light emitting diode or the like that can be turned on and off is used as the retrieval guidance member 382.

The control unit 330 (see FIG. 36A) comprises a programmable controller such as a personal computer and a sequencer. A local area network (LAN) connects the control unit 330 to the retrieval guidance members 382 and the medical resource detecting members 383 via, for example, a rack controller 331. Alternatively, the control unit 330, the retrieval guidance members 382 and the medical resource detecting members 383 are in direct star connection (not shown). The connection enables retrieving detection results of the medical resource detecting members 383 and controlling the lighting of the retrieval guidance members 382.

The control unit 330 (see FIG. 36B) is provided with a display 332 for screen display, a keyboard 333 for key entry, a mouse 334 for inputting instructions etc. on a screen, a bar code reader 335 for reading identification information, a printer 336 for delivering printouts, an interface for a local area network (LAN) 337 which is responsible for communication with a prescription order-entry system etc., and a hard disk 338 as a secondary storage.

A retrieval guidance routine 341, a medical resource detection routine 342, a medical resource information configuration routine 343, and a manual partition condition configuration routine 344 are installed in the control unit 330, as programs for managing the storage status of the medical resources, based on the detection by the medical resource detecting members 383, and for operating selected retrieval guidance members 382 in response to an input designating retrieval. The hard disk 338 stores medical resource availability data 346, a medical resource information table 347, partition availability data 348, and log data 349, which are divided into individual files or are unified in an appropriate database. The figures show (see FIGS. 37A-37B) the data 346, the table 347 and the data 348 maintained in a table format. Each table comprises a 5×21 matrix, in association with the fact that the racks 380 form five tiers and the maximum number of partitions in each rack 380 (i.e., the maximum number of the partition members 385, the retrieval guidance members 382 and the medical resource detecting members 383) is twenty one.

Each field in the medical resource information table 347 (see FIG. 37A) contains an identification code and a name displayed on a screen for the medical resource 310 which is stored or can be stored in an associated location. "1" or "0" is written in the medical resource availability data 346 (see FIG. 37B), "1", indicating that the medical resource 310 is stored in the associated location, and "0", indicating that no medical resources 310 are stored. "1" or "0" is written in the partition availability data 348 (see FIG. 37C), "1", indicating that the partition member 385 is inserted, and "0", indicating that the partition member 385 is removed from the associated location. The medical resource information table 347 should be configured at least once before operating the apparatus for the first time since its installation. Therefore, the table is usually initialized upon starting the apparatus and updated when the operation is stopped. The partition availability data 348 is also initialized so that the insertion condition of the partition member 385 is reflected before the initial operation. Configuration inputs for update are also provided when the partition member 385 is attached or detached. The medical resource availability data 346 is all cleared by initialization before the initial operation, and are subsequently updated with each storage or retrieval of the medical resource 310.

The medical resource information configuration routine 343 is started by the keyboard 333 or mouse 334 operation. When dumping from a medicine master file located on a host computer via the LAN-337 is dictated in an environment where such an action is possible, the medical resource information configuration routine 343 dumps the data. The routine 343 also allows the user to set the code or name of the medical resource 310 in the medical resource information table 347 by selecting an item using the mouse 334 or entering data using the keyboard 333, while viewing screen display on the display 332.

The manual partition condition configuration routine 344 is also started by the keyboard 333 or mouse 334 operation. The routine 344 allows the user to provide an input for configuration to designate in the partition availability data 348 whether the partition member 385 is inserted into the depression 381 in the rack 380, by selecting an item or toggling using the mouse 334 or the keyboard 333, while viewing screen display on the display 332.

The medical resource detection routine 342 is started periodically and automatically by a timer, etc. or irregularly and automatically started by an interruption initiated in the event of a change in a detection signal from the medical resource detecting member 383. The medical resource detection routine 342 manages the storage status of the medical resources 310 based on the detection by the medical resource detecting members 383. More specifically, each time the medical resource detection routine 342 is started, it imports the detection results from all medical resource detecting members 383 or those results changed since its last import, and writes "1" or "0" in the medical resource availability data 346 in association with the on-off condition. When the detection result from the medical resource detecting member 383 undergoes an on/off change and the storage or retrieval of the medical resource 310 is detected accordingly, the medical resource detection routine 342 appends information indicating the detection to the log data 349 with a time stamp, causes the printer 336 to deliver a printout which carries the name listed in the associated field in the medical resource information table 347, and submits a report to a host medical management computer via the LAN 337.

The retrieval guidance routine 341 is started when the code of the medical resource 310 or a prescription ID number is entered by allowing the barcode reader 335 to scan the code or the ID, or by using the keyboard 333 or the mouse 334, in order to operate one of the retrieval guidance members 382 in response to an input designating retrieval. The retrieval guidance routine 341 searches the medical resource information table 347 to determine the location of storage of the medical resource 310 designated to be retrieved via the reading or via the mouse or keyboard operation, and lights the medical resource detecting member 383 at the associated location. The medical resource detection routine 342 is responsible for turning the medical resource detecting member 383 off when the retrieval of the medical resource 310 at the associated location is detected.

The retrieval guidance routine 341 and the medical resource detection routine 342 learn whether or not the partition member 385 is inserted, and collectively process the medical resource detecting members 383 and the retrieval guidance members 382 identified as being located on both sides of the depression 381 from which the partition member 385 is removed. If the results of detection by the medical resource detecting members 383 in the block to be processed collectively continue to fail to match beyond a predetermined period of time, an alarm is issued.

More specifically, the retrieval guidance routine 341 refers to the medical resource availability data 346 to check whether the partition member 385 is inserted to the left or right of a location of storage, before lighting the medical resource detecting member 383. If "0" is entered left or right, indicating that the partition member 385 there is removed, the associated, adjacent retrieval guidance member 382 is also lighted. In association with this, the medical resource detection routine 342 performs a similar check by referring to the medical resource availability data 346 in turning off the retrieval guidance member 382, and turns off the retrieval guidance members 382 in the block at a time.

The medical resource detection routine 342 also performs, upon detecting the storage or retrieval of the medical resource 310, a similar check by referring to the medical resource availability data 346 before changing the value of the medical resource availability data 346. If a series of adjacent partitions are to be processed collectively as a single block, the medical resource detection routine 342 examines whether the values from the medical resource detecting members 383 in the single block match. If the values match, the routine 342 terminates the process normally; if the values do not match, the routine 342 continues the monitoring. If the values from the medical resource detecting members 383 in a block continue to fail to match beyond a maximum period of time required for storage or retrieval of the medical resource 310 while the monitoring is proceeding, the medical resource detection routine 342 displays an alarm on the display 332 or sounds an alarm buzzer (not shown).

In order to help the routines 341 and 342 to collectively process a block where the partition member 385 is removed, the manual partition condition configuration routine 344 configures, in designating in the partition availability data 348 that the partition member 385 is removed, the associated fields in the medical resource information table 347 such that field values (i.e., codes and names maintained) corresponding to the locations of storage identified as being located on both sides of the depression 381 from which the partition member 385 is removed, match. The manual partition condition configuration routine 344 returns the field values to their original values in designating in the partition availability data 348 that the partition member 385 is inserted.

In addition, the control unit 330 acquires operator identification information by requesting an operator to input operator identification information each time an operation is carried out. Alternatively, the control unit 330 acquires operator identification information input by an operator in advance of an operation. The control unit 330 also stores, in the log data 349, related information then collected by automatic detection etc. together with a time stamp. The data stored is also output via the LAN 337. The process is performed in the manual partition condition configuration routine 344 as well as in the retrieval guidance routine 341.

The mode of using the medical resource storage and management apparatus according to the illustrative embodiment 4-1 and its operation will be described with reference to the drawings. FIGS. 38A-4B illustrate the operation of the medical resource storage and management apparatus. FIG. 38A shows an empty condition; and FIG. 38B shows a condition in which a small medical resource is stored. FIGS. 39A-39D also illustrate the operation of the medical resource storage and management apparatus. FIG. 39A shows a condition in which one partition member is removed from the rack while the partition is empty; FIG. 39B shows a condition in which a medium-sized medical resource is stored; FIG. 39C shows a condition in which a large medical resource is stored where two partition members are removed; and FIG. 39D shows a condition in which detection results from medical resource detecting members do not match.

Prior to the operation of the medical resource storage and management apparatus 320, a desired number of racks 380 are set in the storage part of the housing 322, the partition members 385 are inserted into the depressions 381 in each rack 380, and the connecting members 388 with the respective medical resource name plates 387 are fitted to the name plate support member 389. The medical resource information configuration routine 343 in the control unit 330 is started by an operation using the keyboard 333 or the mouse 334 so as to set the identification code and the displayed name of the medical resources 310 in the respective fields in the medical resource information table 347. In this process, it is also favorable to perform a comparison check with the product name of the medical resource currently written in the medical resource name plate 387. The manual partition condition configuration routine 344 in the control unit 330 is started by an operation using the keyboard 333 or the mouse 334 so as to designate whether the partition members 385 are inserted into the depressions 381 in the rack 380, in the respective fields in the partition availability data 348. The medical resource availability data 346 and the log data 349 are cleared by a suitable initialization routine (not shown).

This completes preparation for operation. The operating conditions of the medical resource storage and management apparatus 320 will be described specifically. The operation for storage (replenishment or return) and associated updating of data, and the operation for retrieval and associated updating of data will now be described in the cases where: the partition members 385 are inserted into all of the depressions 381 (FIGS. 38A and 38B); a partition member 385 is removed from one of the depressions 381 (see FIGS. 39A and 39B); and two partition members 385 are removed from two adjacent depressions 381 (FIGS. 39C and 39D).

When the partition members 385 are inserted into all of the depressions 381 (see FIGS. 38A and 38B) and when the medical resources 310 are not stored yet (see the top row of FIG. 38A), the fields in the medical resource information table 347 contain individual values (see A-E in the second row from top in FIG. 38A, where A-E denote different codes and names). The fields in the medical resource availability data 346 all contain "0", indicating the absence of medical resources (see the third row from top in FIG. 38A), and the fields in the partition availability data 348 all contain "1", indicating that the presence of the partition members (see the fourth row from top in FIG. 38A).

When the medical resource 310 is stored on the rack 380 in this condition (see the top row of FIG. 38B), only the medical resource name plate 387 at the location of storage of the medical resource 310 is elevated above the rack 380, revealing the retrieval guidance member 382 for view. In this process, the medical resource information table 347 and the partition availability data 348 remain unchanged (see the second and fourth rows from top in FIG. 38B). Meanwhile, the associated field in the medical resource availability data 346 is updated by the medical resource detection routine 342 to "1", indicating the presence of a medical resource (see the third row from top in FIG. 38B). The medical resource detection routine 342 retrieves the code and name of the medical resource 310 (in the illustrated example, "C") from the medical resource information table 347. The medical resource detection routine 342 further requests the input of operator identification information. These items of information are appended to the log data 349, printed by the printer 336 and reported to the host medical management computer via the LAN 337.

For retrieval of the medical resource 310 thus stored from the medical resource storage and management apparatus 320, a retrieval instruction including the code "C" and the operator identification information are input to the control unit 330 by an operation using the barcode reader 335 or the like. This prompts the retrieval guidance routine 341 in the control unit 230 to search the medical resource information table 347 and check the associated field in the medical resource availability data 346. In this case, the value "1" is found in the field, showing that the medical resource is available, whereupon the retrieval guidance member 382 at the associated location is lighted (see the bottom row of FIG. 38B). The operator viewing this can take out the target medical resource 310 without fail.

When the medical resource 310 is taken out, the medical resource name plate 387 at the associated location is lowered to the front of the rack 380, shielding the retrieval guidance member 382 and the medical resource detecting member 383 from view. In this process, the medical resource detection routine 342 updates the value entered in the associated field in the medical resource availability data 346 to "0", indicating the absence of medical resources. The information is combined with the code and name (in the illustrated example, "C") supplied from the retrieval guidance routine 341, and with operator identification information. The combined information is appended to the log date 349, printed by the printer 336 and reported to the host medical management computer via the LAN 337. When the retrieval guidance member 382 of the associated location is turned off, the operating condition returns to a pre-storage state (see FIG. 38A).

When a partition member 385 is removed from one of the depressions 381, (see FIGS. 39A and 39B), the medical resource name plates 387 and the connecting members 388 adjacent to the location of removal are removed from the name plate support member 389 so that the medical resource name plate 387 and the connecting member 388 twice as wide are set there. The manual partition condition configuration routine 344 is started by an operation using the keyboard 333 or the mouse 334, before storing a medical resource 310 therein (see the top row of FIG. 39A). An instruction for update is entered so as to change the value in the associated field in the partition availability data 348 to "0", indicating the absence of the partition member (see the fourth row from top in FIG. 39A). This prompts the manual partition condition configuration routine 344 to automatically update the medical resource information table 347 so that the values in the fields, corresponding to the locations of storage located on both sides of the recess 381 from which the partition member 385 is removed, match (see "BB" in the second row from top in FIG. 39A). All the fields in the medical resource availability data 346 contain "0" (see the third row from top in FIG. 39A).

When a medical resource 310 not more than twice as wide is stored in a part on the rack from which the partition member 385 is removed (see the top row of FIG. 39B), the medical resource information table 347 and the partition availability data 348 remain unchanged (see the second and fourth rows from top in FIG. 39B). Meanwhile, the values in the two associated fields in the medical resource availability data 346 are changed by the medical resource detection routine 342 to "1", indicating the presence of the medical resource (see the third row from top in FIG. 39B). The medical resource detection routine 342 retrieves the code and name of the medical resource 310 (in the illustrated example, "B") from the medical resource information table 347. The medical resource detection routine 342 further requests the input of operator identification information. These items of information are appended to the log data 349, printed by the printer 336 and reported to the host medical management computer via the LAN 337.

For retrieval of the medical resource 310 thus stored from the medical resource storage and management apparatus 320, a retrieval instruction including the code "B" and the operator identification information is input to the control unit 330 by an operation using the barcode reader 335 or the like. This prompts the retrieval guidance routine 341 in the control unit 330 to search the medical resource information table 347 and select the two adjacent fields (see "BB" in the second row from top in FIG. 39B), and then to check the two associated fields in the medical resource availability data 346. In this case, the two fields contain "1", indicating that the medical resource is available, whereupon the two adjacent retrieval guidance members 382 at the associated locations are lighted at a time (see the bottom row of FIG. 39B). The operator viewing this will not find any difficulty in taking out the target medical resource 310.

When the wide medical resource 310 is taken out, the wide medical resource name plate 387 at the associated location is lowered to the front of the rack 380, shielding two pairs of retrieval guidance member 382 and medical resource detecting member 383 from view. In this process, the medical resource detection routine 342 updates the value entered in the associated field in the medical resource availability data 346 to "0", indicating the absence of medical resources. The information is combined with the code and name (in the illustrated example, "B") supplied from the retrieval guidance routine 341, and with operator identification information. The combined information is appended to the log date 149, printed by the printer 136 and reported to the host medical management computer via the LAN 137. When the retrieval guidance members 382 at the associated locations are turned off at a time, the operating condition returns to a pre-storage state (see FIG. 39A).

In the case where the two partition members 385 are removed from the adjacent two depressions 381 (see FIG. 39C), the operation will easily be surmised from the above explanation so that a detailed explanation will not be repeated. It will be noted that a medical resource 310 not more than three times as wide can be stored (see the top row of FIG. 39C). When the medical resource name plate 387 and the connecting member 388 not more than three times as wide are set, and when the manual partition condition configuration routine 344 is started so as to update the values in the two associated fields in the partition availability data 348 to "0", indicating the absence of a partition member (see the fourth row from top in FIG. 39C), the values in the three associated fields in the medical resource information table 347 are made to match (see "BBB" in the second row from top in FIG. 39C).

When a medical resource 310 not more than three times as wide is stored (see the top row of FIG. 39C), each of the three associated fields in the medical resource availability data 346 is updated to contain "1" (see the third row from top in FIG. 39C), and relevant information is appended to the log data 349.

When a retrieval instruction including the code "B" is input to the control unit 330, the three associated fields in the medical resource information table 347 (see "BBB" in the second row from top in FIG. 39C) are selected, and then the three associated fields in the medical resource availability data 346 are checked. In this case, the three fields contain "1", showing a match. Thereupon, the three adjacent retrieval guidance members 382 at the associated locations are lighted at a time (see the bottom row of FIG. 39C). The operator viewing this will not find difficulty in taking out the target medical resource 310.

If one of the three medical resource detecting members 383 expected to detect the medical resource name plate 387 three times as wide at a time fails (see FIG. 39D), two of the three associated fields in the medical resource availability data 346 are changed to "1", while one field continues to store "0" (see the third row from top in FIG. 39D). This results in incompatibility between the medical resource availability data 346 and the partition availability data 348 as checked by the medical resource detection routine 342, in respect of the three fields to be collectively processed. If the condition of incompatibility (failure to match) continues beyond a maximum period of time required for storage or retrieval of the medical resource 310, the medical resource detection routine 342 issues an alarm, revealing that there is a failure.

Illustrative Embodiment 4-2

A specific structure of the illustrative embodiment 4-2 of the medical resource storage and management apparatus according to the fourth embodiment will be described with reference to the associated drawings. FIGS. 40A and 40B show the structure of the medical resource storage and management apparatus 320. FIG. 40A is an expanded perspective view of the rack 380 and the partition members 385; and FIG. 40B is a functional block diagram of the control unit 30.

The medical resource storage and management apparatus 320 according to this embodiment differs from that of the illustrative embodiment 4-1 in that partition detecting members 384 are added and the manual partition condition configuration routine 344 is replaced by an automatic partition condition configuration routine 345.

The partition detecting member 384 (see FIG. 40A) is implemented by a mechanical switch, a reflective photosensor, a capacity sensor or the like. The partition detecting member 384 is embedded in the top face of the rack 380 to face upward so as to sense the lower end face of the partition member 385 inserted into the depression 381 on the top face of the rack 380, and is placed at respective locations of insertion of the partition members 385 in the rack 380. In this example, the partition detecting member 384 is provided between a pair of depressions 381 arranged in a width direction in order to detect whether the partition member 385 is inserted in its location. The partition member 384 outputs a binary signal which turns on and off according to whether the partition member 385 is available.

The automatic partition condition configuration routine 345 (see FIG. 40B) is started periodically and automatically by a timer, etc. or irregularly and automatically started by an interruption initiated in the event of a change in a detection signal from the partition detecting member 384. The automatic partition condition configuration routine 345 updates the partition availability data 348 based on the detection by the partition detecting member 384. More specifically, each time the automatic partition condition configuration routine 345 is started, it imports the detection results from all partition detecting members 384 or those results changed since its last import, and writes "1" or "0" in the partition availability data 348 in association with the on-off condition. The other functions (e.g., automatic updating of the medical resource information table 347) are the same as those of the manual partition condition configuration routine 344.

This arrangement allows the control unit 330 to collectively process a block of medical resource detecting members 383 and retrieval guidance members 382 identified as being located on both sides of the depression 381 from which the partition member 385 is removed, in accordance with the detection by the partition detecting members 384.

The form of the fitting 386 of the partition member 385 and the depression 381 in the rack 380 is also slightly modified. More specifically, the fitting 386 and the depression 381 are curved instead of being straight. By inserting the partition member 385 in the rack 380 and then pulling and locking the partition member 385, the partition member 385 is prevented from being disengaged.

In this case, removal of the partition member 385 from the depression 381 on the rack 380 or insertion of the partition member 385 into the depression 381 in the rack 380 need not be designated by manual input for configuration. The removal or insertion is detected by the partition detection routine 384, and the partition availability data 348 is automatically configured by the automatic partition condition configuration routine 345. This will prevent incompatibility between the insertion condition of the partition member 385 and the partition availability data 348 from occurring due to a failure to provide an input for configuration.

The other usage modes and operations are the same as those of the illustrative embodiment 4-1 described above.

Illustrative Embodiment 4-3

The partition member 385 and the rack 380 shown in a perspective view of FIG. 41A differ from those of the illustrative embodiments 4-1 and 4-2 in that the partition member 385 is formed by bending a round bar instead of as a plate, and that the depression 381 is a bottomed hole instead of a through hole. The partition detecting member 384 is embedded in the rack 380 so as to face a light-emitting device 384a across the depression 381. Whether or not the partition member 385 is inserted is detected depending on whether light emitted from the light-emitting device 384a is shielded by the fitting 386 at the end of the partition member 385 or received by the partition detecting member 384.

The partition member 385 and the rack 380 shown in a perspective view of FIG. 41B differ from those of the illustrative embodiments 4-1 and 4-2 in that the longitudinal cross section of the partition member 385 is of an inverted T shape, and that the depression 381 is formed as a groove. In this case, the partition member 385 is inserted into the depression 381 by slipping the fitting 386 at the lower end of the partition member 385 into the depression 381.

The partition member 385 and the rack 380 shown in a perspective view of FIG. 41C differ from those of the illustrative embodiments 4-1 and 4-2 in that the partition member 385 is formed by bending a round bar instead of as a plate, and that the depression 381 is formed as a notch or bore formed at the front and back of the rack 380 instead of on the top face thereof. In this case, the partition 385 is inserted into the depression 381 and secured and stabilized therein by a snapping force, by extending the fittings 386 at both ends of the partition member 385 before inserting them in the depression 381.

Illustrative Embodiment 4-4

A specific structure of the illustrative embodiment 4-4 of the medical resource storage and management apparatus according to the fourth embodiment will be described with reference to the associated drawings. FIGS. 42A-42C show the structure of the medical resource storage and management apparatus 320. FIG. 42A is a front view showing the door 324 opened; FIG. 42B is an expanded perspective view of a rack 370 and partition members 375; and FIG. 42C is a functional block diagram of the control unit 330.

The medical resource storage and management apparatus 320 according to this embodiment differs from those of the illustrative embodiments 4-1 through 4-3 in that the racks 370, instead of the racks 380, are placed in an area in the storage part (see FIG. 42A).

The rack 370 is configured such that the name plate support member 389 and the support posts 389b are omitted from the rack 380. The medical resource name plate 387 and the connecting member 388 are also omitted (see FIG. 42B). Therefore, instead of the medical resource detecting members 383, medical resource detecting members 373 are provided on the top face of the rack 370 to directly detect whether the medical resource 310 is placed by sensing the bottom of the medical resource 310. A depression 371, a retrieval guidance member 372, a partition detecting member 374, a partition member 375 and a fitting 376 are of the same structure or function as the depression 381, the retrieval guidance member 382, the partition detecting member 384, the partition member 385 and the fitting 386, respectively, although they differ in the destination of installation.

The control unit 330 is expanded in its capabilities so that access to the retrieval guidance member 372, the medical resource detecting member 373 and the partition detecting member 374, as well as to the retrieval guidance member 382, the medical resource detecting member 383 and the partition detecting member 384, is enabled. The routines 341-345 and the data 346-349 of the control unit 330 are also altered to reflect the structure by, for example, fine-tuning the definition of addresses storing the components or the size of tables.

The basic usage mode and operation are the same as those in the illustrative embodiments already described. For detection of the medical resource 310, the rack 370 is designed for direct detection, while the rack 380 is designed for indirect detection. As a mixture of two types is provided in the storage part of the medical resource storage and management apparatus 320, medical resources 310 of different types can be stored for accurate and automatic management.

The medical resource 310 may be packaged, bundled or contained in a case or a container. Suitable for storage on the rack 370 of direct detection type are those relatively stable in form that can stand on its own while in storage (for example, those contained in a container with the shape of a CD case or a rectangular box). Examples of such medical resources are tube sets for injection/infusion, small and short-length catheters and sets of articles including the same.

Suitable for storage on the rack 380 of indirect detection type are those relatively thick and unstable in form that do not stand on its own while in storage (for example, those contained in a round, hard case, those in a blister package or those in a soft package). Examples of such medical resources are those for respirator medicine such as filters, resources for medical operations, and resources for artificial replacement.

Illustrative Embodiment 4-5

An illustrative embodiment 4-5 of the medical resource storage and management apparatus according to the fourth embodiment will be described with reference to the associated drawings. FIGS. 43A-43C show conditions of replenishment of medical resources. FIGS. 43A-43C are screen shots. FIGS. 44A-44C also show conditions of replenishment of medical resources. FIG. 44A is a perspective view of the rack fitted with partition members; FIG. 44B is a perspective view showing how identification information is read from a medical resource; and FIG. 44C is a perspective view of the rack storing a medical resource.

This medical resource storage and management apparatus differs from the aforementioned embodiments of the apparatus in that guidance is displayed in replenishing as well as in retrieving a medical resource, that the display 332, the keyboard 333 and the mouse 334 are implemented as a touch panel 339, and that, even in an empty condition, the retrieval guidance member 382 is viewable and not shielded from view by the medical resource name plate 387.

In a normal operation (see FIG. 43A), information on the medical resource 310 retrieved from the medical resource storage and management apparatus is arranged chronologically and displayed on the touch panel 339 on a real time basis. A direct finger-touch selection of any of the items 339a displayed on the screen causes relevant details to be displayed for review. Guidance for replenishment is also displayed in accordance with a specific operation for selection.

More specifically, selecting a replenishment button 339b displayed on the screen while in a normal operation (see FIG. 43A) switches the display of the touch panel 339 to a replenishment mode selection screen (see FIG. 43B). By entering information on an operator who replenishes a medical resource, selection of a "registered" button 339c and/or a "new registration" button is available. By selecting the "new registration" button, the operator can register the code (code No.) identifying the medical resource 310 that can be stored in a location of storage (address) and the name for screen display (medical resource name). If the registration is complete, selection of the "registered" button 339c is enabled. The "registered" button 339c is selected if the display of guidance for replenishment is desired.

The selection switches to the screen of the touch panel 339 showing a list of registered resources (see FIG. 43C). After confirming that a location for storage is shown as being empty, the operator scrolls the screen as necessary by using a scroll button 339f so as to directly select a field 339d for a relevant medical resource with the finger.

If the number of empty locations 339e designated as capable of storing the medical resource (e.g., a filter in a bag) is three (i.e., three bags can be stored), the three retrieval guidance members 382 in the empty locations are all lighted because, in this example, the retrieval guidance member 382 also serves as a replenishment destination guidance member (see FIG. 44A).

The operator proceeds to scan the barcode (identification information) assigned to the medical resource 310 about to be stored, by using the barcode reader 335 (see FIG. 44B) for checking, before storing the medical resource 310 in one of the locations on the rack 380 lighted by the guidance member. This turns off all of the guidance members (see FIG. 44C), and the log data, indicating the identity of the operator who replenished the resource, the identity of the resource replenished and the location of replenishment, is recorded with a time stamp.

Thus, guidance display is provided properly and a job record is maintained properly for replenishment. In this example, the selection of the field 339d on the screen showing a list of registered resources, and the scanning of the identification information assigned to the medical resource 310 by using the barcode reader 335 are both performed to reinforce checking. However, only one of the tasks may be performed since it serves the purpose of identifying a medical resource 310. In another alternative, the operator may be allowed to complete both tasks, but guidance display guiding the operator to the destination of replenishment may not require completion of both tasks but may be immediately provided upon completion of one of the tasks.

Illustrative Embodiment 4-6

An illustrative embodiment 4-6 of the medical resource storage and management apparatus according to the fourth embodiment will be described with reference to the associated drawings. FIGS. 45A-45C show the mechanical structure of the medical resource storage and management apparatus. FIG. 45A is a front view showing a door opened; FIG. 45B is a perspective view of a rack and partition members; and FIG. 45C is a perspective view showing the appearance of the rack in which the partition members are fitted. FIGS. 46A-46D show the mechanical structure of a part of the medical resource storage and management apparatus. FIG. 46A is a front view of the horizontal-bridging case and the hanger member; FIGS. 46B and 46C are left side views of the horizontal-bridging case and the hanger member showing the cross section of the horizontal-bridging member; and FIG. 46D is a schematic functional block diagram of the control unit.

The medical resource storage and management apparatus 320 according to this embodiment differs from that of the illustrative embodiment 4-4 of FIGS. 42A-42C in that a rack 360 and a horizontal-bridging case 350, as well as the racks 380 and 370, are placed in an area in the storage part (see FIG. 45A).

The rack 360 (see FIGS. 45B and 45C) is similar to the racks 370 and 380 in that a partition member 365 is removably fitted. The rack 360 differs from the rack 370 in that the rack is provided with a medical name plate 367 supported by a connecting member 368 so as to be swingable up and down. The rack 360 differs from the rack 380 in that the connecting member 368 is fitted to the partition member 365 via a pivot shaft 369.

The rack 360 is implemented by a horizontally extending plate with a flat top face. Partition members 365 formed as thin plates are fitted to the top face thereof at regular or irregular pitches in a longitudinal direction (in the figure, sideways) in order to place a large number of medical resources 310 in respective partitions retrievably. Two rows of depressions 361 to fit partition members are formed on the top face of the rack 360 at regular or irregular pitches in a longitudinal direction. Two fittings 366 are formed to protrude from the bottom of each of the partition members 365. In this example, the fitting 366 is a small round bar and the depression 361 is a through hole. By inserting the fitting 366 into the depression 361, the partition member 365 is removably fitted to the depression 361 in the rack 360. A medical resource name plate 367, a connecting member 368, and a pivot shaft 369 are attached to one side (in the illustrated example, the right side) of the partition member 365.

One end of the pivot shaft 369 is secured to the partition member 365 toward the back thereof; one end of the connecting member 368 is pivotally connected to the other end of the pivot shaft 369; and the medical resource name plate 367 is secured to the other end of the connecting member 368 extending to the front. Thus, by pivotally moving the connecting member 368, the medical resource name plate 367 is moved up and down in association with the connecting member 368 in an easy-to-view space where retrieval of a medical resource takes place (more specifically, slightly in front of the front of the rack 360). In the illustrated example, the connecting member 368 is formed as a rod. Alternatively, like the connecting member 388, the connecting member 368 may be formed as a plate.

The front of the rack 360 exposed when the door 324 is opened is equipped with retrieval guidance members 362 and medical resource detecting members 363 in close proximity with each other. The retrieval guidance members 362 and the medical resource detecting members 363 are arranged in the rack 360 so as to alternate with the depressions 361 in a direction in which the depressions 361 are arranged, i.e., in the longitudinal direction of the rack 360.

When the partition member 365 is inserted into the depression 361 on the top face of the rack 360 and when the connecting member 368 and the medical resource name plate 367 are allowed to make a pivotal movement freely, the member 368 and the plate 367 are lowered under their own weight until the connecting member 368 comes into contact with the top face of the rack 360 and the medical resource name plate 367 in front thereof is lowered to the front of the rack 360. This shields the retrieval guidance member 362 and the medical resource detecting member 363 at the front of the rack 360 from view. The medical resource name plate 367, as it is lowered in response to the retrieval of the medical resource from the associated location, shields the associated retrieval guidance member 362 from view.

When the medical resource name plate 367 is raised so as to store a medical resource 310 on the rack 360, the connecting member 368 rests on the medical resource 310 instead of on the rack 360, causing the medical resource name plate 367 to remain at an elevated position. The medical resource name plate 367 is located above the associated retrieval guidance member 362, revealing the retrieval guidance member 362 and the medical resource detecting member 363 at the front of the rack 360 for view. The medical resource detecting member 363 provided at the front of the rack 360 does not sense the medical resource 310 placed on the rack 360 but senses the medical resource name plate 367 immediately in front of the rack 360. Due to this and the fact that the medical resource name plate 367 is moved up and down in response to the storage/retrieval of the medical resource 310 as a result of interference between the connecting member 368 and the medical resource 310, the medical resource detecting member 363 indirectly detects whether or not the medical resource 310 is placed by detecting whether the medical resource name plate 367 is raised or lowered.

In order to detect the medical resource name plate 367 for indirect detection of the medical resource 310, each of the medical resource detecting members 363 is implemented by a mechanical switch, a reflective photosensor, a capacity sensor or the like, so as to output a binary signal which turns on and off according to whether the medical resource name plate 367 is raised or lowered.

In order to visually guide a user to the location of placement of the medical resource 310 to be retrieved, a miniature bulb, a light emitting diode or the like that can be turned on and off is used as the retrieval guidance member 362.

The horizontal-bridging case 350 (horizontal-bridging member) (see FIG. 45A and FIGS. 46A-46C) comprises a rectangular cylinder. A series of arm-shaped hanger members 355 are hung from the lower part or the bottom of the case 350 in a longitudinal direction (in FIG. 46A, sideways) at regular or irregular pitches so as to arrange a large number of medical resources by retrievably hanging them. In order to hang and store relatively longer medical resources 310 by the hanger members 355, hanging storage space is secured below the horizontal-bridging case 350. In the illustrated example, there is only one horizontal-bridging case 350 provided so as to extend horizontally above the hanging storage space.

In the hollow interior of the horizontal-bridging case 350 (see FIGS. 46A-46C) is housed a horizontal-bridging bar 351 (horizontal-bridging member) extending in a longitudinal direction. The series of hanger members 355 are fitted to the horizontal-bridging bar 351. More specifically, the hanger member 355 comprises a bar member substantially T-shaped in side view. The lower end of an vertical bar is bent into a hook, forming an engaging part 356. One end of a top side bar is formed into a weight part 357 by bulging or by being provided with a weight. The other end of the top side bar is provided with a permanent magnet and is formed into a target of detection 358.

A through hole through which the horizontal-bridging bar 351 can be movably inserted is formed in the middle of the top side bar toward the weight part 357. Alternatively, a bearing is fitted thereto. By introducing the bar 351 through the hole or the bearing, the hanger member 355 is supported by the bar 351 so as to be pivotable around the bar 351. The center of gravitation of the hanger member 355 is displaced from the pivot center toward the weight part 357. Therefore, at the time of retrieving a medical resource, the pivotal movement of the hanger member 355 causes the engaging part 356 to be elevated and moved toward an operator (see FIG. 46B). At the time of hanging a medical resource, the pivotal movement causes the engaging part 356 engaged with a medical resource 310 to be lowered and moved toward the back (see FIG. 46C).

On the underside of the horizontal-bridging case 350 (see FIGS. 46B and 46C), a series of oblong holes 350a (hanger member fitting parts) are formed in a longitudinal direction at regular or irregular pitches. As the hanger member 355 is movably introduced into the oblong hole 350a, the hanger member 355 is allowed to move back and forth freely, while substantially being prevented from moving sideways in a front view (see FIG. 46A). The provision maintains the hanger members 355 in an aligned state (lined up in a longitudinal direction), without inhibiting the pivotal movement thereof.

Further (see FIGS. 46B and 46C), a medical resource detecting member 353 is provided on the interior face of the horizontal-bridging case 350 where the target of detection 358 leaves or comes into contact as a result of the pivotal movement of the hanger member 355. A retrieval guidance member 352 is provided on the front of the horizontal-bridging case 350 which becomes viewable when the door 324 is opened. The retrieval guidance member 352 and the medical resource detecting member 353 are provided in the horizontal-bridging case 350 so as to be alignment with the oblong hole 350a and are provided for each hanger member 355, i.e., at each location of storage.

In this example, the medical resource detecting member 353 is implemented by a sensor using a Hall device that senses the magnetic field of the magnet of the target of detection 358, in order to detect whether the medical resource 310 is hung in accordance with the pivotal movement of the hanger member 355. The hanger member 355 is pivotally moved as the medical resource 310 is hung or removed therefrom. As the target of detection 358 leaves or comes into contact with the medical resource detecting member 353 as a result of the pivotal movement, the medical resource detecting member 353 outputs a binary signal which turns on and off. The medical resource detecting member 353 may be implemented by other devices so long as detection in association with the pivotal movement is enabled. For example, the medical resource detecting member 353 may be implemented by a mechanical switch, a reflective photosensor, a capacity sensor.

In order to visually guide a user to the location of placement of the medical resource 310 to be retrieved, a miniature bulb, a light emitting diode or the like that can be turned on and off is used as the retrieval guidance member 352.

The control unit 330 (see FIG. 46D) is expanded in its capabilities so that access to the retrieval guidance member 362, the medical resource detecting member 363, the partition detecting member 364, the retrieval guidance member 352, the medical resource detecting member 353 and the hanger member detecting member 354, as well as to the retrieval guidance member 382, the medical resource detecting member 383, the partition detecting member 384, the retrieval guidance member 372, the medical resource detecting member 373 and the partition detecting member 374, is enabled. The routines 341-345 and the data 346-349 of the control unit 330 are also altered to reflect the structure by, for example, fine-tuning the definition of addresses storing the components or the size of tables.

The basic usage mode and operation are the same as those in the illustrative embodiments already described. For detection of the medical resource 310, the rack 370 is designed for direct detection, while the racks 380, 360 and the horizontal-bridging case 350 are designed for indirect detection. A difference in the scheme employed to store medical resources 310 is that the racks 380, 370 and the rack 360 are designed so that medical resources 310 are placed thereon, while the horizontal-bridging case 350 is designed to hang medical resources 310. As a mixture of three types is provided in the storage part of the medical resource storage and management apparatus 320, medical resources 310 of different types can be stored for accurate and automatic management. The medical resource 310 may be packaged, bundled or contained in a case or a container. Suitable for storage on the rack 370 of direct detection type are those relatively stable in form that can stand on its own while in storage (for example, those contained in a container with the shape of a CD case or a rectangular box). Examples of such medical resources are tube sets for injection/infusion, small and short-length catheters and sets of articles including the same.

Suitable for storage on the rack 380 and the rack 360 of indirect detection and placement type are those relatively thick and unstable in form that do not stand on its own while in storage (for example, those contained in a round, hard case, those in a blister package or those in a soft package). Examples of such medical resources are those for respirator medicine such as filters, resources for medical operations, and resources for artificial replacement.

Suitable for storage on the horizontal-bridging case 350 of indirect detection and hanger type are those that are long and relatively unstable in form, those that are light or thin but heavy enough to be detected by being hung. Examples of such medical resources are long sterilized catheters of not less than 0.5 cm, long tubes, or resources for medical operations that are light or thin.

Illustrative Embodiment 4-7

An illustrative embodiment 4-7 of the medical resource storage and management apparatus according to the fourth embodiment will be described with reference to the associated drawings. FIGS. 47A and 47B show the structure of the medical resource storage and management apparatus. FIG. 47A is a left side view showing a partial cross section of the rack, the medical resource name plate and the connecting member; and FIG. 47B is a perspective view showing an essential part of the rack, the medical resource name plate and the connecting member. FIG. 48 shows perspective views of some of the medical resources suitable for storage.

A medical resource name plate 387, a connecting member 388 and a locking piece 388a (see FIGS. 47A and 47B) are integrally formed. For example, they are formed as an injection-molded product of transparent resin. A label sticker 387a adhesively attached to the front of the medical resource name plate 387 is detected by the medical resource detecting member 383. If it is not desired to allow the label sticker 387a to conceal the retrieval guidance member 382 when the medical resource name plate 387 is lowered, it is easily ensured that the retrieval guidance member 382 is always viewable by cutting a part of the label sticker 387a.

Since the connecting member 388 is transparent, the medical resource 310 is visually identifiable from diagonally above even in a state where the connecting member 388 rests on the medical resource 310.

Suitable for storage in the rack 380 of this type (see FIG. 48) are a 0.1 L or 0.5 L glass bottle 310a, a 0.05 L plastic bottle 310b, a cylindrical object 310b resembling a film case for a camera, an artificial substitute 310d of a complex form, a box (not shown) and a blister pack (PTP package) (not shown).

Other Points of Note

The locking piece 388a of the fourth embodiment is described as being locked into the locking groove 389a of the name plate support member 389. Alternatively, the connecting member 388 may be locked into the name plate support member 389 using an attachment fitted so as to be slidable in the longitudinal direction of the name plate support member 389 and to be capable of locking the connecting member 388. For prevention of the detachment of the locking piece 388a from the destination of locking as the connecting member 388 makes a pivotal movement, a spring clip or a retainer may be attached to the locking piece 388a.

In the fourth embodiment, the control unit 330 is accommodated in the electric equipment 321. Alternatively, the control unit 330 may be placed outside the housing 322. The input and output means of the control unit 330 may not be restricted to the display 332, the keyboard 333 and the like mentioned above and may be implemented by a touch panel or a mobile information terminal.

In the fourth embodiment, the medical resource detection routine 342 is designed to associate the on and off states of the result of detection by the medical resource detecting member 383 with the storage and retrieval of the medical resource 310, respectively. It is easy to expand the capabilities to automatically manage the return of a medical resource 310 once taken out and not used. For example, a determination may be made that a resource is not replenished but returned, if retrieval and storage are conducted successively in a short time span, or if a resource is stored in one of the modes of operation introduced in the control unit 330 in which mode an action of retrieval is restricted. In this case, information indicating the return may suitably be appended to the log data 349 or other output data. In addition to data storage and output, provisions may also be made for management of expiration dates, stock control, preparation of drug history and inspection.

Some forms of medical resources require that the medical resource be contained in an atypical package with irregular surfaces. Some medical resources do not fit into a soft package, while other medical resources need be contained in a container due, for example, to their lightness or small size. All of these types of resources may be stored in the rack provided with the above-described function, using a detachable lid (case with a name plate).

FIFTH EMBODIMENT

A fifth embodiment of the present invention relates to a medical resource storage and management apparatus which arranges and stores medical resources and also performs management of storage status, and, more particularly, to a medical resource storage and management apparatus which automatically manages availability of medical resources at each location of storage and also guides a user for retrieval.

A summary of the fifth embodiment will be given.

A first medical resource storage and management apparatus according to the fifth embodiment comprises: a rack plate in which are provided a series of medical resource detecting members for detecting whether or not a medical resource is placed on the rack plate and a series of retrieval guidance members for visual guidance; a control unit which manages the storage status of the medical resources, based on the detection by the medical resource detecting members and which operates one of the retrieval guidance members in response to an input designating retrieval; a storage case which is bounded at the bottom, sides and back thereof by a fixed plate, in which a movable medical resource name plate is provided in front of the case, and in which a connecting member extending backward from the medical resource name plate is adapted to make a vertical pivotal movement about the rear end thereof, wherein the medical resource name plate is moved up and down as a result of interference between the medical resource stored in the storage case and the connecting member, and whether the medical resource is placed or not is indirectly detected by detecting the up and down movement of the medical resource name plate, based on the fact that the up and down movement of the medical resource name plate causes the plate to enter or leave a range of detection by the medical resource detecting member in a state in which the storage case is placed on the rack plate.

A second medical resource storage and management apparatus according to the fifth embodiment is a modification to the first medical resource storage and management apparatus wherein the storage case stores the medical resource on the connecting member, and the up and down movement of the medical resource name plate are associated with the nonavailability and availability of the medical resource, respectively.

A third medical resource storage and management apparatus according to the fifth embodiment is a modification to the first medical resource storage and management apparatus wherein a series of case detecting member for detecting the storage case are arranged on the top face of the rack plate in association with the medical resource detecting members and the retrieval guidance members, wherein the storage case stores the medical resource underneath the connecting member, and wherein the up and down movement of the medical resource name plate are associated with the availability and nonavailability of the medical resource, respectively.

A fourth medical resource storage and management apparatus according to the fifth embodiment is a modification to the first through third medical resource storage and management apparatuses, wherein the control unit allows manual or automatic data configuration to indicate whether medical resource detecting members and retrieval guidance members are partitioned, and wherein the control unit collectively processes the medical resource detecting members and the retrieval guidance members identified as being located on both sides of the location configured as not being partitioned.

A fifth medical resource storage and management apparatus according to the fifth embodiment is a modification to the fourth medical resource storage and management apparatus, wherein the control unit issues an alarm if the results of detection by the medical resource detecting members in a block to be processed collectively continue to fail to match beyond a predetermined period of time.

In the first medical resource storage and management apparatus, medical resources are arranged on the rack. The medical resources are not aligned and stored in the cassettes but accommodated in the storage cases which is bounded at the bottom, sides and back thereof by a fixed plate, and in which a movable medical resource name plate is provided in front of the case. By arranging the storage cases on the rack, the medical resources are aligned and stored as a result of the alignment and storage of the storage cases. Therefore, it is easy to retrievably align and store medical resources without accommodating them in cassettes and to prevent disarrangement of the medical resources stored and resultant disorganization. Since the medical resource name plate is provided in each storage case and in an easy-to-view front space where retrieval of a medical resource takes place, the product name or the like of the medical resource to be stored can be identified at a glance.

Since the medical resource detecting member and the retrieval guidance member are placed in respective locations of storage on the rack, it is possible to detect whether each medical resource is stored for automatic management and to properly guide a user to the location of storage of the medical resource to be retrieved. As a medical resource is stored in or taken out from the storage case on the rack, the medical resource name plate is moved up or down in association with the connecting member. The medical resource detecting member indirectly and automatically detects whether or not the medical resource is placed by detecting whether the medical resource name plate is raised or lowered. Accordingly, availability of the medical resource is visually confirmed even if the medical resource name plate is in front of the medical resource. This makes it possible to indirectly detect a medical resource even when it is difficult to detect, for example, the bottom thereof due to the form or material of the medical resource. When the medical resource is placed on or removed from the rack along with the storage case, availability of the medical resource can still be detected indirectly and automatically because the medical resource name plate subject to detection is also placed on or removed from the rack along with the storage case.

Thus, by employing a storage case of a structure specifically adapted for indirect detection, a simple apparatus, in which medical resources are accommodated in storage cases and arranging the cases on the rack, enables storing a large variety of large and small medical resources in the least confusing manner. Even those resources that are not suitable for direct detection can also be detected properly for automatic management. Either the storage and retrieval of a medical resource along with a storage case, or the storage and retrieval of a medical resource with the storage case remaining placed on the rack can be performed without inconvenience.

Thus, the first medical resource storage and management apparatus provides capability for easily and properly storing and retrieving medical resources, and automatically and accurately keeping track of storage status.

In the second medical resource storage and management apparatus, the medical resource is placed on the connecting member and stored in the storage case. A determination is made that the medical resource is placed when the medical resource name plate is lowered in association with the storage. A determination is made that the medical resource is not placed when the medical resource name plate is raised. In this way, by detecting the up and down movement of the medical resource name plate using the medical resource detecting member in front of the rack, the medical resource is properly detected irrespective of whether the medical resource is stored and retrieved in the rack along with the storage case or with the storage case remaining on the rack.

In the third medical resource storage and management apparatus, the case detecting member is provided in each location of storage to detect whether or not the storage case is placed. The medical resource is placed underneath the connecting member and stored in the storage case. A determination is made that the medical resource is placed when the medical resource name plate is raised in association with the storage. A determination is made that the medical resource is not placed when the medical resource name plate is lowered. In this way, by detecting the up and down movement of the medical resource name plate using the medical resource detecting member in front of the rack when the storage case is detected as being placed, the medical resource is properly detected irrespective of whether the medical resource is stored and retrieved in the rack along with the storage case or with the storage case remaining on the rack.

In the fourth medical resource storage and management apparatus, whether or not each of locations of storage available on the rack as a result of arranging medical resource detecting members and retrieval guidance members is partitioned is configured in the control unit so that the control unit collectively process medical resource detecting members and retrieval guidance members in a block. Therefore, a user will not be at a loss or face any inconvenience in handling and management even if there are multiple medical resource detecting members or retrieval guidance members where a single, large medical resource resides.

According to the firth medical resource storage and management apparatus, reliability is enhanced while avoiding an increase in hardware cost, by taking advantage of redundancy of results of detection by multiple medical resource detecting members in a single block so as to detect an error accordingly.

Specific embodiments of the medical resource storage and management apparatus according to the fifth embodiment will be described using illustrative embodiments 5-1 through 5-7.

The illustrative embodiment 5-1 shown in FIGS. 49A-53D is an embodiment of the first, second, fourth and fifth medical resource storage and management apparatus mentioned above. The illustrative embodiment 5-2 shown in FIGS. 54A and 54B is a variation thereof. The illustrative embodiment 5-3 shown in FIGS. 55A-55B is an embodiment of the third medical resource storage and management apparatus mentioned above. The illustrative embodiment 5-4 shown in FIGS. 56A-56C, the illustrative embodiment 5-5 shown in FIGS. 57A-58C, the illustrative embodiment 5-6 shown in FIGS. 59A-60, and the illustrative embodiment 5-7 shown in FIGS. 61A-64D are variations.

In the illustration, fasteners such as bolts, connectors such as hinges, electronic circuits such as drivers are omitted for brevity, highlighting those elements necessary to explain the embodiment and related elements.

Illustrative Embodiment 5-1

A specific structure of the illustrative example 5-1 of the medical resource storage and management apparatus according to the fifth embodiment will be described with reference to the associated drawings. FIGS. 49A-49E show the mechanical structure of the medical resource storage and management apparatus. FIG. 49A is a front view showing a door closed; FIG. 49B is a front view showing the door opened; FIG. 49C is a perspective view showing the appearance of a rack; FIG. 49D is an expanded perspective view of a storage case; FIG. 49E is a perspective view showing the appearance of the rack on which the storage case and a medical resource are placed. FIGS. 50A and 50B show the schematic structure of a control unit. FIG. 50A is a schematic block diagram showing the connection between the control unit and retrieval guidance members; and FIG. 50B is a functional block diagram of the control unit. FIGS. 51A-51C show the data structure of the control unit. FIG. 51A relates to a medical resource information table; FIG. 51B relates to medical resource availability data; and FIG. 51C relates to partition availability data.

A medical resource storage and management apparatus 420 is provided with a housing 422 a large portion of which is for storage and a part of which comprises electric equipment 421. The electric equipment 421 stores a control unit 430 and a power supply unit etc. (not shown). The front of the storage part of the housing 422 is provided with an openable door 424 with a handle 423. The door 424 may be implemented by a shutter or the like, or may be omitted. Inside the storage part exposed when the door 424 is opened is provided a rack 490. Although there may be only one rack 490, an orthodox apparatus would comprise multiple tiers. The pitch between the racks 490 may be selectable. The rack 490 is implemented by a horizontally extending plate with a flat top face so that a large number of storage cases 495 can be placed at regular or irregular pitches in a longitudinal direction (in the figure, sideways). As described later, the storage case 495 may be placed on the rack 490 with or without storing a medical resource 410.

The front of the rack 490 exposed when the door 424 is opened (see FIG. 49C) is equipped with retrieval guidance members 492 and medical resource detecting members 493 in close proximity with each other. The retrieval guidance members 492 and the medical resource detecting members 493 are arranged in the rack 490 so as to correspond to the locations of storage in the storage cases 495 on the rack 490. A typical length of the rack 490 is 900 mm or 1800 mm. A typical distance between the racks 490 and a typical pitch between locations of storage in the storage cases 495 is 30 mm or multiples thereof but not restricted thereto.

The storage case 495 (see FIGS. 49D and 49E) is configured such that a medical resource name plate 497 and a connecting member 498 are attached to a box which is bounded at the bottom, sides and back thereof by a fixed plate (bounding member) and open at the front and top. The medical resource name plate 497 is provided at the front of the storage case 495 to allow clear view. The connecting member is connected and secured to the back of the medical name plate 497 and extends toward the back of the case. Engaging parts 499 that serve as ends of a pivot axis is provided at the rear end of the connecting member 498. The engaging parts 499 are inserted into engaging parts 495a provided in the rear part of the storage case 495 and implemented as a bearing or a hole, so that the connecting member 498 can make a vertical pivotal movement about the rear end thereof and the medical resource name plate 497 is moved up and down in association with the pivotal movement.

When the medical resource 410 is stored in the storage case 495, the medical resource name plate 497 is moved up and down as a result of interference between the medical resource 410 and the connecting member 498. The storage case 495 of the illustrative embodiment 5-1 is of a type which accommodates the medical resource 410 such that the medical resource 410 is placed on the connecting member 498 as a base plate which is moved up and down. Therefore, the connecting member 498 is formed as a plate member that can be movably inserted into the storage case 495, and the engaging parts 495a are provided toward the back and bottom of the storage case 495. An biasing member 496 such as a coil spring for biasing the neighborhood of the front end of the connecting member 498 upward is provided toward the front in the interior bottom of the storage case 495. When the storage case 495 is empty, the medical resource name plate 497 is raised. When the medical resource 410 is placed upon the connecting member 498, the medical resource name plate 497 is lowered.

The medical resource name plate 497 enters a range of detection by the associated medical resource detecting member 493 at the front of the rack 490 and is detected accordingly in one of the two ways. In a first way, the storage case 495 is placed on a location of storage on top of the rack 490 with the medical resource name plate 497 facing a user and then the medical resource 410 is accommodated in the storage case 495, so that the connecting member 498 is pivotally moved and the medical resource name plate 497 is lowered. In the other way, the storage case 495 which stores the medical resource 410, with the connecting member 498 and the medical resource name plate 497 are lowered, is placed on a location of storage on top of the rack 490 such that the medical resource name plate 497 faces the user. The form of the medical resource name plate 497, the connection between the plate 497 and the connecting member 498 and the location of the medical resource detecting member 493 are designed to achieve the above detection.

When the empty storage case 495 with the medical resource name plate 497 in an elevated position is placed on the rack 490, or when the storage case 495 is removed from the rack 490, there will no longer be a target of detection by the medical resource detecting member 493 at the associated location. Therefore, whether the medical resource 410 is placed or not is indirectly detected by the up and down movement of the medical resource name plate 497 by using a detection output of the medical resource detecting member 493 as it is. More specifically, a determination that a medical resource is placed is made when the medical resource name plate 497 enters a range of detection by the medical resource detecting member 493. A determination that a medical resource is not placed is made when the medical resource name plate 497 leaves the range of detection by the medical resource detecting member 493.

In order to detect the medical resource name plate 497 for indirect detection of the medical resource 410, each of the medical resource detecting members 493 is implemented by a mechanical switch, a reflective photosensor, a capacity sensor or the like, so as to output a binary signal which turns on and off according to whether the medical resource name plate 497 is raised or lowered.

In order to visually guide a user to the location of placement of the medical resource 410 to be retrieved, a miniature bulb, a light emitting diode or the like that can be turned on and off is used as the retrieval guidance member 492.

The control unit 430 (see FIG. 50A) comprises a programmable controller such as a personal computer and a sequencer. A local area network (LAN) connects the control unit 430 to the retrieval guidance members 492 and the medical resource detecting members 493 via, for example, a rack controller 431. Alternatively, the control unit 430, the retrieval guidance members 492 and the medical resource detecting members 493 are in direct star connection (not shown). The connection enables retrieving detection results of the medical resource detecting members 493 and controlling the lighting of the retrieval guidance members 492.

The control unit 430 (see FIG. 50B) is provided with a display 432 for screen display, a keyboard 433 for key entry, a mouse 434 for inputting instructions etc. on a screen, a bar code reader 435 for reading identification information, a printer 436 for delivering printouts, an interface for a LAN 437 which is responsible for communication with a prescription order-entry system etc., and a hard disk 438 as a secondary storage.

A retrieval guidance routine 441, a medical resource detection routine 442, a medical resource information configuration routine 443, and a manual partition condition configuration routine 444 are installed in the control unit 430, as programs for managing the storage status of the medical resources, based on the detection by the medical resource detecting members 493, and for operating selected retrieval guidance members 492 in response to an input designating retrieval. The hard disk 438 stores medical resource availability data 446, a medical resource information table 447, partition availability data 448, and log data 449, which are divided into individual files or are unified in an appropriate database. The figures show (see FIGS. 51A-51B) the data 446, the table 447 and the data 448 maintained in a table format. Each table comprises a 6×21 matrix, in association with the fact that the racks 490 form six tiers and the maximum number of locations of storage in each rack 490 (i.e., the maximum number of the retrieval guidance members 492 and the medical resource detecting members 493) is twenty one.

Each field in the medical resource information table 447 (see FIG. 51A) contains an identification code and a name displayed on a screen for the medical resource 410 which is stored or can be stored in an associated location. "1" or "0" is written in the medical resource availability data 446 (see FIG. 51B), "1", indicating that the medical resource 410 is stored in the associated location, and "0", indicating that no medical resource 410 is stored. "1" or "0" is written in the partition availability data 448 (see FIG. 12C), "1", indicating that the partition member 165 is inserted, and "0", indicating that the partition member 165 is removed from the associated location.

The retrieval guidance members 493 and the medical resource detecting members 493 are not partitioned physically. Instead, partition is determined logically and virtually in accordance with the required operation. Partition is configured in the partition availability data 448 for use in guidance for retrieval of medical resources or detection of whether or not a medical resource is placed. More specifically, if the storage case 495 is not so wide and there is only one pair of retrieval guidance member 492 and medical resource detecting member 493 at the front of the rack 490 corresponding to the associated location of storage, the associated location is partitioned. In contrast, if the storage case 495 is wide and there are two or more pairs of retrieval guidance member 492 and medical resource detecting member 493 at the front of the rack 490 corresponding to the associated location of storage, the associated location is not partitioned in order to collectively process the retrieval guidance members 492 and the medical resource detecting members 493.

In connection with this, the partition availability data 448 is initialized so that the scheduled storage status of the storage case 495 is reflected before the initial operation. Configuration inputs for update are also provided when the number of retrieval guidance members 492 and medical resource detecting members 493 collectively processed is changed as a result of, for example, a change in the size of the storage case 495. The medical resource information table 447 should be configured at least once before operating the apparatus for the first time since its installation. Therefore, the table is usually initialized upon starting the apparatus and updated when the operation is stopped. The medical resource availability data 446 is all cleared by initialization before the initial operation and is subsequently updated with each storage or retrieval of the medical resource 410.

The medical resource information configuration routine 443 is started by the keyboard 433 or mouse 434 operation. When dumping from a medicine master file located on a host computer via the LAN 437 is dictated in an environment where such an action is possible, the medical resource information configuration routine 443 dumps the data. The routine 443 also allows the user to set the code or name of the medical resource 410 in the medical resource information table 447 by selecting an item using the mouse 434 or entering data using the keyboard 433, while viewing screen display on the display 432.

The manual partition condition configuration routine 444 is also started by the keyboard 433 or mouse 434 operation. The routine 444 allows the user to provide an input for configuration to designate in the partition availability data 448 how the retrieval guidance members 492 and the medical resource detecting members 493 of the rack 490 are operationally partitioned by selecting an item or toggling using the mouse 434 or the keyboard 433, while viewing screen display on the display 432.

The medical resource detection routine 442 is started periodically and automatically by a timer, etc. or irregularly and automatically started by an interruption initiated in the event of a change in a detection signal from the medical resource detecting member 493. The medical resource detection routine 442 manages the storage status of the medical resources 410 based on detection by the medical resource detecting members 493. More specifically, each time the medical resource detection routine 442 is started, it imports the detection results from all medical resource detecting members 493 or those results changed since its last import, and writes "1" or "0" in the medical resource availability data 446 in association with the on-off condition. When the detection result from the medical resource detecting member 493 undergoes an on/off change and the storage or retrieval of the medical resource 410 is detected accordingly, the medical resource detection routine 442 appends information indicating the detection to the log data 449 with a time stamp, causes the printer 436 to deliver a printout which carries the name listed in the associated field in the medical resource information table 447, and submits a report to a host medical management computer via the LAN 437.

The retrieval guidance routine 441 is started when the code of the medical resource 410 or a prescription ID number is entered by allowing the barcode reader 435 to scan the code or the ID, or by using the keyboard 433 or the mouse 434, in order to operate one of the retrieval guidance members 72 in response to an input designating retrieval. The retrieval guidance routine 441 searches the medical resource information table 447 to determine the location of storage of the medical resource 410 designated to be retrieved via the reading or via the mouse or keyboard operation, and lights the retrieval guidance member 492 at the associated location. The medical resource detection routine 442 is responsible for turning the retrieval guidance member 492 off when the retrieval of the medical resource 410 at the associated location is detected.

The retrieval guidance routine 441 and the medical resource detection routine 442 collectively process the medical resource detecting members 493 and the retrieval guidance members 492 defined as corresponding to the location of storage of one storage case 495 for the required operation, even if there are multiple pairs of members 492 and 493. The routine 441 and the routine 442 issue an alarm if the results of detection by the medical resource detecting members 493 in a block to be processed collectively continue to fail to match beyond a predetermined period of time.

More specifically, the retrieval guidance routine 441 refers to the partition availability data 448 to check how the retrieval guidance member 492 is partitioned to the right and to the left, before lighting the retrieval guidance member 492. If "0" is entered left or right, indicating that the member 492 is not partitioned, the associated, adjacent retrieval guidance member 492 is also lighted. In association with this, the medical resource detection routine 442 performs a similar check by referring to the medical resource availability data 446 in turning off the retrieval guidance member 492, and turns off the retrieval guidance members 492 in the block at a time.

The medical resource detection routine 442 also performs, upon detecting the storage or retrieval of the medical resource 410, a similar check by referring to the partition availability data 448 before changing the value of the medical resource availability data 446. If a series of adjacent partitions are to be processed collectively as a single block, the medical resource detection routine 442 examines whether the values from the medical resource detecting members 493 in the single block match. If the values match, the routine 442 terminates the process normally; if the values do not match, the routine 442 continues the monitoring. If the values from the medical resource detecting members 493 in a block continue to fail to match beyond a maximum period of time required for storage or retrieval of the medical resource 410 while the monitoring is proceeding, the medical resource detection routine 442 displays an alarm on the display 432 or sounds an alarm buzzer (not shown).

In order to help the routines 441 and 442 to collectively process the medical resource detecting members 493 and the retrieval guidance members 492 not partitioned, the manual partition condition configuration routine 444 configures, in designating in the partition availability data 448 that the members are not partitioned, the associated fields in the medical resource information table 447 such that field values (i.e., codes and names maintained) corresponding to the locations of storage match. The manual partition condition configuration routine 444 returns the field values of the associated fields in the medical resource information table 447 to their original values in designating in the partition availability data 448 that the members are partitioned.

In addition, the control unit 430 acquires operator identification information by requesting an operator to input operator identification information each time an operation is carried out. Alternatively, the control unit 430 acquires operator identification information input by an operator in advance of an operation. The control unit 430 also stores, in the log data 449, related information then collected by automatic detection etc. together with a time stamp. The data stored is also output via the LAN 437. The process is performed in the manual partition condition configuration routine 444 as well as in the retrieval guidance routine 441.

The mode of using the medical resource storage and management apparatus according to the illustrative example 5-1 and its operation will be described with reference to the drawings. FIGS. 52A-52B illustrate the operation of the medical resource storage and management apparatus. FIG. 52A shows small empty storage cases arranged on the rack; and FIG. 52B shows a condition in which a medical resource is stored in one of them. FIGS. 53A-53D also illustrate the operation of the medical resource storage and management apparatus. FIG. 53A shows a condition in which an empty medium-sized storage case is included; FIG. 53B shows a condition in which a medical resource is stored in the medium-sized case; FIG. 53C shows a condition in which a large-sized storage case is included and a medical resource is stored therein; and FIG. 53D shows a condition in which detection results from medical resource detecting members do not match.

Prior to the operation of the medical resource storage and management apparatus 420, a desired number of racks 490 are set in the storage part of the housing 422. The medical resource information configuration routine 443 in the control unit 430 is started by an operation using the keyboard 433 or the mouse 434 so as to set the identification code and the displayed name of the medical resources 410 in the respective fields in the medical resource information table 447. In this process, it is also favorable to arrange empty storage cases 495 on the rack 490 and perform a comparison check with the product name of the medical resource currently written in the medical resource name plate 497. The manual partition condition configuration routine 444 in the control unit 430 is started by an operation using the keyboard 433 or the mouse 434 so as to designate whether or not the medical resource detecting members 493 and the retrieval guidance members 492 are partitioned, in the respective fields in the partition availability data 448. The medical resource availability data 446 and the log data 449 are cleared by a suitable initialization routine (not shown).

This completes preparation for operation. The operating conditions of the medical resource storage and management apparatus 420 will be described specifically. The operation for storage (replenishment or return) and associated updating of data, and the operation for retrieval and associated updating of data will now be described in the cases where: the storage cases 495 are all small-sized and all of the medical resource detecting members 493 and the retrieval guidance members 492 are partitioned (see FIGS. 52A and 52B); one of the storage cases 495 is medium-sized and one of the partitions which partition the medical resource detecting members 493 and the retrieval guidance members 492 in FIGS. 52A and 52B is lacking (see FIGS. 53A and 53B); and one of the storage cases 495 is large-sized and two adjacent ones of the partitions which partition the medical resource detecting members 493 and the retrieval guidance members 492 in FIGS. 52A and 52B are lacking (see FIGS. 53C and 53D).

When the empty storage cases 495 are placed on the respective locations of storage on the rack 490 corresponding to respective pairs of the medical resource detecting members 493 and the retrieval guidance members 492 (see FIGS. 52A and 52B) and when the medical resources 410 are not stored yet (see the top row of FIG. 52A), the fields in the medical resource information table 447 contain individual values (see A-E in the second row from top in FIG. 52A, where A-E denote different codes and names). The fields in the medical resource availability data 446 all contain "0", indicating the absence of medical resources (see the third row from top in FIG. 52A), and the fields in the partition availability data 448 all contain "1", designating that the partition members are provided (see the fourth row from top in FIG. 52A).

When the medical resource 410 is stored in the storage case 495 on the rack 490 (see the top row of FIG. 52B) in this condition, only the medical resource name plate 497 connected to the connecting member 498 on which the medical resource 410 is placed for storage is lowered in front of the rack 490 and enters a range of detection by the medical resource detecting member 493. The retrieval guidance member 492 remains viewable. In this condition, the medical resource information table 447 and the partition availability data 448 remain unchanged (see the second and fourth rows from top in FIG. 52B). Meanwhile, the associated field in the medical resource availability data 446 is updated by the medical resource detection routine 442 to "1", indicating the presence of a medical resource (see the third row from top in FIG. 52B). The medical resource detection routine 442 retrieves the code and name of the medical resource 410 (in the illustrated example, "C") from the medical resource information table 447. The medical resource detection routine 442 further requests the input of operator identification information. These items of information are appended to the log data 449, printed by the printer 436 and reported to the host medical management computer via the LAN 437.

For retrieval of the medical resource 410 thus stored from the medical resource storage and management apparatus 420, a retrieval instruction including the code "C" and the operator identification information are input to the control unit 430 by an operation using the barcode reader 435 or the like. This prompts the retrieval guidance routine 441 in the control unit 430 to search the medical resource information table 447 and check the associated field in the medical resource availability data 446. In this case, the value "1" is found in the field, showing that the medical resource is available, whereupon the retrieval guidance member 492 at the associated location is lighted (see the bottom row of FIG. 52B). The operator viewing this can take out the target medical resource 410 without fail.

When the medical resource 410 is taken out, the medical resource name plate 497 of the associated location is raised and leaves the range of detection by the medical resource detecting member 493 so that the medical resource detection routine 442 updates the value entered in the associated field in the medical resource availability data 446 to "0", indicating the absence of medical resources. The information is combined with the code and name (in the illustrated embodiment, "C") supplied from the retrieval guidance routine 441, and with operator identification information. The combined information is appended to the log date 449, printed by the printer 436 and reported to the host medical management computer via the LAN 437. When the retrieval guidance member 492 of the associated location is turned off, the operating condition returns to a pre-storage state (see FIG. 52A).

When the storage case 495 is medium-sized and one of the partitions which partition the medical resource detecting members 493 and the retrieval guidance members 492 is lacking (see FIGS. 53A and 53B), the storage case 495 twice as wide is set there. Since the medical resource name plate 497 and the connecting member 498 of the storage case 495 are also twice as wide, a medical resource 410 that takes up much space can be stored therein. The manual partition condition configuration routine 444 is started by an operation using the keyboard 433 or the mouse 434, before storing the medical resource 410 therein (see the top row of FIG. 53A). An instruction for update is entered so as to change the value in the associated field in the partition availability data 448 to "0", designating the absence of the partition member (see the fourth row from top in FIG. 53A). This prompts the manual partition condition configuration routine 444 to automatically update the medical resource information table 447 so that the values in the fields, corresponding to the locations of storage of the storage case 495 twice as wide, match (see "BB" in the second row from top in FIG. 53A). All the fields in the medical resource availability data 446 contain "0" (see the third row from top in FIG. 53A).

When the medical resource 410 not more than twice as wide is stored in this condition in the storage case 495 twice as wide placed on the rack 490 (see the top row of FIG. 53B), the wide medical resource name plate 497 is lowered and enters the range of detection by the medical resource detecting member 493 in association with the downward pivotal movement of the connecting member 498 on which the medical resource 410 is placed. In this condition, the medical resource information table 447 and the partition availability data 448 remain unchanged (see the second and fourth rows from top in FIG. 53B). Meanwhile, the two associated fields in the medical resource availability data 446 are updated by the medical resource detection routine 442 to "1", indicating the presence of a medical resource (see the third row from top in FIG. 53B). The medical resource detection routine 442 retrieves the code and name of the medical resource 410 (in the illustrated example, "B") from the medical resource information table 447. The medical resource detection routine 442 further requests the input of operator identification information. These items of information are appended to the log data 449, printed by the printer 436 and reported to the host medical management computer via the LAN 437.

For retrieval of the medical resource 410 thus stored from the medical resource storage and management apparatus 420, a retrieval instruction including the code "B" and the operator identification information is input to the control unit 430 by an operation using the barcode reader 435 or the like. This prompts the retrieval guidance routine 441 in the control unit 430 to search the medical resource information table 447 and select the two adjacent fields (see "BB" in the second row from top in FIG. 53B), and then to check the two associated fields in the medical resource availability data 446. In this case, the two fields contain "1", indicating that the medical resource is available, whereupon the two adjacent retrieval guidance members 492 at the associated locations are lighted at a time (see the bottom row of FIG. 53B). The operator viewing this will not find any difficulty in taking out the target medical resource 410.

When the medical resource 410 is taken out, the wide medical resource name plate 497 at the associated location is raised to leave the range of detection by the medical resource detecting member 163. In this process, the medical resource detection routine 442 updates the values entered in the two associated fields in the medical resource availability data 446 to "0", indicating the absence of medical resources. The information is combined with the code and name (in the illustrated example, "B") supplied from the retrieval guidance routine 441, and with operator identification information. The combined information is appended to the log date 449, printed by the printer 436 and reported to the host medical management computer via the LAN 437. When the retrieval guidance members 492 at the associated locations are turned off, the operating condition returns to a pre-storage state (see FIG. 53A).

In the case where one of the storage cases 495 is large-sized and two adjacent ones of the partitions which partition the medical resource detecting members 493 and the retrieval guidance members 492 are missing (see FIGS. 53C and 53D), the operation will easily be surmised from the above explanation so that a detailed explanation will not be repeated. It will be noted that a medical resource 410 three times as wide can be stored (see the top row of FIG. 53C). In this case, the storage case 495 three times as wide provided with the medical resource name plate 497 and the connecting member 498 three times as wide is used. Three pairs of the medical resource detecting members 493 and the retrieval guidance members 492 correspond to the location of storage. When the manual partition condition configuration routine 444 is started so as to update the values in the two associated fields in the partition availability data 448 to "0", indicating the absence of a partition member (see the fourth row from top in FIG. 53C), the values in the three associated fields in the medical resource information table 447 are made to match (see "BBB" in the second row from top in FIG. 53C).

When a medical resource 410 not more than three times as wide is stored (see the top row of FIG. 53C), each of the three associated fields in the medical resource availability data 446 is updated to contain "1" (see the third row from top in FIG. 53C), and relevant information is appended to the log data 449.

When a retrieval instruction including the code "B" is input to the control unit 430, the three associated fields in the medical resource information table 447 (see "BBB" in the second row from top in FIG. 53C) are selected, and then the three associated fields in the medical resource availability data 446 are checked. In this case, the three fields contain "1", showing a match. Thereupon, the three adjacent retrieval guidance members 492 in the associated locations are lighted at a time (see the bottom row of FIG. 53C). The operator viewing this will not find difficulty in taking out the target medical resource 410.

If one of the three medical resource detecting members 493 expected to detect the medical resource name plate 497 three times as wide at a time fails (see FIG. 53D), two of the three associated fields in the medical resource availability data 446 are changed to "1", while one field continues to store "0" (see the third row from top in FIG. 53D). This results in incompatibility between the medical resource availability data 446 and the partition availability data 448 as checked by the medical resource detection routine 442, in respect of the three fields to be collectively processed. If the condition of incompatibility (failure to match) continues beyond a maximum period of time required for storage or retrieval of the medical resource 410, the medical resource detection routine 442 issues an alarm, revealing abnormality.

Given above is an explanation of a case where the storage case 495 remains placed on the rack 490 while the medical resource 410 is taken out. The medical resource detecting member 493 is designed to detect whether or not the medical resource 410 is placed by detecting the medical resource name plate 497, such that the mere placement of the storage case 495 does not invoke a determination of placement. Therefore, resources are equally properly detected and managed even if the storage case 495 storing the medical resource 410 is placed on or removed from the rack 490. The description will be omitted for brevity.

Illustrative Embodiment 5-2

A specific structure of the illustrative example 5-2 of the medical resource storage and management apparatus according to the fifth embodiment will be described with reference to the associated drawings. FIGS. 54A-54B show the mechanical structure of the medical resource storage and management apparatus 420. FIG. 54A is a perspective view showing the appearance of the rack in which the empty storage cases 495 are arranged; FIG. 54B is an expanded front view showing an essential part.

The medical resource storage and management apparatus 420 differs from that of the illustrative embodiment 5-1 is that storage location indicators 491a and 497a (partition configuration members) are added.

The storage location indicators 491a and 497a are sticker paper or adhesive labels with adhesive back. A storage location address, comprising the number identifying the rack, and the number identifying the retrieval guidance member 492 or the medical resource detecting member 493 in the rack, is printed on the front. The storage location indicator 491a is adhesively attached to, for example, the front of the rack 490 and the storage location indicator 497a is adhesively attached to, for example, the medical resource name plate 497. The same storage address location is written in the corresponding storage location indicators 491a and 497a so that correspondence between them occurring as the storage case 495 is placed on the rack 490 is visually identified.

In this case, the storage location indicator 497a is adhesively attached to each of the medical resource name plate 497. The storage location indicator 491a is adhesively attached to the front of the rack 490 where the retrieval guidance members 492 and the medical resource detecting members 493 are operationally partitioned. The indicator 491a is not adhesively attached to the front of the rack 490 where the members 492 and 493 are not operationally partitioned.

This allows the operator to store the storage cases 495 and the medical resources 410 of various sizes without any difficulty.

Illustrative Embodiment 5-3

A specific structure of the illustrative example 5-3 of the medical resource storage and management apparatus according to the fifth embodiment will be described with reference to the associated drawings. FIGS. 55A-55B show the mechanical structure of the medical resource storage and management apparatus. FIG. 55A is an expanded perspective of the storage case; and FIG. 55B is a perspective view showing the appearance of the rack on which the storage case or a medical resource is placed.

The medical resource storage and management apparatus 420 differs from those of the illustrative embodiments 5-1 and 5-2 is that the storage case 495 is of a type in which the medical resource 410 is stored in the storage case 495 such that the connecting member 498 as a cover plate movable up and down, and the case bottom and the connecting member 498 sandwich the medical resource 410. Another difference is that a series of case detecting members 493a are provided on top of the rack 490.

More specifically, the case detecting member 493a is provided to correspond to the retrieval guidance member 492 and the medical resource name plate 493 so as to detect the storage case 495 placed on the location of storage. Like the medical resource detecting member 493, the case detecting member 493a is also implemented by a mechanical switch, a reflective photosensor, a capacity sensor or the like, so as to output a binary signal which turns on and off according to whether or not the storage case 495 is placed.

The biasing member 496 is omitted from the storage case 495. The engaging parts 495a are provided toward the top at the back of the storage case 495. The connecting member 498 is bent in the neighborhood of the back end thereof so that interference between the connecting member 498 and a thin medical resource 410 placed under the member 498 occurs properly. The storage case 495 is bounded at the bottom, sides and back thereof by a fixed plate. The movable medical resource name plate 497 is provided in front of the case. The connecting member 498 extending backward from the medical resource name plate 497 can make a vertical pivotal movement about the rear end thereof. The medical resource name plate 497 is moved up and down as a result of interference between the medical resource 410 stored and the connecting member 498. In these respects, the storage case 495 in this embodiment is the same as that of the foregoing embodiment but differs in that the medical resource 410 is stored underneath the connecting member 498.

Unlike the case of the foregoing embodiments, the up and down movement of the medical resource name plate 497 of the storage case 495 shall be associated with the availability/nonavailability of the medical resource 410, respectively. When the storage case 495 is placed on the rack 490 and when the connecting member 498 and the medical resource name plate 497 are allowed to make a pivotal movement freely, the member 498 and the plate 497 are lowered under their own weight until the connecting member 498 comes into contact with the bottom of the storage case 495 and the medical resource name plate 497 in front thereof is lowered to the front of the rack 490. This results in the medical resource name plate 497 entering the range of detection by the medical resource detecting member 493. In contrast, when the medical resource name plate 497 is raised so as to store a medical resource 410 underneath the connecting member 498, the connecting member 498 rests on the medical resource 410, causing the medical resource name plate 497 to remain at an elevated position and placing the medical resource name plate 497 outside the range of detection by the medical resource detecting member 493.

As a result of this arrangement, the binary logic of the output signal of the medical resource detecting member 493 of this embodiment is reversed from that of the foregoing embodiments. Therefore, a mere detection by the medical resource detecting member 493 cannot differentiate between a condition in which the storage case 495 is removed from the rack 490 so that the medical resource name plate 497 cannot be detected accordingly, and a condition in which the medical resource 410 is stored in the storage case 495 on the rack 490 so that the medical resource name plate 497 cannot be detected accordingly. In order to prevent this, the case detecting member 493*a* is added. By causing the medical resource detection routine 442 to combine the detection result of the medical resource detecting member 493 with the detection result of the case detecting member 493*a*, indirect detection of whether or not the medical resource 410 is placed can be properly made by the up and down movement of the medical resource name plate 497.

As in the case of the foregoing embodiments, the storage case 495 may remain placed on the rack 490 while the medical resource 410 is being stored or taken out. Alternatively, the storage case 495 storing the medical resource 410 may be placed on or removed from the rack 490. Storage status of the medical resource 410 can be properly detected and managed in either mode of use.

Illustrative Embodiment 5-4

A specific structure of the illustrative example 5-4 of the medical resource storage and management apparatus according to the fifth embodiment will be described with reference to the associated drawings. FIGS. 56A-56C show the structure of the medical resource storage and management apparatus 420. FIG. 56A is an expanded perspective view of the storage case 495 and the rack 490; FIG. 56B is a perspective view showing the appearance of the rack 490 on which the storage case 495 and the medical resource 410 are placed; and FIG. 56C is a functional block diagram of the control unit 430.

The medical resource storage and management apparatus 420 according to this embodiment differs from that of the illustrative embodiments 5-1 through 5-3 in that storage location indicators 491*a* (partition configuration members) are detachable, partition detecting members 494 are added and the manual partition condition configuration routine 444 is replaced by an automatic partition condition configuration routine 445.

On the front of the rack 490 (see FIGS. 56A and 56B) are provided a depression 491 and a partition detecting member 494 in close proximity with each other at all locations where the storage location indicators 491*a* could be provided. More specifically, each pair of the retrieval guidance member 492 and the medical resource detecting member 493 is associated with each pair of the depression 491 and the partition detecting member 494. The depressions 491 and the partition detecting members 494 are also provided in series on the rack 490 in the longitudinal direction thereof. The storage location indicator 491*a* (see FIGS. 56A and 56B) is formed as a rigid plastic plate provided with small projections on the back (not shown). By engaging the small projections with the depression 491, the indicator 491*a* is fitted to the rack 490. By pulling the plate toward the operator, the small projections slip out of the depression 491 and are removed from the rack 490. Each of the partition detecting members 494 is implemented by a mechanical switch, a reflective photosensor, a capacity sensor or the like, so as to detect whether the storage location indicator 491*a* (partition configuration member) is provided in the associated location, by sensing the bottom of the storage location indicator 491*a* fitted to the front of the rack 490 and output a binary signal which turns on and off.

The automatic partition condition configuration routine 445 (see FIG. 56C) is started periodically and automatically by a timer, etc. or irregularly and automatically started by an interruption initiated in the event of a change in a detection signal from the partition detecting member 494. The automatic partition condition configuration routine 445 updates the partition availability data 448 based on detection by the partition detecting member 494. More specifically, each time the automatic partition condition configuration routine 445 is started, it imports the detection results from all partition detecting members 494 or those results changed since its last import, and writes "1" or "0" in the partition availability data 448 in association with the on-off condition. The other functions (e.g., automatic updating of the medical resource information table 447) are the same as those of the manual partition condition configuration routine 444. This arrangement allows the control unit 430 to collectively process a block of medical resource detecting members 493 and retrieval guidance members 492 identified as being located on both sides of the depression 491 from which the storage location indicator 491*a* (partition configuration member) is removed, in accordance with the detection by the partition detecting members 494.

In this case, removal of the storage location indicator 491*a* (partition configuration member) from the depression 491 in the rack 490 or fitting of the storage location indicator 491*a* (partition configuration member) to the depression 491 in the rack 490 need not be designated by manual input for configuration. The removal or insertion is detected by the partition detecting member 494, and the partition availability data 448 is automatically configured by the automatic partition condition configuration routine 445. This will prevent incompatibility between the availability of the storage location indicator 491*a* (partition configuration member) and the partition availability data 448 from occurring due to a failure to provide an input for configuration.

The other usage modes and operations are the same as those of the illustrative embodiments 5-1 through 5-3 described above.

Illustrative Embodiment 5-5

An illustrative embodiment 5-5 of the medical resource storage and management apparatus according to the fifth embodiment will be described with reference to the associated drawings. FIGS. 57A-57C show conditions of replenishment of medical resources. FIGS. 57A-57C are screen shots. FIGS. 58A-58C also show conditions of replenishment of medical resources. FIG. 58A is a perspective view of the rack 490 on which the empty storage cases 495 are arranged; FIG. 59B is a perspective view showing how identification information is read from the medical resource 410; and FIG. 58C is a perspective view of the rack 490 storing the medical resource 410.

This medical resource storage and management apparatus differs from the aforementioned embodiments of the apparatus in that guidance is displayed in replenishing as well as in retrieving a medical resource, and that the display 432, the keyboard 433 and the mouse 434 are implemented as a touch panel 439.

In a normal operation (see FIG. 57A), information on the medical resource 410 retrieved from the medical resource storage and management apparatus is arranged chronologically and displayed on the touch panel 439 on a real time basis. A direct finger-touch selection of any the items 439*a* displayed on the screen causes relevant details to be displayed for review. Guidance for replenishment is also displayed in accordance with a specific operation for selection.

More specifically, selecting a replenishment button 439*b* displayed on the screen while in a normal operation (see FIG. 57A) switches the display of the touch panel 439 to a replenishment mode selection screen (see FIG. 57B). By entering information on an operator who replenishes a medical resource, selection of a "registered" button 439*c* and/or a "new registration" button is available. By selecting the "new registration" button, the operator can register the code (code No.) identifying the medical resource 410 that can be stored in a location of storage (address) and the name for screen display (medical resource name). If the registration is complete, selection of the "registered" button 439*c* is enabled. The "registered" button 439*c* is selected when the display of guidance for replenishment is desired.

The selection switches to the screen of the touch panel 439 showing a list of registered resources (see FIG. 57C). After confirming that a location for storage is shown as being empty, the operator scrolls the screen as necessary by using a scroll button 439*f* so as to directly select a field 439*d* for a relevant medical resource with the finger.

If the number of empty locations 439*e* designated as capable of storing the medical resource (e.g., a filter in a bag) is three (i.e., three bags can be stored), the three retrieval guidance members 492 in the empty locations are all lighted because, in this example, the retrieval guidance member 492 also serves as a replenishment destination guidance member (see FIG. 58A).

The operator proceeds to scan the barcode (identification information) assigned to the medical resource 410 about to be stored, by using the barcode reader 435 (see FIG. 58B) for checking, before storing the medical resource 410 in one of the storage cases 495 on the rack 490 lighted by the guidance member. This turns off all of the guidance members 492 (see FIG. 58C), and the log data, indicating the identity of the operator who replenished the resource, the identify of the resource replenished and the location of replenishment, is recorded with a time stamp. In the illustrated example, the empty storage case 495 is placed on the rack 490 so that only the medical resource 410 is replenished. The medical resource 410 can also be replenished properly and detected and managed properly, by leaving a space above the rack 490 empty and then placing the storage case 495 containing the medical resource 410 on the rack 490.

Thus, guidance display is provided properly and a job record is maintained properly for replenishment. In this example, the selection of the field 439*d* on the screen showing a list of registered resources, and the scanning of the identification information assigned to the medical resource 410 by using the barcode reader 435 are both performed to reinforce checking. However, only one of the tasks may be performed since it serves the purpose of identifying a medical resource 410. In another alternative, the operator may be allowed to complete both tasks, but guidance display guiding the operator to the destination of replenishment may not require completion of both tasks but may be immediately provided upon completion of one of the tasks.

Illustrative Embodiment 5-6

An illustrative example 5-6 of the medical resource storage and management apparatus according to the fifth embodiment will be described with reference to the associated drawings. FIGS. 59A and 59B show the structure of an essential part of the medical resource storage and management apparatus. FIG. 59A is a left side view showing a partial cross section of the rack 490, the medical resource name plate 497 and the connecting member 498; FIG. 59B is a perspective view showing an essential part of the rack 490, the medical resource name plate 497 and the connecting member 498. FIG. 60 shows perspective views of some of the medical resources suitable for storage. Illustration of the bounding member of the storage case 495 is omitted.

The medical resource name plate 497, the connecting member 498 and the hook-shaped locking piece 499 (see FIGS. 47A and 47B) are integrally formed. For example, they are formed as an injection-molded product of transparent resin. A label sticker 387*a* adhesively attached to the front of the medical resource name plate 387 is detected by the medical resource detecting member 383. If it is not desired to allow the label sticker 497*b* to conceal the retrieval guidance member 492 when the medical resource name plate 497 is lowered, it is easily ensured that the retrieval guidance member 492 is always viewable by cutting a part of the label sticker 497*b*.

Since the connecting member 498 is transparent, the medical resource 410 is visually identifiable from diagonally above even in a state where the connecting member 498 rests on the medical resource 410.

Suitable for storage in the rack 490 of this type (see FIG. 60) are a 0.1 L or 0.5 L glass bottle 410*a*, a 0.05 L plastic bottle 410*b*, a cylindrical object 410*c* resembling a film case for a camera, an artificial substitute 410*d* of a complex form, a box (not shown) and a blister pack (PTP package) (not shown).

Illustrative Embodiment 5-7

An illustrative example 5-7 of the medical resource storage and management apparatus according to the fifth embodiment will be described with reference to the associated drawings.

FIGS. 61A-61D show the mechanical structure of the medical resource storage and management apparatus 420. FIG. 61A is a front view showing the door 424 opened; FIG. 61B is an expanded perspective view of a rack 460 and partition members 465; and FIG. 61C is a perspective view showing the appearance of the rack 460 to which the partition members 465 are fitted. FIGS. 62A and 62B show the mechanical structure of a part of the medical resource storage and management apparatus 420. FIG. 62A is an expanded perspective view of a rack 470 and partition members 475; and FIG. 62B is a perspective view showing the appearance of the rack 470 to which the partition members 475 are fitted. FIG. 63 shows the mechanical structure of another part of the medical resource storage and management apparatus 420. FIG. 63 is an expanded perspective view of a rack 480 and partition members 485.

FIGS. 64A-64D show the structure of the medical resource storage and management apparatus 420. FIG. 64A is a front view of a horizontal-bridging case 450 (horizontal-bridging member) and hanger members 455; FIGS. 64B and 64C are left side views of the horizontal-bridging member and the hanging member showing the longitudinal cross section of the horizontal-bridging case 450 and a horizontal-bridging bar 451; and FIG. 64D is a schematic functional block diagram of the control unit 430.

The medical resource storage and management apparatus 420 according to this embodiment differs from those of the illustrative examples 5-1 through 5-6 in that the racks 480, 470 and 460 and the horizontal-bridging case 450 are placed in the storage part in addition to the rack 490 (see FIG. 61A).

The rack 460 (see FIGS. 61B and 61C) is implemented by a horizontally extending plate with a flat top face. The partition members 465 formed as thin plates are fitted to the top face thereof at regular or irregular pitches in a longitudinal direction (in the figure, sideways) in order to place a large number of medical resources 410 in respective partitions retrievably. Two rows of depressions 461 to fit partition members are formed on the top face of the rack 460 at regular or irregular pitches in a longitudinal direction. Two fittings 466 are formed to protrude from the bottom of each of the partition members 465. In this example, the fitting 466 is a small round bar and the depression 461 is a through hole. By inserting the fitting 466 into the depression 461, the partition member 465 is removably fitted to the depression 461 in the rack 460. A medical resource name plate 467, a connecting member 468, and a pivot shaft 469 are attached to one side (in the illustrated example. the right side) of the partition member 465.

One end of the pivot shaft 469 is secured to the partition member 465 toward the back thereof; one end of the connecting member 468 is pivotally connected to the other end of the pivot shaft 469; and the medical resource name plate 467 is secured to the other end of the connecting member 468 extending to the front. Thus, by pivotally moving the connecting member 468, the medical resource name plate 467 moves up and down in association with the connecting member 468 in an easy-to-view space where retrieval of a medical resource takes place (more specifically, slightly in front of the front of the rack 460).

The front of the rack 460 exposed when the door 424 is opened is equipped with retrieval guidance members 462 and medical resource detecting members 463 in close proximity with each other. The retrieval guidance members 462 and the medical resource detecting members 463 are arranged in the rack 460 so as to alternate with the depressions 461 in a direction in which the depressions 461 are arranged, i.e., in the longitudinal direction of the rack 460.

When the partition member 465 is inserted into the depression 461 on the top face of the rack 460 and when the connecting member 468 and the medical resource name plate 467 are allowed to make a pivotal movement freely, the member 468 and the plate 467 are lowered under their own weight until the connecting member 468 comes into contact with the top face of the rack 460 and the medical resource name plate 467 in front thereof is lowered to the front of the rack 460. This shields the retrieval guidance member 462 and the medical resource detecting member 463 at the front of the rack 460 from view. The medical resource name plate 467, as it is lowered in response to the retrieval of the medical resource from the associated location, shields the associated retrieval guidance member 462 from view.

When the medical resource name plate 467 is raised so as to store a medical resource 410 on the rack 460, the connecting member 468 rests on the medical resource 410 instead of on the rack 460, causing the medical resource name plate 467 to remain at an elevated position. The medical resource name plate 467 is located above the associated retrieval guidance member 462, revealing the retrieval guidance member 462 and the medical resource detecting member 463 at the front of the rack 460 for view. The medical resource detecting member 463 provided at the front of the rack 460 does not sense the medical resource 410 placed on the rack 460 but senses the medical resource name plate 467 immediately in front of the rack 460. Due to this and the fact that the medical resource name plate 467 moves up and down in response to the storage/retrieval of the medical resource 410 as a result of interference between the connecting member 468 and the medical resource 410, the medical resource detecting member 463 indirectly detects whether or the medical resource 410 is placed by detecting whether the medical resource name plate 467 is raised or lowered.

In order to detect the medical resource name plate 467 for indirect detection of the medical resource 410, each of the medical resource detecting members 463 is implemented by a mechanical switch, a reflective photosensor, a capacity sensor or the like, so as to output a binary signal which turns on and off according to whether the medical resource name plate 467 is raised or lowered.

In order to visually guide a user to the location of placement of the medical resource 410 to be retrieved, a miniature bulb, a light emitting diode or the like that can be turned on and off is used as the retrieval guidance member 462 as in the case of the retrieval guidance member 492.

The rack 470 is for inserting the partition member 475 (see FIGS. 62A and 62B). The partition member 475 is configured such that the medical resource name plate 467, the connecting member 468 and the pivot shaft 469 are omitted from the partition member 465. Therefore, instead of the medical resource members 463, medical resource detecting members 473 are provided on the top face of the rack 470 to directly detect whether the medical resource 410 is placed by sensing the bottom of the medical resource 410. A depression 471, a retrieval guidance member 472, a partition detecting member 474 and a fitting 476 may be of the same structure or function as the depression 461, the retrieval guidance member 462, the partition detecting member 464 and the fitting 466, respectively, although they differ in the destination of installation.

The rack 480 (see FIG. 63) is similar to the racks 460 and 470 in that the partition member 485 is removably fitted. The rack 480 differs from the rack 470 in that the rack is provided with a medical name plate 487 supported by a connecting member 488 so as to be swingable up and down. The rack 480 differs from the rack 460 in that the connecting member 488 is fitted to the rack 480 via a name plate support member 489 instead of the partition member 485.

The rack 480 is implemented by a horizontally extending plate with a flat top face. The partition members 485 formed as thin plates are fitted to the top face thereof at regular or irregular pitches in a longitudinal direction (in the figure, sideways) in order to place a large number of medical resources in respective partitions retrievably.

Two rows of depressions 481 to fit partition members are formed on the top face of the rack 480 at regular or irregular pitches in a longitudinal direction (in the figures, sideways). Two fittings 486 are formed to protrude from the bottom of each of the partition members 485. In this example, the fitting 486 is a small round bar and the depression 481 is a through hole. By inserting the fitting 486 into the depression 481, the partition member 485 is removably fitted to the depression 481 in the rack 480.

The name plate support member 489 is provided above the rack 480 so as to be in parallel to the rack 480 and behind the partition member 485 as it is fitted to the rack 480. In the illustrated example, the name plate support member 489 is a round bar or shaft extending straight. The ends of the member 489 is supported by support posts 489b provided to stand on the rack 480 so that the member 489 can be accommodated in or removed from the housing 422 along with the rack 480. Locking groove 489a are formed at appropriate locations in the name plate support member 489 at a fine pitch, or at least at a pitch determined by the pitch at which the depressions 481 are provided. Each of the locking grooves 489a is formed by engraving the entire circumference of the name plate support member 489 to a regular width and depth.

The connecting member 488 is removably fitted to the name plate support member 489. More specifically, the connecting member 488 is of a form that would be made by bending a plate of a width slightly smaller than the pitch at which the depressions 481 are provided. A locking piece 488a lockable with the locking groove 489a of the name plate support member 489 is provided at the rear end of the connecting member 488. The medical resource name plate 487 is secured to the other end of the connecting member 488 extending forward. As the locking piece 488a is engaged with the locking groove 489a, slight play therebetween allows the connecting member 488 to rotate in both directions around the name plate support member 489 as a pivot axis or an axis of rotation. Meanwhile, travel of the connecting member 488 in the longitudinal direction of the name plate support member 489 is restricted. Thus, by pivotally moving the connecting member 488, the medical resource name plate 487 moves up and down in association with the connecting member 488 in an easy-to-view space where retrieval of a medical resource takes place (more specifically, slightly in front of the front of the rack 480).

The front of the rack 480 exposed when the door 424 is opened is equipped with retrieval guidance members 482 and medical resource detecting members 483 in close proximity with each other. The retrieval guidance members 482 and the medical resource detecting members 483 are arranged in the rack 480 so as to alternate with the depressions 481 in a direction in which the depressions 481 are arranged, i.e., in the longitudinal direction of the rack 480. When the partition member 485 is inserted into the depression 481 on the top face of the rack 480, when the connecting member 488, with a width adapted to the interval between adjacent partition members 485, is fitted to the name plate support member 489, and when the connecting member 488 and the medical resource name plate 487 are allowed to swing freely, the member 488 and the plate 487 are lowered under their own weight until the connecting member 488 comes into contact with the top face of the rack 480 and the medical resource name plate 487 in front thereof is lowered to the front of the rack 480. This shields the retrieval guidance member 482 and the medical resource detecting member 483 at the front of the rack 480 from view. The medical resource name plate 487, as it is lowered in response to the retrieval of the medical resource from the associated location, shields the associated retrieval guidance member 482 from view.

When the medical resource name plate 487 is raised so as to store the medical resource 410 on the rack 480, the connecting member 488 rests on the medical resource 410 instead of on the rack 480, causing the medical resource name plate 487 to remain at an elevated position. The medical resource name plate 487 is located above the associated retrieval guidance member 482, revealing the retrieval guidance member 482 and the medical resource detecting member 483 at the front of the rack 480 for view. The medical resource detecting member 483 provided at the front of the rack 480 does not sense the medical resource 410 placed on the rack 480 but senses the medical resource name plate 467 immediately in front of the rack 480. Due to this and the fact that the medical resource name plate 487 moves up and down in response to the storage/retrieval of the medical resource 410 as a result of interference between the connecting member 488 and the medical resource 410, the medical resource detecting member 483 indirectly detects whether or not the medical resource 410 is placed by detecting whether the medical resource name plate 487 is raised or lowered.

In order to detect the medical resource name plate 487 for indirect detection of the medical resource 410, each of the medical resource detecting members 483 is implemented by a mechanical switch, a reflective photosensor, a capacity sensor or the like, as in the case of the medical resource detecting members 463, 473 and 493 described above, so as to output a binary signal which turns on and off according to whether the medical resource name plate 487 is raised or lowered.

In order to visually guide a user to the location of placement of the medical resource 410 to be retrieved, a miniature bulb, a light emitting diode or the like that can be turned on and off is used as the retrieval guidance member 482, as in the case of the retrieval guidance members 462, 472 and 492 described above.

The horizontal-bridging case 450 (horizontal-bridging member) comprises a rectangular cylinder (see FIGS. 64A-64C). A series of arm-shaped hanger members 455 are hung from the lower part or the bottom of the case 450 in a longitudinal direction (in FIGS. 61A and 64A, sideways) at regular or irregular pitches so as to arrange a large number of medical resources by retrievably hanging them. In order to hang and store relatively longer medical resources 410 by the hanger members 455, hanging storage space is secured below the horizontal-bridging case 450 (see FIG. 61A). In the illustrated example, there is only one horizontal-bridging case 450 provided so as to extend horizontally above the hanging storage space.

In the hollow interior of the horizontal-bridging case 450 (see FIGS. 64C-64C) is housed the horizontal-bridging bar 451 (horizontal-bridging member) extending in a longitudinal direction. The series of hanger members 455 are fitted to the horizontal-bridging bar 451. More specifically, the hanger member 455 comprises a bar member substantially T-shaped in side view (see FIGS. 64B and 64C). The lower end of an vertical bar is bent into a hook, forming an engaging part 456. One end of a top side bar is formed into a weight part 457 by bulging or by being provided with a weight. The other end of the top side bar is provided with a permanent magnet and is formed into a target of detection 458.

A through hole through which the horizontal-bridging bar 451 can be movably inserted is formed in the middle of the top side bar toward the weight part 457. Alternatively, a bearing is fitted thereto. By introducing the bar 451 through the hole or the bearing, the hanger member 455 is supported by the bar 451 so as to be pivotable around the bar 451. The center of gravitation of the hanger member 455 is displaced from the pivot center toward the weight part 457. Therefore, at the time of retrieving a medical resource, the pivotal movement of the hanger member 455 causes the engaging part 456 to be elevated and moved toward an operator (see FIG. 64B). At the time of hanging a medical resource, the pivotal movement causes the engaging part 456 engaged with the medical resource 410 to be lowered and moved toward the back (see FIG. 64C).

On the underside of the horizontal-bridging case 450 (see FIGS. 64B and 64C), a series of oblong holes 450a (hanger member fitting parts) are formed in a longitudinal direction at regular or irregular pitches. As the hanger member 455 is movably introduced into the oblong hole 450a, the hanger member 455 is allowed to move back and forth freely, while substantially being prevented from moving sideways in a front view (see FIG. 64A). The provision maintains the hanger members 455 in an aligned state (lined up in a longitudinal direction), without inhibiting the pivotal movement thereof.

Further (see FIGS. 64B and 64C), a medical resource detecting member 453 is provided on the interior face of the horizontal-bridging case 450 where the target of detection 458 comes into contact as a result of the pivotal movement of the hanger member 455. A retrieval guidance member 452 is provided on the front of the horizontal-bridging case 450 which becomes viewable when the door 424 is opened. The retrieval guidance member 452 and the medical resource detecting member 453 are provided in the horizontal-bridging case 450 so as to be alignment with the oblong hole 250a and are provided for each hanger member 455, i.e., at each location of storage.

In this example, the medical resource detecting member 453 is implemented by a sensor using a Hall device that senses the magnetic field in the magnet of the target of detection 458, in order to detect whether the medical resource 410 is hung in accordance with the pivotal movement of the hanger member 455. The hanger member 455 pivotally moves as the medical resource 410 is hung or removed therefrom. As the target of detection 458 leaves or comes into contact with the medical resource detecting member 453 as a result of the pivotal movement, the medical resource detecting member 453 outputs a binary signal which turns on and off. The medical resource detecting member 453 may be implemented by other devices so long as detection in association with the pivotal movement is enabled. For example, the medical resource detecting member 453 may be implemented by a mechanical switch, a reflective photosensor, a capacity sensor.

In order to visually guide a user to the location of placement of the medical resource 410 to be retrieved, a miniature bulb, a light emitting diode or the like that can be turned on and off is used as the retrieval guidance member 452.

The control unit 430 is expanded in its capabilities so that access to the retrieval guidance member 482, the medical resource detecting member 483, the partition detecting member 484, the retrieval guidance member 472, the medical resource detecting member 473, the partition detecting member 474, the retrieval guidance member 462, the medical resource detecting member 463, the partition detecting member 464, the retrieval guidance member 452, the medical resource detecting member 453 and the partition detecting member 454, as well as to the retrieval guidance member 492, the medical resource detecting member 493 and the hanger member detecting member 494, is enabled. The routines 441-445 and the data 446-449 of the control unit 430 are also altered to reflect the structure by, for example, fine-tuning the definition of addresses storing the components or the size of tables.

The basic usage mode and operation may be largely the same as those in the illustrative embodiments already described. For detection of the medical resource 410, the rack 470 is designed for direct detection, while the racks 460, 480 and 460 and the horizontal-bridging case 450 are designed for indirect detection. A difference in the scheme employed to store medical resources 410 is that the racks 490, 480 and 470 and the rack 460 are designed so that medical resources 410 are placed thereon, while the horizontal-bridging case 450 is designed to hang medical resources 410. As a mixture of three types is provided in the storage part of the medical resource storage and management apparatus 420, medical resources 410 of different types can be stored for accurate and automatic management. The medical resource 410 may be packaged, bundled or contained in a case or a container. Suitable for storage on the rack 470 of direct detection type are those relatively stable in form that can stand on its own while in storage (for example, those contained in a container with the shape of a CD case or a rectangular box). Examples of such medical resources are tube sets for injection/infusion, small and short-length catheters and sets of articles including the same.

Suitable for storage on the racks 490, 480 and 460 of indirect detection and placement type are those relatively thick and unstable in form that do not stand on its own while in storage (for example, those contained in a round, hard case, those in a blister package or those in a soft package). Examples of such medical resources are those for respirator medicine such as filters, resources for medical operations, and resources for artificial replacement. The rack 490 of a type on which resources contained in a case are placed, medical resources 410 of even more unstable form may be stored in a stable manner.

Suitable for storage on the horizontal-bridging case 450 of indirect detection and hanger type are those that are long and relatively unstable in form, those that are light or thin but heavy enough to be detected by being hung. Examples of such medical resources are long sterilized catheters of not less than 0.5 cm, long tubes, or resources for medical operations that are light or thin.

Other Points of Note

In the fifth embodiment, the control unit 430 is accommodated in the electric equipment 421. Alternatively, the control unit 430 may be placed outside the housing 422. The input and output means of the control unit 430 may not be restricted to the display 432, the keyboard 433 and the like mentioned above and may be implemented by a touch panel or a mobile information terminal.

In the fifth embodiment, the medical resource detection routine 442 is designed to associate the on and off states of the result of detection by the medical resource detecting member 493 with the storage and retrieval of the medical resource 410, respectively. It is easy to expand the capabilities to automatically manage the return of a medical resource 410 once taken out and not used. For example, a determination may be made that a resource is not replenished but returned, if retrieval and storage are conducted successively in a short time span, or if a resource is stored in one of the modes of operation introduced in the control unit 430 in which mode an action of retrieval is restricted. In this case, information indicating the return may suitably be appended to the log data 449 or other output data. In addition to data storage and output, provisions may also be made for management of expiration dates, stock control, preparation of drug history and inspection.

SIXTH EMBODIMENT

A sixth embodiment of the present invention relates to a medical supply management system for managing medical supplies in a medical institution.

Medical institutions such as hospitals handle a variety of medical resources and medicines for treatment (e.g. operation) and inspection of patients suffering from various diseases and injuries. This calls for stock control of medical supplies whereby the amount of different types of medical supplies in stock and the expiration date of medical supplies are kept track of. For replenishment of those medical supplies that are running short, an order for a necessary amount should be placed with a manufacturer of medical supplies. In the event that a medical supply runs short and causes a trouble in treatment or inspection, it may lead to mishaps in medical practice. Accordingly, stock control of medical supplies in a medical institution is a task of utmost importance.

Recently, institutions like hospitals use computers for stock control of medical supplies. The amount of respective types of medical supplies in stock is calculated and recorded by inputting the amount of respective types of medical supplies delivered and the amount of respective types of medical supplies consumed in treatment or inspection. Input of the amount of medical supplies consumed is manually provided. Therefore, it is required that the amount of respective types of medical supplies consumed be input without fail, in order to acquire the accurate amount of respective types of medical supplies in stock.

Various techniques are conceivable for computer-based stock control of medical supplies. For maintenance of the proper amount of respective types of medical supplies in stock, it is necessary to monitor the amount of stock, determine the amount replenished and place an order for the required amount. The process imposes a heavy burden on medical workers. In this background, patent document No. 2 discloses a medical resource management system configured such that a management server is connected via the Internet to terminals at medical institutions and terminals at logistics centers for communication of information. The management server is responsible for stock control of medial resources at the medical institutions, determination of the type and amount of medical resources to be ordered, and placement of orders with the logistics centers.

Because hospitals handle an extremely large variety of medical supplies, utmost care is necessary in selecting from the vast variety and making available medical supplies used in treatment or inspection of patients without fail. Any error may lead to mishaps in medical practice. As shown in patent document No. 3, we have made available a medicine storage and management apparatus comprising multiple medicine storage units, multiple medicine sensors and multiple indicator lamps. The indicator lamp of a medicine storage unit accommodating a medicine to be administered to a patient is turned on by referring to information on the medicine.

Conventional management of medical supplies at medical institutions such as hospitals is such that the amount of medical supplies consumed is manually input, even if a computer is used for stock control. This gives rise to failure to input the amount consumed or an error in input, preventing the amount of respective types of medical supplies in stock to be acquired efficiently, easily and accurately. This will result in failure to place an order with a manufacturer of medical supplies for the required amount of medical supplies that have been consumed and run short in an efficient and proper manner.

A resultant shortage of medical supplies may lead to mishaps in medical practice. Conversely, an excessive amount of medical supplies in stock may result. In this case, a large amount of medical supplies are wasted as they are past expiration date. Consequently, the amount of respective types of medical supplies in stock cannot be maintained at a proper level neither insufficient nor excessive. The medical resource management system of patent document No. 2 uses, for example, a barcode reader to input the amount of medical resources consumed at a medical institution. Since this still involves manual operation, the same problem as described above occurs, preventing the amount of respective types of medical supplies in stock to be acquired in a reliable manner.

Medicine storage and management apparatuses such as that of patent document No. 3, which support making available a stock of medicines administered to patients, are indeed available. However, apparatuses that support making available a stock of medical resources necessary for treatment or inspection of patients have not been put into use. For example, a medical operation department of a hospital uses a large variety of medical resources. Conventionally, it is difficult to make available medical resources easily and properly that are necessary in an operation on a patient. That is, it is difficult to improve efficiency of the work of making available medical resources.

A general purpose of the sixth embodiment is to provide a medical supply management system wherein: medical supplies necessary for treatment and inspection of patients are retrieved easily and properly; the type and amount of medical supplies consumed and the amount of respective types of medical supplies in stock are acquired efficiently, easily and properly; and an order for the required amount of medical supplies that have been consumed and run short is placed efficiently and properly for replenishment.

A summary of the sixth embodiment will be given.

A first medical supply management system according to the sixth embodiment is for managing medical supplies in a medical institution and comprises a plurality of storage and management apparatuses, wherein each of the plurality of storage and management apparatuses comprises: a plurality medical supply storage parts capable of storing a plurality of types of medical supplies; medical supply detecting means which detects whether a medical supply is stored in each of the medical supply storage parts; computer means which creates management information pertaining to the medical supplies in the plurality of medical supply storage parts on the basis of information detected by the medical supply detecting means; and retrieval guidance means which is controlled by the computer means so as to guide a user to the medical supply to be taken out, wherein the computer means in each storage and management apparatus is operable to control the retrieval guidance means on the basis of information on the medical supply to be taken out, and to create and output consumed medical supply information related to the type and amount of medical supplies consumed, the system further comprising stock control means which is communicably connected to the plurality of storage and management apparatuses, and which calculates and stores the amount of respective types of medical supplies in stock, on the basis of the latest amount of respective types of medical supplies in stock stored in the stock control means, and on the basis of the consumed medical supply information received from the storage and management apparatuses.

Since a plurality of medical supply storage parts capable of storing a plurality of types of medical supplies are provided in each storage and management apparatus and since a medical supply detection sensor detects whether a medical supply is stored in each of the medical supply storage parts, the computer means is operable to create management information related to the medical supplies in the plurality of medical supply storage parts, by mapping the plurality of types of medical supplies into the plurality of medical supply storage parts, respectively. The management information indicating whether a medical supply is stored in each of the medical supply storage parts, the type and amount of medical supplies stored in each of the medical supply storage parts, the type and amount of medical supplies taken out from each of the medical supply storage parts, the type and amount of medical supplies accepted (replenished or returned) in each of the medical supply storage parts, etc. Preferably, the medical supply detecting means is implemented by a plurality of medical supply detection sensors respectively provided in the plurality of medical supply storage parts.

The computer means in each storage and management apparatus controls the indicator retrieval guidance means on the basis of information related to the medical supply needed in treatment or inspection of each patient (medical supply to be taken out) so as to allow the retrieval guidance means to indicate the medical supply to be taken out. For example, the information on the medical supply to be taken out may be created by a data processor outside the storage and management apparatus. Preferably, the retrieval guidance means may be implemented by multiple indicator lamps respectively provided in the plurality of medical supply storage parts.

By using the management information and by designating, in the event of accepting a medical supply in the medical supply storage part, whether the acceptance is replenishment or return, the computer means determines the type and amount of medical supplies consumed (i.e., no longer in stock). The computer means then creates the consumed medical supply information related to the type and amount of consumed medical supplies. The stock control means is communicably connected to the multiple storage and management apparatuses so that the storage and management apparatuses output the consumed medical supply information to the stock control means.

The stock control means calculates and stores the amount of respective types of medical supplies in stock on the basis of the latest amount of respective types of medical supplies in stock stored in the stock control means, and on the basis of the consumed medical supply information received from the storage and management apparatuses. The stock control means may be provided in the medical institution and connected to the storage and management apparatuses via a local area network. Alternatively, the stock control means may be provided in a management server outside the medical institution and connected to the storage and management apparatuses via the Internet or a local area network.

The following structure may be employed in the sixth embodiment.

In a second medical resource storage and management apparatus according to the sixth embodiment, the stock control means may receive the amount of respective types of medical supplies delivered to the medical institution from an external source, and calculate and store the amount of respective types of medical supplies in stock on the basis of the delivered amount. In a third medical resource storage and management apparatus according to the sixth embodiment, the plurality of types of medical supplies stored may include at least one of injection/infusion resources, catheters, tubes, resources for anesthesia, resources for oxygen inhalation, oxygen masks, sterilized filters, artificial bones and artificial joints.

In a fourth medical resource storage and management apparatus according to the sixth embodiment, at least one of the plurality of types of medical supplies may be an ampule, a vial or a medicine contained in an infusion package. In a fifth medical resource storage and management apparatus according to the sixth embodiment, the medical institution may be a hospital. One or multiple storage and management apparatuses may be provided in each section of the hospital where a stock of medical supplies is necessary. In a sixth medical resource storage and management apparatus according to the sixth embodiment, the stock control means may calculate and store the amount of respective types of medical supplies in stock for each of the one or multiple storage and management apparatuses in each section.

In a seventh medical resource storage and management apparatus according to the sixth embodiment, the stock control means may be connected to medical supply supplier terminals of medical supply suppliers delivering medical supplies to the medical institution. The system may be provided with an order determining means which determines the type and amount of medical supplies to be ordered from the medical supply suppliers, on the basis of the amount of respective types of medical supplies in stock maintained in the stock control means. The system may further be provided with an ordering means which places an order by outputting order information, which contains the type and amount of medical supplies determined by the order determining means, to the medical supply supplier terminal.

In an eighth medical resource storage and management apparatus according to the sixth embodiment, the stock control means may be provided with a target stock amount setting means which sets a target amount of respective types of medical supplies in stock. The order determining means may determine the type and amount of medical supplies to be ordered from the medical supply suppliers, on the basis of the stock amount and the target stock amount. In a ninth medical resource storage and management apparatus according to the sixth embodiment, a local area network may be formed in the medical institution to communicably connect at least the multiple medical resource storage and management apparatuses and the medical institution terminal. The stock control means may comprise a data processor of a management server connected to the medical institution terminal via a communicating means. In a tenth medical resource storage and management apparatus according to the sixth embodiment, multiple medical institutions each provided with the local area network, and multiple medical supply suppliers each provided with the medical supply supplier terminal may be adapted to be connected to the management server.

According to the first medical supply management system, the system comprises a storage and management apparatus each comprising a plurality medical supply storage parts, a medical supply detecting means, a computer means and a retrieval guidance means. The medical supply detecting means in each storage and management apparatus detects whether a medical supply is stored in each of the medical supply storage parts. The computer means controls the retrieval guidance means on the basis of information related to the medical supply needed in treatment or inspection of each patient (medical supply to be taken out) so as to allow the retrieval guidance means to indicate the medical supply to be taken out. Accordingly, the target medical supply is retrieved from the medical supply storage part easily and properly. The efficiency in making available medical supplies is improved and the likelihood of mishaps in medical practice due to failure to retrieve proper medical supplies is minimized. The computer means in each storage and management apparatus creates management information pertaining to the medical supplies in the plurality of medical supply storage parts, the management information indicating whether a medical supply is stored in each of the medical supply storage parts, the type and amount of medical supplies stored in each of the medical supply storage parts, the type and amount of medical supplies taken out from each of the medical supply storage parts, the type and amount of medical supplies accepted (replenished or returned) in each of the medical supply storage parts, etc. The management information may be utilized to achieve, before and after the retrieval of medical supplies, a proper stock status in which necessary medical supplies are stored in just the right amount. If the medical supply to be taken out is not stored, the management information may be utilized to indicate as such.

By using the management information and by designating, in the event of accepting a medical supply in the medical supply storage part, whether the acceptance is replenishment or return, the computer means in each storage and management apparatus determines the type and amount of medical supplies consumed (i.e., no longer in stock). The computer means then creates the consumed medical supply information related to the type and amount of consumed medical supplies. Because the information on the type and amount of medical supplies used is recorded, a request for heal insurance coverage can be made properly without failure. The stock control means communicably connected to the multiple storage and management apparatuses calculates and stores the amount of respective types of medical supplies in stock, on the basis of the latest type-by-type amount of stock maintained in the stock control means and the consumed medical supply information received from each of the storage and management apparatuses. Accordingly, the type and amount of consumed medical supplies, and the amount of respective types of medical supplies in stock can be acquired efficiently, easily and accurately. An order for a required amount of medical supplies that have been consumed and run short can be placed efficiently and properly for replenishment. As a result, the amount of respective types of medical supplies in stock in the medical institution can be maintained at just the right level. As described, the inventive system can contribute to the operation (management) of the medical institution such as a hospital.

According to the second medical supply management system, the stock control means receives the amount of respective types of medical supplies delivered to the medical institution from an external source, and calculates and stores the amount of respective types of medical supplies in stock on the basis of the delivered amount. Therefore, the amount of respective types of medical supplies in stock in the medical institution can be properly acquired.

According to the third medical supply management system, the plurality of types of medical supplies include at least one of injection/infusion resources, catheters, tubes, resources for anesthesia, resources for oxygen inhalation, oxygen masks, sterilized filters, artificial bones and artificial joints. Therefore, at least one of multiple types of medical resources can be managed properly.

According to the fourth medical supply system, at least one of the multiple types of medical supplies is an ampule, a vial or a medicine contained in an infusion package. Therefore, at least one of the multiple types of medicines can be managed properly.

According to the fifth medical supply management system, the medical institution is a hospital. One or multiple storage and management apparatuses is provided in each section of the hospital where a stock of medical supplies is necessary. Therefore, the sections provided with storage and management apparatuses can manage medical supplies properly.

According to the sixth medical supply management system, the stock control means calculates and stores the amount of respective types of medical supplies in stock for each of the one or multiple storage and management apparatuses in each section. Accordingly, each section provided with the storage and management apparatuses can manage the amount of respective types of medical supplies in stock and maintain the amount of stock at just the right level.

According to the seventh medical supply management system, the stock control means is connected to medical supply supplier terminals of medical supply suppliers delivering medical supplies to the medical institution. The system is provided with an order determining means which determines the type and amount of medical supplies to be ordered from the medical supply suppliers, on the basis of the amount of respective types of medical supplies in stock maintained in the stock control means. The system is further provided with an ordering means which places an order by outputting order information, which contains the type and amount of medical supplies determined by the order determining means, to the medical supply supplier terminal. Therefore, the type and amount of medical supplies to be ordered from the medical supply suppliers are properly determined, and the order for the required type and amount of medical supplies is placed with the medical supply suppliers smoothly and properly.

According to the eighth medical supply management apparatus, the stock control means comprises a target stock amount setting means which sets a target amount of respective types of medical supplies in stock. The order determining means determines the type and amount of medical supplies to be ordered from the medical supply suppliers, on the basis of the stock amount and the target stock amount. Therefore, by setting the target amount of respective types of medical supplies in stock, the type and amount of medical supplies to be ordered from the medical supply suppliers is determined automatically.

According to the ninth medical supply management system, a local area network is formed in the medical institution to communicably connect at least the multiple medical resource storage and management apparatuses and the medical institution terminal. The stock control means comprises a data processor of a management server connected to the medical institution terminal via a communicating means. Therefore, the majority of the processes in the medical supply management system for managing medical supplies can be performed by the data processor of the management server, which is outside the medical institutions. The medical institutions can benefit from the medical supply management system while incurring the minimizing the cost to build the system. Thus, the system is highly effective.

According to the tenth medical supply management system, multiple medical institutions each provided with the local area network, and multiple medical supply suppliers each provided with the medical supply supplier terminal are adapted to be connected to the management server. Therefore, the multiple medical institutions can share the management server of the medical supply management server, and the medical institutions can order a large variety of medical supplies from appropriate ones of the multiple medical supply suppliers via the management server.

The medical supply management system according to the sixth embodiment is for managing medical supplies in a medical institution and, more particularly, comprises a plurality of storage and management apparatuses, wherein each of the plurality of storage and management apparatuses comprises: a plurality medical supply storage parts capable of storing a plurality of types of medical supplies (medical resources and medicines); medical supply detecting means which detects whether a medical supply is stored in each of the medical supply storage parts; computer means which creates management information pertaining to the medical supplies in the plurality of medical supply storage parts on the basis of information detected by the medical supply detecting means; and retrieval guidance means which is controlled by the computer means so as to guide a user to the medical supply to be taken out.

Illustrative Embodiment 6-1

As shown in FIG. 65, a medical institution 1001 (general hospital) is provided with multiple sections such as a medical operation department 1002, a dispensary 1003 and a medical ward 1004 (other sections may include an emergency department, central care unit, dialysis department, X-ray department, ICU, HICU, NICU, etc.). One or multiple medical resource storage and management apparatus 1005 and/or one or multiple of medicine storage and managements 1006 are provided in each section where maintenance of a stock of medical supplies (medical resources and medicines) is necessary. For example, the medical resource storage and management apparatus 1005 and the medicine storage and management apparatus 1006 are provided in the operation department 1002; the medicine storage and management apparatus 1005 is provided in the dispensary 1003; and the medical resource storage and management apparatus 1005 and the medicine storage and management apparatus 1006 are provided in the medical ward 1004.

The medical institution 1001 is also provided with a stock control apparatus 1007 and an incoming management apparatus 1008. A local area network 1009 (LAN 1009) is formed to communicably connect the multiple medical resource storage and management apparatuses 1005, multiple medicine storage and management apparatuses 1006, the stock control apparatus 1007 and the incoming management apparatus 1008. Various data processors provided in the medical institution 1001 can be connected to the LAN 1009. The medical supply management system MS1 of the illustrative embodiment 6-1 comprises multiple medical resource storage and management apparatuses 1005, multiple medicine storage and management apparatuses 1006, the stock control apparatus 1007, the incoming management apparatus 1008, the LAN 1009 and the like.

As shown in FIG. 66, the medical resource storage and management apparatus 1005 and the medicine storage and management apparatus 1006 each comprises: multiple medical supply storage parts 1010 capable of storing multiple types of medical supplies (medical resources and medicines); a medical supply detection sensor 1011 (medical supply detecting means) which is provided in each of the medical supply storage parts 1010 and which detects whether a medical supply is stored in the part 1010; a computer 1012 (computer means) which creates management information pertaining to the medical supplies in the multiple medical supply storage parts 1010 on the basis of information detected by the medical supply detection sensor 1011; and an indicator lamp 1013 which is provided in association with the multiple medical supply storage parts 1010 (retrieval guidance means) and which is controlled by the computer 1012 so as to guide a user to the medical supply to be taken out.

The computer 1012 is provided with a CPU, ROM, RAM and I/O (input and output interface). Multiple medical supply detection sensors 1011 and multiple indicator lamps 1013 are connected to the I/O. Each medical supply storage part 1010 is configured to store only one medical supply. Alternatively, each medical supply storage part 1010 may be configured to store multiple medical supplies. In this case, it is favorable that multiple medical supply detection sensors 1011 be provided in each medical supply storage part 1010.

The medical resource storage and management apparatus 1005 and the medicine storage and management apparatus 1006 each comprises: a storage device 1014 such as a hard disk; a display device 1015 such as a liquid crystal display; an input device 1016 such as a keyboard, mouse or touch panel; a reader device 1017 such as a barcode reader or IC reader; and a printing device 1018 such as an inkjet printer. These equipment 1014-1018 are connected to the I/O of the computer 1012. At least some of the equipment 1014-1018 may be omitted.

As shown in FIG. 67, the storage device 1014 stores a storage management program executed by the CPU of the computer 1012 and stores a medical supply master file 1020, a correspondence information file 1021 and a management information file 1022.

As shown in FIG. 68, the medical supply master file 1020 stores medical supply information related to multiple types of medical supplies. The medical supply information contains a medical supply code, a medical supply name and information on specification or amount. As shown in FIG. 69, the correspondence information file 1021 contains medical supply storage part codes for multiple medical supply storage parts 1010. Each of medical supply codes preset to identify corresponding types of medical supplies is stored in association with each of the medical supply storage part codes (correspondence information table).

The computer 1012 of the storage and management apparatuses 1005 and 1006 creates management information related to medical supplies in the multiple medical supply storage parts 1010, on the basis of the information detected by the multiple medical supply detection sensors 1011 and of the correspondence information table stored in the correspondence information file 1021. As shown in FIG. 70, the management information indicating whether a medical supply is stored in each of the medical supply storage parts 1010, the type and amount of medical supplies stored in each of the medical supply storage parts 1010, the type and amount of medical supplies taken out from each of the medical supply storage parts 1010, the type and amount of medical supplies accepted (replenished or returned) in each of the medical supply storage parts 1010.

A description will now be given of specific structures of four types of medical resource storage and management apparatuses 1005A-1005D that can be employed to implement the medical resource storage and management apparatus 1005 of the medical supply management system MS1. The multiple types of medical supplies stored in the medical resource storage and management apparatus 1005 include at least one of injection/infusion resources, catheters, tubes, resources for anesthesia, resources for oxygen inhalation, oxygen masks, sterilized filters, artificial bones and artificial joints.

A description will be given of the medical resource storage and management apparatus 1005A by referring to FIGS. 71-74.

The medical resource storage and management apparatus 1005A is provided with a cuboid housing 1030 provided with a computer 1012A, a door 1031 which opens and closes the front of the housing 1030, and multiple racks 1032 provided inside the housing 1030. Each rack 1032 is formed as a horizontally extending plate. Multiple partition members 1033 partition the top part of the rack so as to form multiple medical supply storage parts 1010A. In each medical supply storage part 1010A, the medical supply is placed on top of the rack 1032. Multiple pairs of front and rear mounting holes 1032a are formed in each rack 1032 at regular intervals in the horizontal direction. Each partition member 1033 is fitted to the rack 1032 by inserting a pair of front and rear insertion fittings 1033a into a pair of front and rear mounting holes 1032a, respectively.

Medical resources such as catheters are stored in the medical supply storage part 1010A such that they are accommodated in a medical resource case designed to stand on its own and having a relatively small horizontal width. The medical resource cases do not have a regular horizontal width. Therefore, the interval between the mounting holes 1032a that are adjacent in the horizontal direction is defined in accordance with the minimum horizontal width of the medical resource case. The horizontal storage width of each medical supply storage part 1010A can be adjusted in accordance with the horizontal width of the medical supply case to be stored, by adjusting the position of fitting the partition member 1033.

Multiple medical supply detection sensors 1011A are fitted on top of each rack 1032 such that a medical supply sensor 1011A is located between the mounting holes 1032a that are adjacent to each other in the horizontal direction (or between the mounting hole 1032*a* at the horizontal end and the edge of the rack 1032). Multiple indicator lamps 1013A are fitted to the front of each rack 1032 so as to make respective pairs with the multiple medical supply detection sensors 1011A. Each medical supply detection sensor 1011A is a sensor for directly detecting the medical supply and is implemented by a mechanical switch, a photosensor or a capacity sensor. The indicator lamp 1013A may be implemented by a light-emitting diode or a miniature bulb.

In this storage and management apparatus 1005A, the position of fitting the multiple partition members 1033, i.e., the layout of the multiple medical supply storage parts 1010A is variable. By providing an attachment sensor for detecting whether the partition member 1033 is fitted to the mounting hole 1032*a*, the computer 1012A can known the layout of the multiple medical supply storage parts 1010A on the basis of information from the attachment sensor.

A description will be given of the medical resource storage and management apparatus 1005B by referring to FIGS. 75-77.

The medical resource storage and management apparatus 1005B is provided with a cuboid housing 1040 provided with a computer 1012B, a door 1041 which opens and closes the front of the housing 1040, and multiple racks 1042 provided inside the housing 1040. Each rack 1042 is formed as a horizontally extending plate. Multiple partition members 1043 partition the top part of the rack so as to form multiple medical supply storage parts 1010B. A movable member 1044 is provided in each medical supply storage part 1010B so that the medical supply is placed on top of the rack 1042 below the movable member 1044. Multiple pairs of front and rear mounting holes 1042*a* are formed in each rack 1042 at regular intervals in the horizontal direction. Each partition member 1043 is fitted to the rack 1042 by inserting a pair of front and rear insertion fittings 1043*a* into a pair of front and rear mounting holes 1042*a*, respectively.

A support shaft 1045 is fitted above the rear end of each rack 1042 so as to extend horizontally. Each movable member 1044 is pivotally fitted such that an engaging part 1044*a* at the rear end is engaged with the support shaft 1045. Each movable member 1044 is provided with the engaging part 1044*a*, a connecting part 1044*b* extending from the engaging part 1044*a* to the front, and a name plate part 1044*c* provided at the front of the connecting part 1044*b*. The movable member 1044 of the medical supply storage part 1010B which does not store a medical supply is as shown in FIG. 76. The name plate part 1044*c* covers the front of the rack 1042. When the medical supply is stored in the medical supply storage part 1010B, the connecting part 1044*b* of the movable member 1044 of the medical supply storage part 1010B is swung upward by being pressed by the medical supply inserted below the movable member 1044.

Medical resources such as injection/infusion resources are stored in the medical supply storage part 1010B such that they are accommodated in a medical resource case of a relatively large horizontal width designed to lie horizontally. The medical resource cases do not have a regular horizontal width. Therefore, the interval between the mounting holes 1042*a* that are adjacent in the horizontal direction is defined in accordance with the minimum horizontal width of the medical resource case. The horizontal storage width of each medical supply storage part 1010B can be adjusted in accordance with the horizontal width of the medical supply case to be stored, by adjusting the position of fitting the partition member 1043. It is desirable that the movable member 1044 with a size compatible with the horizontal width of the medical supply storage part 1010B be provided therein.

Multiple medical supply detection sensors 1011B and indicator lamps 1013B are fitted to the front of each rack 1042 such that a medical supply sensor 1011B and an indicator lamp 1013B are located in front of the interval between the mounting holes 1042*a* that are adjacent to each other in the horizontal direction (or between the mounting hole 1042*a* at the horizontal end and the edge of the rack 1042). Multiple indicator lamps 1013A are fitted to the front of each rack 1032 so as to make respective pairs with the multiple medical supply detection sensors 1011A. The medical supply detection sensor 1011B is a sensor for indirectly detecting the medical supply via the movable member 1044. The name plate part 1044*c* of the movable member 1044 of the medical supply storage part 1101B which does not store a medical supply comes close to the medical supply detection sensor 1011B so as to cover the indicator lamp 1013. When the medical supply is stored in the medical supply storage part 1010B, the name plate part 1044*c* is raised and removed from the medical supply detection sensor 1011B, allowing the indicator lamp 1013B to be viewed.

In this storage and management apparatus 1005B, the position of fitting the multiple partition members 1043, i.e., the layout of the multiple medical supply storage parts 1010B is variable. By providing an attachment sensor for detecting whether the partition member 1043 is fitted to the mounting hole 1042*a*, the computer 1012A can know the layout of the multiple medical supply storage parts 1010B on the basis of information from the attachment sensor. The medical supply detection sensor 1011B and the indicator lamp 1013B may be implemented in the same way as in the case of the storage and management apparatus 1005A.

A description will be given of the medical resource storage and management apparatus 1005C by referring to FIGS. 78-81.

The medical resource storage and management apparatus 1005C is provided with a cuboid housing 1050 provided with a computer 1012C, a door 1051 which opens and closes the front of the housing 1050, and a horizontal-bridging member 1052 provided toward the upper end of the interior of the housing 1050. The horizontal-bridging member 1052 is formed as a horizontally extending hollow case with rectangular longitudinal cross section. Multiple oblong holes 1052*a* are formed on the bottom plate of the horizontal-bridging member 1052 so as to be aligned in the horizontal direction. There are also provided multiple hanger members 1053 which are introduced into the respective oblong holes 1052. The neighborhood of the multiple hanger members 1053 and a space below form multiple medical supply storage parts 1101C. In each medical supply storage part 1101C, medical supplies such as tubes are stored by being hung from the hanger members 1053.

Each hanger member 1053 is substantially T-shaped in side view. A connecting part 1053*a* at its upper end is accommodated in the horizontal-bridging member 1052. A straight swinging part 1053*b* extending downward from the connecting part 1053*a* is introduced into the insertion hole 1052*a*. A hook part 1053*c* is formed at the lower end of the swinging part 1053*b*. A support shaft 1054 extending horizontally is fitted inside the horizontal-bridging member 1052. The connecting part 1053*a* of each hanger member 1053 is fitted onto and pivotally supported by the support shaft 1054. A target of detection 1053*d* is provided at the front end of the connecting part 1053*a* and a weight part 1053*e* is provided at the rear end thereof.

Multiple medical supply detection sensors 1011C corresponding to the targets of detection 1053*d* of the multiple hanger members 1053 are fitted inside the horizontal-bridging member 1052. Multiple indicator lamps 1013C corresponding to the multiple hanger members 1053 are fitted at the front of the horizontal-bridging member 1052. As shown in FIG. 80, the hanger member 1053 from which a medical supply is not hung is tilted backward due to the weight part 1053e, with the result that the target of detection 1053d is removed from the medical supply detection sensor 1011C. When a medical supply is hung from the hanger member 1053, the hanger member 1053 becomes vertically oriented with the result that the target of detection 1053 comes close to the medical supply detection sensor 1011C. The medical supply detection sensor 1011C and the indicator lamp 1013C may be implemented in the same way as in the case of the storage and management apparatus 1005A.

A description will be given of the medical resource storage and management apparatus 1005D with reference to FIGS. 82 and 83.

The medical resource storage and management apparatus 1005D is provided with a cuboid housing 1060 provided with a computer 1012D, and multiple racks 1062 provided inside the housing 1060. Each rack 1062 is formed as a horizontally extending plate. Inside each rack 1062 is fitted multiple antennas 1011D for IC readers corresponding to medical supply detecting means. A space above the antennas 1011D forms a medical supply storage part 1010D. In each medical supply storage part 1010D, a medical supply fitted with an IC tag 1063 is placed on top of the rack 1062. The IC reader is connected to the computer 1012D. An IC chip of the IC tag 1063 stores information on the medical supply fitted with the IC tag 1063.

A description of the specific structure of the medicine storage and management apparatus 1006 that could be employed in the medical supply management system MW1 is omitted. At least one of multiple types of medicines stored in the medicine storage and management apparatus 1006 is an ampule, a vial or a medicine contained in an infusion package.

The computer 1012 of the storage and management apparatuses 1005 and 1006 controls the multiple indicator lamps 1013, on the basis of information on the medical supply to be taken out, so as to turn on the indicator lamp 1013 of one or multiple medical supply storage parts 1010 which store the medical supply to be taken out. The information on the medical supply to be taken out represents information for each patient's prescription, for each treatment (operation) or for each inspection. The information may be read by the reader device 1017 from a barcode or an IC chip attached to a document such as a form, received from a predetermined data processor via the LAN 1009, or separately input via the input device 1015.

The computer 1012 of the storage and management apparatus 1005 and 1006 is designed to create consumed medical supply information related to the type and amount of medical supplies taken out from the storage and management apparatuses 1005 and 1006 and consumed, and to output the information to the stock control apparatus 1007. While most of the medical supplies taken out from the storage and management apparatuses 1005 and 1006 are actually used (or discarded, in some cases) and consumed, some are not used and returned to the storage and management apparatuses 1005 and 1006. Medical supplies that are returned are not dealt with as consumed medical supplies.

In this regard, the computer 1012 of the storage and management apparatuses 1005 and 1006 may be designed to create consumed medical supply information indicating the type and amount of medical supplies consumed, on the basis the type and amount of medical supplies taken out and returned since the task of making available medical supplies is started until it is ended, which task is carried out for each patient's prescription, each treatment or each inspection. The computer 1012 may also be configured to output the information to the stock control apparatus 1007 after the task of making available is completed. The consumed medical supply information may be the type and amount of medical supplies taken out and returned, which are directly output from the computer 1012 of the storage and management apparatuses 1005 and 1006 to the stock control apparatus 1007. In this case, the stock control apparatus 1007 may determine the type and amount of medical supplies taken out from the storage and management apparatuses 1005 and 1006 and consumed.

A description will now be given of the stock control apparatus 1007 and the incoming management apparatus 1008.

As shown in FIGS. 84 and 85, the stock control apparatus 1007 comprises a data processor such as a personal computer. The stock control apparatus 1007 is provided with a processor main body 1070, a mouse 1071, a keyboard 1072 and a display 1073. The processor main body 1070 is provided with a CPU 1080, a ROM 1081, a RAM 1082, a hard disk drive 1083 (HDD) and a hard disk 1084 (HD), a CD drive 1085 (CDD) for a compact disk 1085a (CD), an FDD 1086 for a floppy disk (FD), an input and output interface (I/O) 1087, and the like. The elements 1080-1087 are connected to each other via a bus 1088. The mouse 1071, the keyboard 1072 and a display drive circuit 1073a for the display 1073 are connected to the I/O 1087.

As shown in FIG. 86, the storage unit of the HD 1084 or the like stores a stock control program executed by the CPU 1080. A type-by-type incoming medical supply file 1090, a type-by-type medical supply consumption file 1091 and a type-by-type medical supply stock file 1092 are also stored.

As shown in FIG. 87, the type-by-type medical supply stock file 1092 stores the amount of respective types of medical supplies in stock in the whole medical institution 1001, and the amount of respective types of medical supplies in stock in each section (medical operation unit, dispensary, medical ward and the like) in which is provided the storage and management apparatuses 1005 and 1006, i.e., the amount in each of the one or multiple storage and management apparatuses 1005 and 1006 provided in each section. The stock control apparatus 1007 calculates, stores and updates the amount of respective types of medical supplies in stock, on the basis of the latest amount maintained in the type-by-type medical supply stock file 1092, and on the basis of the consumed medical supply information received from the storage and management apparatuses 1005 and 1006. The process is carried out each time the consumed medical supply information is received from either of the storage and management apparatuses 1005 and 1006.

The incoming management apparatus 1008. (not shown) comprises a data processor such as a personal computer and is of structure similar to that of the stock control apparatus 1007. The apparatus 1008 is further provided with a reader device such as a barcode reader and an IC reader. The incoming management apparatus 1008 creates incoming medical supply information related to the type and amount of incoming medical resources and to the destination sections to which the medical supplies are delivered, on the basis of information read by the reader device from barcodes assigned to the cases containing the delivered medical supplies. The information thus created is transmitted to the stock control apparatus 1007. The incoming management apparatus 1008 is provided in a section responsible for accepting incoming medical supplies and/or in each of the sections in which the storage and management apparatuses 1005 and 1006 are provided.

The stock control apparatus 1007 calculates, stores and updates the amount, as shown in FIG. 87, of respective types of medical supplies stored, on the basis of the latest amount maintained in the type-by-type medical supply stock file 1092, and on the basis of the incoming medical supply information received from the incoming management apparatus 1008 (the amount of respective types of medical supplies delivered to the medical institution 1001 and communicated from outside via the incoming management apparatus 1008). The process is carried out each time the incoming medical supply information is received from the incoming management apparatus 1008.

The type-by-type incoming medical supply file 1090 chronologically stores the type and amount of medical supplies delivered to the medical institution 1001 as a whole and to the respective sections, in association with information such as date and time of delivery. The type-by-type medical supply consumption file 1091 chronologically stores the type and amount of medical supplies consumed in the medical institution 1001 as a whole and in the respective sections, in association with information such as date and time of consumption. The stock control apparatus 1007 is operable to output the information or a modified version thereof.

The medical supply management system MS1 described above provides the following advantages.

The medical supply management system MS1 is provided with the multiple storage and management apparatuses 1005 and 1006 each provided with multiple medical supply storage parts 1010, multiple medical supply detection sensors 1011, the computer 1012 and the multiple indicator lamps 1013. The medical supply detection sensor 1011 in each of the storage and management apparatuses 1005 and 1006 detects whether a medical supply is stored in the medical supply storage part 1010. The computer 1012 controls the indicator lamp 1013 on the basis of information related to the medical supply needed in treatment or inspection of each patient (medical supply to be taken out) so as to allow the indicator lamp 1013 to indicate the medical supply to be taken out. Accordingly, the target medical supply is taken out from the medical supply storage part 1010 easily and properly. The efficiency in making available medical supplies is improved and the likelihood of mishaps in medical practice due to failure to make available proper medical supplies is minimized.

The computer 1012 in each of the storage and management apparatuses 1005 and 1006 creates management information related to the medical supplies in the multiple medical supply storage parts 1010, the management information indicating the availability of a medical supply in the medical supply storage parts 1010, the type and amount of medical supplies stored in the medical supply storage parts 1010, the type and amount of medical supplies taken out from the medical supply storage parts 1010, the type and amount of medical supplies accepted (replenished or returned) in the medical supply storage parts 1010. The management information may be utilized to achieve, before and after the retrieval of medical supplies, a proper stock status in which necessary medical supplies are stored in just the right amount. If the medical supply to be taken out is not stored, the management information may be utilized to indicate as such.

By using the management information and by designating, in the event of accepting a medical supply in the medical supply storage part 1010, whether the acceptance is replenishment or return, the computer 1012 in each of the storage and management apparatuses 1005 and 1006 determines the type and amount of medical supplies consumed (i.e., no longer in stock). The computer 1012 then creates the consumed medical supply information related to the type and amount of consumed medical supplies. Because the information on the type and amount of medical supplies used is recorded, a request for heal insurance coverage can be made properly without failure.

The stock control apparatus 1007 communicably connected to the multiple storage and management apparatuses 1005 and 1006 calculates and stores the amount of respective types of medical supplies in stock, on the basis of the latest type-by-type amount of stock maintained in the stock control apparatus 1007 and the consumed medical supply information received from each of the storage and management apparatuses 1005 and 1006. Accordingly, the type and amount of consumed medical supplies, and the amount of respective types of medical supplies in stock can be acquired efficiently, easily and accurately. An order for a required amount of medical supplies that have been consumed and run short can be placed efficiently and properly for replenishment. As a result, the amount of respective types of medical supplies in stock in the medical institution 1001 can be maintained at just the right level. As described, the inventive system can contribute to the operation (management) of the medical institution 1001 such as a hospital.

The stock control apparatus 1007 receives the amount of respective types of medical supplies delivered to the medical institution 1001 from an external source, and calculates and stores the amount of respective types of medical supplies in stock on the basis of the delivered amount. Therefore, the amount of respective types of medical supplies in stock in the medical institution 1001 can be properly acquired. The medical institution 1001 is a hospital where each section (e.g. a medical operation unit 1002) requiring a stock of medical supplies is provided with one or multiple storage and management apparatuses 1005 and 1006. Therefore, the sections provided with storage and management apparatuses 1005 and 1006 can manage medical supplies properly. The stock control apparatus 1007 calculates and stores the amount of respective types of medical supplies in stock for each of the one or multiple storage and management apparatuses 1005 and 1006 in the each section. Accordingly, each section provided with the storage and management apparatuses 1005 and 1006 can manage the amount of respective types of medical supplies in stock and maintain the amount of stock at just the right level.

The stock control apparatus 1007 can manage the expiration date of the medical supplies in stock. For example, the type-by-type medical supply stock file 1092 stored in the storage unit of the HD 1084 or the like of the stock control apparatus 1007 may additionally store information on the expiration date of the medical supplies. As shown in FIG. 88, the amount may be stored for each medical supply (e.g. a medical supply N) and for each predetermine range of expiration dates (e.g., ten-day range of expiration dates). In this way, it is possible to properly acquire the type and amount of medical supplies past the expiration date and the type and amount of medical supplies close to the expiration date.

Illustrative Embodiment 6-2

As shown in FIG. 89, in a medical supply management system MS2 of an illustrative embodiment 6-2, the stock control apparatus 1007 for the medical institution 1001 is connected to medical supply supplier terminals 1101 of multiple medical supply suppliers 1100A-1100C delivering medical supplies to the medical institution 1001 via the LAN 1009 and the Internet 1105 (communicating means). The apparatus 1007 is provided with a target stock amount setting means 1110 which sets a target amount of respective types of medical supplies in stock, and an order determining means 1111 which determines the type and amount of medical supplies to be ordered from the medical supply suppliers 1100A-1100C, on the basis of the amount of respective types of medical supplies in stock maintained in the stock control apparatus 1006 (the type-by-type medical supply stock file 1092 of FIG. 87) and of the target amount of respective types of medical supplies set by the target stock amount setting means 1110.

As shown in FIG. 90, the storage unit of the HD 1084 or the like of the stock control apparatus 1007 stores a type-by-type target medical supply stock file 1093, a type-by-type medical supply order file 1094 and a medical supply supplier master file 1095. The medical supply supplier master file 1095 stores information such as the name, address, telephone number, fax number, mail address, URL and the like of multiple medical supply suppliers. In addition, the file 1095 stores medical supply information on one or multiple types of medical supplies that can delivered by each medical supply supplier.

As shown in FIG. 91, the type-by-type target medical supply stock file 1093 stores the target amount of respective types of medical supplies in stock in the whole medical institution 1001, and the target amount of respective types of medical supplies in stock in each section (medical operation unit, dispensary, medical ward and the like) in which is provided the storage and management apparatuses 1005 and 1006, i.e., the amount in each of the one or multiple storage and management apparatuses 1005 and 1006 provided in each section. The medical institution 1001 may use the target stock amount setting means 1110 to set any target amount of stock desired. Alternatively, an automatic determination may be made as to whether the amount in stock is excessive or insufficient in relation to the past target amount of stock, whereupon an appropriate target amount of stock may be set up that would not cause excessive or insufficient stock of medical supplies.

As shown in FIG. 92, the type-by-type medical supply order file 1094 stores the type and amount of medical supplies to be ordered from each of the medical supply suppliers 1100A-1100C. The medical supply to be ordered from each of the medical supply suppliers 1100A-1100C is determined by the order determining means 1111 on the basis of the type-by-type medical supply stock file 1092 of FIG. 87, the type-by-type target medical supply stock file 1093, and the medical supply supplier master file 1095. When there are multiple medical supply suppliers that deal with the medical supply to be ordered, a determination may be made on the medial supply supplier that offers a low unit price for the medical supply or on the medical supply supplier that provides the earliest date of delivery of the medical supply. The information necessary for this purpose should be stored in the medical supply supplier master file 1095.

As shown in FIG. 89, the medical supply management system MS2 is provided with a medical institution terminal 1112 connected via the LAN 1009 to the multiple storage and management apparatuses 1005 and 1006, the stock control apparatus 1007 and the incoming management apparatus 1008. The medical institution terminal 1112 is connected to the medical supply supplier terminals 1101 of the multiple medical supply suppliers 1100A-1100C via the Internet 1105. The medical institution terminal 1112 is provided with an ordering means 1113 which places an order by outputting order information, which contains the type and amount of medical supplies determined by the order determining means 1111 of the stock control apparatus 1007, to the medical supply supplier terminal 1101, splitting the information and directing them to selected ones of the medical supply suppliers 1100A-1100C from which the supplies should be ordered. The ordering means 1113 may automatically order at predetermined intervals (e.g., at intervals of one week or one month), or when it is determined, as a result of monitoring each type of medical supply, that the amount of stock falls below a predetermined level.

The medical supply supplier terminals 1101 of the medical supply suppliers 1100A-1100C may preferably be configured to receive the order information from the medical institute 1001 and transmit, when the order for the medical supply is accepted, acknowledgement to the medical institution terminal 1112 of the medical institute 1001 via the Internet 1105. The other aspects of the structure of the storage and management apparatuses 1005 and 1006, the stock control apparatus 1007, and the incoming management apparatus 1008 at the medical institute 1001 constituting the medical supply management system MS2 is basically the same as those of the medical supply management system MS1 of the illustrative embodiment 6-1.

The medical supply management system MS2 provides the following advantages.

The stock control apparatus 1007 is connected to the medical supply supplier terminals 1101 of the medical supply suppliers 1100A-1100C delivering medical supplies to the medical institution 1001 via the LAN 1009 and the Internet 1105. The apparatus 1007 is provided with the order determining means 1111 which determines the type and amount of medical supplies to be ordered from the medical supply suppliers 1100A-1100C, on the basis of the amount of respective types of medical supplies in stock maintained in the stock control apparatus 1007. The stock control apparatus 1007 is also provided with the ordering means 1113 which places an order by outputting order information, which contains the type and amount of medical supplies determined by the order determining means 1111, to the medical supply supplier terminal 1101. Therefore, the type and amount of medical supplies to be ordered from the medical supply suppliers 1100A-1100C are properly determined, and the order for the required type and amount of medical supplies is placed with the medical supply suppliers 1100A-1100C smoothly and properly.

The stock control apparatus 1007 is provided with the target stock amount setting means 1110 which sets a target amount of respective types of medical supplies in stock. The order determining means 1111 determines the type and amount of medical supplies to be ordered from the medical supply suppliers 1100A-1100C, on the basis of the stock amount and the target stock amount. Therefore, by setting the target amount of respective types of medical supplies in stock, the type and amount of medical supplies to be ordered from the medical supply suppliers 1100A-1100C is determined automatically. The system also enables various transaction data to be exchanged between the medical institution 10001 and the medical supply suppliers 1100A-1100C, thereby reducing the burden of administrative work in the medical institution 1001 and the medical supply suppliers 1100A-1100C. The other advantages of the system MS2 are basically the same as those of the medical supply management system MS1 of the illustrative embodiment 6-1.

Illustrative Embodiment 6-3

As shown in FIG. 93, a medical supply management system MS3 according to an illustrative embodiment 6-3 is provided with multiple medical institutions 1001A-1001C. Multiple medical resource storage and management apparatuses 1005, multiple medicine storage and management apparatuses 1006, the incoming management apparatus 1008 and a medical institution terminal 1120 are provided in each of the medical institutions 1001A-1001C. The LAN 1009 is built to communicably connect the storage and management apparatuses 1005 and 1006, the incoming management apparatus 1008 and medical institution terminal 1120. A data processor 1131 of a management server 1130 connected to the medical institution terminal 1120 of each of the medical institutions 1001A-1001C via the Internet 1105 corresponds to the stock control apparatus 1007 of the illustrative embodiments 6-1 and 6-2. Each of the medical supply supplier terminal 1101s of the multiple medical supply suppliers 1100A-1100C is connected to the data processor 1131 via the Internet 1105 (communicating means).

As shown in FIG. 94, the storage unit 1132 of the HD or the like of the data processor 1131 of the management server 1130 stores a stock control program, a medical supply master file 1140, a medical supply supplier master file 1141 and a management file 1142 for managing the multiple medical institutions 1001A-1001C. The management file 1142 for managing each of the multiple medical institutions 1001A-1001C stores a type-by-type incoming medical supply file 1150, a type-by-type medical supply consumption file 1151, a type-by-type medical supply stock file 1152, a type-by-type target medical supply stock file 1153 and a type-by-type medical supply order file 1154.

By executing the stock control program on the basis of the files 1140-1142 and 1150-1154, the data processor 1131 can calculate and store the amount of respective types of medical supplies in stock in the medical institutions 1001A-1001C, calculate and store the amount of respective types of medical supplies in stock in each of the one or multiple storage and management apparatuses 1005 and 1006 in the respective sections, set the target amount of respective types of medical supplies in stock in each of the one or multiple storage and management apparatuses 1005 and 1006, determine the type and amount of medical supplies to be ordered from the medical supply suppliers 1100A-1100C, and place an order by outputting order information, which contains the type and amount of medical supplies to be ordered, to the medical supply supplier terminal 1101 of the medical supply suppliers 1100A-1100C.

Consumed medical supply information related to the type and amount of medical supplies consumed is created at each of the medical institutions 1001A-1001C and is output to the management server 1130 via the Internet 1105. For example, the consumed medical supply information is created by the medical institution terminal 1120. The medical management system MS3 is a variation to the medical management system MS2 of the illustrative embodiment MS2 such that the stock control apparatus 1007 of the medical institution 1001 is omitted, the function of the apparatus 1007 is assigned to the data processor 1131 of the management server 1130, and the medical institution 1001 is replaced by the multiple medical institutions 1001A-1001C. Information in the files 1140-1142 and 1150-1154 is basically the same as that of the medical management systems MS1 and MS2 of the illustrative embodiments 6-1 and 6-2, respectively.

The medical management system MS3 provides the following advantages.

The LAN 1009 is built in each of the medical institutions 1001A-1000C to communicably connect the storage and management apparatuses 1005 and 1006, and the medical institution terminal 1120. The data processor 1131 of the management server 1130 connected to the medical institution terminal 1120 via the Internet 1105 corresponds to the stock control apparatus 1007 of the illustrative embodiments 6-1 and 6-2. Therefore, the majority of the processes in the medical management system MS3 for managing medical supplies can be performed by the data processor 1131 of the management server 1130, which is outside the medical institutions 1001A-1001C. The medical institutions 1001A-1001C can benefit from the medical supply management system MS3 while incurring the minimizing the cost to build the system MS3. Thus, the system MS3 is highly versatile.

The multiple medical institutions 1001A-1001C provided with the LAN 1009, and the multiple medical supply suppliers 1100A-1100C each provided with the medical supply supplier terminal 1101 are adapted to be connected to the management server 1130. Therefore, the multiple medical institutions 1001A-1001C can share the management server 1130 of the medical supply management server MS3, and the medical institutions 1001A-1001C can order a large variety of medical supplies from appropriate ones of the multiple medical supply suppliers 1100A-1100C via the management server 1130.

Illustrative Embodiment 6-4

In an illustrative embodiment 6-4, a description will be given, with reference to FIGS. 95-98, of the process of reconfiguring the target amount of respective types of medical supplies in stock performed by the target stock amount setting means 1110 (i.e., the computer constituting the target stock amount setting means 1110) in the medical supply management system MS2 of the illustrative embodiment 6-2 and in the medical supply management system MS3 of the illustrative embodiment 6-3. Si ($i=1, 2, 3 \ldots$) in the flowchart of FIGS. 95 and 97 indicates each step.

As mentioned before, the target stock amount setting means 1110 is a means for setting the target amount of respective types of medical supplies in stock and determines the type and amount of medical supplies to be ordered from the medical supply suppliers, on the basis of the target amount of stock thus set and the amount of respective types of medical supplies in stock. For example, when the target amount of one type of medical supply in stock is set to X and when the amount of that type of medical supply in stock is Y, the amount of medical supplies is (X-Y).

The amount consumed (frequency of use) differs between types of medical supplies. The amount of a given type of medical supply also differs depending on the form of medical institution (e.g., hospital for internal diseases, surgical hospital, general hospital, etc.), the number of patients using the medical institution, age group, distribution of diseases, season or the like. As is known, such parameters are subject to variation. It is a significantly difficult task to reconfigure the target amount of respective types of medical supplies in stock at a proper level in accordance with the parameters for the purpose of ordering just the right amount of medical supplies. Reconfiguration may be implemented by the target stock amount setting means 1111.

The flowchart of FIG. 95 is designed so that the target stock amount is reconfigured at predetermined intervals defined for evaluation of stock of each type of medical supply. In the illustrated process for reconfiguring the target stock amount, a determination is first made in S1 as to whether the predetermined interval defined to evaluate the stock of each type of medical supply has elapsed. For example, a determination is made as to whether several days (one week, etc.) have passed since the last evaluation, and the predetermined interval for evaluation of stock is set to expire concurrently with the placement of order. If the determination is affirmative in S1, the amount A of the medical supply in stock, the target stock amount B, the lower limit A1 of stock amount and the upper limit A2 are read in s2.

In S2, the amount A of the medical supply in stock is read from the type-by-type medical supply stock file and the target stock amount B is read from the type-by-type target medical supply stock file. The stock amount currently determined (i.e., the stock amount determined on one occasion since the last evaluation of stock) may represent the amount A of the medical supply in stock. Alternatively, an average of the stock amount evaluated on several occasions including the current and past occasions may represent the stock amount A. In this case, the stock amount evaluated on past occasions may be cumulatively stored. The lower limit A1 and the upper limit A2 are set up at the outset of the process for reconfiguring the target stock amount but are subject to reconfiguration. In this case, the operator may reconfigure the limits at will, or the limits may be automatically reconfigured to a proper level.

As shown in FIG. 96, when medical supplies are delivered since the last order, the stock amount A is found to be substantially equal to the target stock amount B (in actuality, the stock is reduced by the amount consumed between the placement of order and the delivery). Upon expiry of the predefined interval for stock evaluation, it is determined that the stock amount A is reduced as a result of consumption. An evaluation is made in S3 as to whether the stock amount A is within the range between the lower limit A1 and the upper limit A2, i.e., whether $A1 \leq A \leq A2$.

If the determination is affirmative in S3, it means that the stock amount is found to be proper upon evaluation of stock. The target stock amount B remains unchanged, and control proceeds to RETURN. If the determination is negative in S3, it means that the stock amount is not found to be proper upon evaluation of stock. In S4, excess or insufficiency $\alpha = A - $ preset stock amount value Am is calculated. In S5, the target stock amount B is reconfigured to $(B-\alpha)$. For example, Am may be an average of A1 and A2. That is, as shown in FIG. 96, the target stock amount B is not reconfigured if (1) $A1 \leq A \leq A2$; the target stock amount B is reduced by $(A-Am)$ if (2) $A>A2$; and the target stock amount B is increased by $(Am-A)$ if (3) $A<A1$.

The flowchart of FIG. 97, which shows a variation, is designed so that the target stock amount is reconfigured to ensure that the target stock amount is reconfigurable each time the stock amount of each type of medical supply is equal to or less than a predetermined lower limit A3. If this target stock amount reconfiguration process, the amount A of each type of medical supply in stock, the target stock amount B, the lower limit A3 of stock amount, a lower limit C1 of a period required to reach the lower limit of stock amount and an upper limit C2 thereof are read in S10.

In S10, the amount A of the medical supply in stock is read from the type-by-type medical supply stock file and the target stock amount B is read from the type-by-type target medical supply stock file. The lower limit A3, the lower limit C1 and the upper limit C2 are set up at the outset of the process for reconfiguring the target stock amount but are subject to reconfiguration. In this case, the operator may reconfigure the limits at will, or the limits may be automatically reconfigured to a proper level.

A evaluation is made in S11 as to whether the stock amount A is equal to or less than the lower limit A3, i.e., whether $A \leq A3$. If the determination is affirmative in S11, a period C, which was required to reach the lower limit of amount of medical supplies in stock since the last order for the medical supply, is calculated in S12. A evaluation is made in S13 as to whether the period C required to reach the lower limit of stock amount is within the range between the lower limit C1 and the upper limit C2, i.e., whether $C1 \leq C \leq C2$.

If the determination is affirmative in S13, it means that the period required to reach the lower limit of stock amount is proper. The target stock amount B remains unchanged, and control proceeds to RETURN. If the determination is negative in S13, it means that the period C required to reach the lower limit of stock amount is improper. A ratio $\beta$ between Cm and the period C (=Cm/C) is calculated in S14, where Cm denotes a preset lower limit of period required to reach the lower limit of stock amount. Thereupon the target stock amount B is reconfigured to $(B \times \beta)$ in S15. For example, Cm may be an average of C1 and C2.

As shown in FIG. 98, when medical supplies are delivered since the last order, the stock amount A is found to be substantially equal to the target stock amount B (in actuality, the stock is reduced by the amount consumed between the placement of order and the delivery). When the stock amount A is equal to or less than the lower limit A3 as a result of consumption, the target stock amount B remains unchanged if (1) $C1 \leq C \leq C2$, and the target stock amount B is reconfigured to $(B \times \beta)$ if (2) $C>C2$ or (3) $C<C1$.

Thus, it is possible to reconfigure the target stock amount B to a proper level automatically. Therefore, the type and amount of medical supplies to be ordered from the medical supply suppliers can be properly determined so that the amount of respective types of medical supplies in stock can be maintained at just the right level. In ordering medical supplies, a comparison may be made between the type and amount of medical supplies used in the past and the type and amount of medical supplies scheduled to be used, in order to know, for example, whether the amount of a particular type of medical supply scheduled to be used is in increase or decrease. The amount of medical supplies ordered may be increased or decreased depending on the information.

The medical management systems of the illustrative embodiments 6-1 through 6-4 may be applied to various medical institutions other than hospitals. For example, the systems may be applied to dispensaries or welfare institutions. Various modifications other than the matters disclosed above may be introduced and practiced without departing from the scope of the present invention.

The following technical ideas are encompassed by the embodiments described above and variations thereof.

(1) A medical resource storage and management apparatus comprising: a rack in which a series of depressions for insertion of partition members are formed so that a large number of medical resources are retrievably placed in respective partitions; partition members which are removably inserted into the depressions; medical resource detecting members which are arranged on the rack so as to alternate with the depressions in a direction in which the depressions are arranged, and each of which detects whether or not a medical resource is placed; retrieval guidance members for visual guidance which are arranged on the rack so as to alternate with the depressions in a direction in which the depressions are arranged; and a control unit which manages the storage status of the medical resources, based on the detection by the medical resource detecting members and which operates one of the retrieval guidance members in response to an input designating retrieval, wherein the control unit allows providing an input for configuration to designate whether or not the partition member is inserted into the depression, and the control unit collectively processes a block of medical resource detecting members and retrieval guidance members identified as being located on both sides of the depression from which the partition member is removed, based on the input for configuration.

(2) A medical resource storage and maintenance apparatus comprising: a rack in which a series of depressions for insertion of partition members are formed so that a large number of medical resources are retrievably placed in respective partitions; partition members which are removably inserted into the depressions; medical resource detecting members which are arranged on the rack so as to alternate with the depressions in a direction in which the depressions are arranged, and each of which detects whether or not a medical resource is placed; retrieval guidance members for visual guidance which are arranged on the rack so as to alternate with the depressions in a direction in which the depressions are arranged; a control unit which manages the storage status of the medical resources, based on the detection by the medical resource detecting members and which operates one of the retrieval guidance members in response to an input designating retrieval; and partition detecting members each of which detects whether the partition member is inserted into the depression, wherein the control unit collectively processes a block of medical resource detecting members and retrieval guidance members identified as being located on both sides of the depression from which the partition member is removed, based on the detection by the partition detecting member.

(3) The medical resource storage and management apparatus of (1) or (2), wherein the control unit issues an alarm if the results of detection by the medical resource detecting members in a block to be processed collectively continue to fail to match beyond a predetermined period of time.

(4) A medical resource storage and management apparatus comprising: a rack in which a series of depressions for insertion of partition members are formed so that a large number of medical resources are retrievably placed in respective partitions; partition members which are removably inserted into the depressions; medical resource detecting members which are arranged on the rack so as to alternate with the depressions in a direction in which the depressions are arranged, and each of which detects whether or not a medical resource is placed; retrieval guidance members for visual guidance which are arranged on the rack so as to alternate with the depressions in a direction in which the depressions are arranged; and a control unit which manages the storage status of the medical resources, based on the detection by the medical resource detecting members and which operates one of the retrieval guidance members in response to an input designating retrieval, wherein a medical resource name plate for visual guidance is attached to a partition member via a connecting member such that the connecting member is moved up and down depending on whether a medical resource is placed and as a result of interference between the connecting member and the medical resource, and that the medical resource name plate is located in a space where retrieval of a medical resource takes place, and is moved in association with the connecting member, and wherein the medical resource detecting member indirectly detects whether or not a medical resource is placed by detecting whether the medical resource name plate is raised or lowered.

(5) The medical resource storage and management apparatus of (4), wherein the medical resource name plate, when elevated in association with the placement of a medical resource in the associated location, is located above the retrieval guidance member in the associated location, and the medical resource name plate, when lowered in response to the retrieval of the medical resource from the associated location, shields the retrieval guidance member in the associated location from view.

(6) The medical resource storage and management apparatus of (4) or (5), wherein the control unit allows providing an input for configuration to designate whether the partition member is inserted into the depression, and, based on the configuration, the control unit collectively processes the medical resource detecting members and the retrieval guidance members identified as being located on both sides of the depression from which the partition member is removed.

(7) The medical resource storage and management apparatus of (4) or (5), further comprising a partition detecting member which detects whether the partition member is inserted into the depression, wherein, based on the detection by the partition, the control unit collectively processes the medical resource detecting members and the retrieval guidance members identified as being located on both sides of the depression from which the partition member is removed.

(8) The medical resource storage and management apparatus of (6) or (7), wherein the control unit issues an alarm if the results of detection by the medical resource detecting members in a block to be processed collectively continue to fail to match beyond a predetermined period of time.

(9) A medical resource storage and management apparatus comprising: a horizontal-bridging member which is provided with a series of hanger member fitting parts operable to hang and arrange a large number of medical resources, a hanger member which is fitted to the hanger member fitting part and is pivotally moved depending on whether a medical resource is hung; a medical resource detecting member which is provided in each of the hanger member fitting parts so as to detect whether a medical resource is hung in an associated location in accordance with the pivotal movement of the associated hanger member; a retrieval guidance member for visual confirmation provided in each of the hanger member fitting parts; and a control unit which manages the storage status of the medical resources, based on the detection by the medical resource detecting member, and which operates the retrieval guidance member in response to an input designating retrieval, wherein, at the time of hanging a medical resource, the pivotal movement of the hanger member causes the engaging part engaged with the medical resource to be lowered, and, at the time of retrieving a medical resource, the pivotal movement causes the engaging part to be elevated and moved toward an operator.

(10) The medical resource storage and management apparatus of (9), wherein the pivotal movement of the hanger member is based on the displacement between the center of gravitation and the pivot center.

(11) The medical resource storage and management apparatus of (9) or (10), wherein the control unit allows providing an input for configuration to designate whether the hanger member is fitted to the hanger member fitting part, and, based on the configuration, the control unit terminates the operation of the retrieval guidance member if it is determined that the hanger member is removed from the associated hanger member fitting part.

(12) The medical resource storage and management apparatus of (9) or (10), wherein the hanger member is detachable, the apparatus further comprising a hanger detecting member which detects whether the hanger member is fitted to the hanger member fitting part, wherein the control unit terminates the operation of the retrieval guidance member if it is determined that the hanger member is removed from the associated hanger member fitting part.

(13) The medical resource storage and management apparatus of (11) or (12), wherein the control unit issues an alarm if informed, by the medical resource detecting member of the hanger member fitting part in which it is determined that the hanger member is removed, that a medical resource is hung.

(14) A medical resource storage and management apparatus comprising: a rack in which a series of depressions for insertion of partition members are formed so that a large number of medical resources are retrievably placed in respective partitions; partition members which are removably inserted into the depressions; medical resource detecting members which are arranged on the rack so as to alternate with the depressions in a direction in which the depressions are arranged, and each of which detects whether or not a medical resource is placed; retrieval guidance members for visual guidance which are arranged on the rack so as to alternate with the depressions in a direction in which the depressions are arranged; and a control unit which manages the storage status of the medical resources, based on the detection by the medical resource detecting members and which operates one of the retrieval guidance members in response to an input designating retrieval, wherein a name plate support member is provided so as to be in parallel to the rack and behind the partition members, and a medical resource name plate for visual guidance is attached to the name plate support member via a detachable connecting member such that the connecting member is moved up and down depending on whether a medical resource is placed and as a result of interference between the connecting member and the medical resource, and that the medical resource name plate is moved in association with the connecting member in a space where retrieval of a medical resource takes place, and wherein the medical resource detecting member indirectly detects whether or not a medical resource is placed by detecting whether the medical resource name plate is raised or lowered.

(15) The medical resource storage and management apparatus of (14), wherein the medical resource name plate, when elevated in association with the placement of a medical resource in the associated location, is located above the retrieval guidance member in the associated location, and the medical resource name plate, when lowered in response to the retrieval of the medical resource from the associated location, shields the retrieval guidance member in the associated location from view.

(16) The medical resource storage and management apparatus of (14) or (15), wherein the control unit allows providing an input for configuration to designate whether the partition member is inserted into the depression, and, based on the configuration, the control unit collectively processes the medical resource detecting members and the retrieval guidance members identified as being located on both sides of the depression from which the partition member is removed.

(17) The medical resource storage and management apparatus of (14) or (15), further comprising a partition detecting member which detects whether the partition member is inserted into the depression, wherein, based on detection by the partition, the control unit collectively processes the medical resource detecting members and the retrieval guidance members identified as being located on both sides of the depression from which the partition member is removed.

(18) The medical resource storage and management apparatus of (16) or (17), wherein the control unit issues an alarm if the results of detection by the medical resource detecting members in a block to be processed collectively continue to fail to match beyond a predetermined period of time.

(19) A medical resource storage and management apparatus comprising: a rack plate in which are provided a series of medical resource detecting members for detecting whether or not a medical resource is placed on the rack plate and a series of retrieval guidance members for visual guidance; a control unit which manages the storage status of the medical resources, based on the detection by the medical resource detecting members and which operates one of the retrieval guidance members in response to an input designating retrieval; a storage case which is bounded at the bottom, sides and back thereof by a fixed plate, in which a movable medical resource name plate is provided in front of the case, and in which a connecting member extending backward from the medical resource name plate is adapted to make a vertical pivotal movement about the rear end thereof, wherein the medical resource name plate is moved up and down as a result of interference between the medical resource stored in the storage case and the connecting member, and whether the medical resource is placed or not is indirectly detected by detecting the up and down movement of the medical resource name plate, based on the fact that the up and down movement of the medical resource name plate causes the plate to enter or leave a range of detection by the medical resource detecting member in a state in which the storage case is placed on the rack plate.

(20) The medical resource storage and management apparatus of (19), wherein the storage case stores the medical resource on the connecting member, and the up and down movement of the medical resource name plate are associated with the nonavailability and availability of the medical resource, respectively.

(21) The medical resource storage and management apparatus of (19), wherein a series of case detecting member for detecting the storage case are arranged on the top face of the rack plate in association with the medical resource detecting members and the retrieval guidance members, wherein the storage case stores the medical resource underneath the connecting member, and wherein the up and down movement of the medical resource name plate are associated with the availability and nonavailability of the medical resource, respectively.

(22) The medical resource storage and management apparatus of any one of (19) through (21), wherein the control unit allows manual or automatic data configuration to indicate whether medical resource detecting members and retrieval guidance members are partitioned, and wherein the control unit collectively processes the medical resource detecting members and the retrieval guidance members identified as being located on both sides of the location configured as not being partitioned.

(23) The medical resource storage and management apparatus of (22), wherein the control unit issues an alarm if the results of detection by the medical resource detecting members in a block to be processed collectively continue to fail to match beyond a predetermined period of time.

(24) A medical supply management system for managing medical supplies in a medical institution, comprising: a plurality of storage and management apparatuses, wherein each of the plurality of storage and management apparatuses comprises: a plurality medical supply storage parts capable of storing a plurality of types of medical supplies; medical supply detecting means which detects whether a medical supply is stored in each of the medical supply storage parts; computer means which creates management information pertaining to the medical supplies in the plurality of medical supply storage parts on the basis of information detected by the medical supply detecting means; and retrieval guidance means which is controlled by the computer means so as to guide a user to the medical supply to be taken out, wherein the computer means in each storage and management apparatus is operable to control the retrieval guidance means on the basis of information on the medical supply to be taken out, and to create and output consumed medical supply information related to the type and amount of medical supplies consumed, the system further comprising stock control means which is communicably connected to the plurality of storage and management apparatuses, and which calculates and stores the amount of respective types of medical supplies in stock, on the basis of the latest amount of respective types of medical supplies in stock stored in the stock control means, and on the basis of the consumed medical supply information received from the storage and management apparatuses.

(25) The medical supply management system of (24), wherein the stock control means receives the amount of respective types of medical supplies delivered to the medical institution from an external source, and calculates and stores the amount of respective types of medical supplies in stock on the basis of the delivered amount.

(26) The medical supply management system of (24) or (25), wherein the plurality of types of medical supplies stored include at least one of injection/infusion resources, catheters, tubes, resources for anesthesia, resources for oxygen inhalation, oxygen masks, sterilized filters, artificial bones and artificial joints.

(27) The medical supply management system of (24) or (25), wherein at least one of the plurality of types of medical supplies is an ampule, a vial or a medicine contained in an infusion package.

(28) The medical supply management system of any one of (24)-(27), wherein the medical institution is a hospital, and one or multiple storage and management apparatuses is provided in each section of the hospital where a stock of medical supplies is necessary.

(29) The medical supply management system of any one of (24)-(28), wherein the stock control means calculates and stores the amount of respective types of medical supplies in stock for each of the one or multiple storage and management apparatuses in each section.

(30) The medical supply management system of any one of (24)-(29), wherein the stock control means is connected to medical supply supplier terminals of medical supply suppliers delivering medical supplies to the medical institution, the system further comprising: order determining means which determines the type and amount of medical supplies to be ordered from the medical supply suppliers, on the basis of the amount of respective types of medical supplies in stock maintained in the stock control means; and ordering means which places an order by outputting order information, which contains the type and amount of medical supplies determined by the order determining means, to the medical supply supplier terminal.

(31) The medical supply management system of (30), wherein the stock control means comprises a target stock amount setting means which sets a target amount of respective types of medical supplies in stock, and the order determining means determines the type and amount of medical supplies to be ordered from the medical supply suppliers, on the basis of the stock amount and the target stock amount.

(32) The medical supply management system of (30) or (31), wherein a local area network is formed in the medical institution to communicably connect at least the multiple medical resource storage and management apparatuses and the medical institution terminal, and the stock control means comprises a data processor of a management server connected to the medical institution terminal via a communicating means.

(33) The medical supply management system of (32), wherein multiple medical institutions each provided with the local area network, and multiple medical supply suppliers each provided with the medical supply supplier terminal are adapted to be connected to the management server.

Given above is an explanation of the present invention based on the embodiments. While the preferred embodiments of the present invention have been described using specific terms, such description is for illustrative purposes only, and it is to be understood that changes and variations may be made without departing from the spirit or scope of the appended claims.

INDUSTRIAL APPLICABILITY

As described above, the present invention is applicable to management of medical resources or medical supplies.

The invention claimed is:

1. A medical resource storage and management apparatus comprising:
a rack in which a series of depressions for insertion of partition members are formed so that a large number of medical resources are retrievably placed in respective partitions;
the partition members which are removably inserted into the depressions;
medical resource detecting sensors which are arranged on the rack so as to alternate with the depressions in a direction in which the depressions are arranged, and each of which detects whether or not a medical resource is placed by sensing a bottom of a medical resource;
retrieval guidance members for visual guidance which are arranged on the rack so as to alternate with the depressions in a direction in which the depressions are arranged; and
a control unit which manages the storage status of the medical resources, based on the detection by the medical resource detecting sensors and which operates one of the retrieval guidance members in response to an input designating retrieval, wherein
the control unit allows providing an input for configuration to designate whether or not the partition member is inserted into the depression, and
the control unit collectively processes a block of medical resource detecting sensors and retrieval guidance members identified as being located on both sides of the depression from which the partition member is removed, based on the input for configuration,
wherein the control unit issues an alarm if the results of detection by the medical resource detecting sensors in a block to be processed collectively continue to fail to match beyond a predetermined period of time.

2. A medical resource storage and maintenance apparatus comprising:
a rack in which a series of depressions for insertion of partition members are formed so that a large number of medical resources are retrievably placed in respective partitions;
the partition members which are removably inserted into the depressions;
medical resource detecting sensors which are arranged on the rack so as to alternate with the depressions in a direction in which the depressions are arranged, and each of which detects whether or not a medical resource is placed by sensing a bottom of the medical resource;
retrieval guidance members for visual guidance which are arranged on the rack so as to alternate with the depressions in a direction in which the depressions are arranged;

a control unit which manages the storage status of the medical resources, based on the detection by the medical resource detecting sensors and which operates one of the retrieval guidance members in response to an input designating retrieval; and partition detecting members each of which detects whether the partition member is inserted into the depression, wherein the control unit collectively processes a block of medical resource detecting sensors and retrieval guidance members identified as being located on both sides of the depression from which the partition member is removed, based on the detection by the partition detecting member, wherein the control unit issues an alarm if the results of detection by the medical resource detecting sensors in a block to be processed collectively continue to fail to match beyond a predetermined period of time.

* * * * *